(12) United States Patent
Montenegro et al.

(10) Patent No.: US 12,219,874 B2
(45) Date of Patent: Feb. 4, 2025

(54) MATERIALS FOR ELECTRONIC DEVICES

(71) Applicant: Merck Patent GmbH, Darmstadt (DE)

(72) Inventors: Elvira Montenegro, Weinheim (DE); Teresa Mujica-Fernaud, Darmstadt (DE); Florian Maier-Flaig, Weinheim (DE); Frank Voges, Bad Duerkheim (DE); Christian Wirges, Weiterstadt (DE)

(73) Assignee: Merck Patent GmbH, Darmstadt (DE)

( * ) Notice: Subject to any disclaimer, the term of this patent is extended or adjusted under 35 U.S.C. 154(b) by 789 days.

(21) Appl. No.: 17/415,990

(22) PCT Filed: Dec. 17, 2019

(86) PCT No.: PCT/EP2019/085517
§ 371 (c)(1),
(2) Date: Jun. 18, 2021

(87) PCT Pub. No.: WO2020/127176
PCT Pub. Date: Jun. 25, 2020

(65) Prior Publication Data
US 2022/0109116 A1   Apr. 7, 2022

(30) Foreign Application Priority Data

Dec. 20, 2018 (EP) ..................... 18214579

(51) Int. Cl.
| | | |
|---|---|---|
| *C07D 307/91* | (2006.01) | |
| *C07D 333/76* | (2006.01) | |
| *C07D 405/12* | (2006.01) | |
| *C07D 409/10* | (2006.01) | |
| *C07D 409/14* | (2006.01) | |
| *H10K 85/60* | (2023.01) | |
| *H10K 50/15* | (2023.01) | |
| *H10K 50/17* | (2023.01) | |
| *H10K 50/18* | (2023.01) | |

(52) U.S. Cl.
CPC ....... *H10K 85/6574* (2023.02); *C07D 307/91* (2013.01); *C07D 333/76* (2013.01); *C07D 405/12* (2013.01); *C07D 409/10* (2013.01); *C07D 409/14* (2013.01); *H10K 85/633* (2023.02); *H10K 85/636* (2023.02); *H10K 85/6572* (2023.02); *H10K 85/6576* (2023.02); *H10K 50/15* (2023.02); *H10K 50/17* (2023.02); *H10K 50/18* (2023.02)

(58) Field of Classification Search
None
See application file for complete search history.

(56) References Cited

U.S. PATENT DOCUMENTS

| | | | |
|---|---|---|---|
| 10,446,761 B2 | 10/2019 | Yabunouchi et al. | |
| 10,505,121 B2 | 12/2019 | Song et al. | |
| 2016/0093810 A1 | 3/2016 | Miyake et al. | |
| 2018/0287069 A1* | 10/2018 | Cha ..................... | H10K 85/633 |
| 2019/0252613 A1 | 8/2019 | Song et al. | |

FOREIGN PATENT DOCUMENTS

| | | | |
|---|---|---|---|
| CN | 107652189 A | 2/2018 | |
| CN | 108623545 A | 10/2018 | |
| CN | 108864012 A | 11/2018 | |
| CN | 108864013 A | 11/2018 | |
| CN | 111683943 A | 9/2020 | |
| EP | 2428512 A2 | 3/2012 | |
| JP | 2011-082238 A | 4/2011 | |
| JP | 2016-066723 A | 4/2016 | |
| KR | 10-2014-0035737 A | 3/2014 | |
| KR | 10-2014-0091487 A | 7/2014 | |
| KR | 10-2017-0088601 A | 8/2017 | |
| KR | 2018-0127905 A | 11/2018 | |
| WO | 2007/125714 A1 | 11/2007 | |
| WO | 2011/021520 A1 | 2/2011 | |
| WO | 2014/042420 A1 | 3/2014 | |
| WO | 2017/148564 A1 | 9/2017 | |
| WO | WO 2017/191896 A1 * | 11/2017 | |
| WO | 2019/151682 A1 | 8/2019 | |

OTHER PUBLICATIONS

International Preliminary Report on Patentability received for PCT Patent Application No. PCT/EP2019/085517, mailed on Jul. 1, 2021, 13 pages.
International Search Report and Written Opinion received for PCT Patent Application No. PCT/EP2019/085517, mailed on Apr. 6, 2020, 17 pages.

* cited by examiner

*Primary Examiner* — Tae H Yoon
(74) *Attorney, Agent, or Firm* — Faegre Drinker Biddle & Reath LLP

(57) ABSTRACT

The present application concerns compounds for use in electronic devices, processes for preparing the compounds, and electronic devices comprising the compounds.

18 Claims, No Drawings

MATERIALS FOR ELECTRONIC DEVICES

CROSS-REFERENCE TO RELATED APPLICATIONS

This application is a national stage application (under 35 U.S.C. § 371) of PCT/EP2019/085517, filed Dec. 17, 2019, which claims benefit of European Application No. 18214579.7, filed Dec. 20, 2018, both of which are incorporated herein by reference in their entirety.

The present application relates to an amine compound comprising a fluorene group, which is suitable for use in electronic devices, in particular organic electroluminescent devices (OLEDs).

Electronic devices in the context of this application are understood to mean what are called organic electronic devices, which contain organic semiconductor materials as functional materials. More particularly, these are understood to mean OLEDs.

The construction of OLEDs in which organic compounds are used as functional materials is common knowledge in the prior art. In general, the term OLEDs is understood to mean electronic devices which have one or more layers comprising organic compounds and emit light on application of electrical voltage.

In electronic devices, especially OLEDs, there is great interest in improving the performance data, especially lifetime, efficiency and operating voltage. In these aspects, it has not yet been possible to find any entirely satisfactory solution.

A great influence on the performance data of electronic devices is possessed by layers having a hole-transporting function, for example hole-injecting layers, hole transport layers, electron blocking layers and also emitting layers. For use in these layers, there is a continuous search for new materials having hole-transporting properties.

In the course of the present invention, it has been found that amine compounds which have a fluorene group and a group selected from dibenzofuran and dibenzothiophene groups, are very well suited for use as materials with hole transporting function, in particular for use as materials of the hole transport layer, the electron blocking layer and/or the emitting layer, more particularly for use in the hole transport layer and/or the electron blocking layer. An electron blocking layer is understood in this context to be a layer which is directly adjacent to the emitting layer on the anode side, and which serves to block electrons which are present in the emitting layer from entering the hole transport layers of the OLED.

When used in electronic devices, in particular in OLEDs, they lead to excellent results in terms of lifetime, operating voltage and quantum efficiency of the devices. The compounds are also characterized by very good hole-conducting properties, very good electron-blocking properties, high glass transition temperature, high oxidation stability, good solubility, high thermal stability, and low sublimation temperature.

The present invention thus relates to a compound of a formula (I)

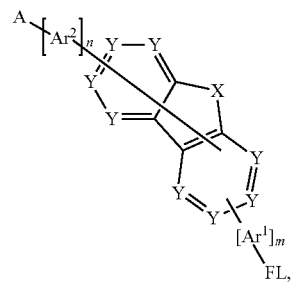

formula (I)

where:
FL is a group of one of formulae (FL-1) and (FL-2)

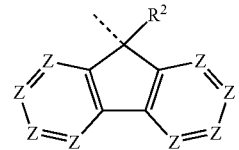

formula (FL-1)

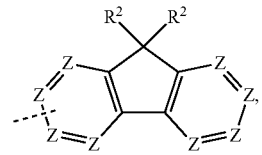

formula (FL-2)

where the dotted bond is the bond to the rest of formula (I); Z is C, if in formula (FL-2), this Z is the bonding position of the formula (FL-2) to the rest of the formula (I); and Z is in all other cases selected, identically or differently at each occurrence, from $CR^1$ and N;

Y is C if a group $-[Ar^2]_n-N(Ar^3)(Ar^4)$ or $-[Ar']_m-FL$ is bonded in this position; and Y is in all other cases selected, identically or differently at each occurrence, from $CR^3$ and N;

X is O or S;

$Ar^1$ is, identically or differently at each occurrence, selected from aromatic ring systems having 6 to 40 aromatic ring atoms, which are substituted by radicals $R^4$, and heteroaromatic ring systems having 5 to 40 aromatic ring atoms, which are substituted by radicals $R^4$;

$Ar^2$ is, identically or differently at each occurrence, selected from aromatic ring systems having 6 to 40 aromatic ring atoms, which are substituted by radicals $R^5$, and heteroaromatic ring systems having 5 to 40 aromatic ring atoms, which are substituted by radicals $R^5$;

A corresponds to the following formula

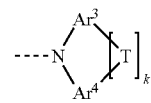

which is bonded via the dotted line;

$Ar^3$ and $Ar^4$ are, identically or differently at each occurrence, selected from aromatic ring systems having 6 to 40 aromatic ring atoms, which are substituted by radicals $R^6$, and heteroaromatic ring systems having 5 to 40 aromatic ring atoms, which are substituted by radicals $R^6$;

T is a single bond or a divalent group selected from $C(R^6)_2$, $Si(R^6)_2$, $N(R^6)$, O, and S;

k is 0 or 1, where k=0 means that T does not occur and the groups $Ar^3$ and $Ar^4$ are not connected;

$R^1$ is selected, identically or differently at each occurrence, from H, D, F, Cl, Br, I, $C(=O)R^7$, CN, $Si(R^7)_3$, $N(R^7)_2$, $P(=O)(R^7)_2$, $OR^7$, $S(=O)R^7$, $S(=O)_2R^7$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^1$ may be connected to each other to form a ring; where the said alkyl, alkoxy, alkenyl and alkynyl groups and the said aromatic and heteroaromatic ring systems are in each case substituted by radicals $R^7$, and where one or more $CH_2$ groups in the said alkyl, alkoxy, alkenyl and alkynyl groups may in each case be replaced by —$R^7C=CR^7$—, —C≡C—, $Si(R^7)_2$, C=O, C=NR$^7$, —C(=O)O—, —C(=O)NR$^7$—, NR$^7$, P(=O)(R$^7$), —O—, —S—, SO or $SO_2$;

$R^2$ is selected, identically or differently at each occurrence, from H, D, F, Cl, Br, I, CN, $Si(R^7)_3$, $N(R^7)_2$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^2$ may be connected to each other to form a ring; where the said alkyl, alkoxy, alkenyl and alkynyl groups and the said aromatic and heteroaromatic ring systems are in each case substituted by radicals $R^7$, and where one or more $CH_2$ groups in the said alkyl, alkoxy, alkenyl and alkynyl groups may in each case be replaced by —$R^7C=CR^7$—, —C≡C—, $Si(R^7)_2$, C=O, C=NR$^7$, —C(=O)O—, —C(=O)NR$^7$—, NR$^7$, P(=O)(R$^7$), —O—, —S—, SO or $SO_2$;

$R^3$ is selected, identically or differently at each occurrence, from H, D, F, Cl, Br, I, $C(=O)R^7$, CN, $Si(R^7)_3$, $N(R^7)_2$, $P(=O)(R^7)_2$, $OR^7$, $S(=O)R^7$, $S(=O)_2R^7$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^3$ may be connected to each other to form a ring; where the said alkyl, alkoxy, alkenyl and alkynyl groups and the said aromatic and heteroaromatic ring systems are in each case substituted by radicals $R^7$, and where one or more $CH_2$ groups in the said alkyl, alkoxy, alkenyl and alkynyl groups may in each case be replaced by —$R^7C=CR^7$—, —C≡C—, $Si(R^7)_2$, C=O, C=NR$^7$, —C(=O)O—, —C(=O)NR$^7$—, NR$^7$, P(=O)(R$^7$), —O—, —S—, SO or $SO_2$;

$R^4$ is selected, identically or differently at each occurrence, from H, D, F, Cl, Br, I, $C(=O)R^7$, CN, $Si(R^7)_3$, $N(R^7)_2$, $P(=O)(R^7)_2$, $OR^7$, $S(=O)R^7$, $S(=O)_2R^7$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^4$ may be connected to each other to form a ring; where the said alkyl, alkoxy, alkenyl and alkynyl groups and the said aromatic and heteroaromatic ring systems are in each case substituted by radicals $R^7$, and where one or more $CH_2$ groups in the said alkyl, alkoxy, alkenyl and alkynyl groups may in each case be replaced by —$R^7C=CR^7$—, —C≡C—, $Si(R^7)_2$, C=O, C=NR$^7$, —C(=O)O—, —C(=O)NR$^7$—, NR$^7$, P(=O)(R$^7$), —O—, —S—, SO or $SO_2$;

$R^5$ is selected, identically or differently at each occurrence, from H, D, F, Cl, Br, I, $C(=O)R^7$, CN, $Si(R^7)_3$, $N(R^7)_2$, $P(=O)(R^7)_2$, $OR^7$, $S(=O)R^7$, $S(=O)_2R^7$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^5$ may be connected to each other to form a ring; where the said alkyl, alkoxy, alkenyl and alkynyl groups and the said aromatic and heteroaromatic ring systems are in each case substituted by radicals $R^7$, and where one or more $CH_2$ groups in the said alkyl, alkoxy, alkenyl and alkynyl groups may in each case be replaced by —$R^7C=CR^7$—, —C≡C—, $Si(R^7)_2$, C=O, C=NR$^7$, —C(=O)O—, —C(=O)NR$^7$—, NR$^7$, P(=O)(R$^7$), —O—, —S—, SO or $SO_2$;

$R^6$ is selected, identically or differently at each occurrence, from H, D, F, Cl, Br, I, $C(=O)R^7$, CN, $Si(R^7)_3$, $N(R^7)_2$, $P(=O)(R^7)_2$, $OR^7$, $S(=O)R^7$, $S(=O)_2R^7$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^6$ may be connected to each other to form a ring; where the said alkyl, alkoxy, alkenyl and alkynyl groups and the said aromatic and heteroaromatic ring systems are in each case be substituted by radicals $R^7$, and where one or more $CH_2$ groups in the said alkyl, alkoxy, alkenyl and alkynyl groups may in each case be replaced by —$R^7C=CR^7$—, —C≡C—, $Si(R^7)_2$, C=O, C=NR$^7$, —C(=O)O—, —C(=O)NR$^7$—, NR$^7$, P(=O)(R$^7$), —O—, —S—, SO or $SO_2$;

$R^7$ is selected, identically or differently at each occurrence, from H, D, F, Cl, Br, I, $C(=O)R^8$, CN, $Si(R^8)_3$, $N(R^8)_2$, $P(=O)(R^8)_2$, $OR^8$, $S(=O)R^8$, $S(=O)_2R^8$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^7$ may be connected to each other to form a ring; where the said alkyl, alkoxy, alkenyl and alkynyl groups and the said aromatic and heteroaromatic ring systems are in each case be substituted by radicals $R^8$, and where one or more $CH_2$ groups in the said alkyl, alkoxy, alkenyl and alkynyl groups may in each case be replaced by —$R^8C=CR^8$—, —C≡C—, $Si(R^8)_2$, C=O, C=NR$^8$, —C(=O)O—, —C(=O)NR$^8$—, NR$^8$, P(=O)(R$^8$), —O—, —S—, SO or $SO_2$;

$R^8$ is selected, identically or differently at each occurrence, from H, D, F, Cl, Br, I, CN, alkyl groups having 1 to 20 C atoms, aromatic ring systems having 6 to 40 C atoms, or heteroaromatic ring systems having 5 to 40 aromatic ring atoms; where two or more radicals $R^8$ may be connected to each other to form a ring; and where the said alkyl groups, aromatic ring systems and heteroaromatic ring systems may be substituted by one or more radicals selected from F and CN;

m is 0, 1, 2, 3, or 4;

n is 0, 1, 2, 3, or 4.

The following definitions apply to the chemical groups used as general definitions. They apply insofar as no more specific definitions are given.

An aryl group here is taken to mean either a single aromatic ring, for example benzene, or a condensed aromatic polycycle, for example naphthalene, phenanthrene, or anthracene. A condensed aromatic polycycle in the sense of the present application consists of two or more single aromatic rings which are condensed with one another. An aryl group in the sense of this invention contains 6 to 40 aromatic ring atoms, of which none is a heteroatom.

A heteroaryl group here is taken to mean either a single heteroaromatic ring, such as pyridine, pyrimidine or thiophene, or a condensed heteroaromatic polycycle, such as quinoline or carbazole. A condensed heteroaromatic polycycle in the sense of the present application consists of two or more single aromatic or heteroaromatic rings, which are condensed with one another, where at least one of the two or more single aromatic or heteroaromatic rings is a heteroaromatic ring. A heteroaryl group in the sense of this invention contains 5 to 40 aromatic ring atoms, at least one of which is a heteroatom. The heteroatoms are preferably selected from N, O and S.

An aryl or heteroaryl group, which may in each case be substituted by the above-mentioned radicals, is taken to mean, in particular, a group derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, benzimidazolo[1,2-a]benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the sense of this invention is a system which does not necessarily contain only aryl groups, but which may additionally contain one or more non-aromatic rings, which are condensed with at least one aryl group. Such non-aromatic rings contain exclusively carbon atoms as ring atoms. Examples of groups embraced by such definition are tetrahydronaphthalene, fluorene, and spirobifluorene. Furthermore, the term aromatic ring system is understood to embrace systems consisting of two or more aromatic ring systems which are connected to each other via single bonds, such as biphenyl, terphenyl, 7-phenyl-2-fluorenyl and quaterphenyl. An aromatic ring system in the sense of this invention contains 6 to 40 C atoms and no heteroatoms as ring atoms of the ring system. An aromatic ring system in the sense of this application does not comprise any heteroaryl groups, as defined above.

A heteroaromatic ring system is defined in analogy to the aromatic ring system above, but with the difference that it must obtain at least one heteroatom as one of the ring atoms. As it is the case for the aromatic ring system, it does not necessarily contain only aryl and heteroaryl groups, but it may additionally contain one or more non-aromatic rings, which are condensed with at least one aryl or heteroaryl group. The non-aromatic rings may contain only carbon atoms as ring atoms, or they may contain additionally one or more heteroatoms, where the heteroatoms are preferably selected from N, O and S. An example for such a heteroaromatic ring system is benzpyranyl. Furthermore, the term heteroaromatic ring system is understood to embrace systems consisting of two or more aromatic or heteroaromatic ring systems, which are connected to each other via single bonds, such as 4,6-diphenyl-2-triazinyl. A heteroaromatic ring system in the sense of this invention contains 5 to 40 ring atoms, which are selected from carbon and heteroatoms, where at least one of the ring atoms is a heteroatom. The heteroatoms are preferably selected from N, O or S.

The terms "heteroaromatic ring system" and "aromatic ring system" according to the definition of the present application differ from each other by the fact that the aromatic ring system cannot comprise any heteroatom as ring atom, whereas the heteroaromatic ring system must comprise at least one heteroatom as ring atom. Such heteroatom may be present as a ring atom of a non-aromatic heterocyclic ring of the system, or as a ring atom of an aromatic heterocyclic ring of the system.

According to the above, any aryl group, as defined above, is embraced by the term "aromatic ring system", as defined above, and any heteroaryl group, as defined above, is embraced by the term "heteroaromatic ring system", as defined above.

An aromatic ring system having 6 to 40 aromatic ring atoms or a heteroaromatic ring system having 5 to 40 aromatic ring atoms is in particular a group which is derived from the above mentioned aryl or heteroaryl groups, or from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, and indenocarbazole, or from any combinations of these groups.

For the purposes of the present invention, a straight-chain alkyl group having 1 to 20 C atoms or a branched or cyclic alkyl group having 3 to 20 C atoms or an alkenyl or alkynyl group having 2 to 20 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl.

An alkoxy or thioalkyl group having 1 to 20 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyl-oxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The phrase "two or more radicals may be connected to each other to form a ring" shall be understood to include the case that the two radicals are connected by a chemical bond. Additionally, the phrase shall be understood to include the case that one of the two radicals is H, this radical H is removed, and the other of the two radicals forms a ring by being connected to the position, to which this radical H was initially bonded. Additionally, this phrase shall be understood to include the case that both of the two radicals are H, they are both removed, and the positions to which the two radicals H were bonded are connected by a single bond to form a ring.

For the purposes of the present application, if a group is depicted as bonded to a ring having multiple bonding positions, and the group has an index which is an integer, this means that the respective group is present multiple times on the ring. E.g. if a group —[R$^1$]$_4$ is shown in a formula, bonded to an aromatic ring of the fluorene moiety of the formula, this means that all four positions on that aromatic ring are substituted with R$^1$.

The group —[Ar$^2$]$_n$-A can be bonded in any of the positions on the dibenzofuran or dibenzothiophene group in formula (I), as represented by the bond which crosses the whole of the dibenzofuran or dibenzothiophene group.

The compound according to formula (I) is preferably a monoamine. A monoamine is understood to be a compound which has only one triarylamine group, preferably a compound which has only one amine group.

Preferably, FL conforms to the formula (FL-1).

The group of formula (FL-2) preferably conforms to the following formula:

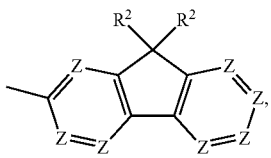

Formula (FL-2-1)

where the dotted bond is the bond to the rest of formula (I).

Preferably, Z is C, if in formula (FL-2), this Z is the bonding position of the formula (FL-2) to the rest of the formula (I); and Z is in all other cases CR$^1$.

Preferably, Y is C, if a group —[Ar$^2$]$_n$—N(Ar$^3$)(Ar$^4$) or —[Ar$^1$]$_m$-FL is bonded in this position; and Y is in all other cases CR$^3$.

X is preferably O.

According to a preferred embodiment, Ar$^1$ is selected from divalent groups derived from phenyl, biphenyl, terphenyl, naphthalene, fluorene, indenofluorene, indenocarbazole, spirobifluorene, dibenzofuran, dibenzothiophene, and carbazole, which are optionally substituted with one or more radicals R$^4$, more preferably selected from divalent groups derived from phenyl, biphenyl and fluorene, which are optionally substituted with one or more radicals R$^4$, most preferably selected from 1,2-phenylene, 1,3-phenylene and 1,4-phenylene, of which 1,4-phenylene is preferred, where the phenylene groups are optionally substituted with one or more radicals R$^4$ and are preferably unsubstituted.

Index m is preferably 0, 1 or 2. For the case where the group FL conforms to the formula (FL-1), m is preferably 1. For the case where the group FL conforms to the formula (FL-2), m is preferably 0.

Preferred groups —[Ar$^1$]$_m$— for the case of m=1 are selected from divalent groups derived from phenyl, biphenyl, terphenyl, naphthalene, fluorene, indenofluorene, indenocarbazole, spirobifluorene, dibenzofuran, dibenzothiophene, and carbazole, which are substituted with radicals R$^4$, more preferably selected from divalent groups derived from phenyl, biphenyl and fluorene, which are substituted with radicals R$^4$, most preferably selected from divalent groups derived from phenyl, of which 1,4-phenylene is preferred, where the phenylene groups are substituted with radicals R$^4$, and where in such case, radicals R$^4$ are preferably H.

Preferred groups Ar$^2$ are selected from divalent groups derived from benzene, biphenyl, terphenyl, naphthalene, fluorene, indenofluorene, indenocarbazole, spirobifluorene, dibenzofuran, dibenzothiophene, and carbazole, which are substituted with radicals R$^5$, more preferably selected from divalent groups derived from benzene, biphenyl, naphthalene and fluorene, which are substituted with radicals R$^5$.

According to a preferred embodiment, index n is 0, so that the group Ar$^2$ is not present, and the groups bonding to group Ar$^2$ in formula (I) are directly connected to each other.

According to an alternative preferred embodiment, index n is 1 or 2, preferably 1.

Preferred groups —[Ar$^2$]$_n$— for the case of n=1 are selected from divalent groups derived from phenyl, biphenyl, terphenyl, naphthalene, fluorene, indenofluorene, indenocarbazole, spirobifluorene, dibenzofuran, dibenzothiophene, and carbazole, which are substituted with radicals R$^5$, more preferably selected from divalent groups derived from phenyl, naphthyl, biphenyl and fluorene, which are substituted with radicals R$^5$.

Particularly preferred groups —[Ar$^2$]$_n$— for the case of n=1 are selected from the following groups

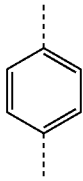

Ar$^2$-1

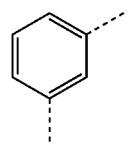

Ar$^2$-2

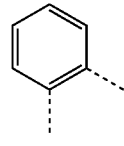

Ar$^2$-3

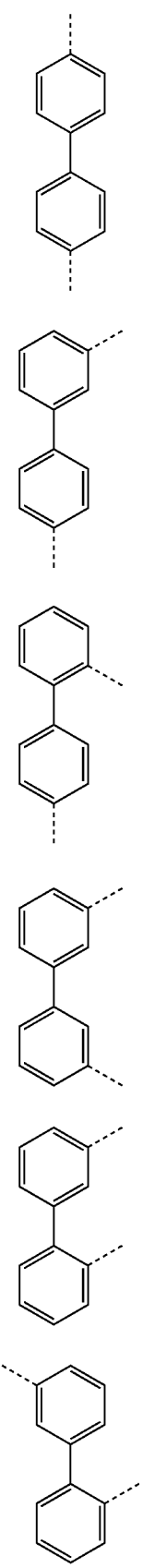
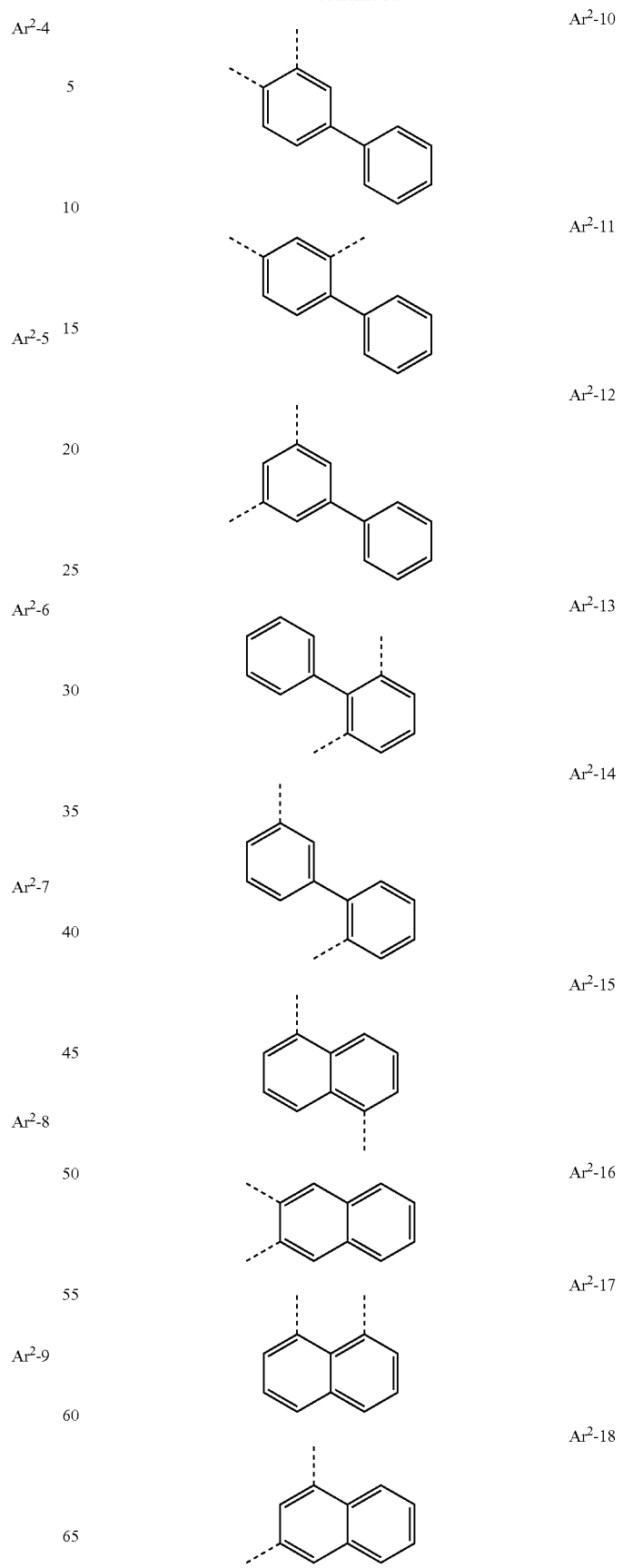

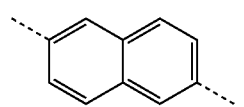 Ar²-19
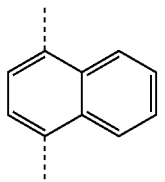 Ar²-20
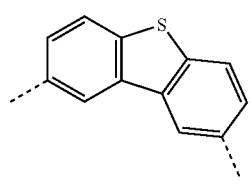 Ar²-21
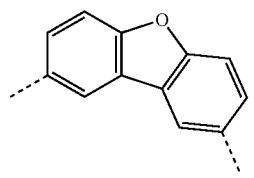 Ar²-22
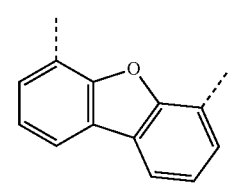 Ar²-23
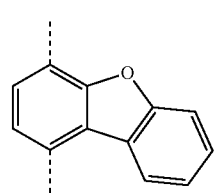 Ar²-24
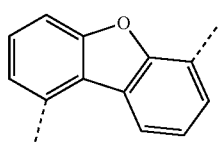 Ar²-25
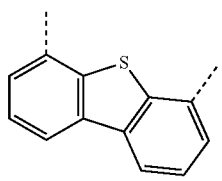 Ar²-26
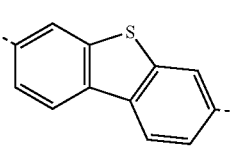 Ar²-27
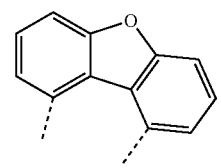 Ar²-28
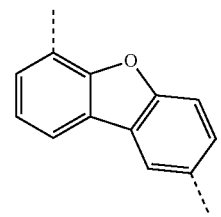 Ar²-29
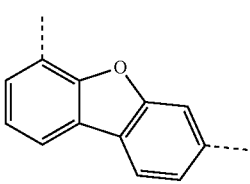 Ar²-30
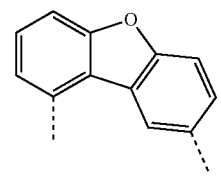 Ar²-31
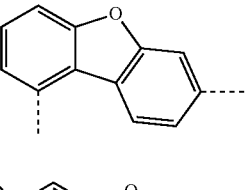 Ar²-32
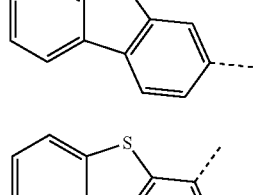 Ar²-33
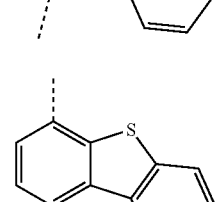 Ar²-34
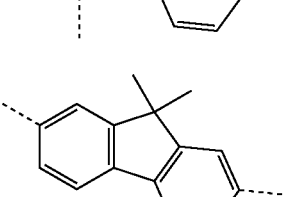 Ar²-35
 Ar²-36

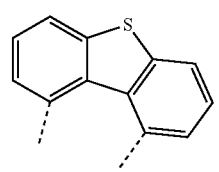 Ar²-37
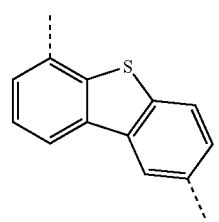 Ar²-38
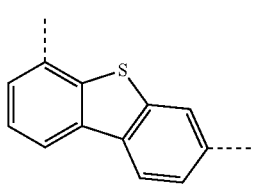 Ar²-39
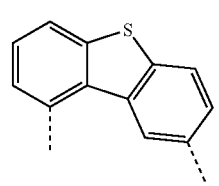 Ar²-40
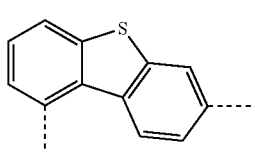 Ar²-41
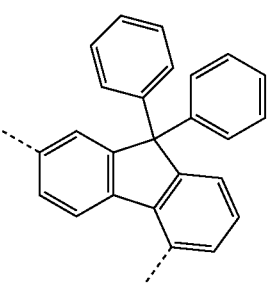 Ar²-42
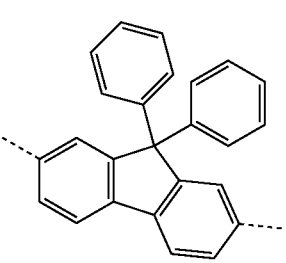 Ar²-43
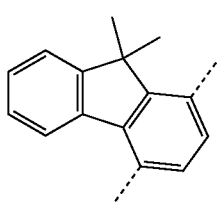 Ar²-44
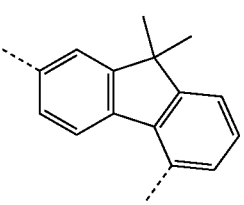 Ar²-45
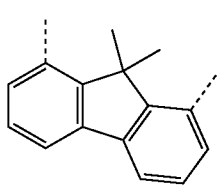 Ar²-46
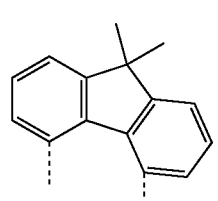 Ar²-47
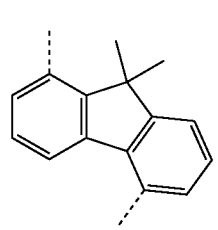 Ar²-48
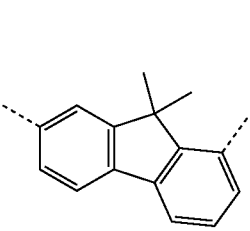 Ar²-49
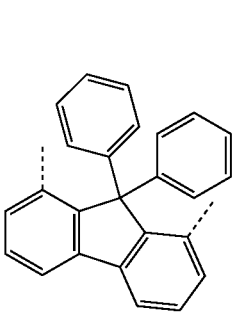 Ar²-50

Ar²-51
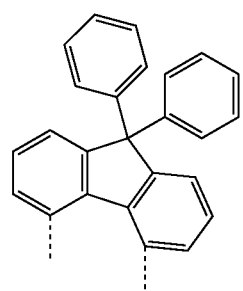
Ar²-52
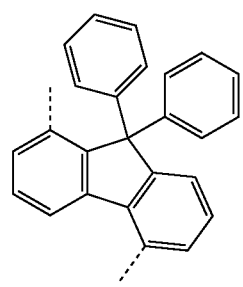
Ar²-53
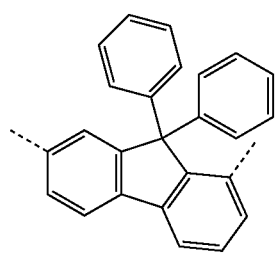
Ar²-54
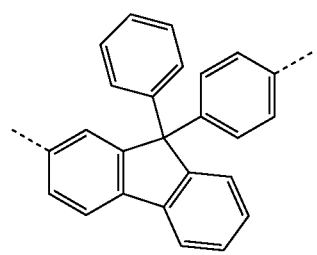
Ar²-55
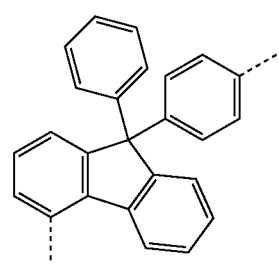
Ar²-56
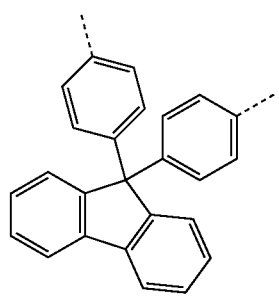
Ar²-57
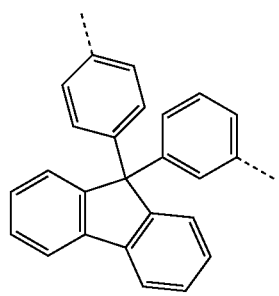
Ar²-58
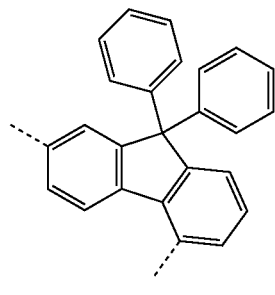
Ar²-59
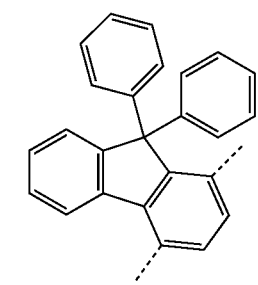
Ar²-60
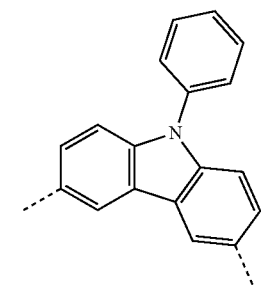

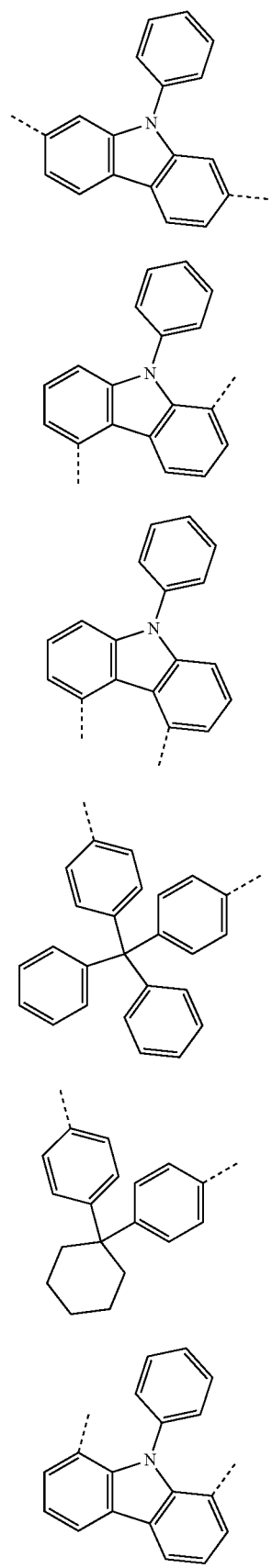

-continued

Ar²-72
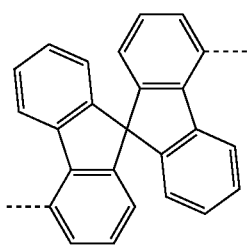

Ar²-73
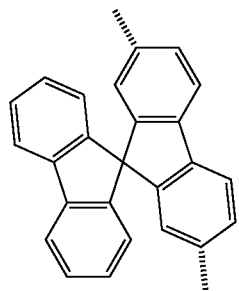

Ar²-74
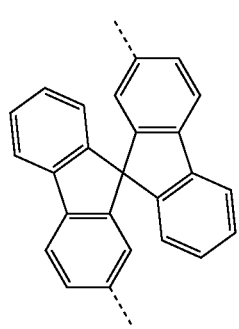

Ar²-75
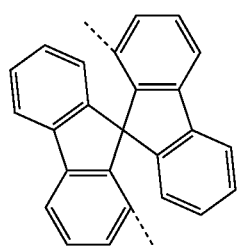

Ar²-76
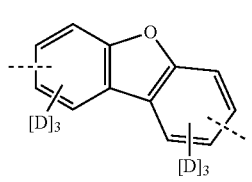

Ar²-77
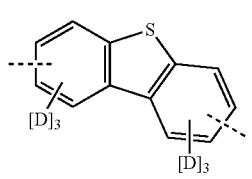

-continued

Ar²-78
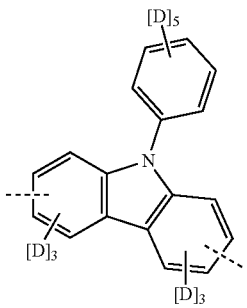

Ar²-79
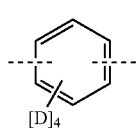

Ar²-80
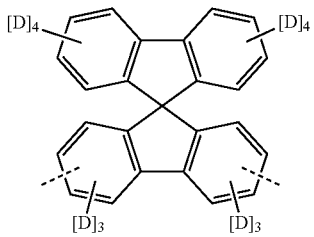

Ar²-81
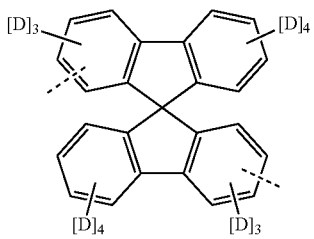

Ar²-82
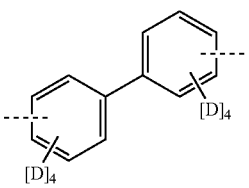

where the dotted bonds are the bonds to the rest of the formula (I), and the groups are substituted with radicals $R^5$ at all free positions.

Among the above-mentioned groups, groups according to formulae (Ar²-1), (Ar²-2), (Ar²-3), (Ar²-4), (Ar²-15), (Ar²-20), (Ar²-25) and (Ar²-36) are particularly preferred.

According to one preferred embodiment of the invention, the groups $Ar^3$ and $Ar^4$ in group A are not linked to each other by a group T, i.e. k is 0.

According to another preferred embodiment, the groups $Ar^3$ and $Ar^4$ are linked to each other by a group T, i.e. k is 1. In this case, T is preferably a single bond. Preferred embodiments of group A for the case k=1 are shown in the following:

(A-cycl-1)
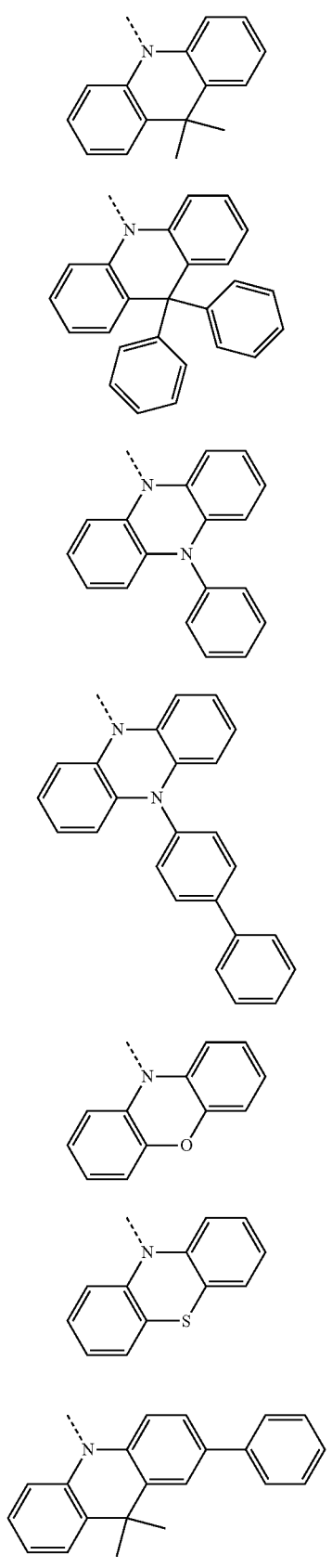
(A-cycl-2)
(A-cycl-3)
(A-cycl-4)
(A-cycl-5)
(A-cycl-6)
(A-cycl-7)
-continued
(A-cycl-8)
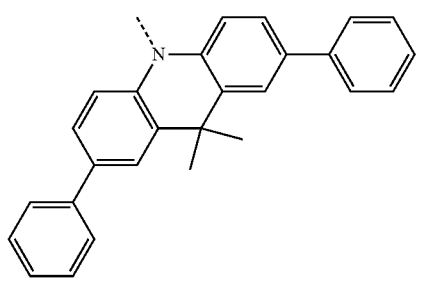
(A-cycl-9)
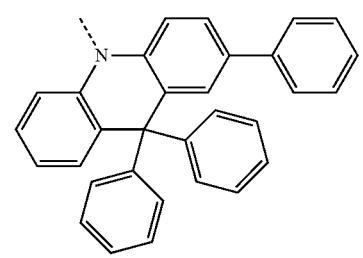
(A-cycl-10)
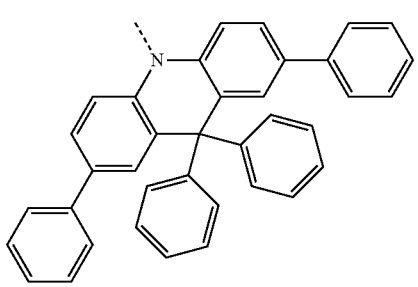
(A-cycl-11)
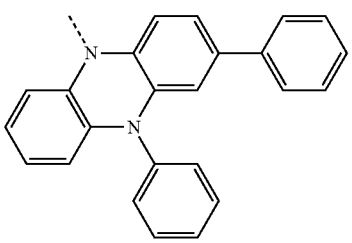
(A-cycl-12)
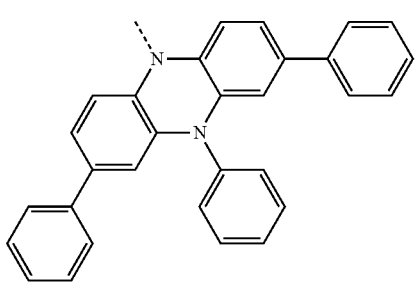
(A-cycl-13)
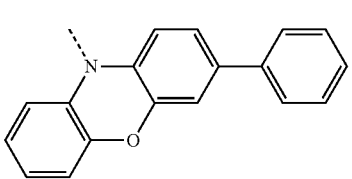

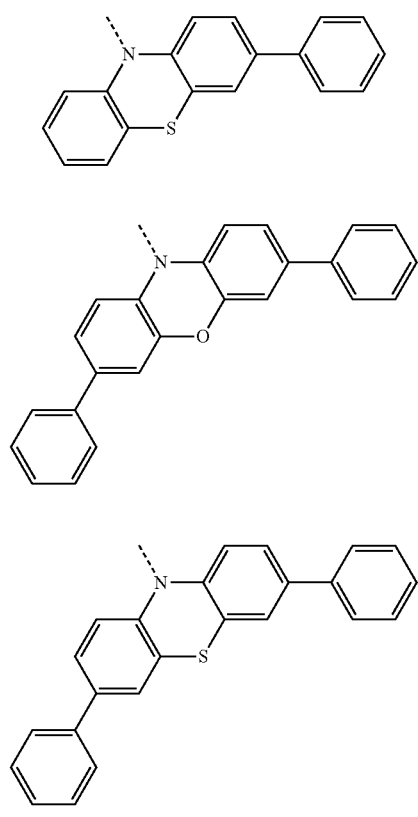
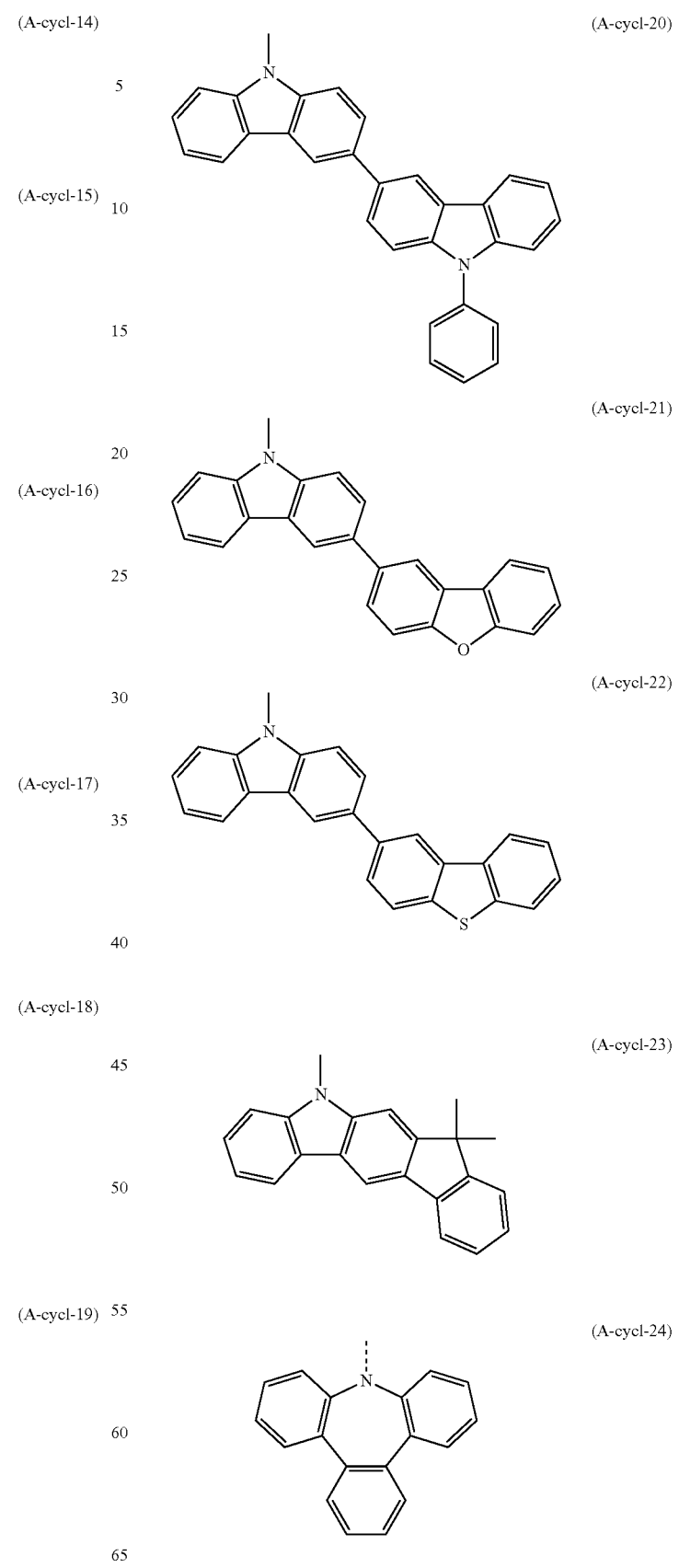

-continued (A-cycl-25)
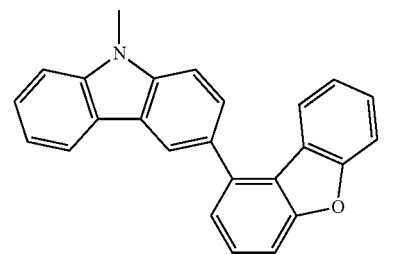

(A-cycl-26)
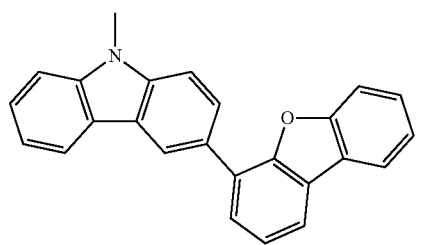

(A-cycl-27)
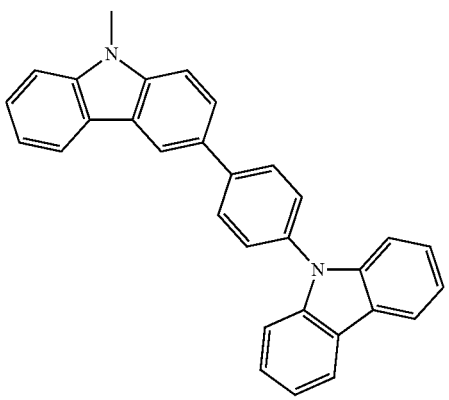

(A-cycl-28)
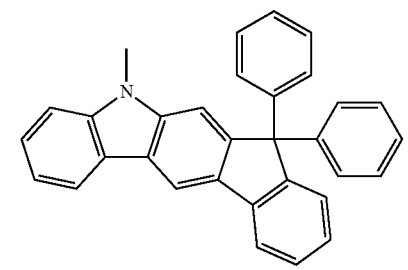

(A-cycl-29)
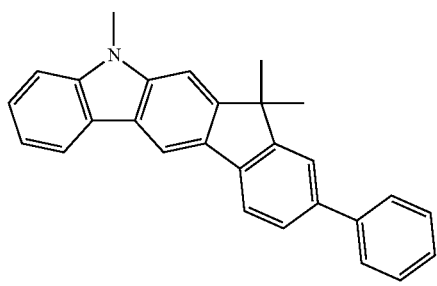

-continued (A-cycl-30)
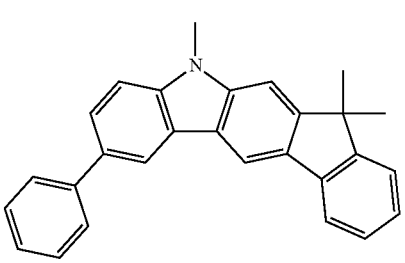

(A-cycl-31)

(A-cycl-32)

where the dotted line is the bond to the rest of formula (I).

According to a preferred embodiment, Ar³ and Ar⁴ are selected, identically or differently, from monovalent groups derived from benzene, biphenyl, terphenyl, quaterphenyl, naphthalene, fluorene, particularly 9,9'-dimethylfluorene and 9,9'-diphenylfluorene, 9-sila-fluorene, particularly 9,9'-dimethyl-9-silafluorene and 9,9'-diphenyl-9-silafluorene, benzofluorene, spirobifluorene, indenofluorene, indenocarbazole, dibenzofuran, dibenzothiophene, benzocarbazole, carbazole, benzofuran, benzothiophene, indole, quinoline, pyridine, pyrimidine, pyrazine, pyridazine, and triazine, where each of the monovalent groups is substituted with radicals R⁶. According to an alternative preferred embodiment, groups Ar³ and Ar⁴ are selected, identically or differently, from combinations of 2 to 4 groups, preferably 2 groups derived from benzene, biphenyl, terphenyl, quaterphenyl, naphthalene, fluorene, particularly 9,9'-dimethylfluorene and 9,9'-diphenylfluorene, 9-sila-fluorene, particularly 9,9'-dimethyl-9-silafluorene and 9,9'-diphenyl-9-silafluorene, benzofluorene, spirobifluorene, indenofluorene, indenocarbazole, dibenzofuran, dibenzothiophene, benzocarbazole, carbazole, benzofuran, benzothiophene, indole, quinoline, pyridine, pyrimidine, pyrazine, pyridazine, and triazine, where each of the groups is substituted with radicals R⁶.

Particularly preferred groups Ar³ and Ar⁴ are selected, identically or differently, from phenyl, biphenyl, terphenyl, quaterphenyl, naphthyl, fluorenyl, particularly 9,9'-dimethylfluorenyl and 9,9'-diphenylfluorenyl, benzofluorenyl, spirobifluorenyl, indenofluorenyl, indenocarbazolyl, dibenzofuranyl, dibenzothiophenyl, carbazolyl, benzofuranyl, benzothiophenyl, benzo-condensed dibenzofuranyl, benzo-condensed dibenzothiophenyl, phenyl substituted with naphthyl, phenyl substituted with fluorenyl, phenyl substituted with spirobifluorenyl, phenyl substituted with dibenzofuranyl, phenyl substituted with dibenzothiophene, phenyl substituted with carbazolyl, phenyl substituted with pyridyl, phenyl substituted with pyrimidyl, and phenyl substituted with triazinyl, where the groups are each substituted with radicals $R^6$.

Preferred embodiments of groups $Ar^3$ and $Ar^4$ are shown in the following:

Ar-1

Ar-2

Ar-3

Ar-4

Ar-5

Ar-6

Ar-7

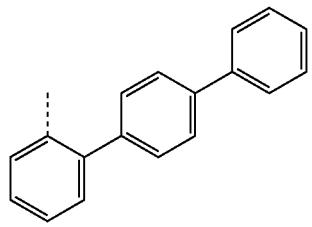

Ar-8

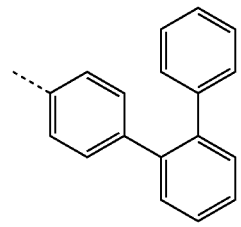

Ar-9

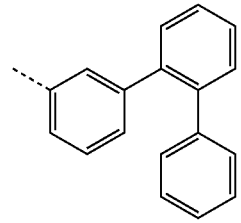

Ar-10

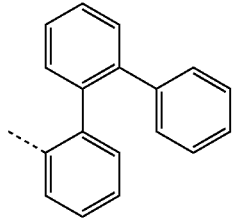

Ar-11

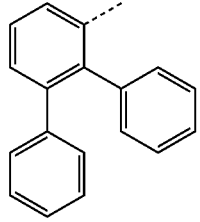

Ar-12

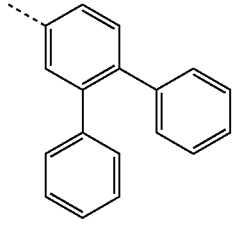

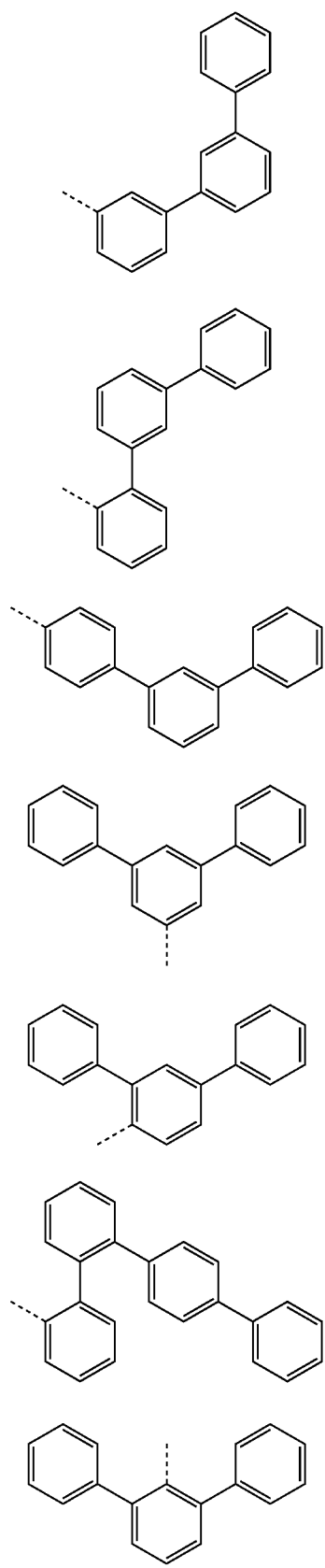
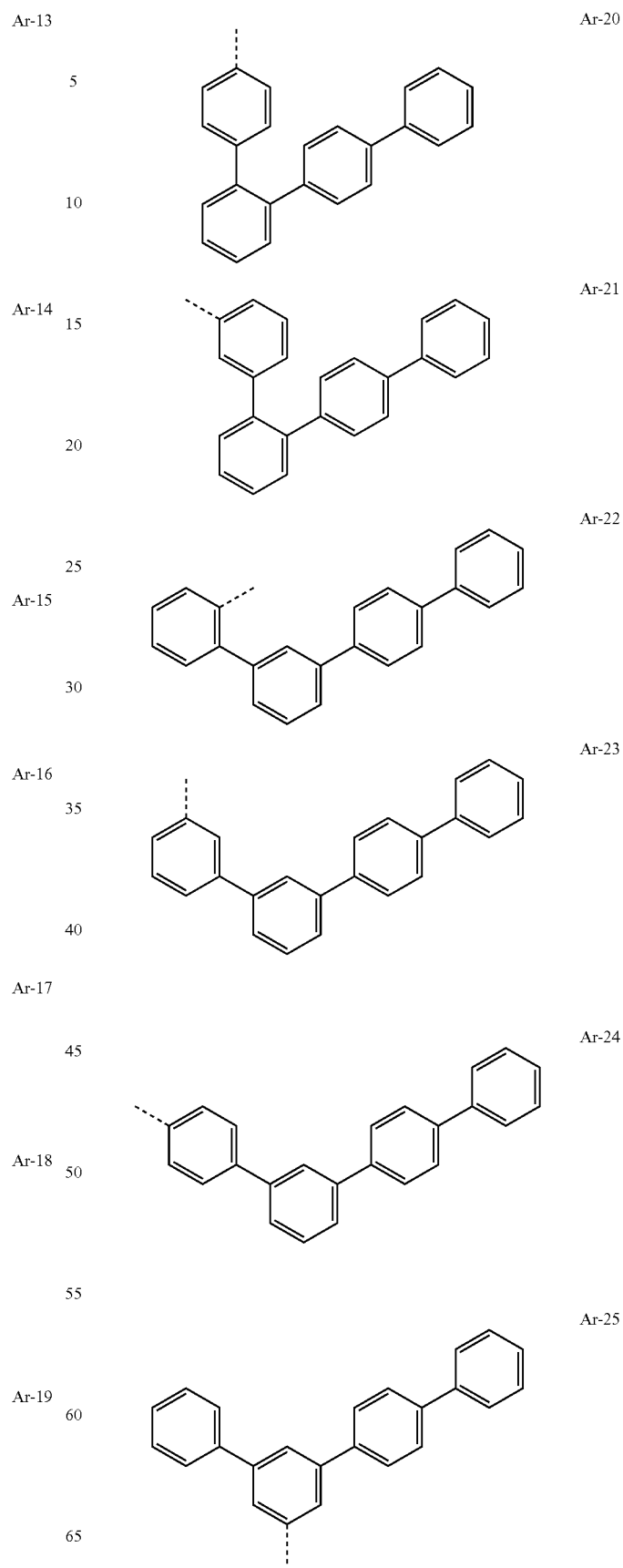

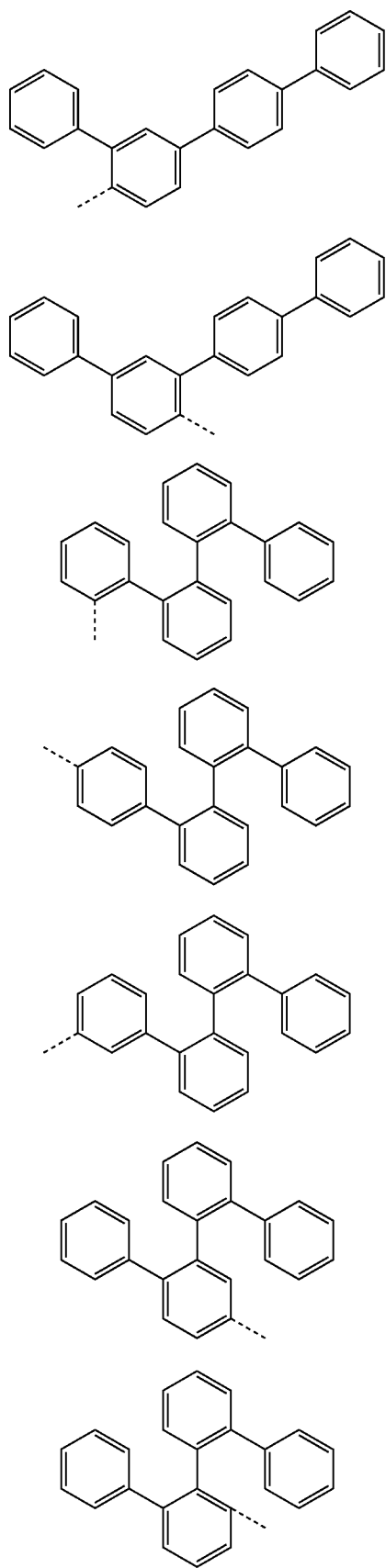
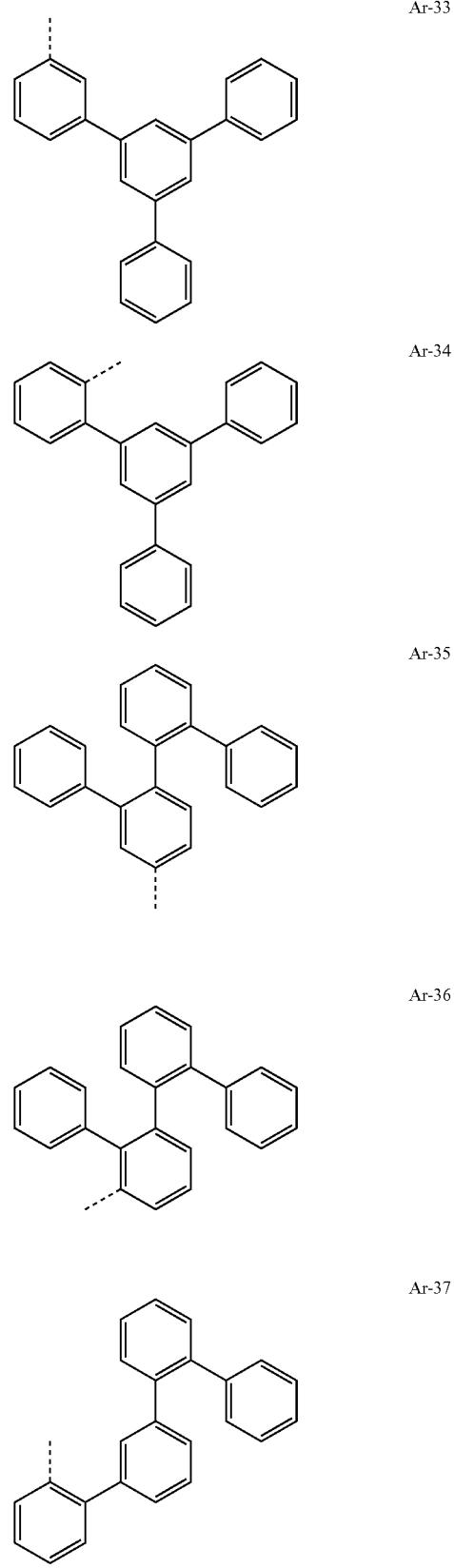

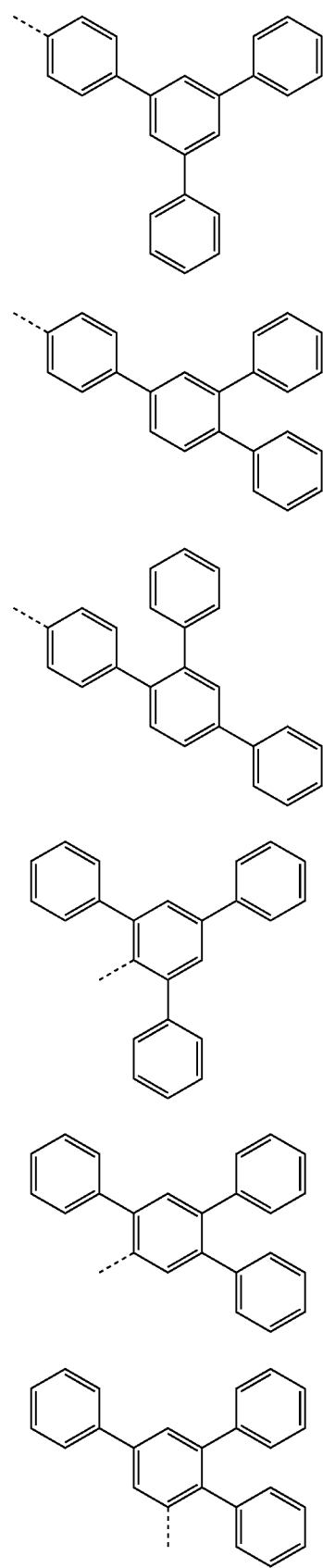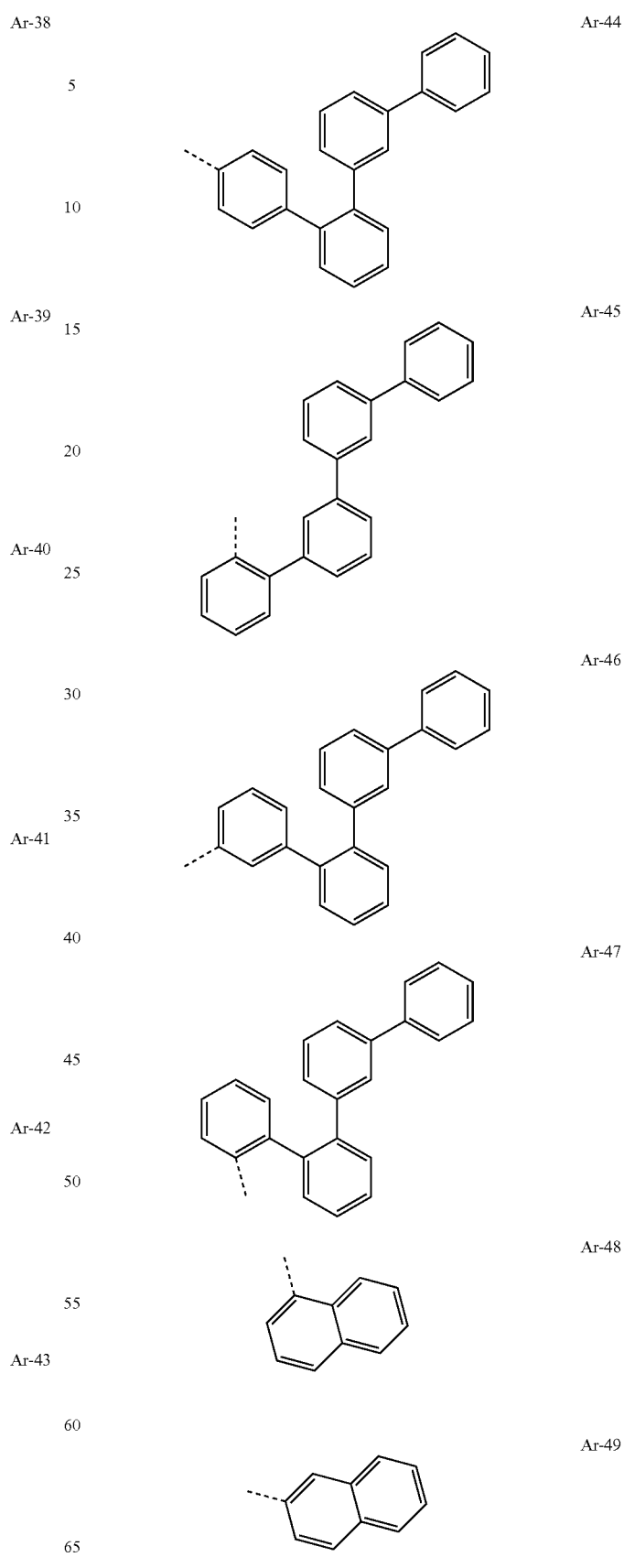

Ar-50
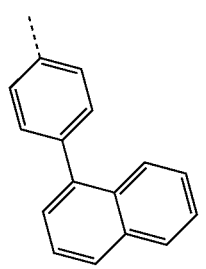
Ar-51
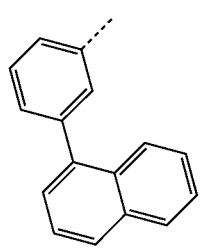
Ar-52
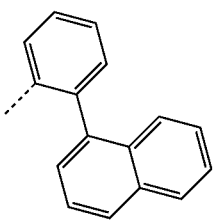
Ar-53
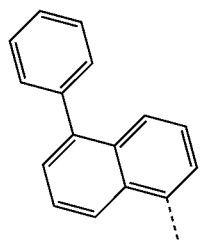
Ar-54
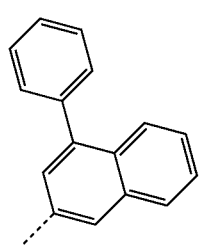
Ar-55
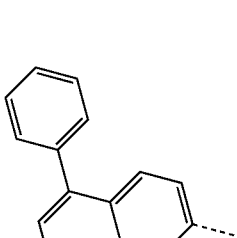
Ar-56
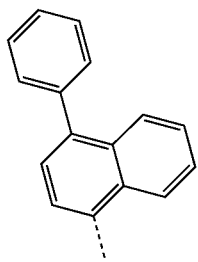
Ar-57
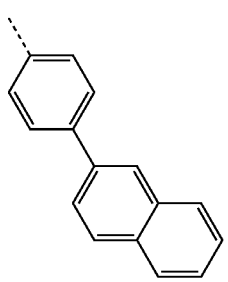
Ar-58
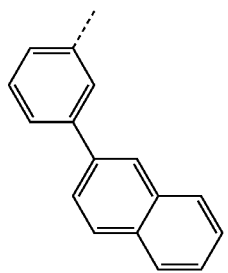
Ar-59
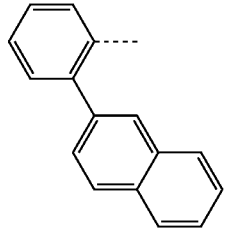
Ar-60
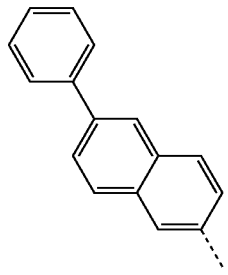
Ar-61
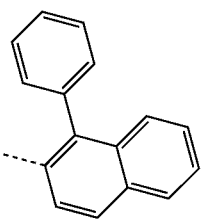

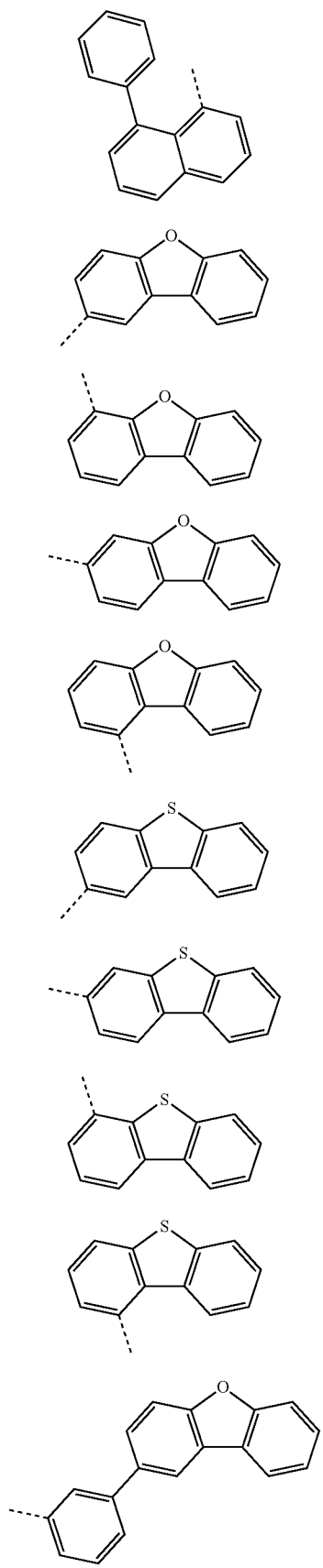
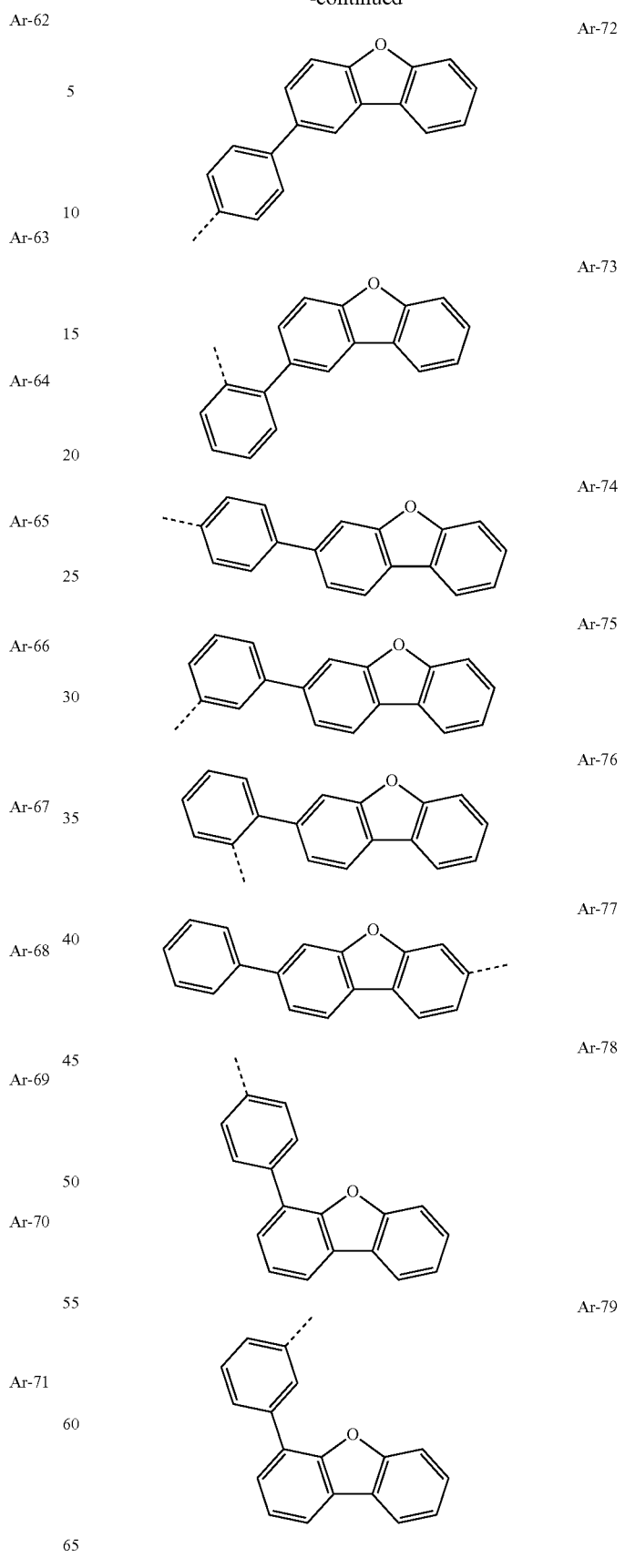

-continued
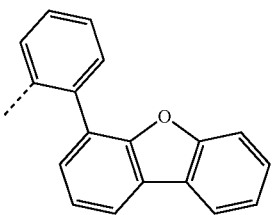
Ar-80
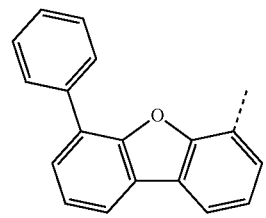
Ar-81
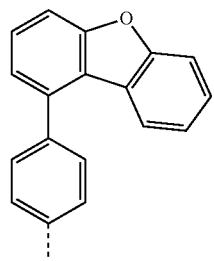
Ar-82
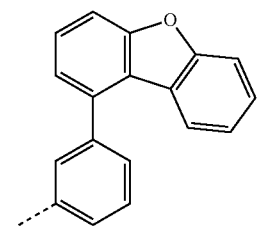
Ar-83
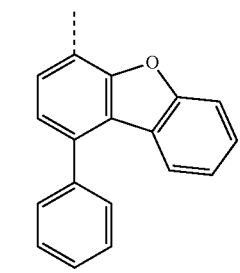
Ar-84
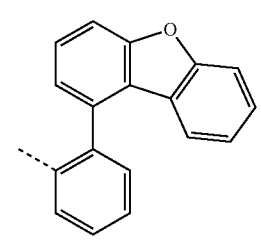
Ar-85
-continued
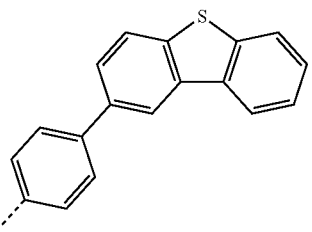
Ar-86
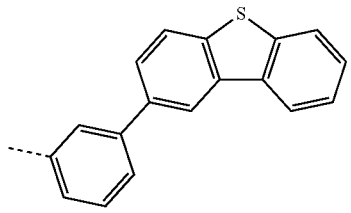
Ar-87
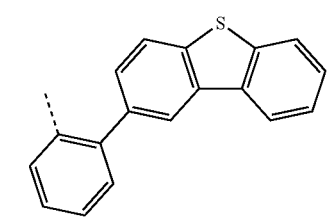
Ar-88
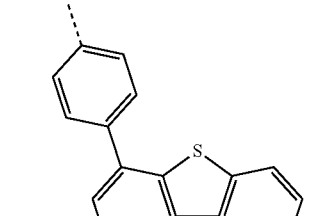
Ar-89
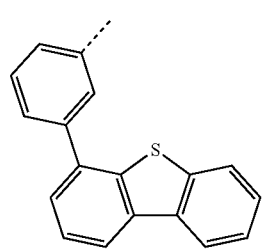
Ar-90
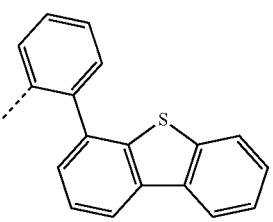
Ar-91
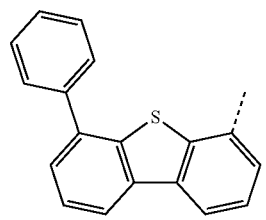
Ar-92

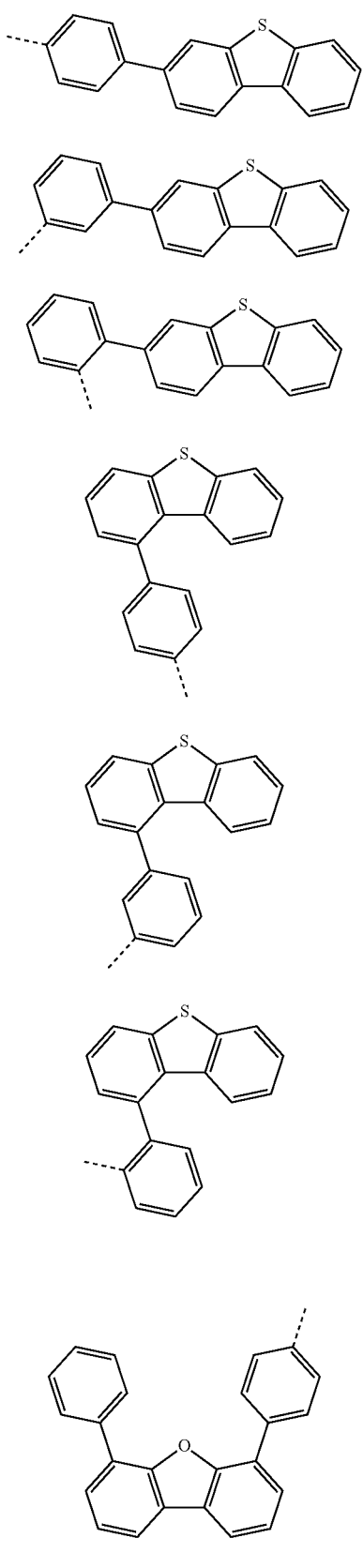
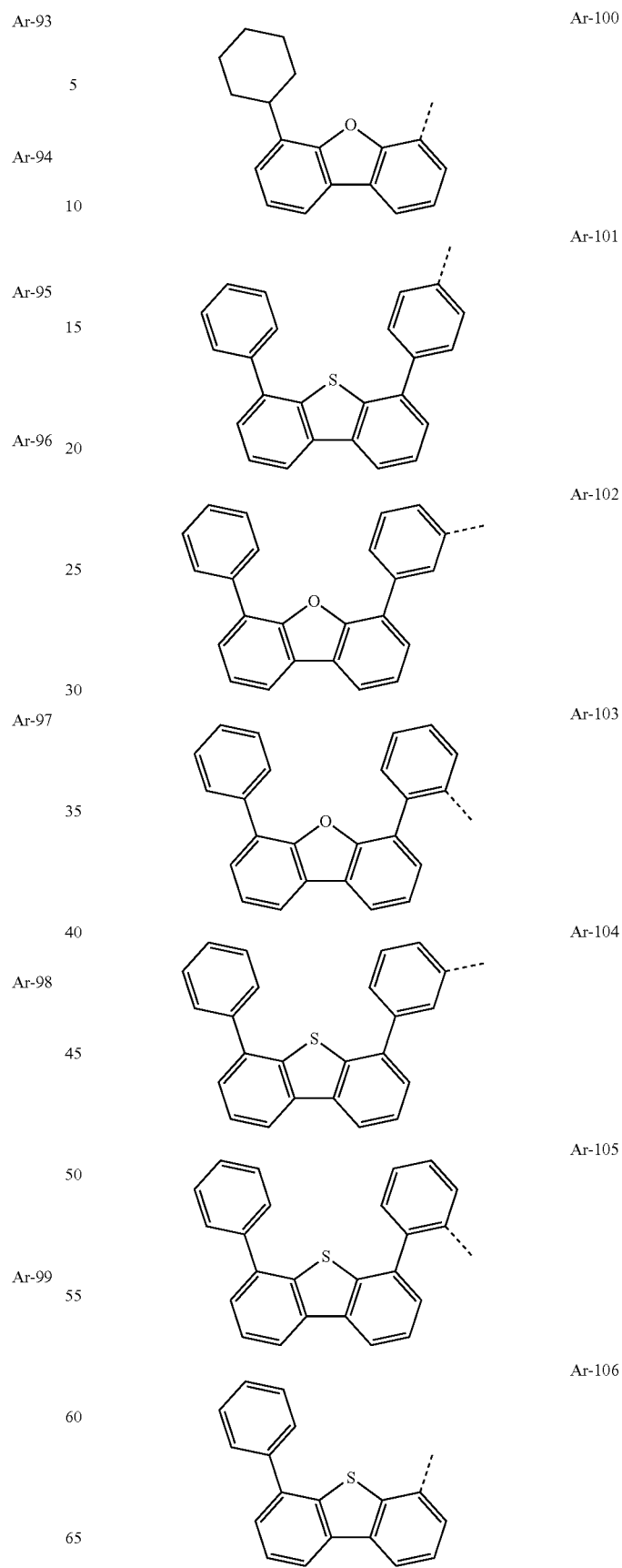

Ar-107
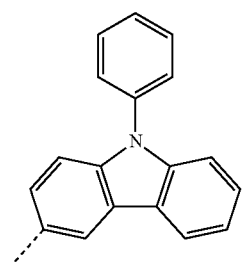
Ar-108
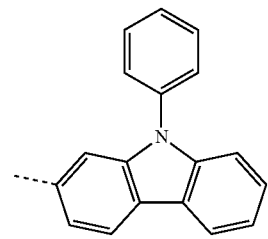
Ar-109
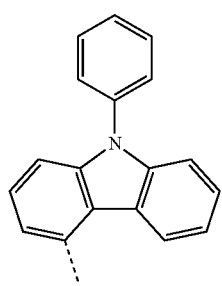
Ar-110
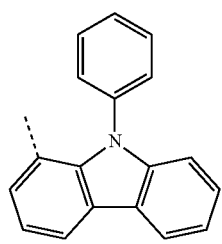
Ar-111
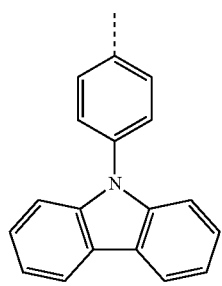
Ar-112
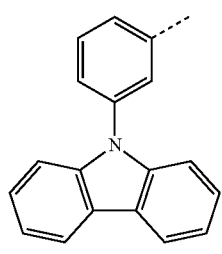
Ar-113
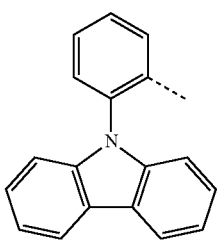
Ar-114
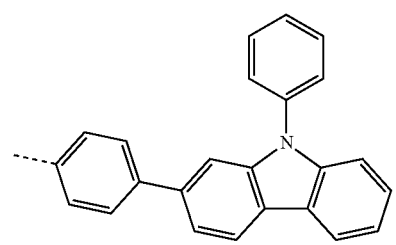
Ar-115
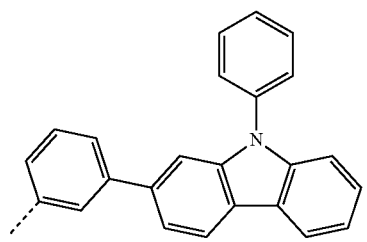
Ar-116
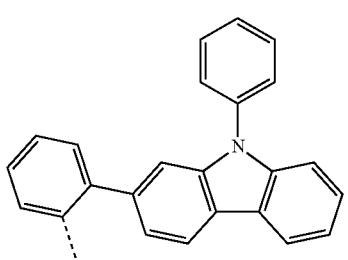
Ar-117
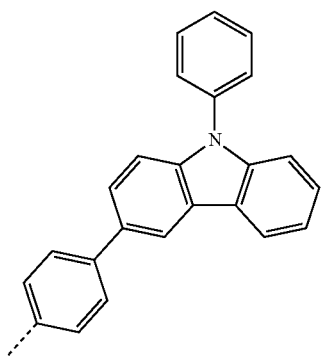

Ar-118
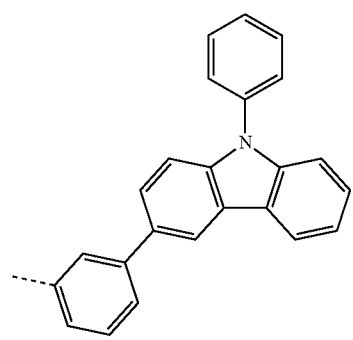
Ar-119
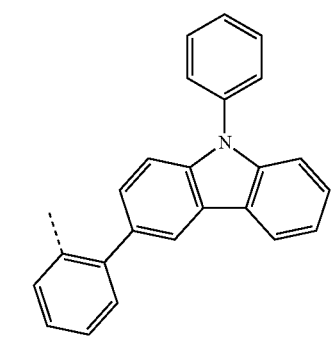
Ar-120
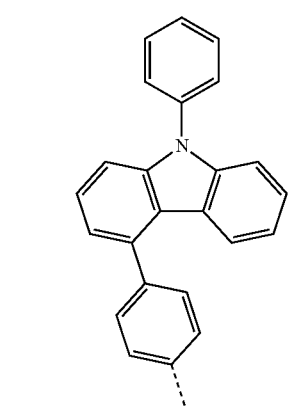
Ar-121
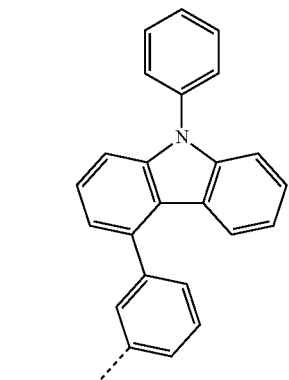
Ar-122
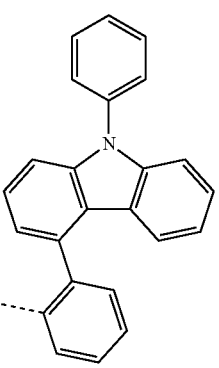
Ar-123
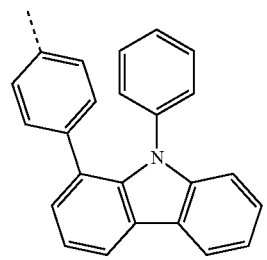
Ar-124
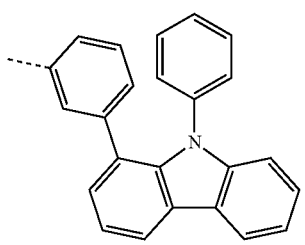
Ar-125
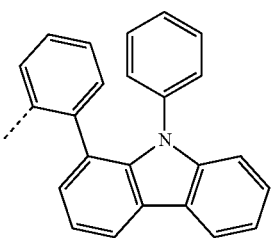
Ar-126
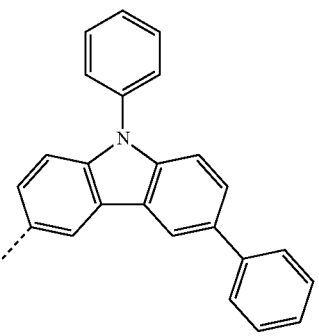

Ar-127 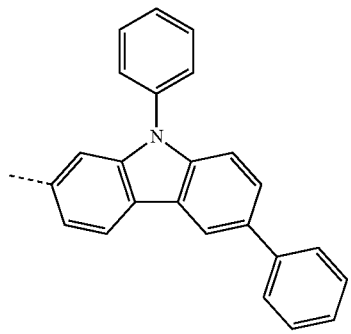
Ar-128 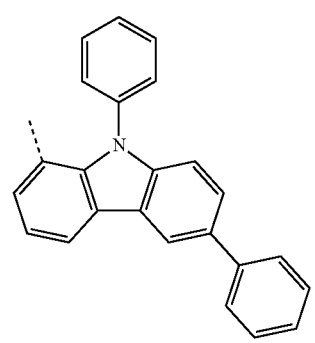
Ar-129 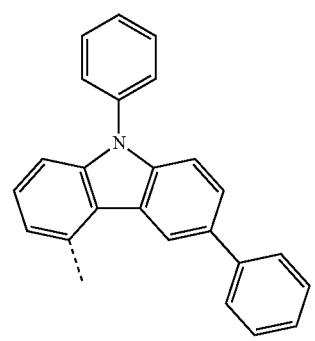
Ar-130 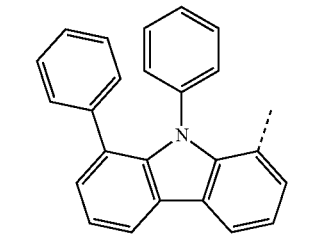
Ar-131 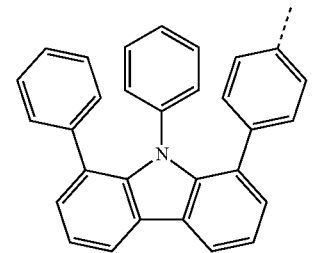
Ar-132 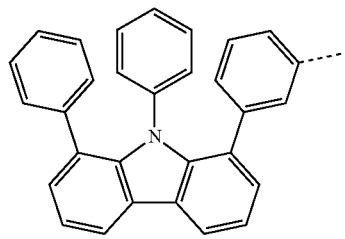
Ar-133 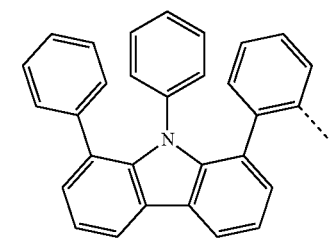
Ar-134 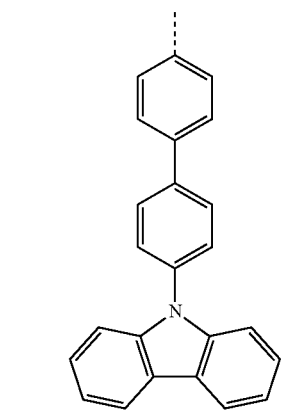
Ar-135 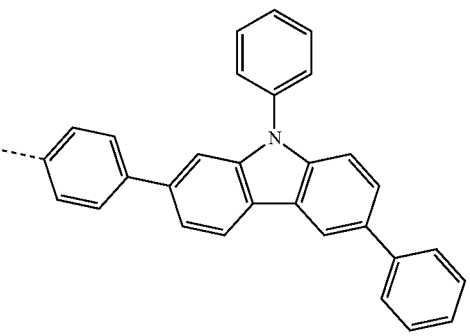
Ar-136 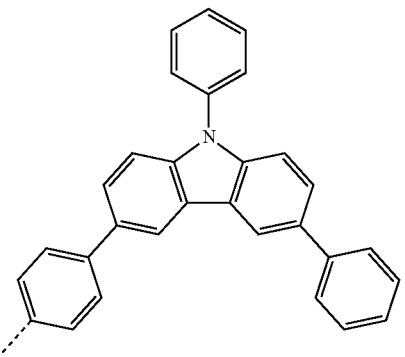

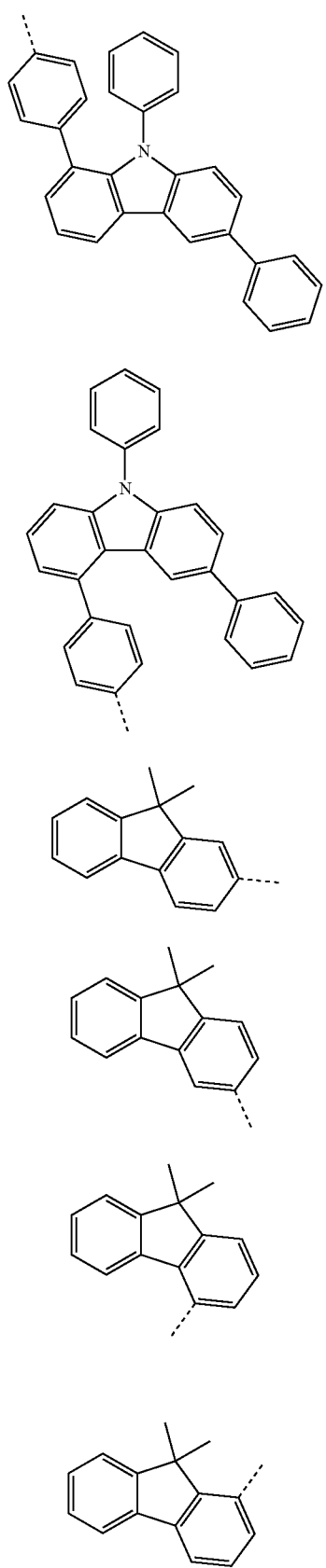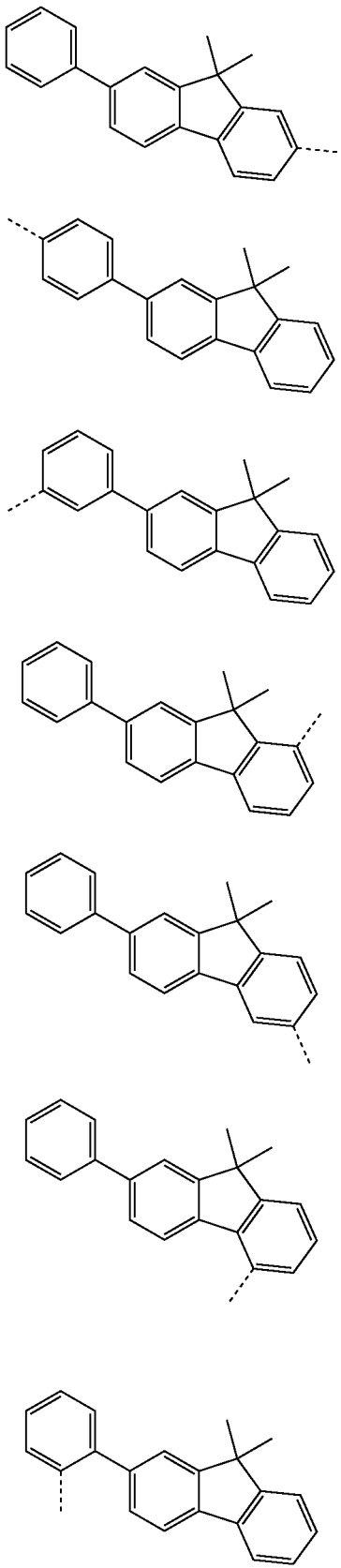

-continued
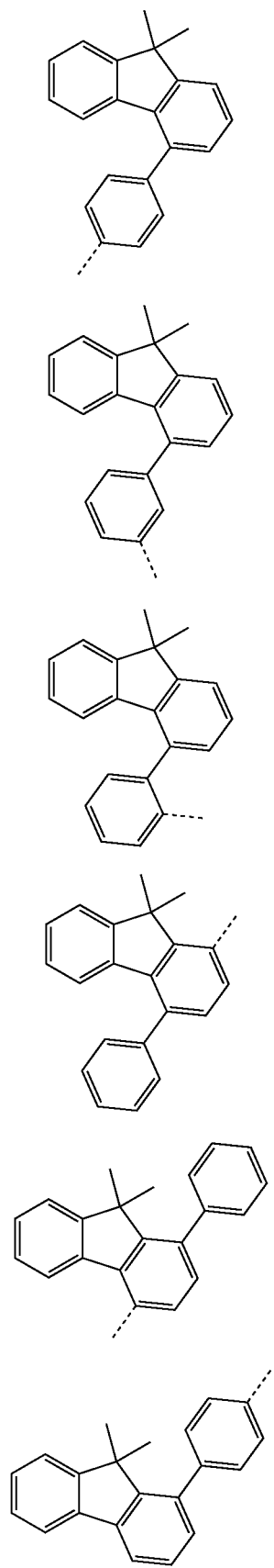
Ar-150
Ar-151
Ar-152
Ar-153
Ar-154
Ar-155
-continued
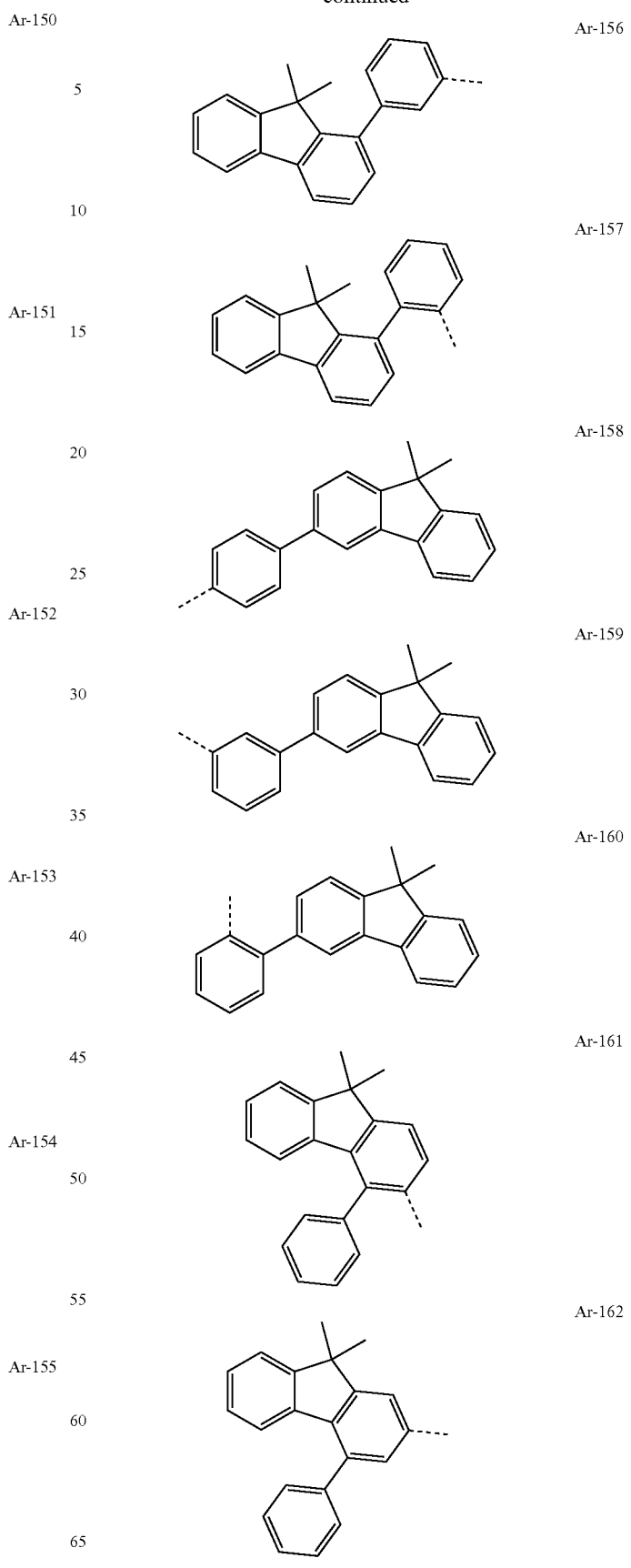
Ar-156
Ar-157
Ar-158
Ar-159
Ar-160
Ar-161
Ar-162

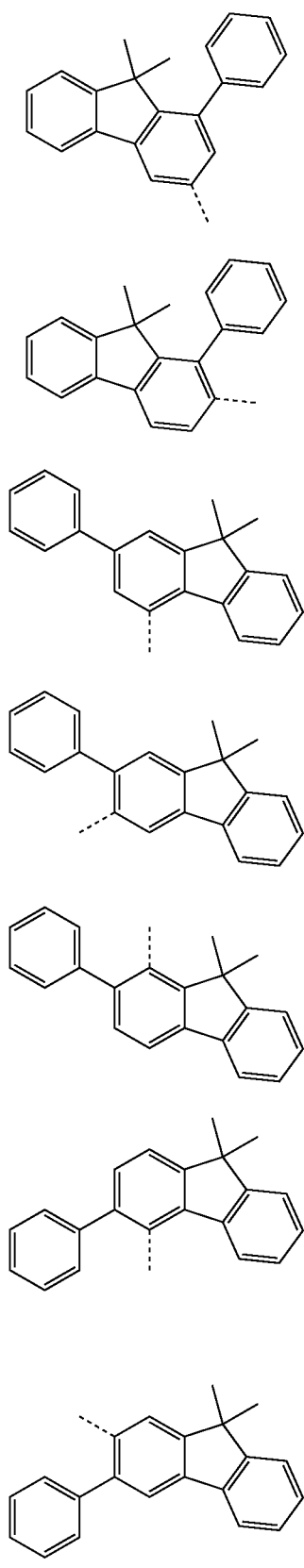
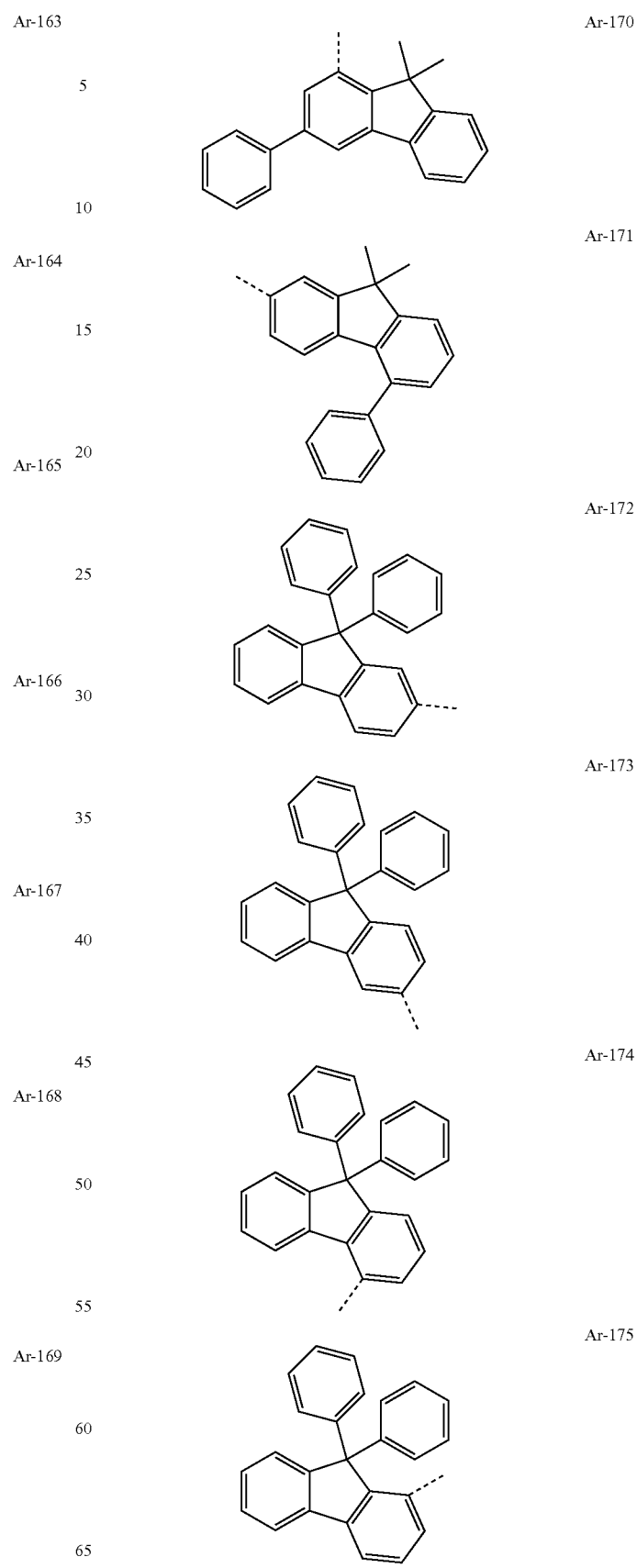

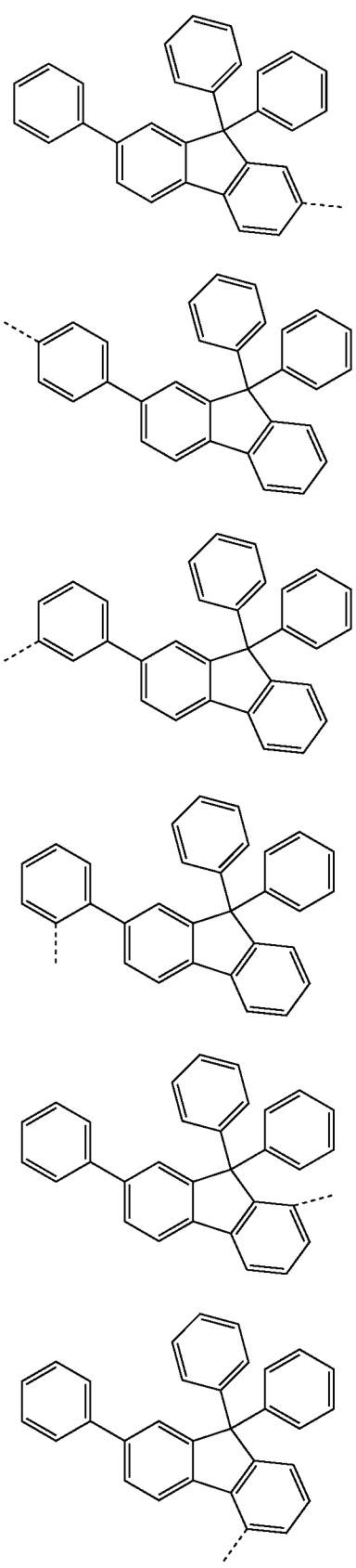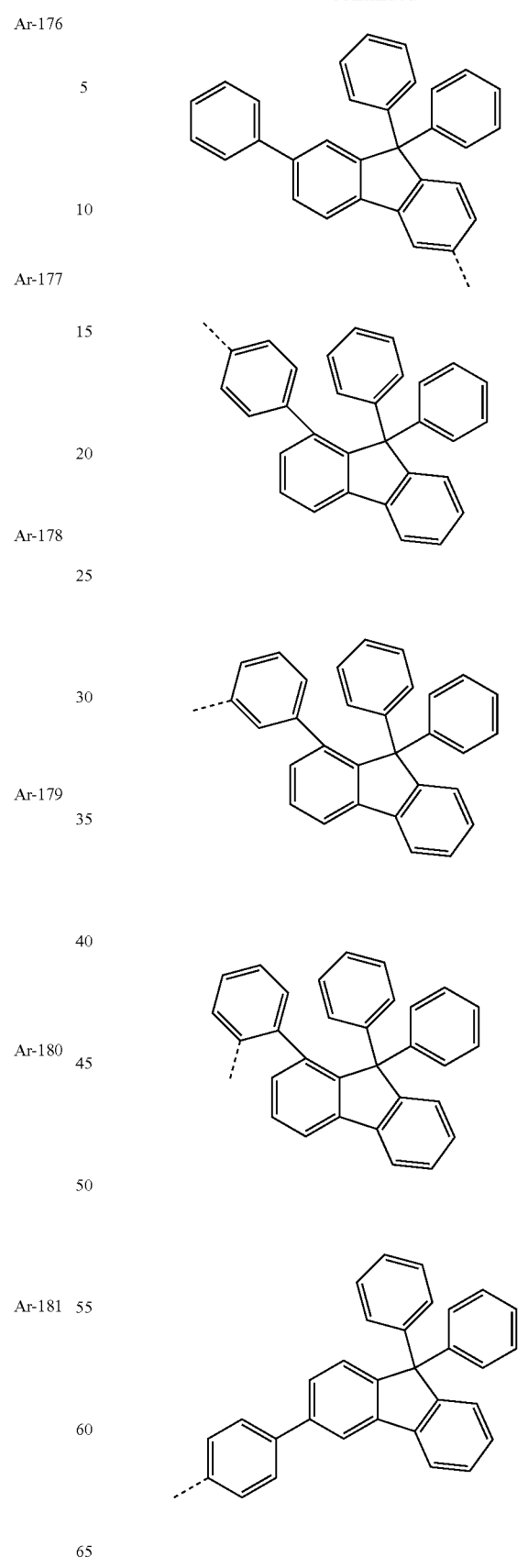

-continued
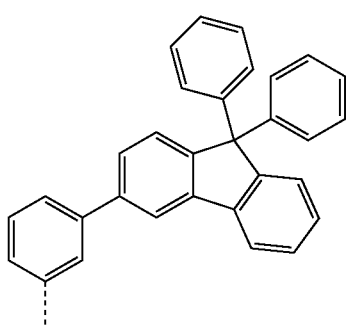
Ar-187
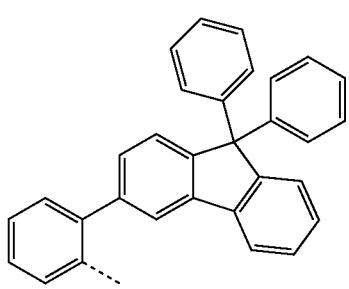
Ar-188
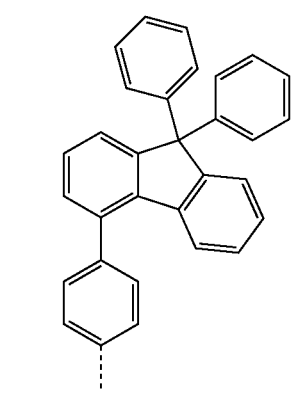
Ar-189
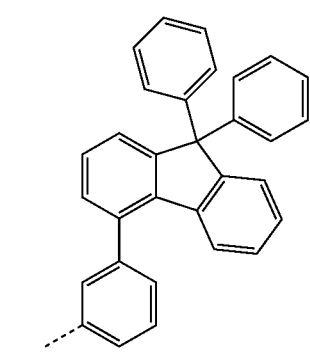
Ar-190
-continued
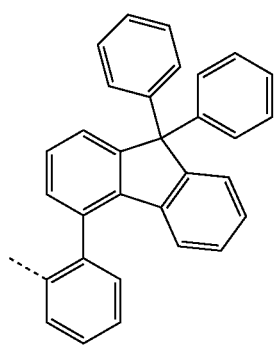
Ar-191
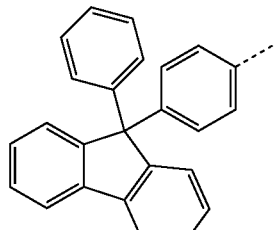
Ar-192
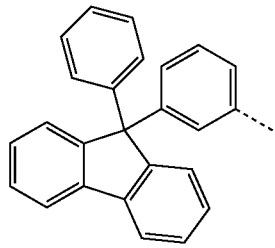
Ar-193
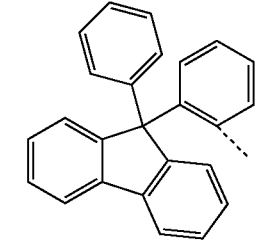
Ar-194
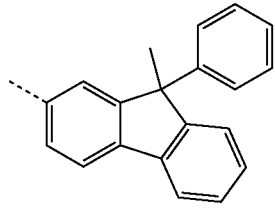
Ar-195
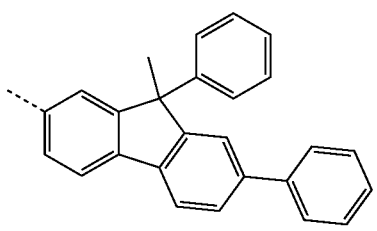
Ar-196

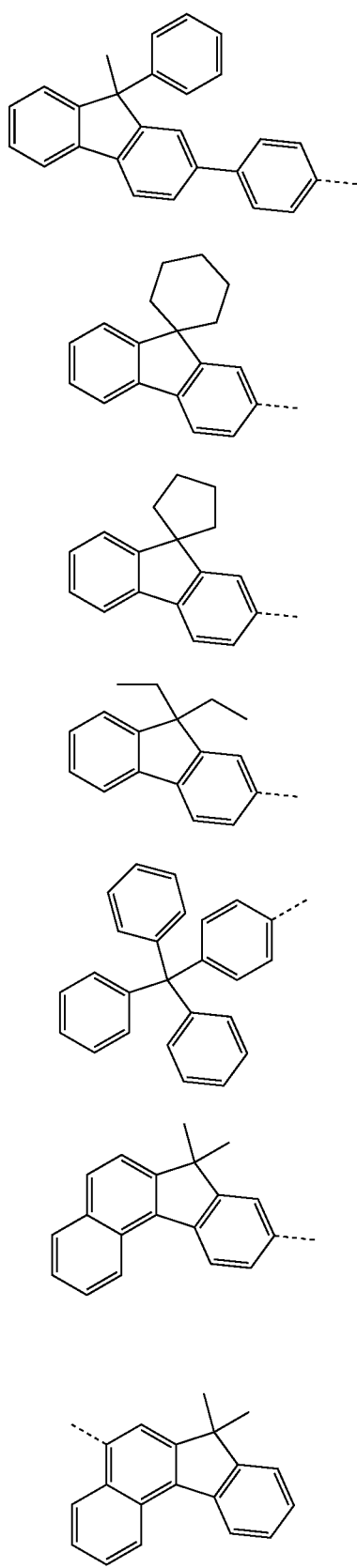
Ar-197
Ar-198
Ar-199
Ar-200
Ar-201
Ar-201
Ar-203
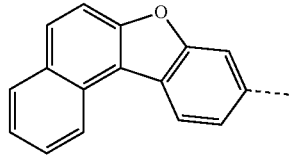
Ar-204
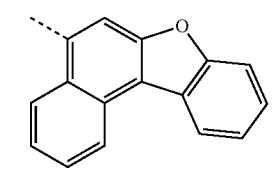
Ar-205
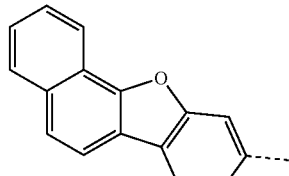
Ar-206
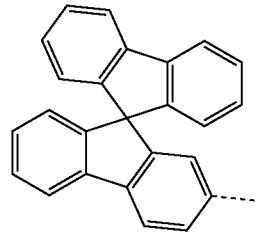
Ar-207
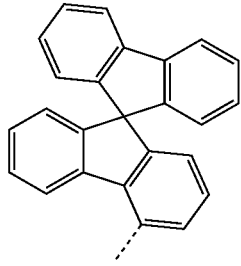
Ar-208
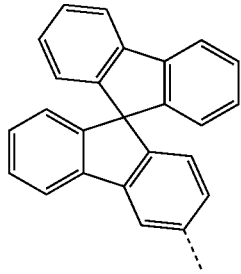
Ar-209
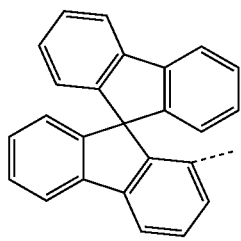
Ar-210

Ar-211
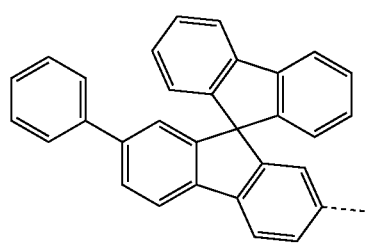
Ar-212
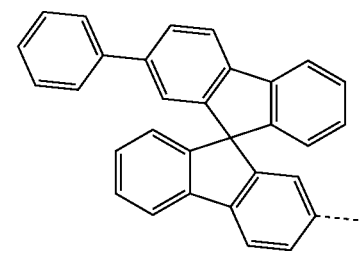
Ar-213
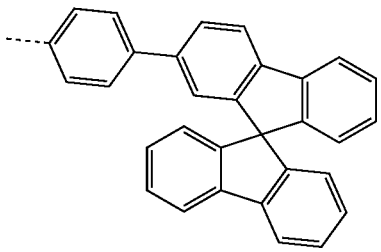
Ar-214
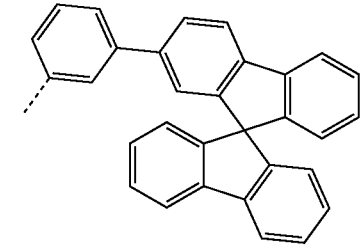
Ar-215
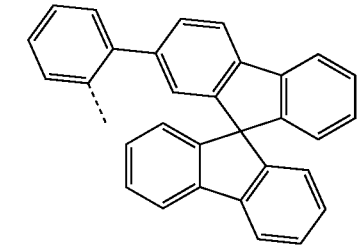
Ar-216
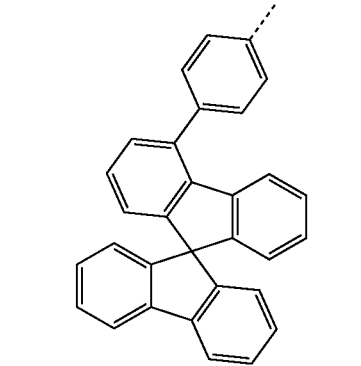
Ar-217
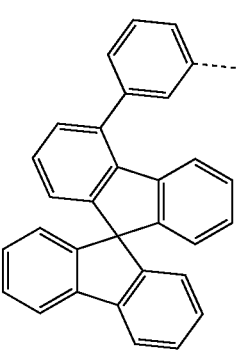
Ar-218
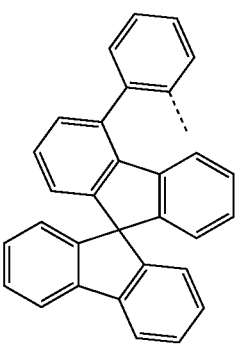
Ar-219
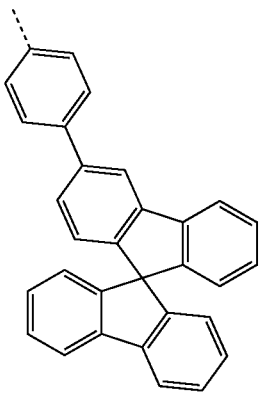
Ar-220
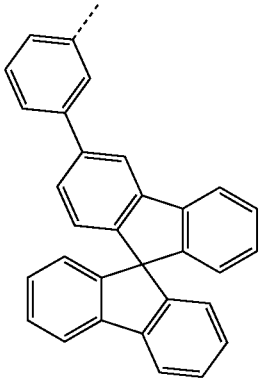

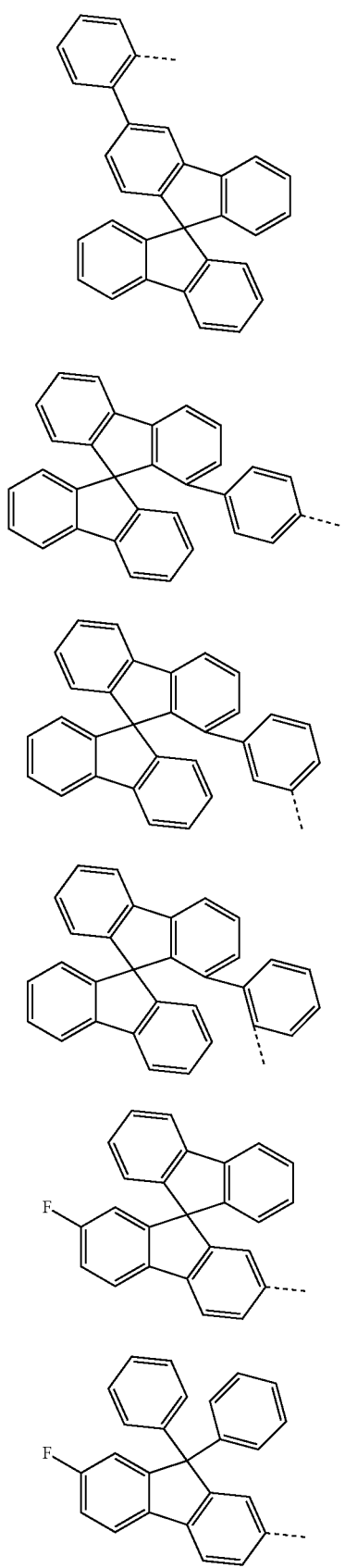
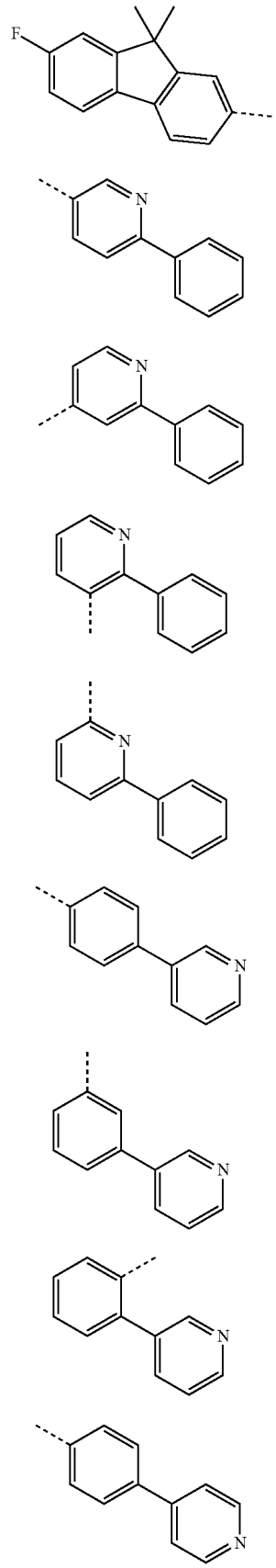

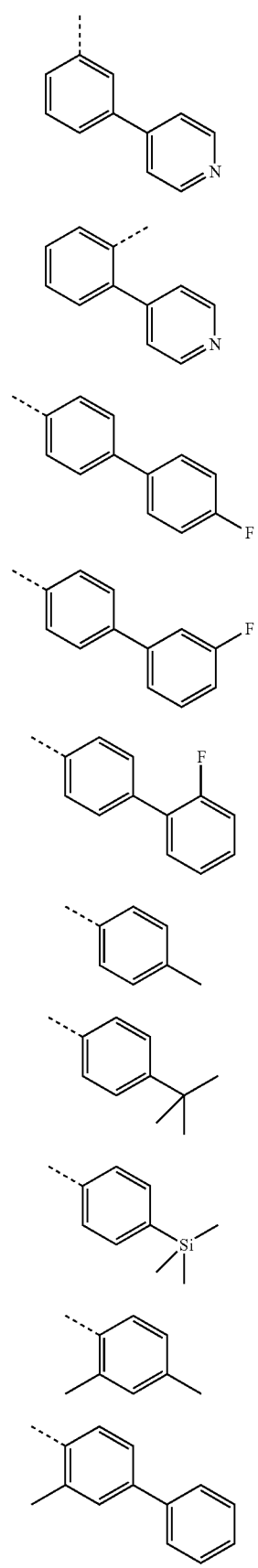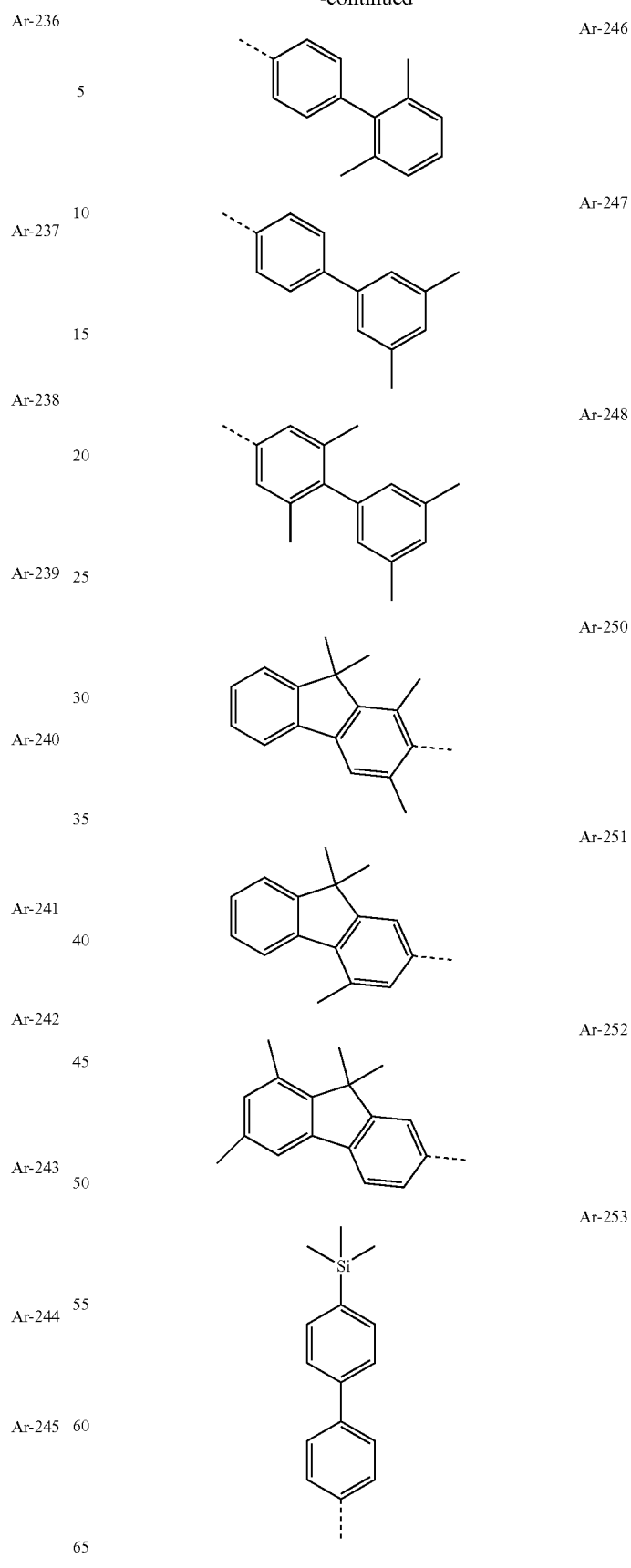

Ar-254 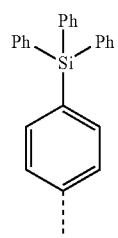
Ar-255 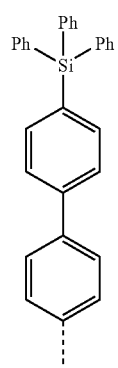
Ar-256 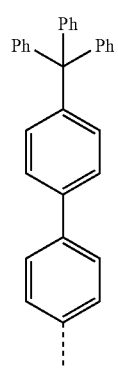
Ar-257 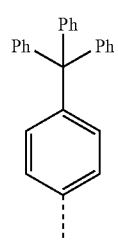
Ar-258 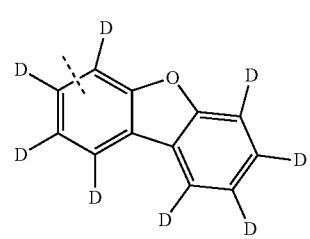
Ar-259 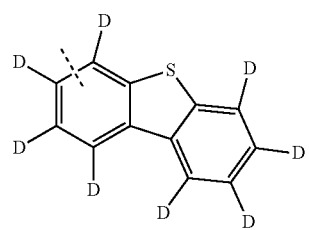
Ar-260 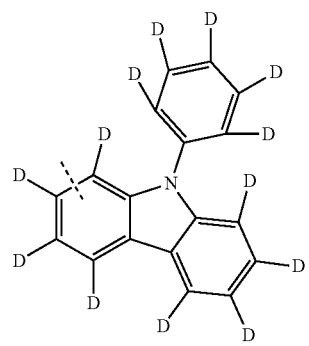
Ar-261 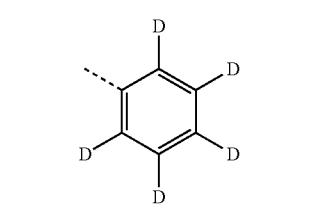
Ar-262 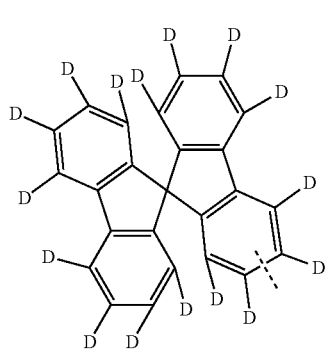
Ar-263 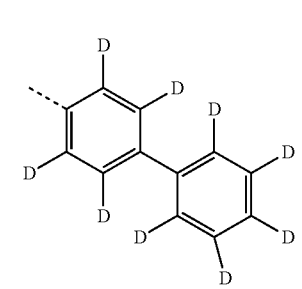

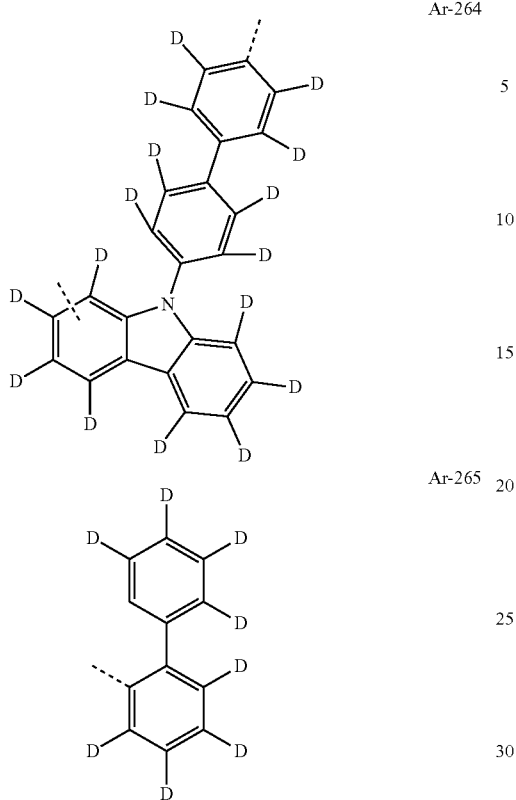

Ar-264

Ar-265

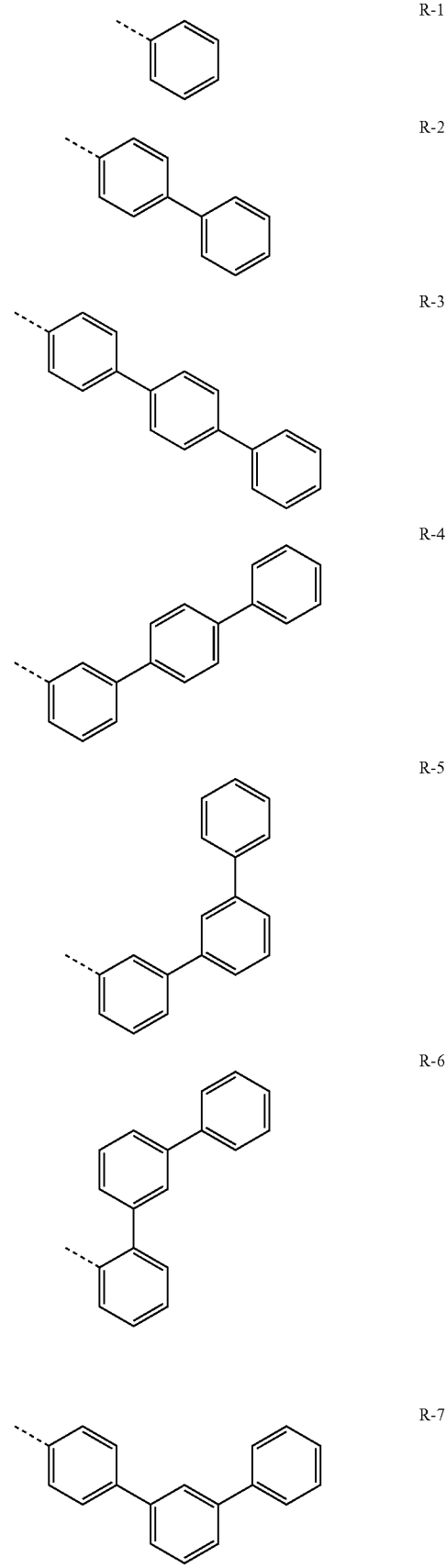

R-1

R-2

R-3

R-4

R-5

R-6

R-7 where the dotted lines are the bonds to the nitrogen atom of the group A.

Particularly preferred among the above formulae are formulae Ar-1, Ar-2, Ar-4, Ar-5, Ar-50, Ar-74, Ar-78, Ar-82, Ar-107, Ar-108, Ar-117, Ar-134, Ar-139, Ar-150, and Ar-172.

Preferably, $R^1$ is selected, identically or differently, from H, D, F, CN, $Si(R^7)_3$, $N(R^7)_2$, straight-chain alkyl or alkoxy groups having 1 to 20 C atoms, branched or cyclic alkyl or alkoxy groups having 3 to 20 C atoms, aromatic ring systems having 6 to 40 aromatic ring atoms, and heteroaromatic ring systems having 5 to 40 aromatic ring atoms; where the said alkyl and alkoxy groups and the said aromatic and heteroaromatic ring systems are substituted by radicals $R^7$, and where one or more $CH_2$ groups in the said alkyl and alkoxy groups may in each case be replaced by —C≡C—, —$R^7$C=C$R^7$—, $Si(R^7)_2$, C=O, C=N$R^7$, —N$R^7$—, —O—, —S—, —C(=O)O— or —C(=O)N$R^7$—. Preferably, $R^1$ is not $N(R^7)_2$. Particularly preferably, $R^1$ does not comprise any amine group. More preferably, $R^1$ is selected, identically or differently, from H, D, F, CN, $Si(R^7)_3$, straight-chain alkyl groups having 1 to 20 C atoms, which are optionally deuterated and/or fluorinated, branched or cyclic alkyl groups having 3 to 20 C atoms, which are optionally deuterated and/or fluorinated, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$. Most preferably, $R^1$ is H.

Preferred embodiments of $R^1$ are selected from the following groups:

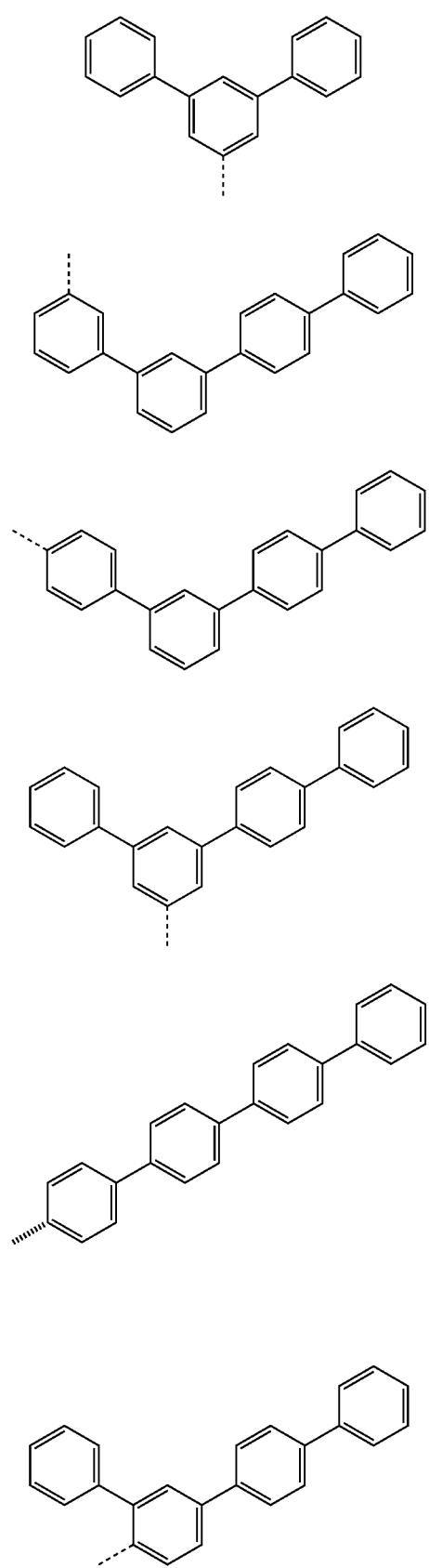
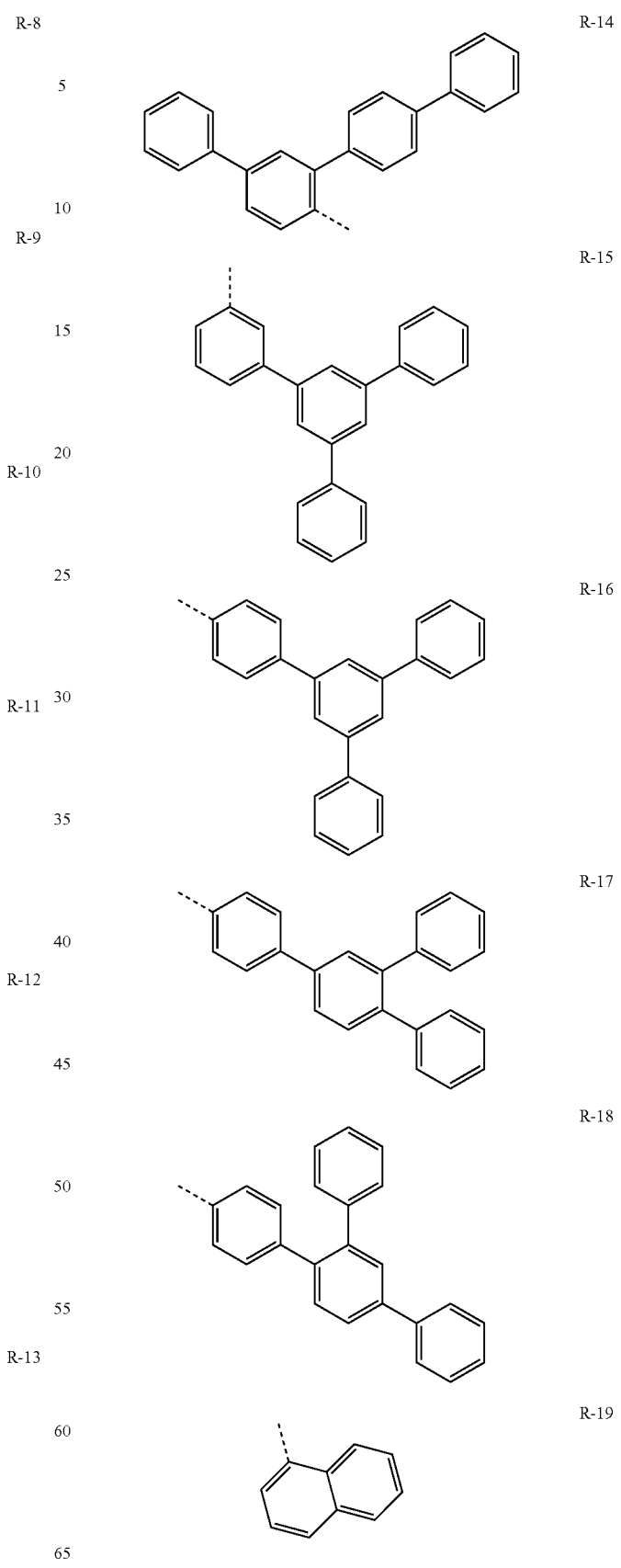

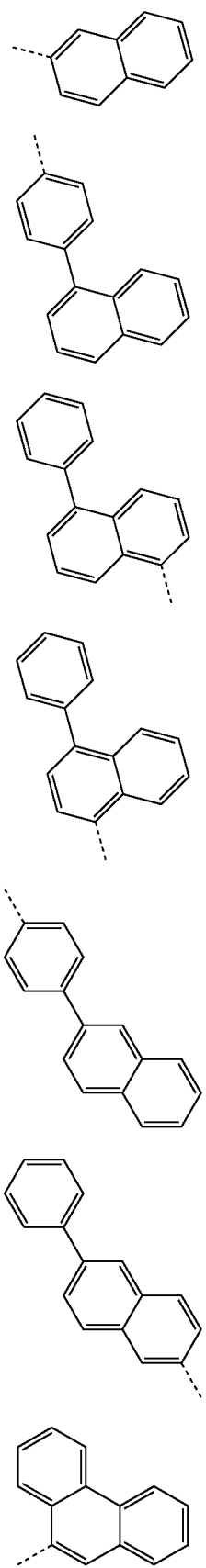
R-20
R-21
R-22
R-23
R-24
R-25
R-26
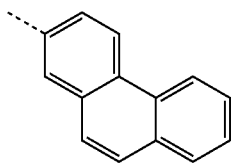
R-27
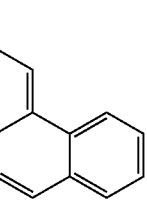
R-28
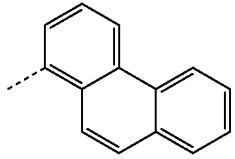
R-29
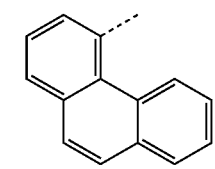
R-30
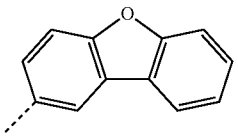
R-31
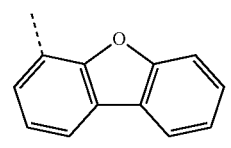
R-32
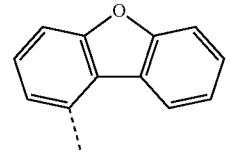
R-33
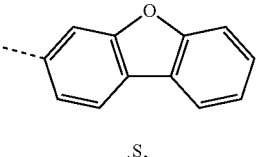
R-34
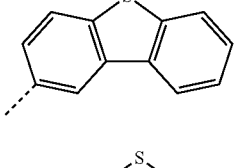
R-35
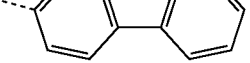
R-36

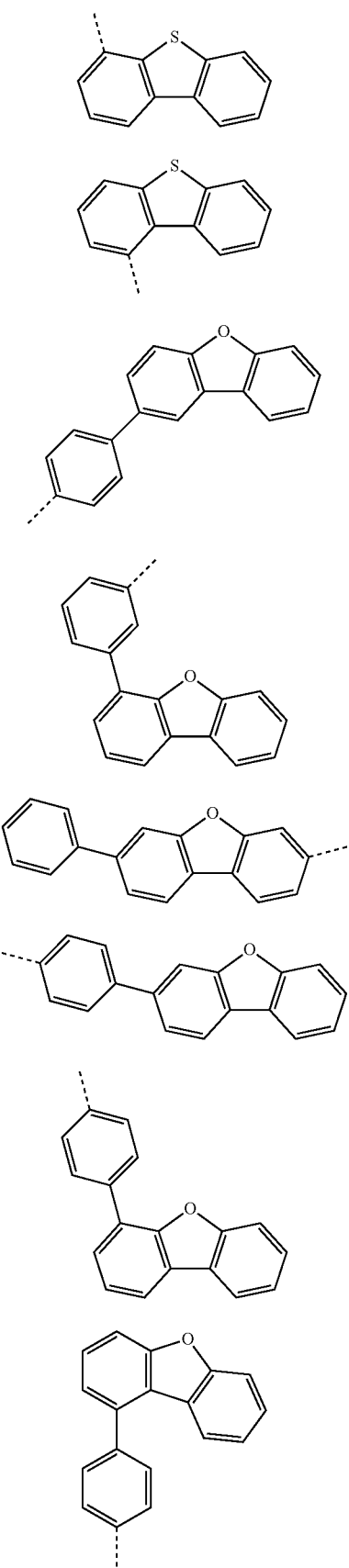
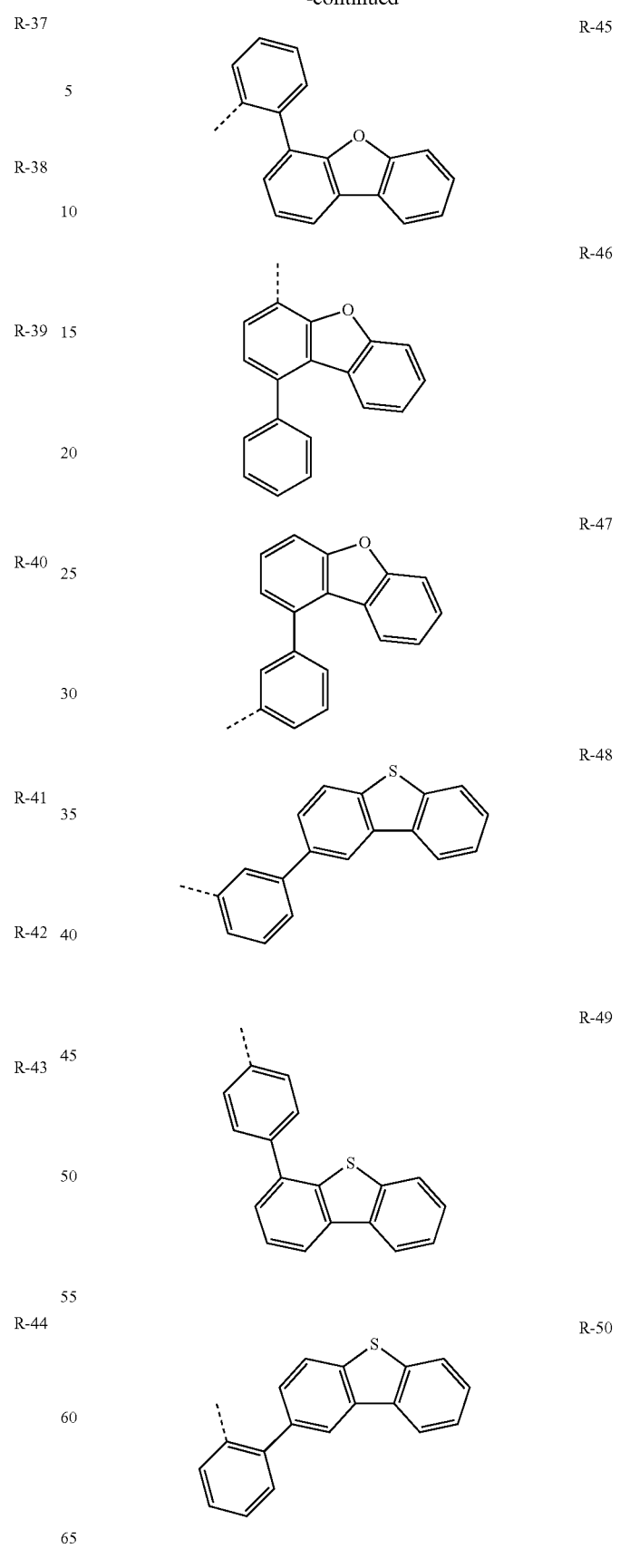

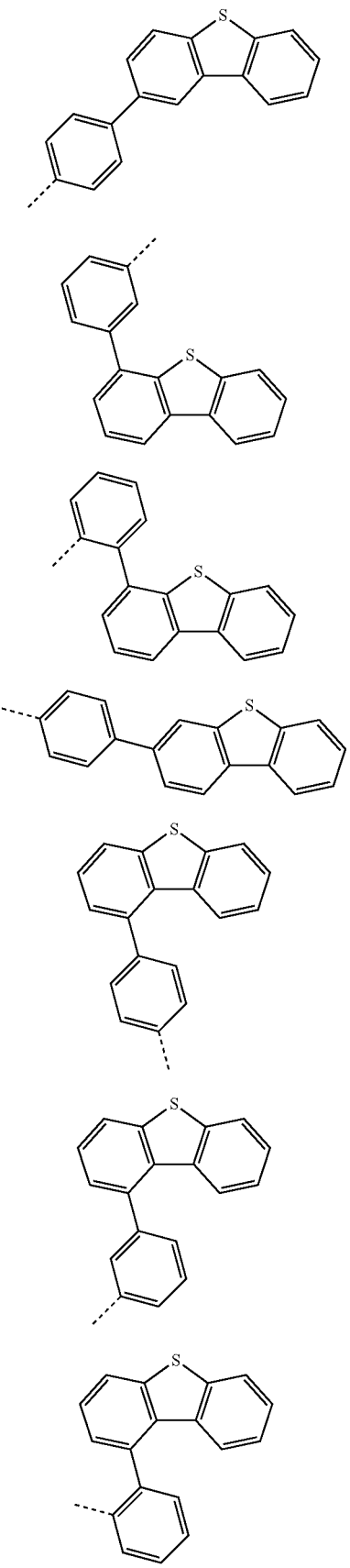
R-51
R-52
R-53
R-54
R-55
R-56
R-57
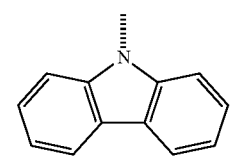
R-58
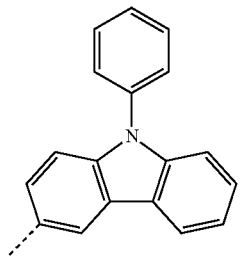
R-59
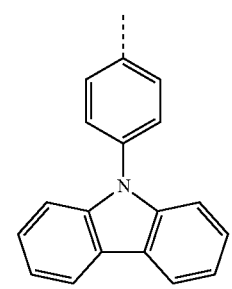
R-60
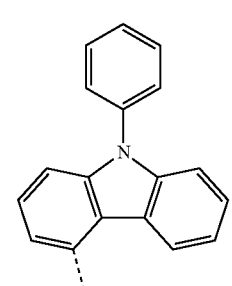
R-61
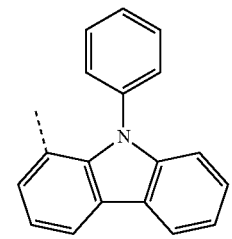
R-62
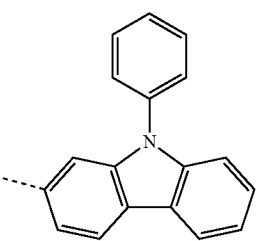
R-63

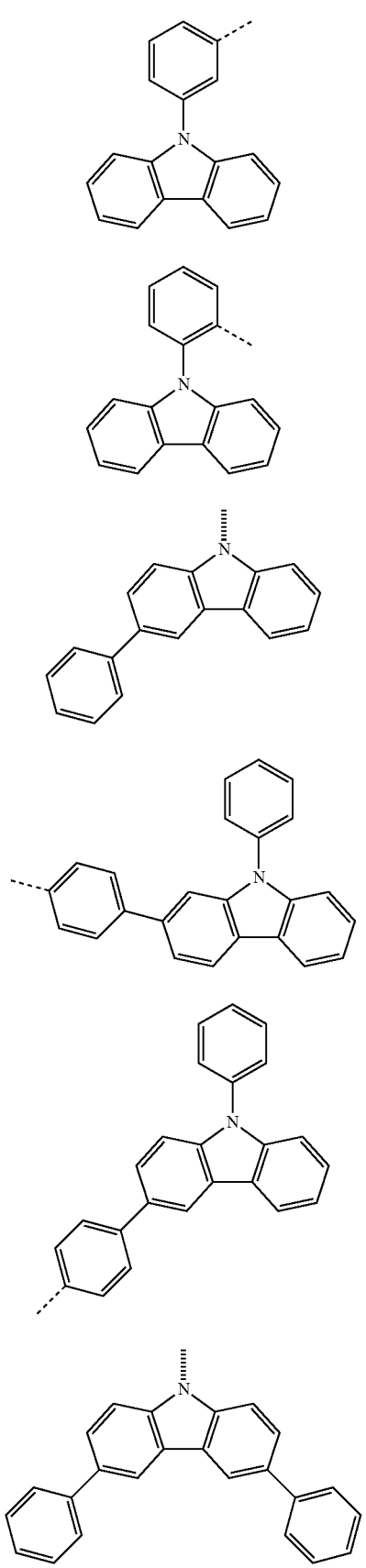
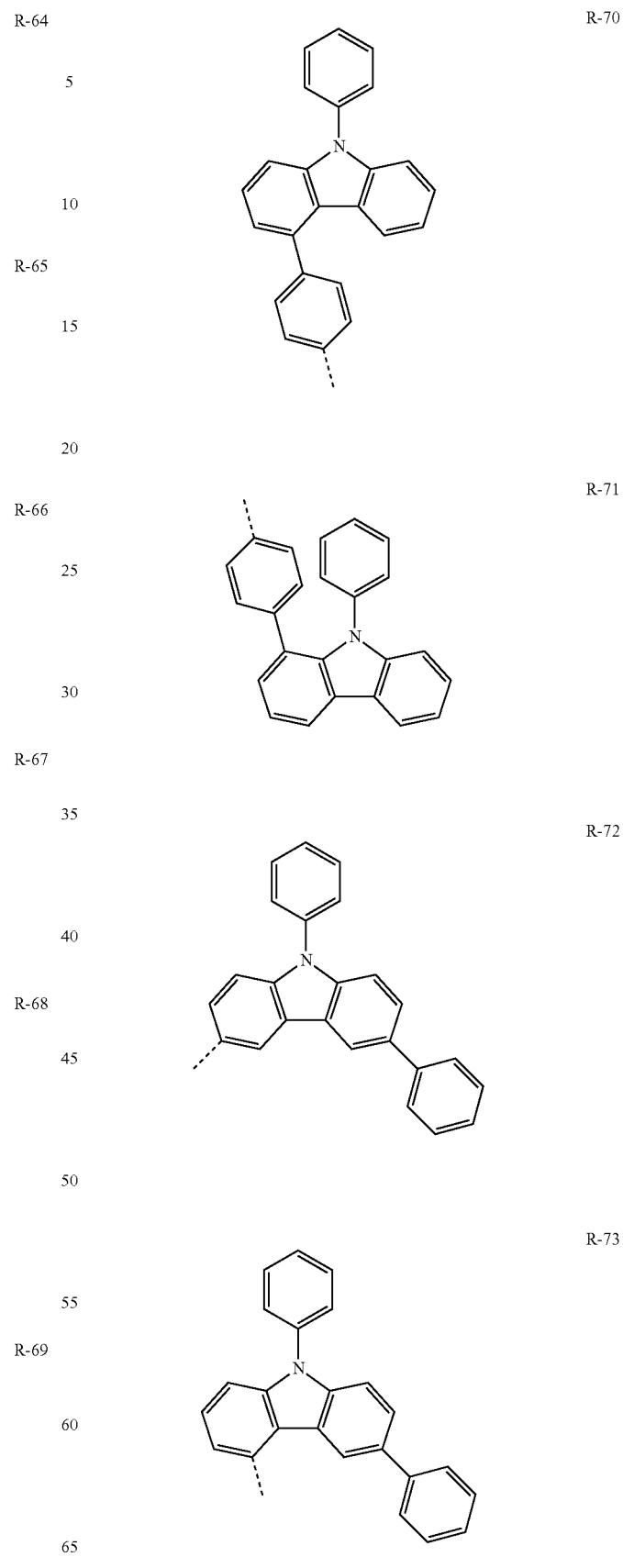

R-74
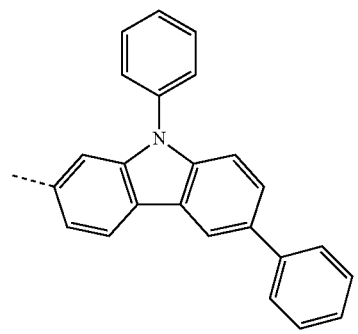
R-75
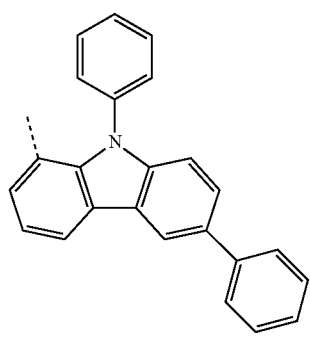
R-76
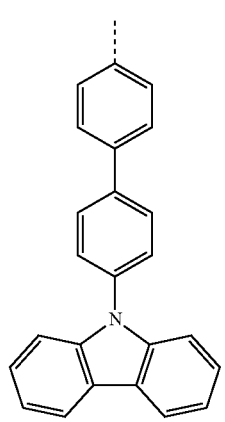
R-77
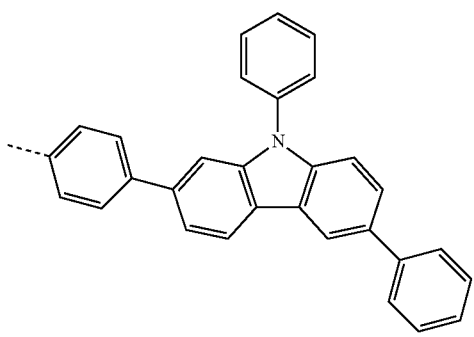
R-78
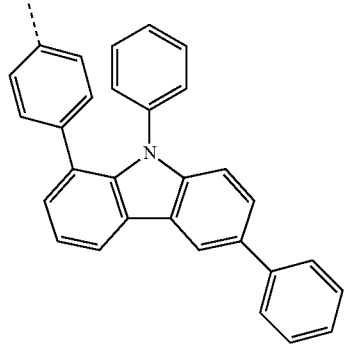
R-79
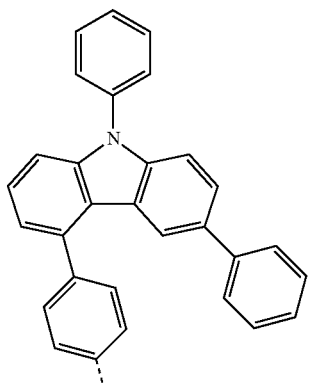
R-80
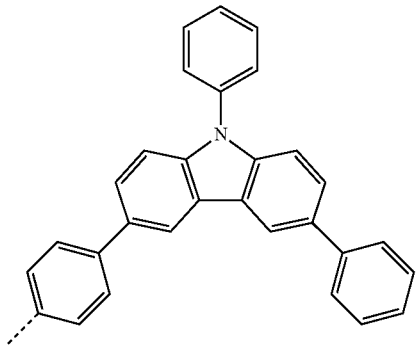
R-81
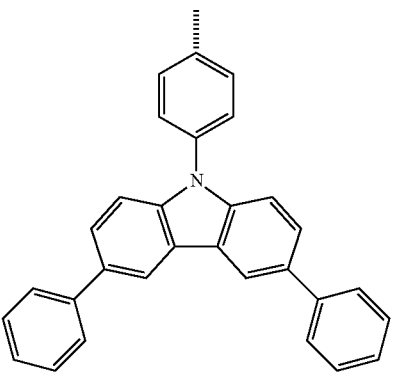

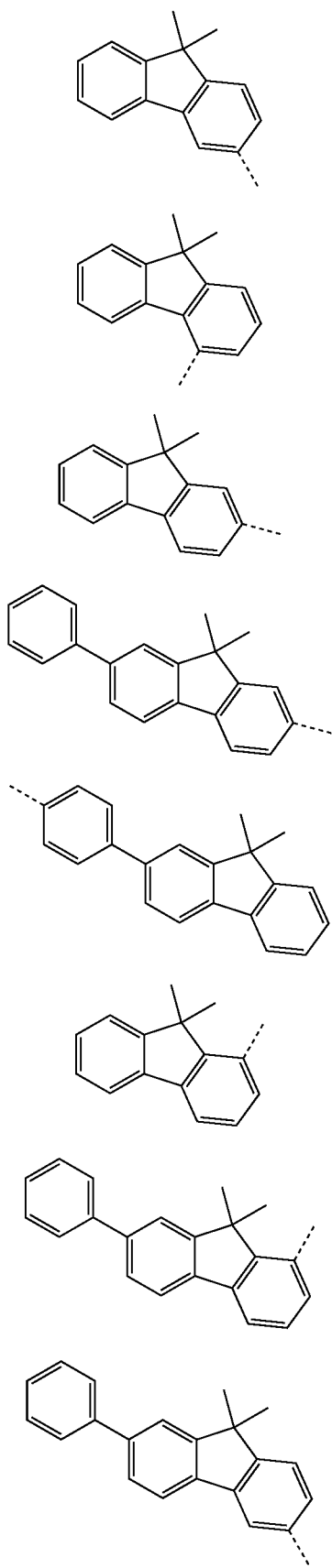
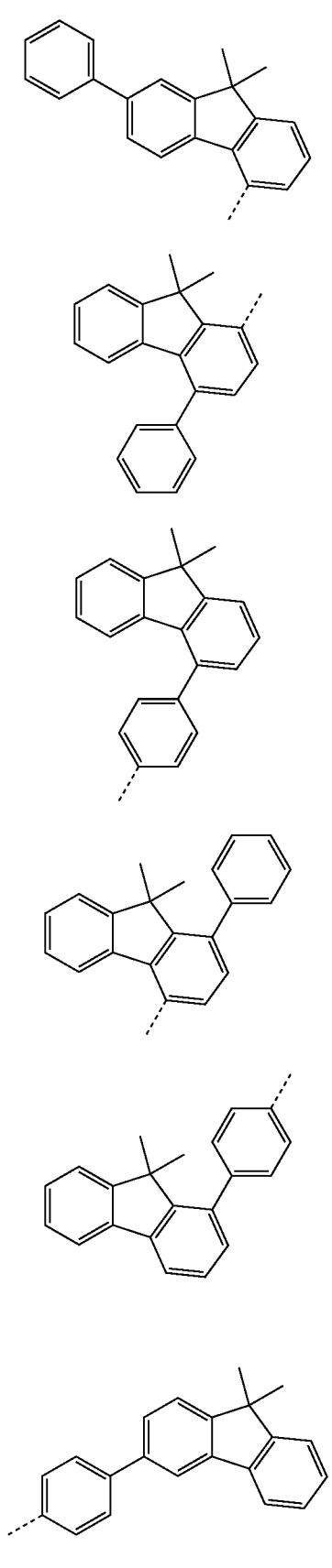

-continued
R-96
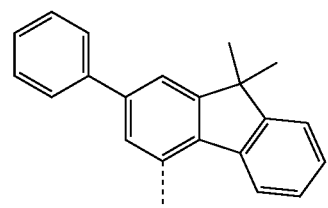
R-97
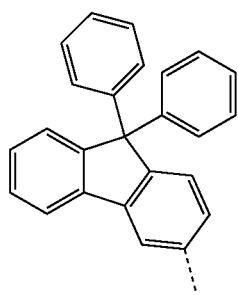
R-98
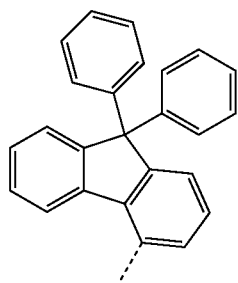
R-99
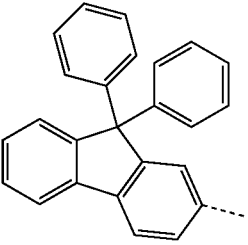
R-100
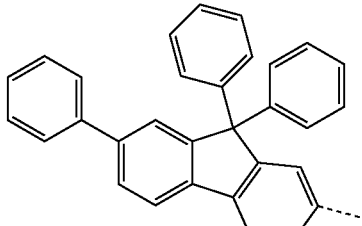
R-101
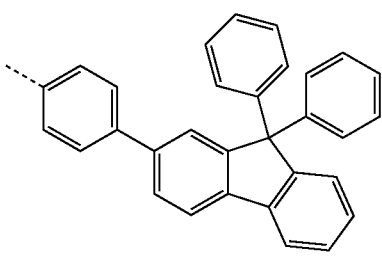
-continued
R-102
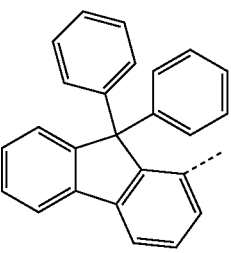
R-103
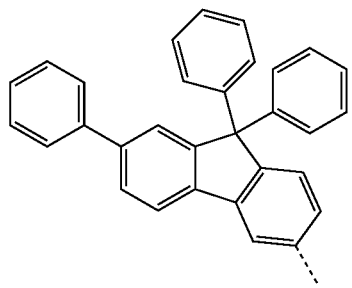
R-104
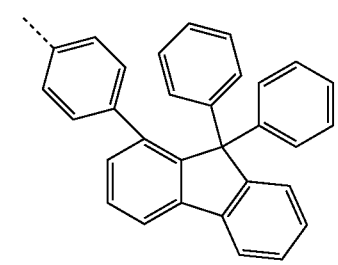
R-105
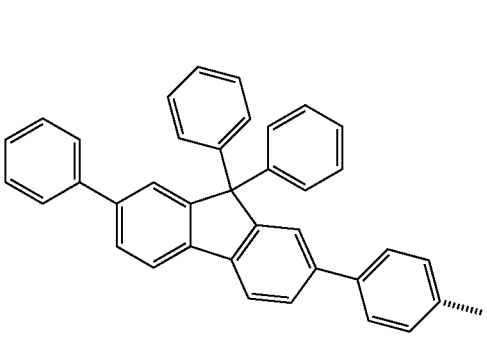
R-106
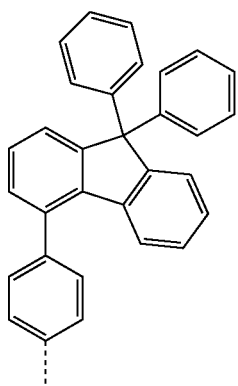

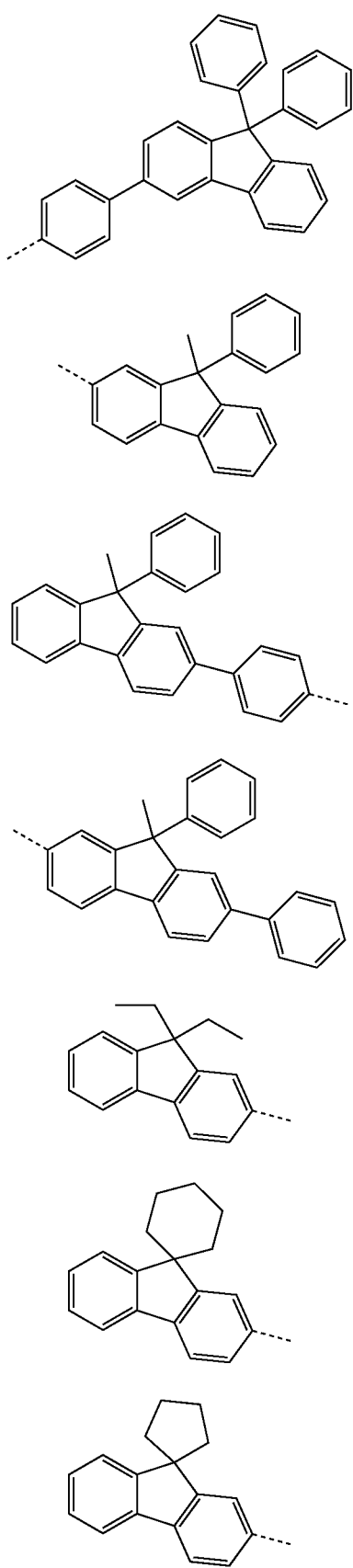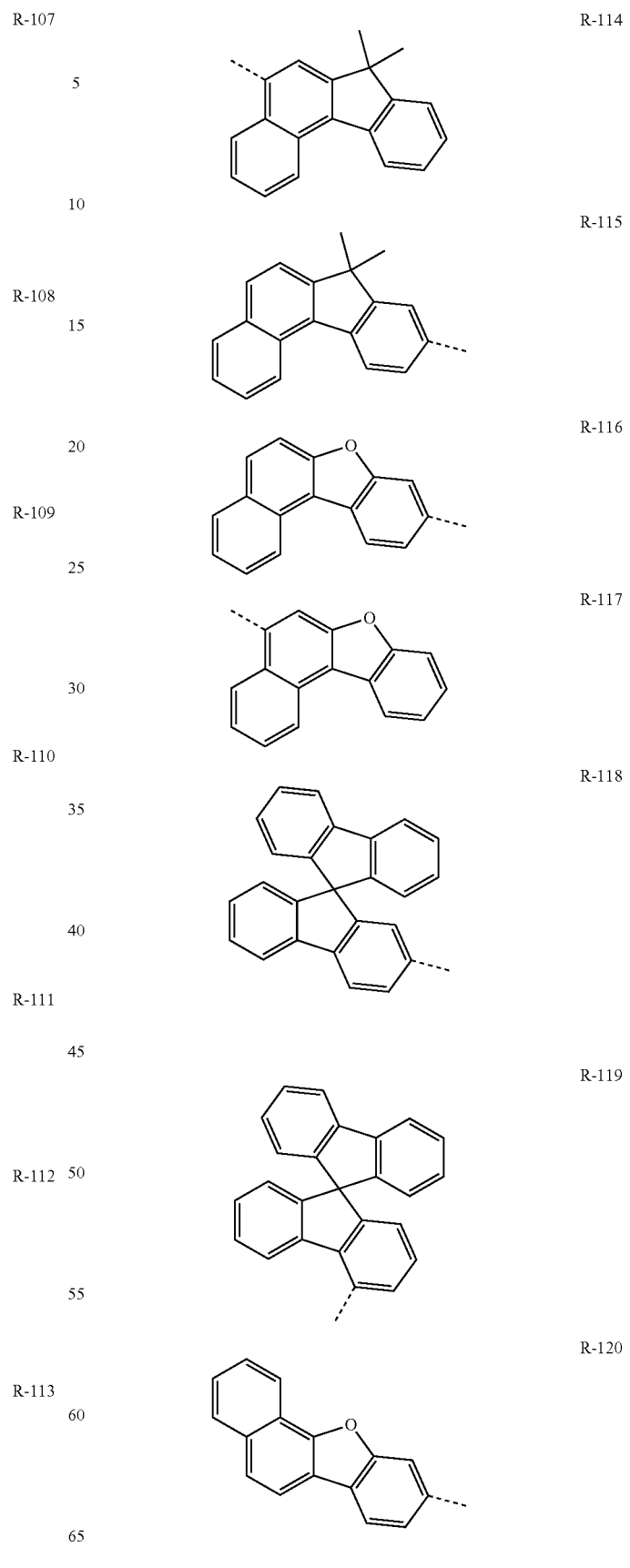

R-121
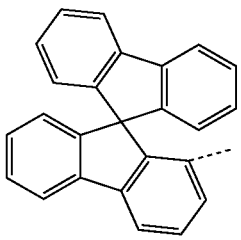
R-122
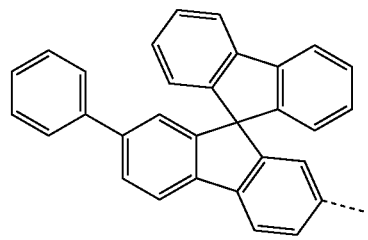
R-123
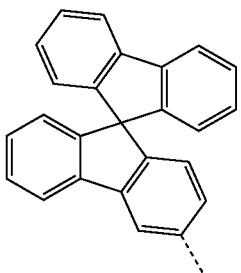
R-124
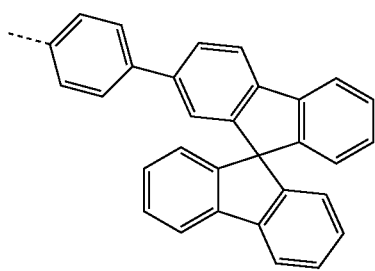
R-125
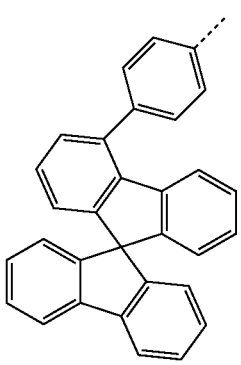
R-126
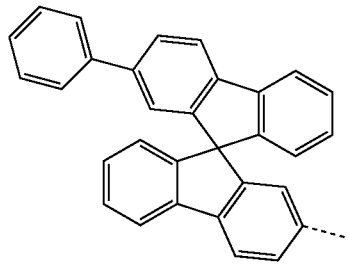
R-127
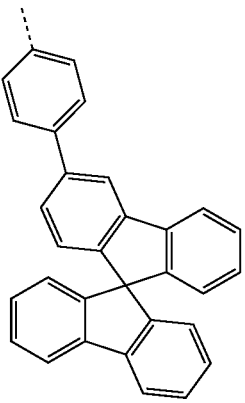
R-128
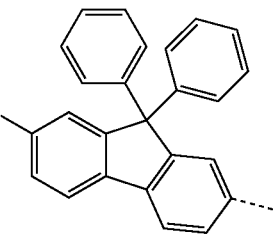
R-129
R-130
R-131
R-132

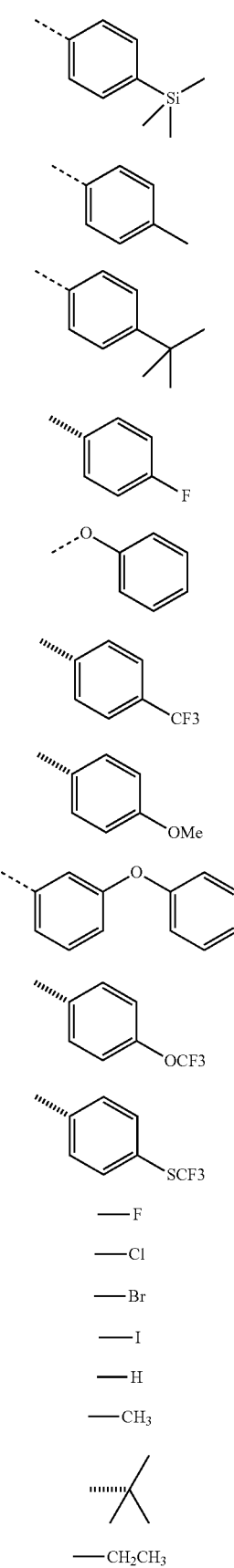
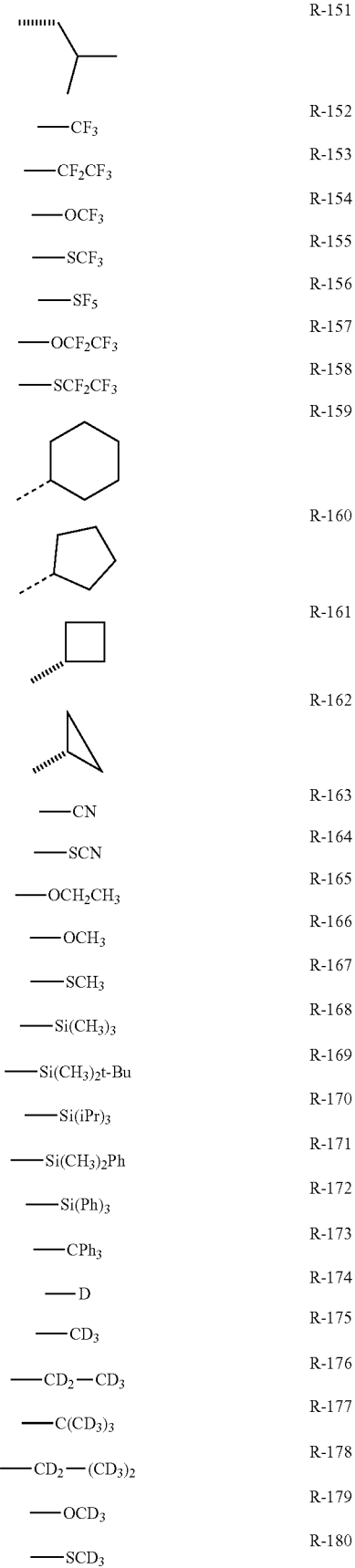

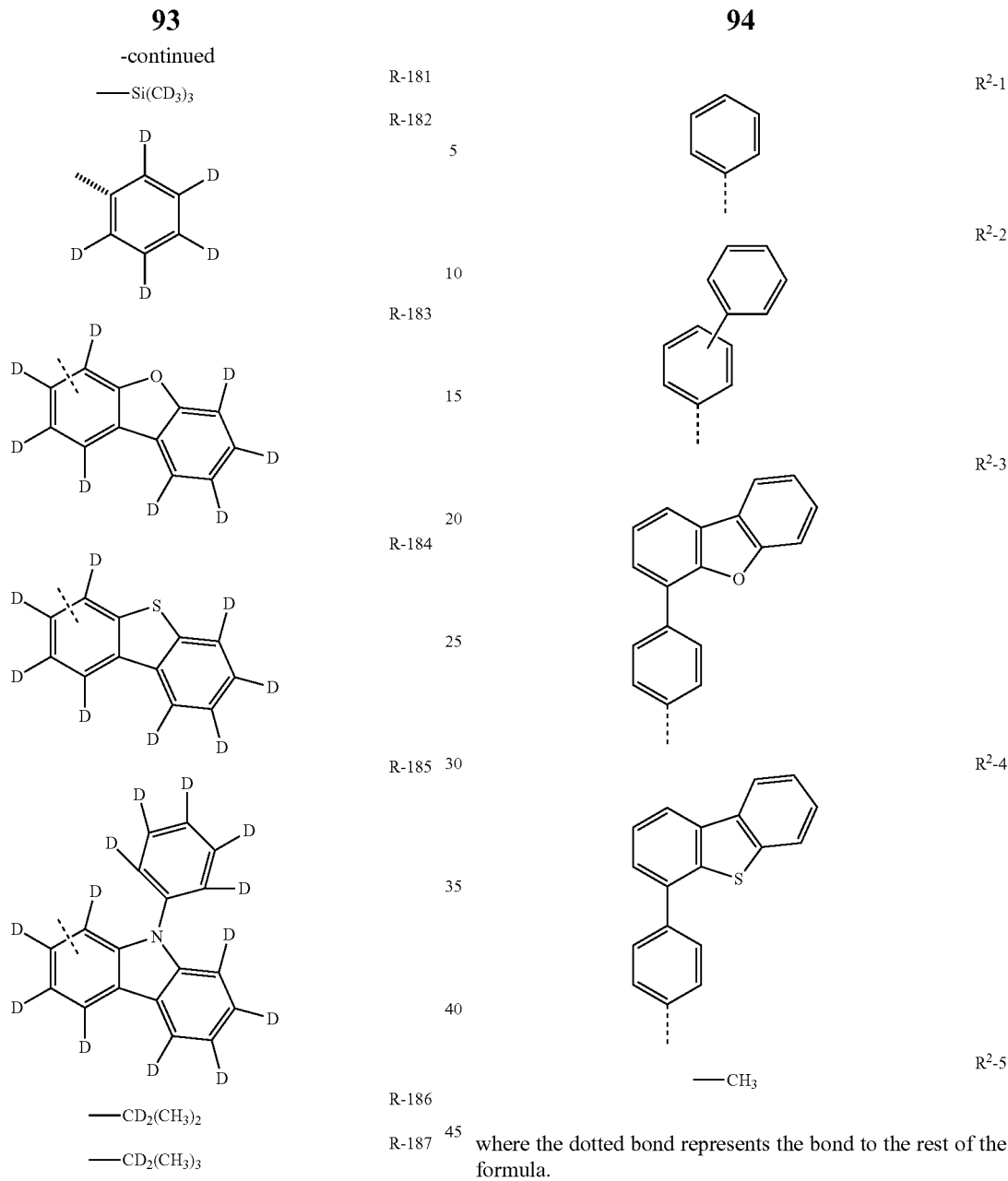

-continued

—Si(CD₃)₃  R-181

R-182

R-183

R-184

R-185

—CD₂(CH₃)₂  R-186

—CD₂(CH₃)₃  R-187 where the dotted bond is the bond to the rest of formula (I).

Preferably, $R^2$ is selected, identically or differently, from F, $Si(R^7)_3$, a straight-chain alkyl group having 1 to 20 C atoms, a branched or cyclic alkyl group having 3 to 20 C atoms, an aromatic ring system having 6 to 40 aromatic ring atoms, or a heteroaromatic ring system having 5 to 40 aromatic ring atoms; where the said alkyl group and the said aromatic or heteroaromatic ring system are substituted by radicals $R^7$. More preferably, $R^2$ is methyl, ethyl, iso-propyl, tert-butyl, phenyl, biphenyl, terphenyl, phenyl substituted with dibenzofuran, or phenyl substituted with dibenzothiophene, where each of the groups is substituted with radicals $R^7$, which are in this case preferably H. The strongest preference is that $R^2$ is methyl or phenyl, which are substituted with radicals $R^7$, which are in this case preferably H.

Preferably, in particular for the case where group FL conforms to formula (FL-1), $R^2$ is selected, identically or differently on each occurrence, from the following groups where the dotted bond represents the bond to the rest of the formula.

Preferably, in particular for the case where group FL conforms to formula (FL-2), $R^2$ is selected, identically or differently on each occurrence, from methyl and phenyl, each of which is substituted with radicals $R^7$, which are in this case preferably H.

Preferably, $R^3$ is selected, identically or differently, from H, D, F, CN, $Si(R^7)_3$, $N(R^7)_2$, straight-chain alkyl or alkoxy groups having 1 to 20 C atoms, branched or cyclic alkyl or alkoxy groups having 3 to 20 C atoms, aromatic ring systems having 6 to 40 aromatic ring atoms, and heteroaromatic ring systems having 5 to 40 aromatic ring atoms; where the said alkyl and alkoxy groups and the said aromatic and heteroaromatic ring systems are substituted by radicals $R^7$, and where one or more $CH_2$ groups in the said alkyl and alkoxy groups may in each case be replaced by —C≡C—, —$R^7$C=C$R^7$—, $Si(R^7)_2$, C=O, C=N$R^7$, —N$R^7$—, —O—, —S—, —C(=O)O— or —C(=O)N$R^7$—. More preferably, $R^3$ is selected, identically or differently, from H, D, F, CN, $Si(R^7)_3$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$. Most preferably, $R^3$ is H.

Preferably, $R^4$ is selected, identically or differently, from H, D, F, CN, $Si(R^7)_3$, $N(R^7)_2$, straight-chain alkyl or alkoxy groups having 1 to 20 C atoms, branched or cyclic alkyl or alkoxy groups having 3 to 20 C atoms, aromatic ring systems having 6 to 40 aromatic ring atoms, and heteroaromatic ring systems having 5 to 40 aromatic ring atoms; where the said alkyl and alkoxy groups and the said aromatic and heteroaromatic ring systems are substituted by radicals $R^7$, and where one or more $CH_2$ groups in the said alkyl and alkoxy groups may in each case be replaced by —C≡C—, —$R^7$C=C$R^7$—, $Si(R^7)_2$, C=O, C=N$R^7$, —N$R^7$—, —O—, —S—, —C(=O)O— or —C(=O)N$R^7$—. More preferably, $R^4$ is selected, identically or differently, from H, D, F, CN, $Si(R^7)_3$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$. Most preferably, $R^4$ is H.

Preferably, $R^5$ is selected, identically or differently, from H, D, F, CN, $Si(R^7)_3$, $N(R^7)_2$, straight-chain alkyl or alkoxy groups having 1 to 20 C atoms, branched or cyclic alkyl or alkoxy groups having 3 to 20 C atoms, aromatic ring systems having 6 to 40 aromatic ring atoms, and heteroaromatic ring systems having 5 to 40 aromatic ring atoms; where the said alkyl and alkoxy groups and the said aromatic and heteroaromatic ring systems are substituted by radicals $R^7$, and where one or more $CH_2$ groups in the said alkyl and alkoxy groups may in each case be replaced by —C≡C—, —$R^7$C=C$R^7$—, $Si(R^7)_2$, C=O, C=N$R^7$, —N$R^7$—, —O—, —S—, —C(=O)O— or —C(=O)N$R^7$—. More preferably, $R^5$ is selected, identically or differently, from H, D, F, CN, $Si(R^7)_3$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$. Most preferably, $R^5$ is H.

Preferably, $R^6$ is selected, identically or differently, from H, D, F, CN, $Si(R^7)_3$, $N(R^7)_2$, straight-chain alkyl or alkoxy groups having 1 to 20 C atoms, branched or cyclic alkyl or alkoxy groups having 3 to 20 C atoms, aromatic ring systems having 6 to 40 aromatic ring atoms, and heteroaromatic ring systems having 5 to 40 aromatic ring atoms; where the said alkyl and alkoxy groups and the said aromatic and heteroaromatic ring systems are substituted by radicals $R^7$, and where one or more $CH_2$ groups in the said alkyl and alkoxy groups may in each case be replaced by —C≡C—, —$R^7$C=C$R^7$—, $Si(R^7)_2$, C=O, C=N$R^7$, —N$R^7$—, —O—, —S—, —C(=O)O— or —C(=O)N$R^7$—. More preferably, $R^6$ is selected, identically or differently, from H, D, F, CN, $Si(R^7)_3$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$. Most preferably, $R^6$ is selected, identically or differently, from H, alkyl groups having 1 to 10 C atoms, preferably methyl, iso-propyl and tert-butyl, and aromatic ring systems having 6 to 40 aromatic ring atoms, which are substituted with groups $R^7$, preferably phenyl.

Preferably, $R^7$ is selected, identically or differently, from H, D, F, CN, $Si(R^8)_3$, $N(R^8)_2$, straight-chain alkyl or alkoxy groups having 1 to 20 C atoms, branched or cyclic alkyl or alkoxy groups having 3 to 20 C atoms, aromatic ring systems having 6 to 40 aromatic ring atoms, and heteroaromatic ring systems having 5 to 40 aromatic ring atoms; where the said alkyl and alkoxy groups and the said aromatic and heteroaromatic ring systems are substituted by radicals $R^8$, and where one or more $CH_2$ groups in the said alkyl and alkoxy groups may in each case be replaced by —C≡C—, —$R^8$C=C$R^8$—, $Si(R^8)_2$, C=O, C=N$R^8$, —N$R^8$—, —O—, —S—, —C(=O)O— or —C(=O)N$R^8$—. More preferably, $R^7$ is selected, identically or differently, from H, D, F, CN, $Si(R^8)_3$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^8$.

Preferably, $R^8$ is H.

According to a preferred embodiment, compounds of formula (I) conform to one of formulae (I-A) and (I-B)

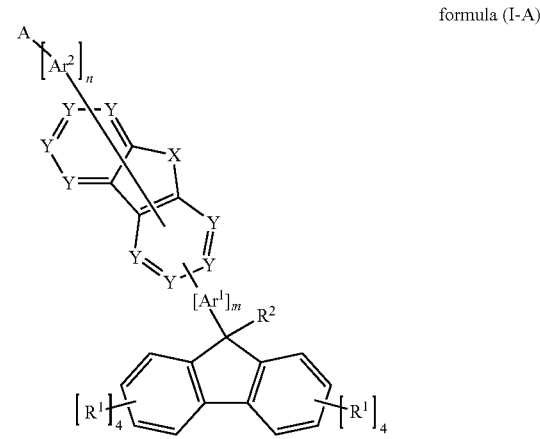

formula (I-A)

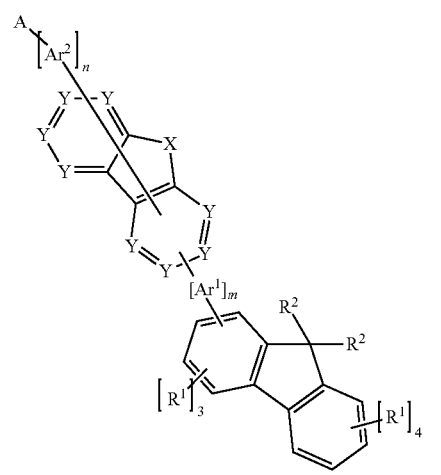

formula (I-B)

where the variables occurring are defined as above. Formula (I-A) is particularly preferred. Furthermore, X is preferably O, and m is preferably 1, and Ar¹ is preferably phenylene, which is substituted with radicals R⁷.

Compounds of formula (I) preferably conform to one of the following formulae

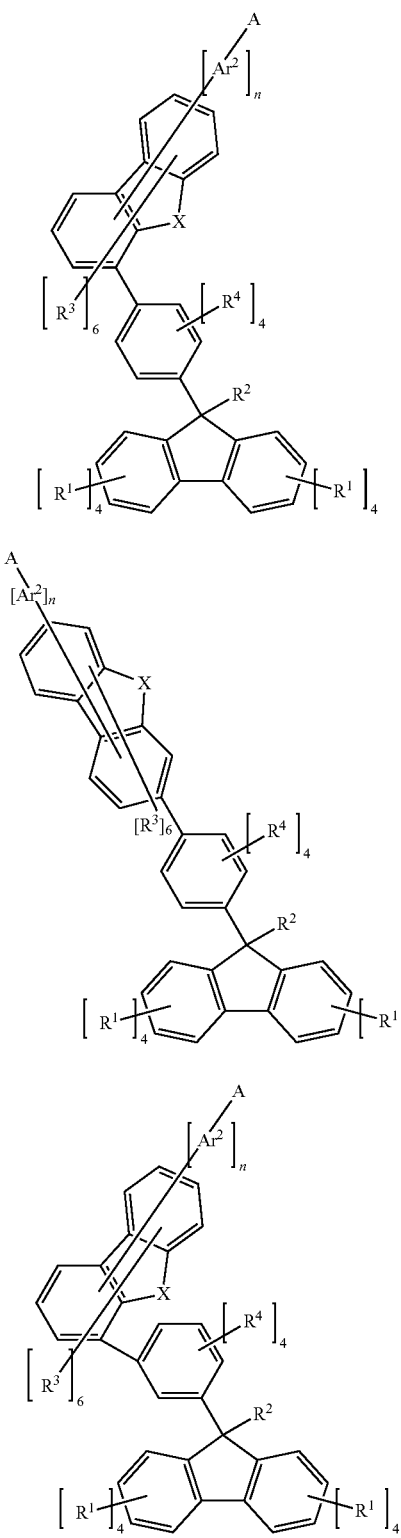

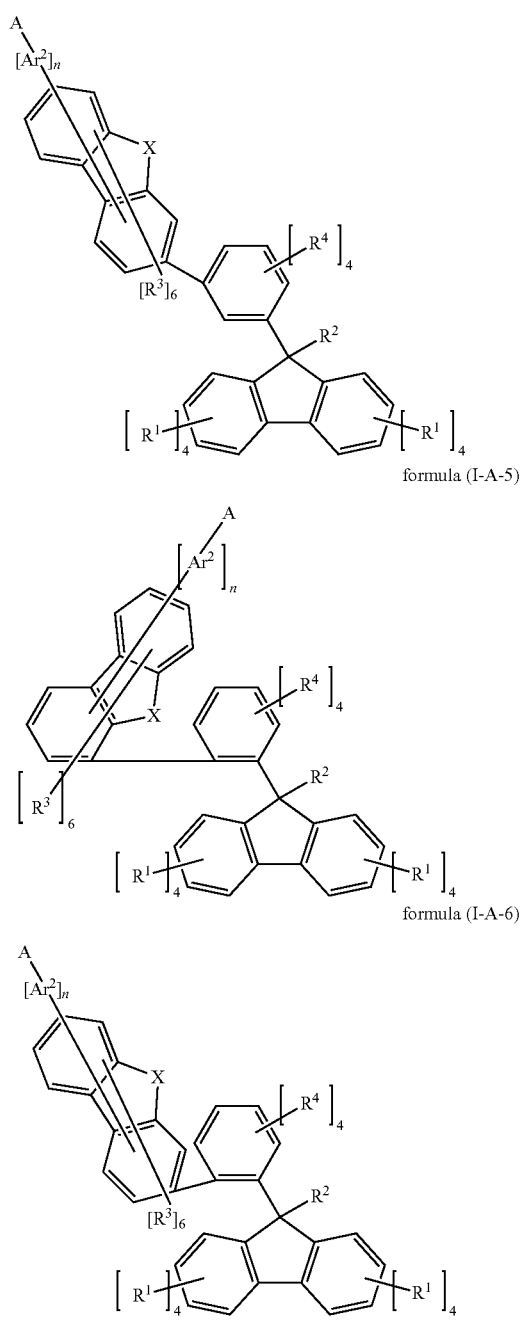

where the variables occurring are defined as above, and where X is preferably O. Furthermore, preferably, k is 0. According to one preferred embodiment, groups $R^1$ are all H. According to an alternative preferred embodiment, two groups $R^1$ are not H, and the other groups $R^1$ are H. The groups $R^1$ which are not H are preferably present in positions 2 and 7 on the fluorenyl group. Furthermore, preferably, the groups $R^2$ which are not H are selected from D, F, CN, $Si(R^7)_3$, straight-chain alkyl groups having 1 to 20 C atoms, which are optionally deuterated and/or fluorinated, branched or cyclic alkyl groups having 3 to 20 C atoms, which are optionally deuterated and/or fluorinated, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$. Furthermore, preferably, in the formulae (I-A-1) to (I-A-6), the group —[Ar$^2$]$_n$-A is bonded to the benzene ring of the dibenzofuran or dibenzothiophene moiety which is opposite to the benzene ring to which the phenylene-fluorenyl group is bonded.

More preferred embodiments of compounds according to formula (I) conform to the following formulae Formula (I-A-1-1)

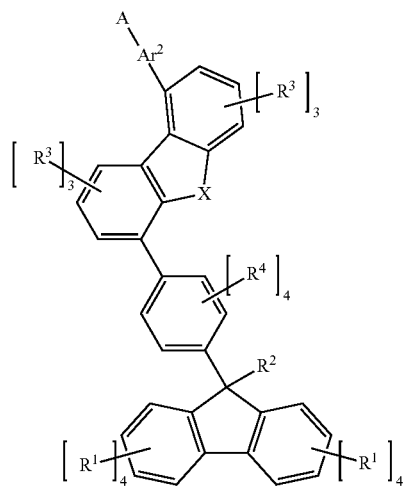

Formula (I-A-1-2)

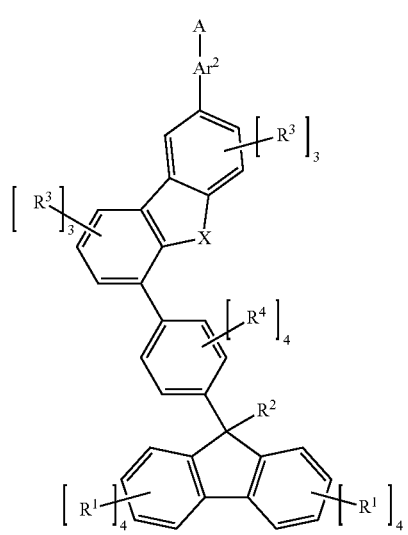

Formula (I-A-1-3)

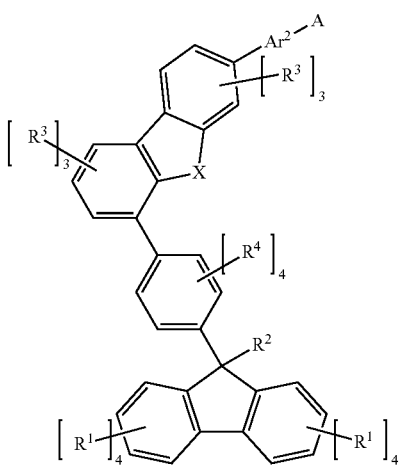

Formula (I-A-1-4)

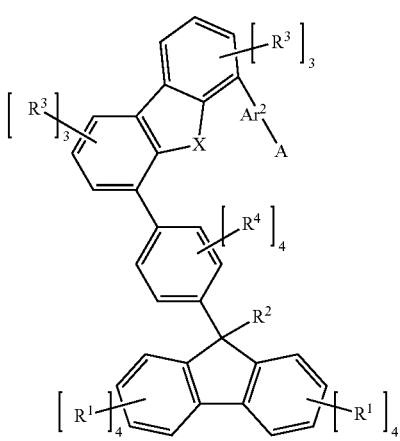

Formula (I-A-1-5)

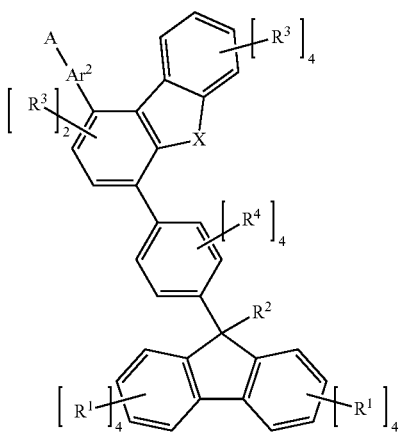

Formula (I-A-1-6)

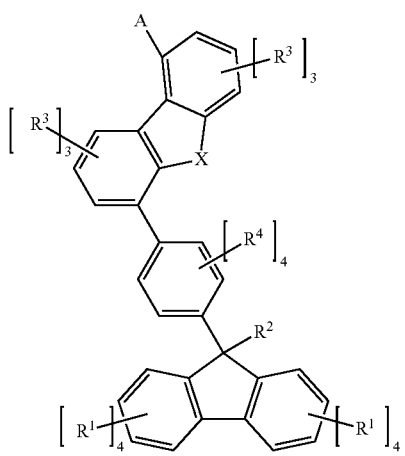

Formula (I-A-1-7)

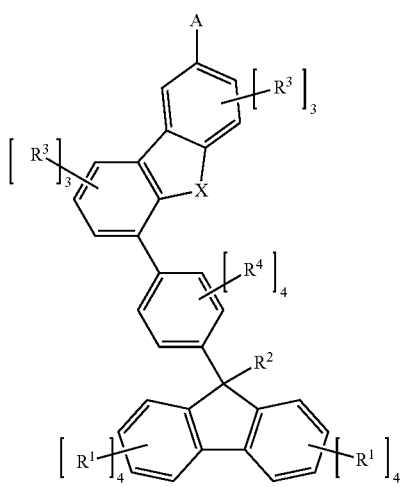

Formula (I-A-1-8)

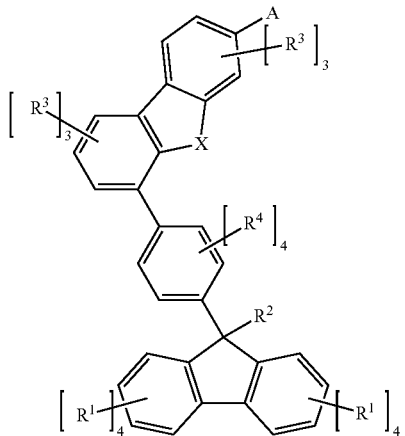

Formula (I-A-1-9)

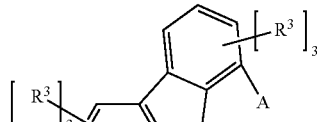
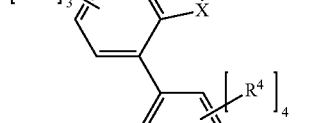
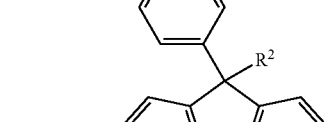

Formula (I-A-1-10)

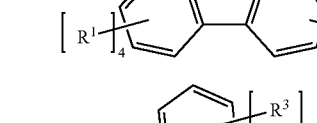
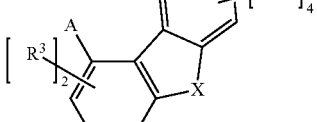
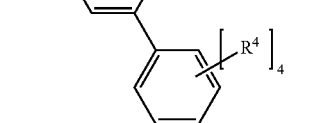
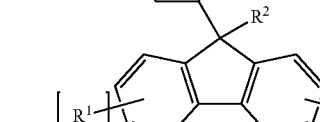
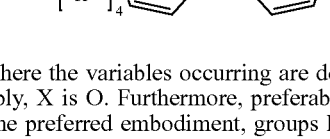

where the variables occurring are defined as above. Preferably, X is O. Furthermore, preferably, k is 0. According to one preferred embodiment, groups $R^1$ are all H. According to an alternative preferred embodiment, two groups $R^1$ are not H, and the other groups $R^1$ are H. The groups $R^1$ which are not H are preferably present in positions 2 and 7 on the fluorenyl group. Furthermore, preferably, the groups $R^2$ which are not H are selected from D, F, CN, $Si(R^7)_3$, straight-chain alkyl groups having 1 to 20 C atoms, which are optionally deuterated and/or fluorinated, branched or cyclic alkyl groups having 3 to 20 C atoms, which are optionally deuterated and/or fluorinated, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$.

Among the above-mentioned formulae, formulae (I-A-1-4) and (I-A-1-9) are particularly preferred.

Particularly preferably, compounds of formula (I) conform to specific embodiments of the formulae (I-A-1-1) to (I-A-1-10) above, where $R^2$ is selected from the following groups $R^2$ $R^2$-1

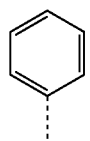

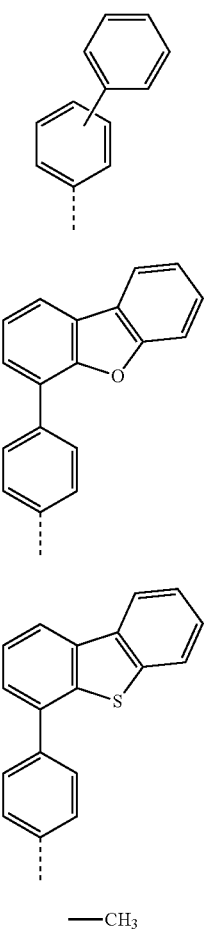

where the dotted bond represents the bond to the rest of the formula.

These specifically preferred embodiment of formula (I) are listed below:

| Formula | Basic formula | $R^2$ |
|---|---|---|
| (I-A-1-1-1) | (I-A-1-1) | $R^2$-1 |
| (I-A-1-1-2) | (I-A-1-1) | $R^2$-2 |
| (I-A-1-1-3) | (I-A-1-1) | $R^2$-3 |
| (I-A-1-1-4) | (I-A-1-1) | $R^2$-4 |
| (I-A-1-1-5) | (I-A-1-1) | $R^2$-5 |
| (I-A-1-2-1) | (I-A-1-2) | $R^2$-1 |
| (I-A-1-2-2) | (I-A-1-2) | $R^2$-2 |
| (I-A-1-2-3) | (I-A-1-2) | $R^2$-3 |
| (I-A-1-2-4) | (I-A-1-2) | $R^2$-4 |
| (I-A-1-2-5) | (I-A-1-2) | $R^2$-5 |
| (I-A-1-3-1) | (I-A-1-3) | $R^2$-1 |
| (I-A-1-3-2) | (I-A-1-3) | $R^2$-2 |
| (I-A-1-3-3) | (I-A-1-3) | $R^2$-3 |
| (I-A-1-3-4) | (I-A-1-3) | $R^2$-4 |
| (I-A-1-3-5) | (I-A-1-3) | $R^2$-5 |
| (I-A-1-4-1) | (I-A-1-4) | $R^2$-1 |
| (I-A-1-4-2) | (I-A-1-4) | $R^2$-2 |
| (I-A-1-4-3) | (I-A-1-4) | $R^2$-3 |
| (I-A-1-4-4) | (I-A-1-4) | $R^2$-4 |
| (I-A-1-4-5) | (I-A-1-4) | $R^2$-5 |
| (I-A-1-5-1) | (I-A-1-5) | $R^2$-1 |
| (I-A-1-5-2) | (I-A-1-5) | $R^2$-2 |
| (I-A-1-5-3) | (I-A-1-5) | $R^2$-3 |
| (I-A-1-5-4) | (I-A-1-5) | $R^2$-4 |
| (I-A-1-5-5) | (I-A-1-5) | $R^2$-5 |
| (I-A-1-6-1) | (I-A-1-6) | $R^2$-1 |
| (I-A-1-6-2) | (I-A-1-6) | $R^2$-2 |
| (I-A-1-6-3) | (I-A-1-6) | $R^2$-3 |
| (I-A-1-6-4) | (I-A-1-6) | $R^2$-4 |
| (I-A-1-6-5) | (I-A-1-6) | $R^2$-5 |
| (I-A-1-7-1) | (I-A-1-7) | $R^2$-1 |
| (I-A-1-7-2) | (I-A-1-7) | $R^2$-2 |
| (I-A-1-7-3) | (I-A-1-7) | $R^2$-3 |
| (I-A-1-7-4) | (I-A-1-7) | $R^2$-4 |
| (I-A-1-7-5) | (I-A-1-7) | $R^2$-5 |
| (I-A-1-8-1) | (I-A-1-8) | $R^2$-1 |
| (I-A-1-8-2) | (I-A-1-8) | $R^2$-2 |
| (I-A-1-8-3) | (I-A-1-8) | $R^2$-3 |
| (I-A-1-8-4) | (I-A-1-8) | $R^2$-4 |
| (I-A-1-8-5) | (I-A-1-8) | $R^2$-5 |
| (I-A-1-9-1) | (I-A-1-9) | $R^2$-1 |
| (I-A-1-9-2) | (I-A-1-9) | $R^2$-2 |
| (I-A-1-9-3) | (I-A-1-9) | $R^2$-3 |
| (I-A-1-9-4) | (I-A-1-9) | $R^2$-4 |
| (I-A-1-9-5) | (I-A-1-9) | $R^2$-5 |
| (I-A-1-10-1) | (I-A-1-10) | $R^2$-1 |
| (I-A-1-10-2) | (I-A-1-10) | $R^2$-2 |
| (I-A-1-10-3) | (I-A-1-10) | $R^2$-3 |
| (I-A-1-10-4) | (I-A-1-10) | $R^2$-4 |
| (I-A-1-10-5) | (I-A-1-10) | $R^2$-5 |

In these formulae, preferably, X is O. Furthermore, preferably, k is 0. According to one preferred embodiment, groups $R^1$ are all H. According to an alternative preferred embodiment, two groups $R^1$ are not H, and the other groups $R^1$ are H. The groups $R^1$ which are not H are preferably present in positions 2 and 7 on the fluorenyl group. Furthermore, preferably, the groups $R^2$ which are not H are selected from D, F, CN, $Si(R^7)_3$, straight-chain alkyl groups having 1 to 20 C atoms, which are optionally deuterated and/or fluorinated, branched or cyclic alkyl groups having 3 to 20 C atoms, which are optionally deuterated and/or fluorinated, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$.

According to an alternative preferred embodiment, compounds of formula (I) preferably conform to the following formula formula (I-B-1)

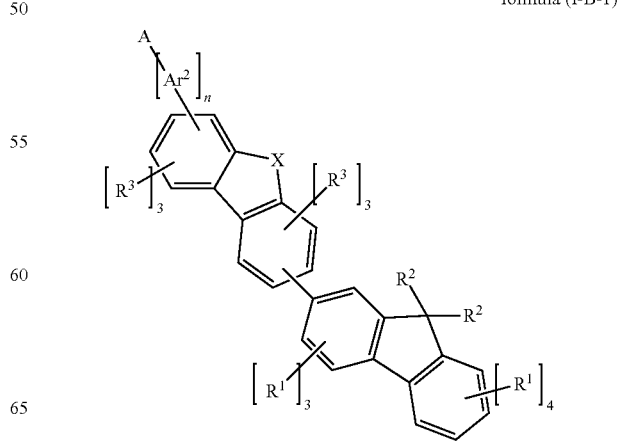

formula (I-B-2)

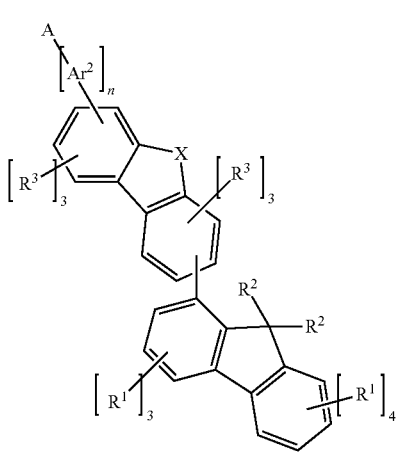

Formula (I-B-1-1)

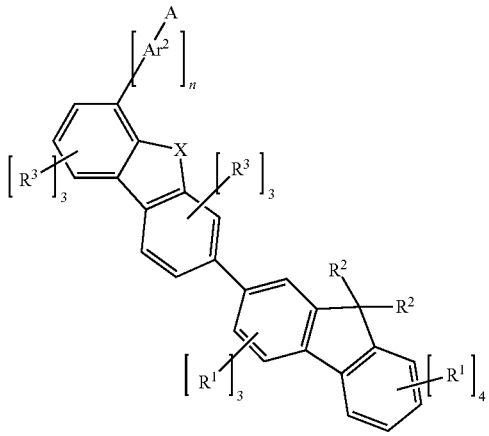

formula (I-B-3)

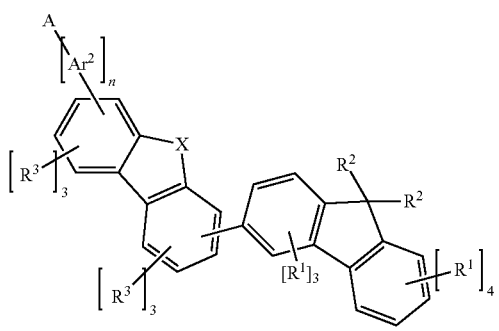

Formula (I-B-1-2)

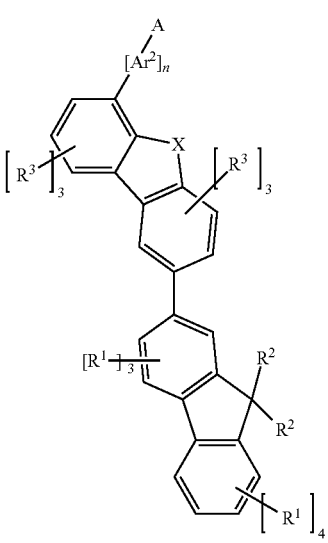

formula (I-B-4)

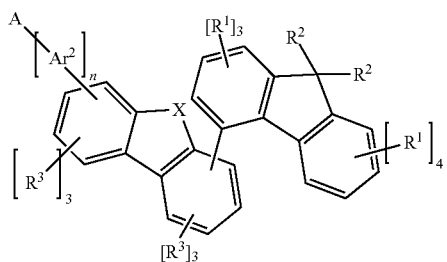

where the variables occurring are defined as above, and where X is preferably O. Furthermore, preferably, k is 0. Furthermore, preferably, $R^2$ is selected, identically or differently on each occurrence, preferably identically, from methyl and phenyl.

Preferably, compounds of formula (I-B-1) conform to one of the following formulae Formula (I-B-1-3)

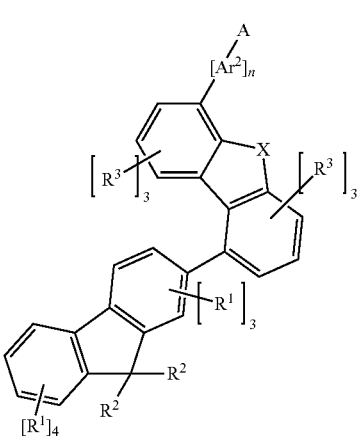

-continued

Formula (I-B-1-4)

Formula (I-B-1-5)

Formula (I-B-1-6)

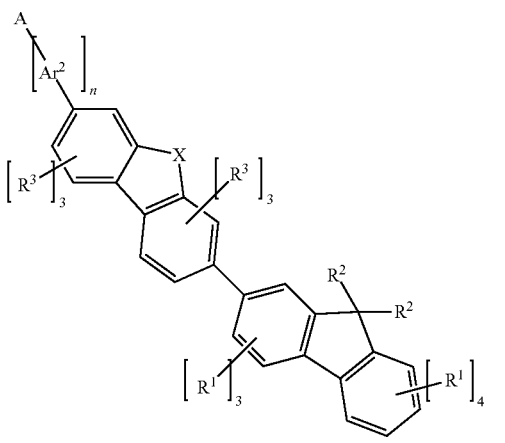

Formula (I-B-2-1)

Formula (I-B-2-2)

Formula (I-B-2-3)

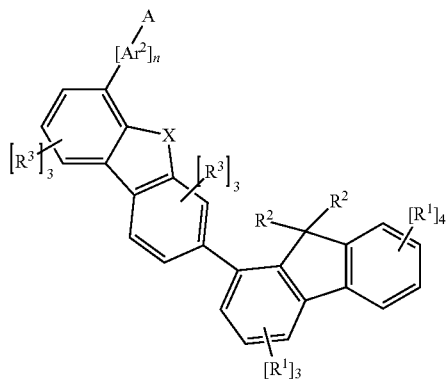

where the variables occurring are defined as above. Preferably, X is O. Furthermore preferably, k is 0. Furthermore, preferably, $R^2$ is selected, identically or differently on each occurrence, preferably identically, from methyl and phenyl.

Preferably, compounds of formula (I-B-2) conform to one of the following formulae Formula (I-B-2-4)

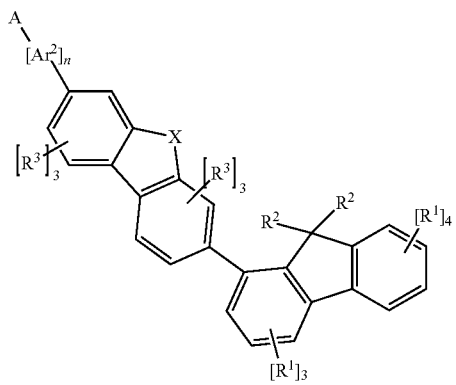

Formula (I-B-2-5)

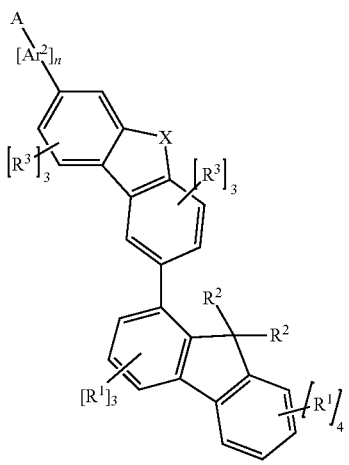

Formula (I-B-2-6)

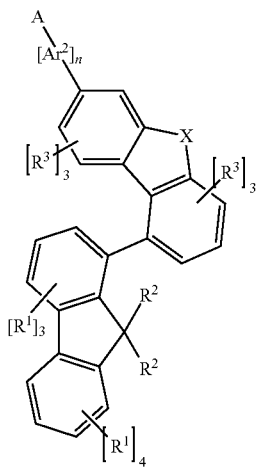

Formula (I-B-1-1-1)

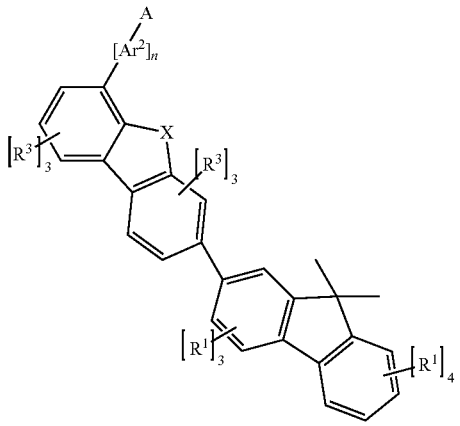

Formula (I-B-1-2-1)

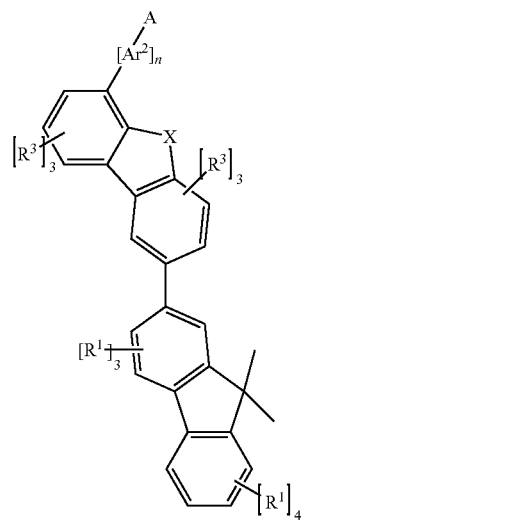

Formula (I-B-1-3-1)

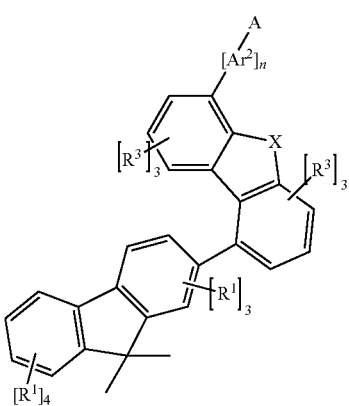

where the variables occurring are defined as above. Preferably, X is O. Furthermore preferably, k is 0. Furthermore, preferably, $R^2$ is selected, identically or differently on each occurrence, preferably identically, from methyl and phenyl.

More preferably, compounds of formula (I-B-1) conform to one of the following formulae -continued
Formula (I-B-1-4-1)
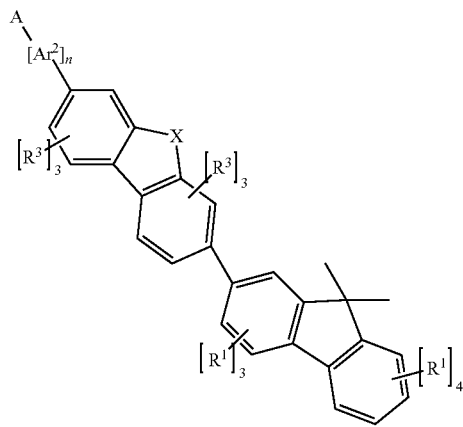
Formula (I-B-1-5-1)
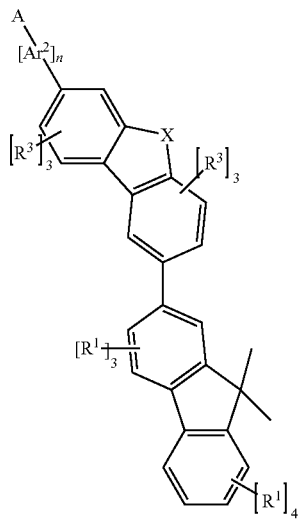
Formula (I-B-1-6-1)
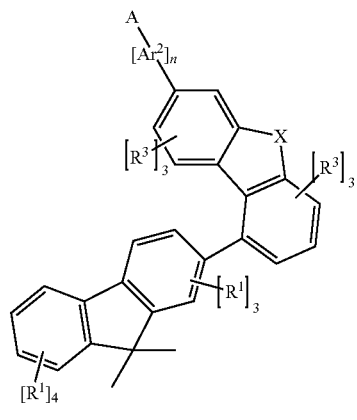
-continued
Formula (I-B-1-1-2)
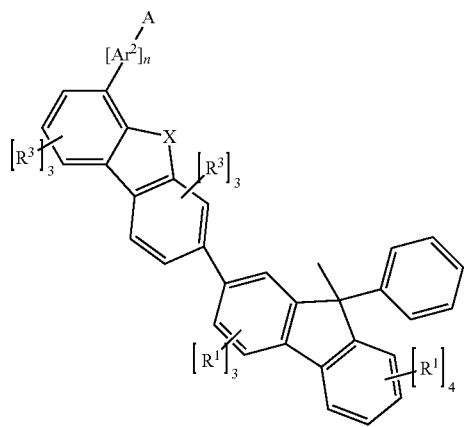
Formula (I-B-1-2-2)
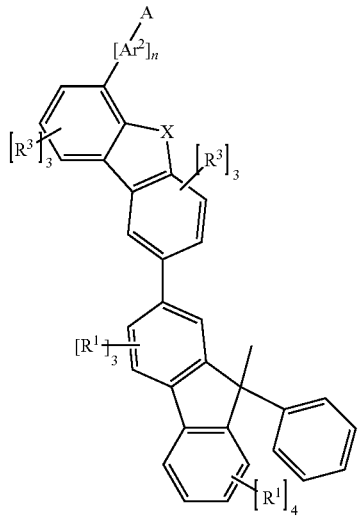
Formula (I-B-1-3-2)
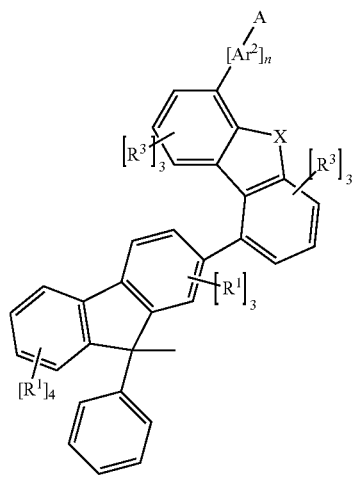

Formula (I-B-1-4-2)
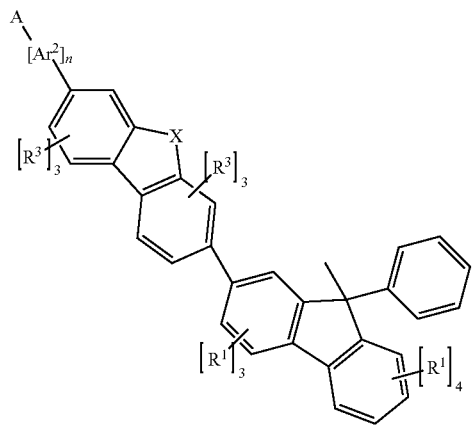
Formula (I-B-1-1-3)
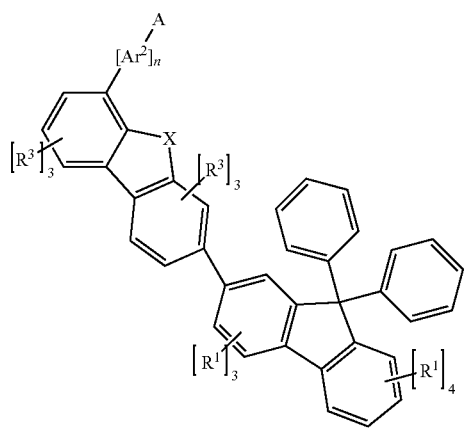
Formula (I-B-1-5-2)
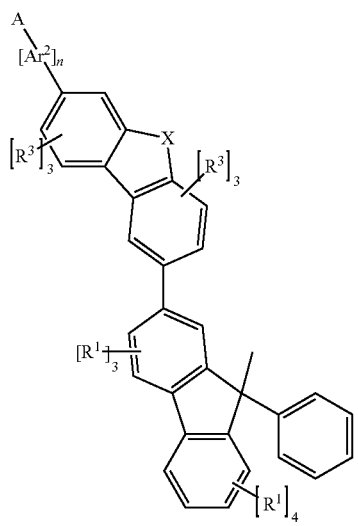
Formula (I-B-1-2-3)
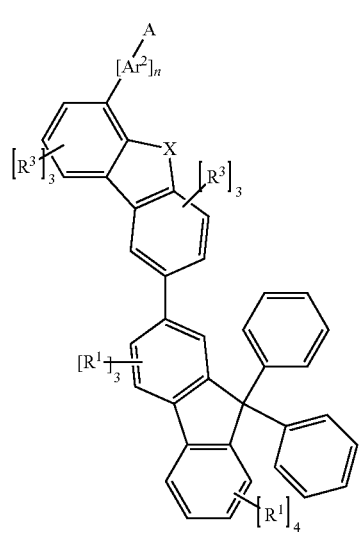
Formula (I-B-1-6-2)
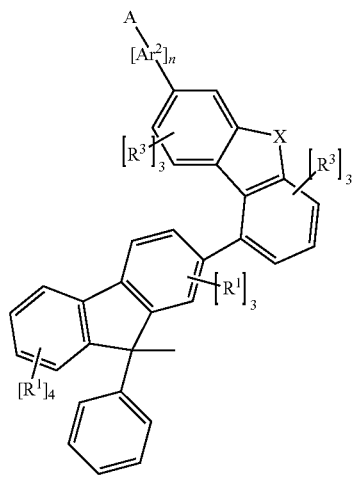
Formula (I-B-1-3-3)
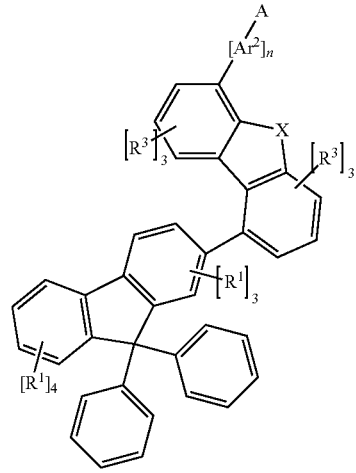

-continued
Formula (I-B-1-4-3)
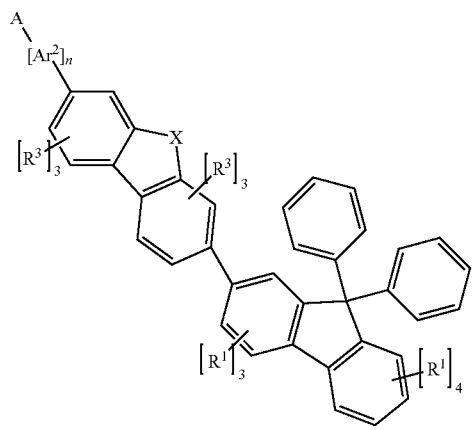
Formula (I-B-1-5-3)
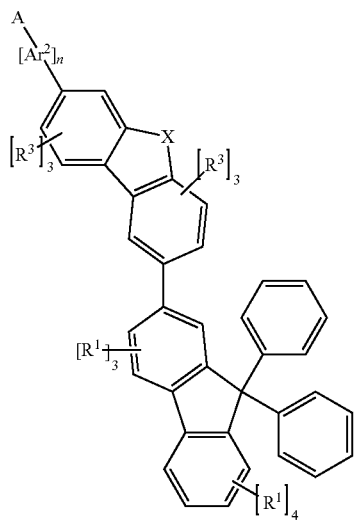
Formula (I-B-1-6-3)
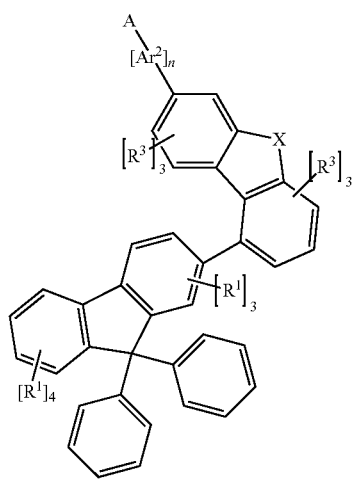
Formula (I-B-2-1-1)
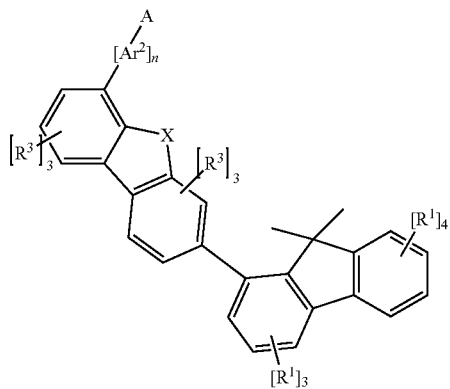
Formula (I-B-2-2-1)
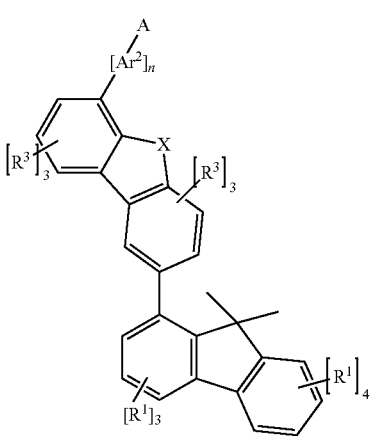
Formula (I-B-2-3-1)
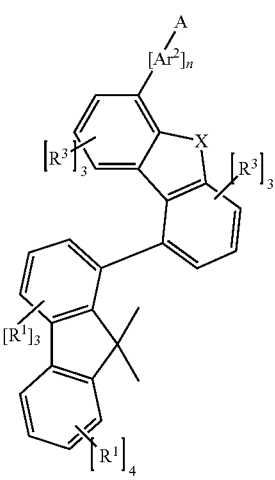
where the variables occurring are defined as above. Preferably, X is O. Furthermore preferably, k is 0.
More preferably, compounds of formula (I-B-2) conform to one of the following formulae Formula (I-B-2-4-1)
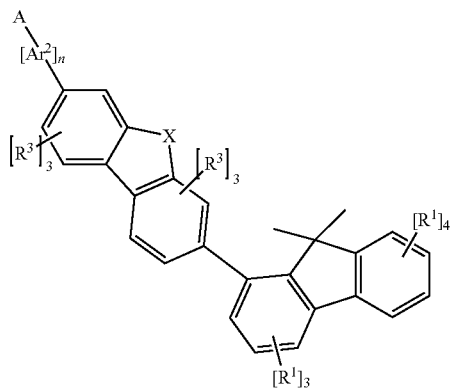
Formula (I-B-2-1-2)
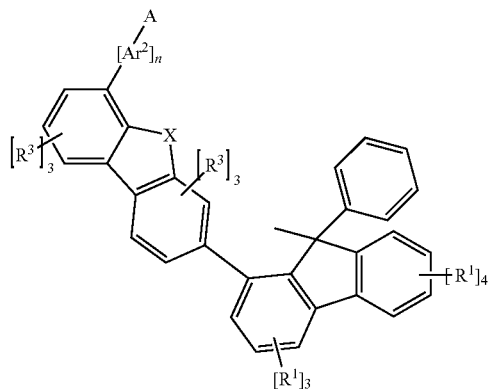
Formula (I-B-2-5-1)
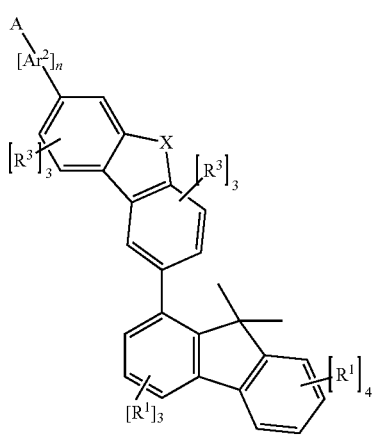
Formula (I-B-2-2-2)
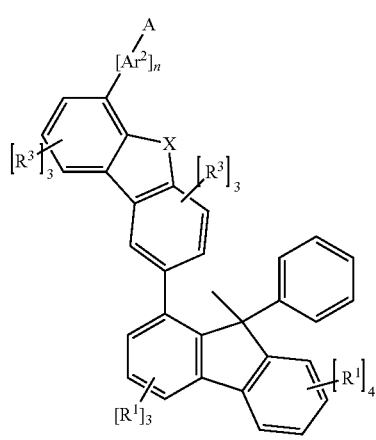
Formula (I-B-2-6-1)
Formula (I-B-2-3-2)
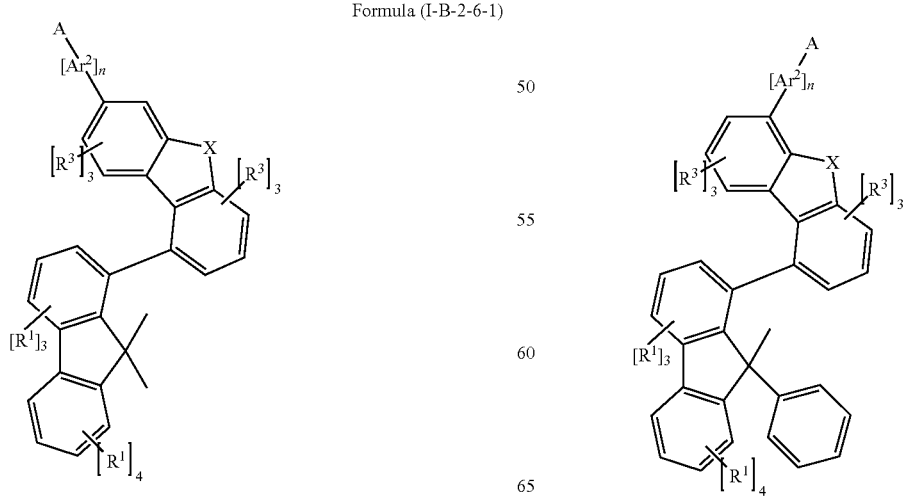

Formula (I-B-2-4-2)
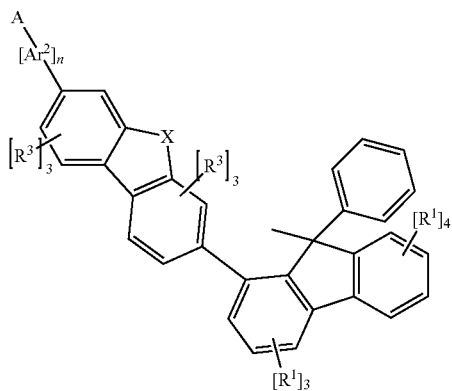
Formula (I-B-2-1-3)
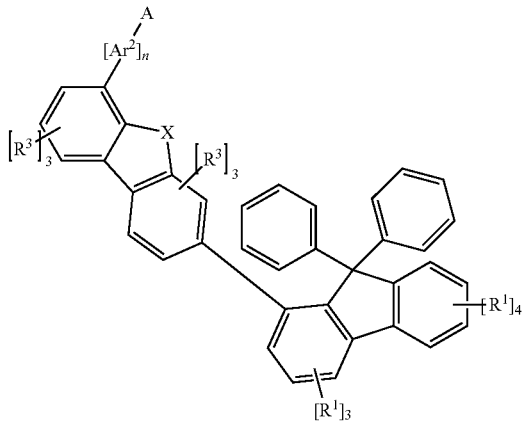
Formula (I-B-2-5-2)
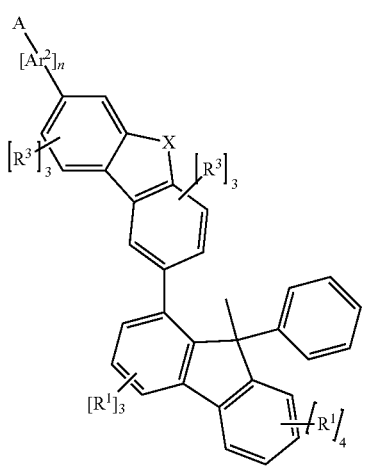
Formula (I-B-2-2-3)
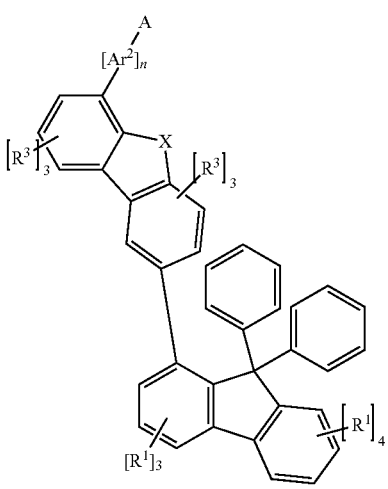
Formula (I-B-2-6-2)
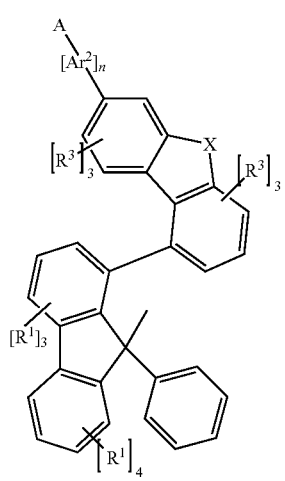
Formula (I-B-2-3-3)
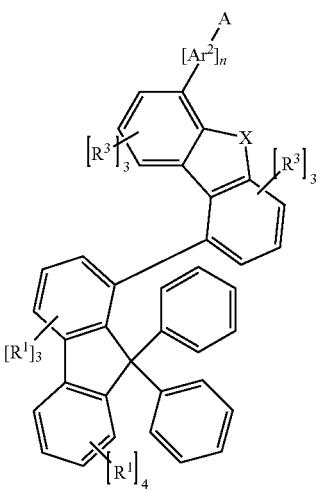

Formula (I-B-2-4-3)
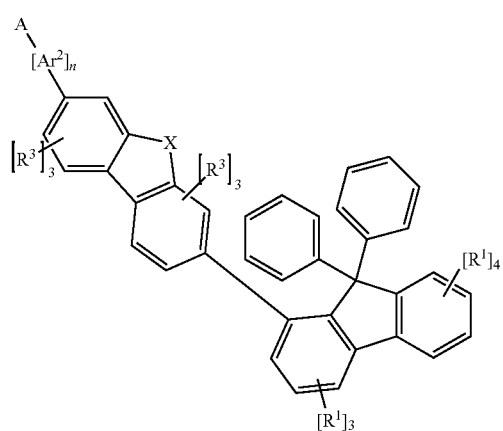
Formula (I-B-2-5-3)
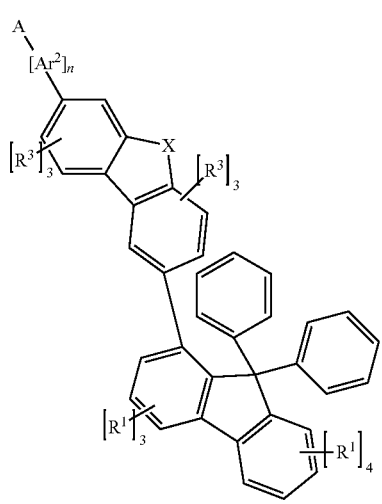
Formula (I-B-2-6-3)
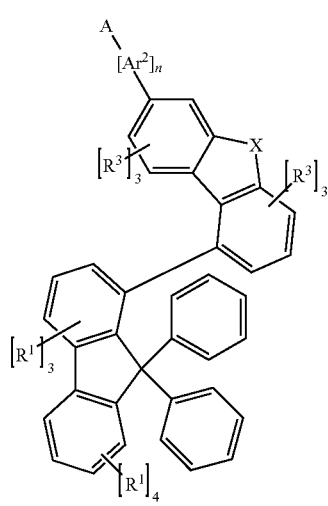
where the variables occurring are defined as above. Preferably, X is O. Furthermore preferably, k is 0.
The following compounds are preferred embodiment of compounds according to formula (I):
(1)
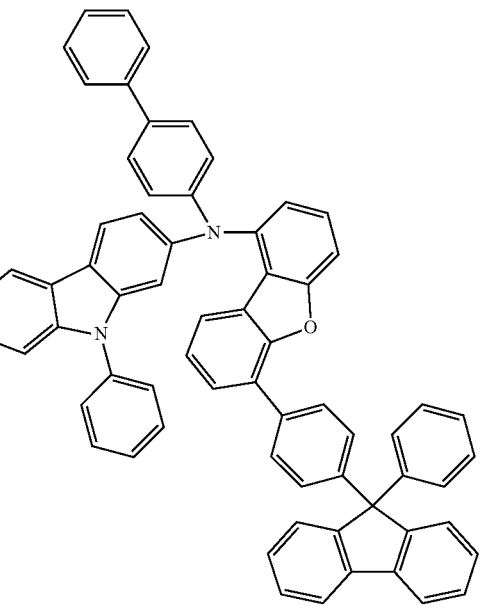
(2)
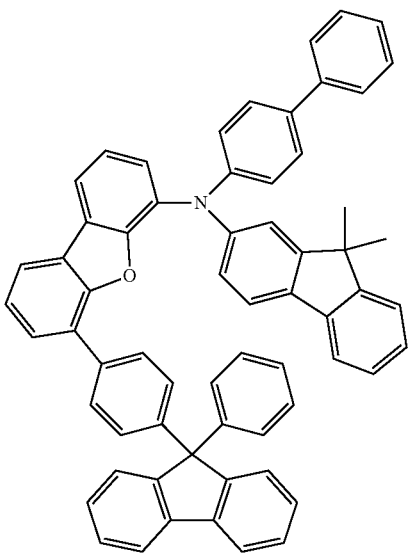
(3)
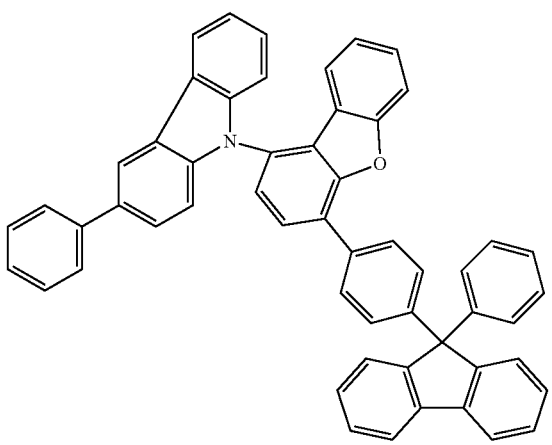

(4)
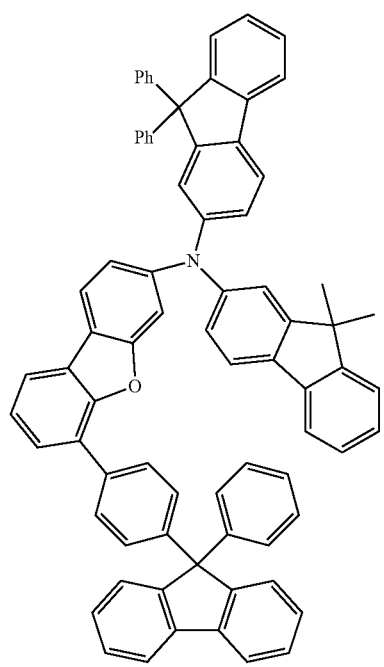
(6)
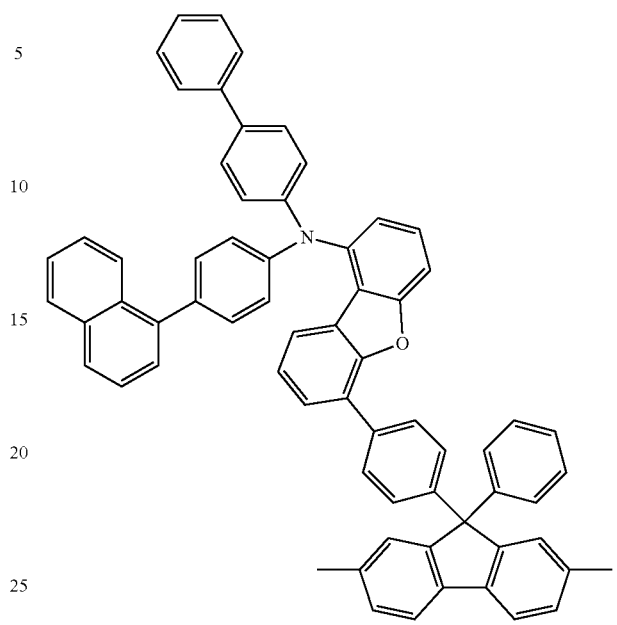
(5)
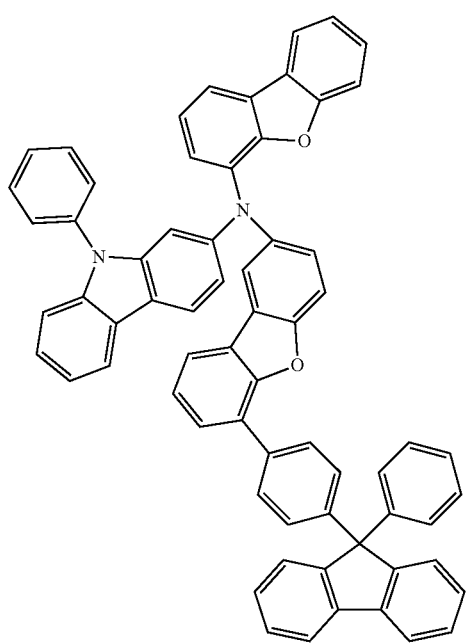
(7)
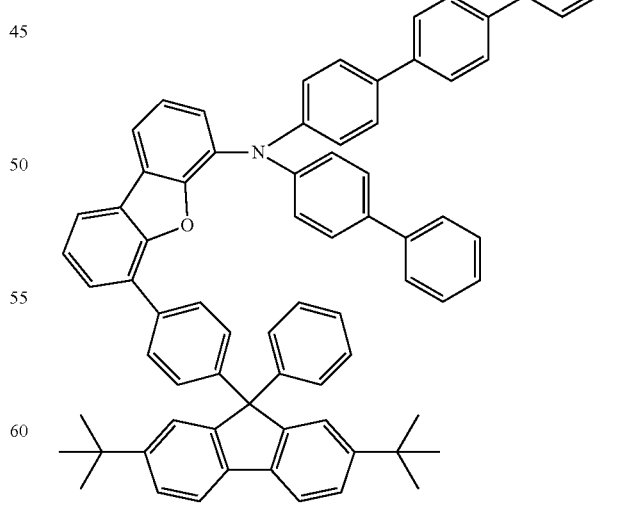

(8)
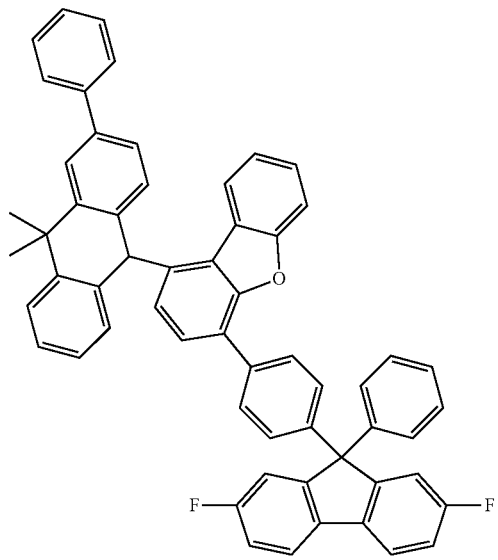
(9)
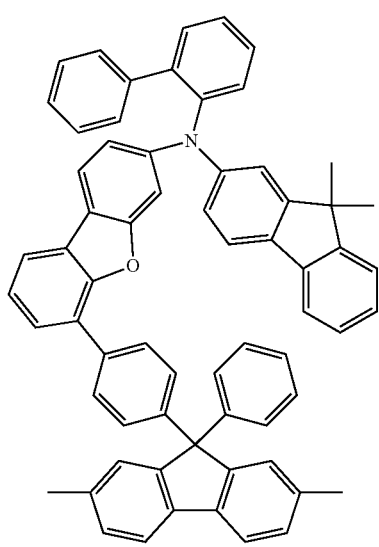
(10)
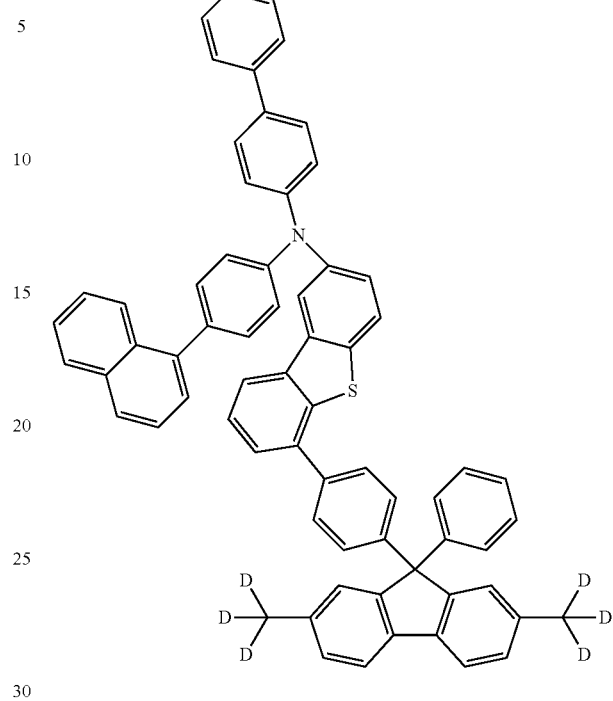
(11)
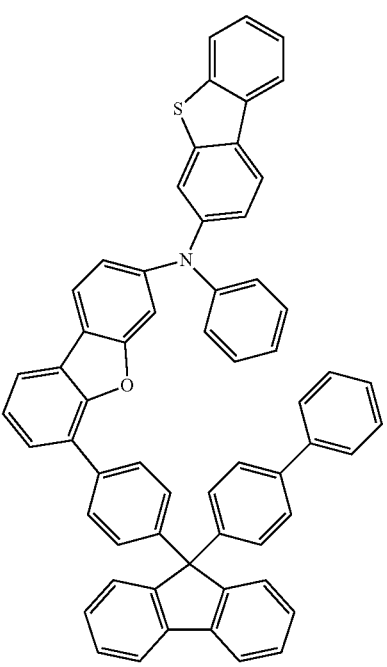

(12)
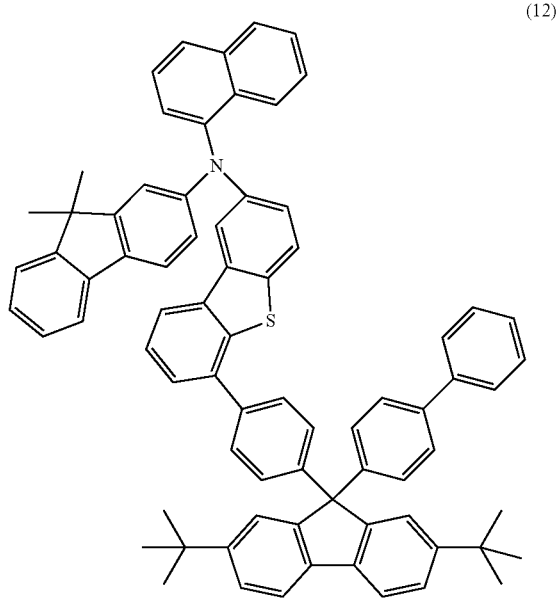
(13)
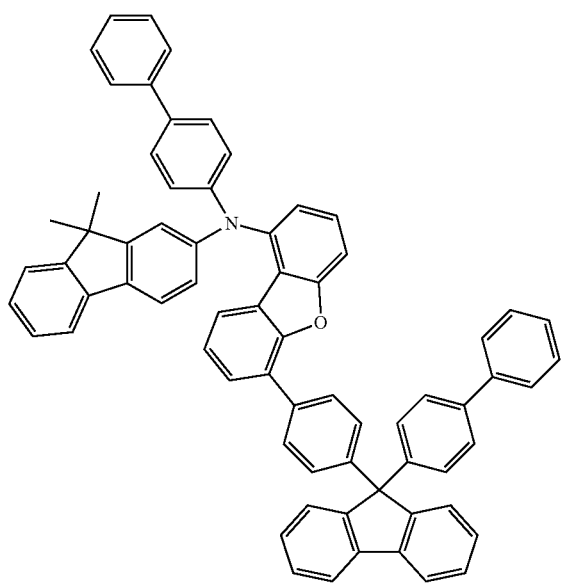
(14)
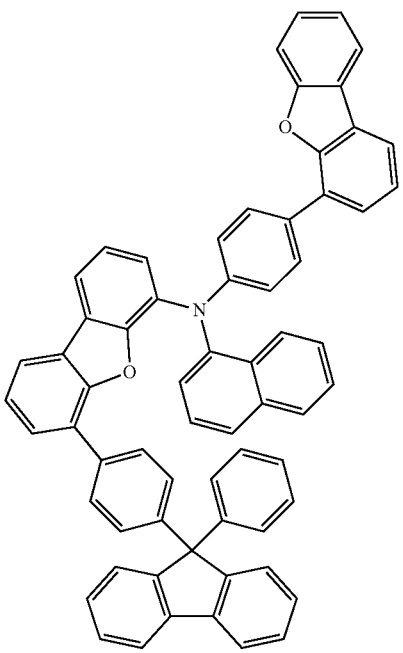
(15)
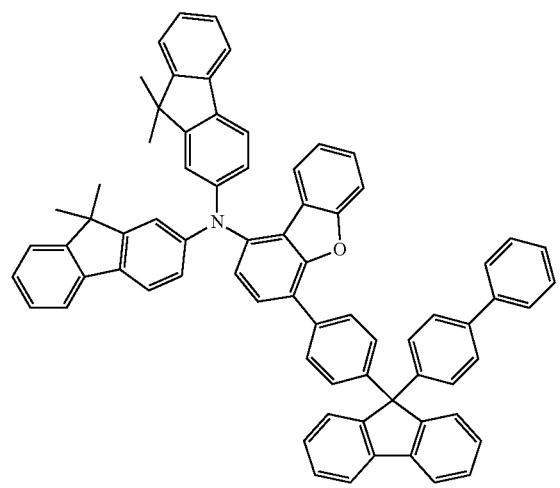

(16)
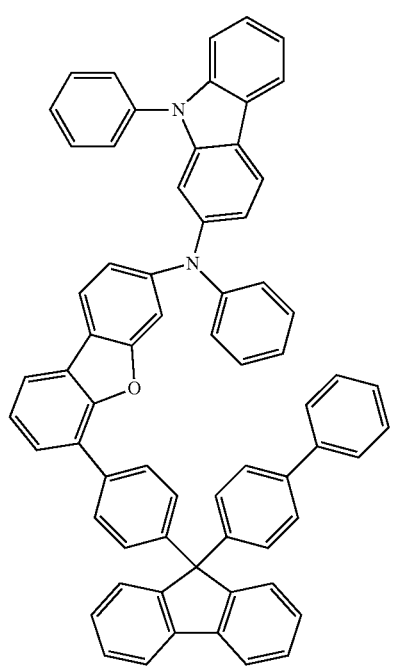
(18)
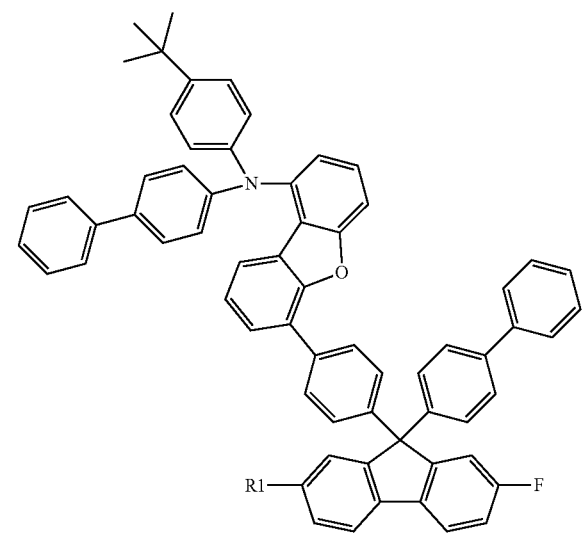
(17)
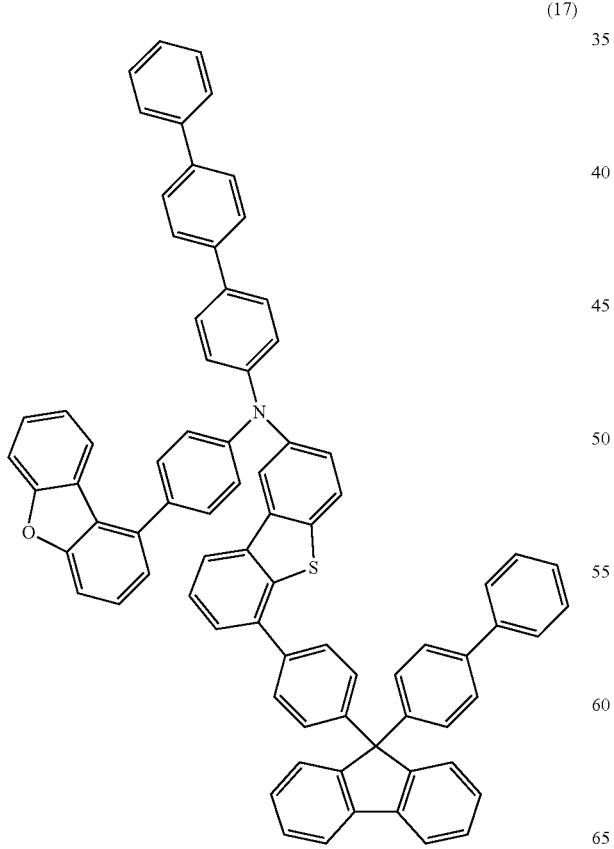
(19)
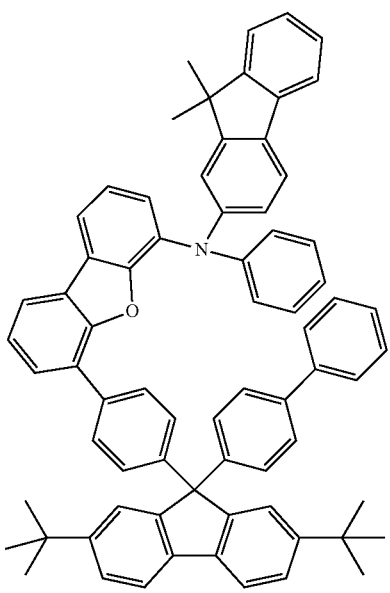

(20)
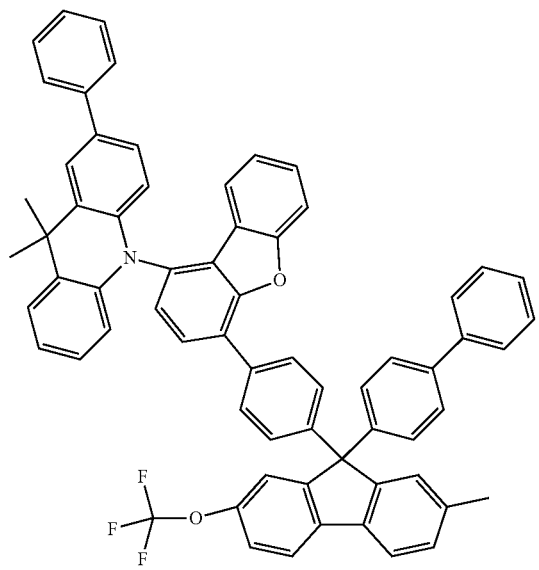
(21)
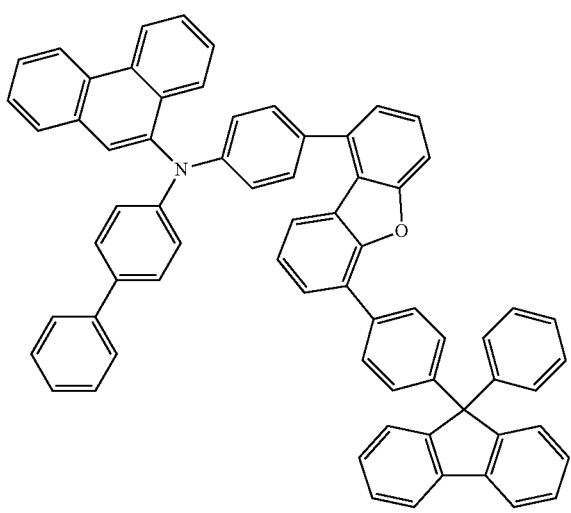
(22)
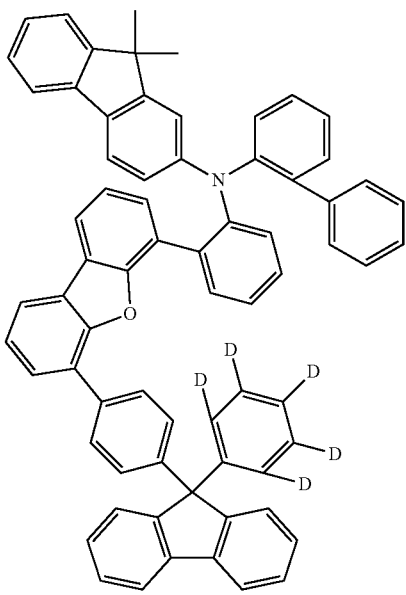
(23)
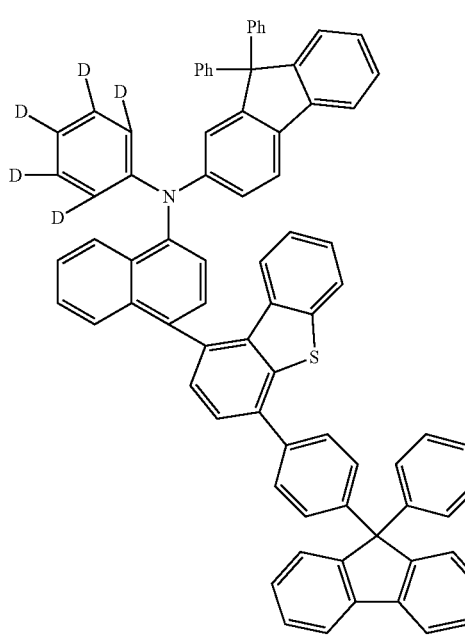

(24)
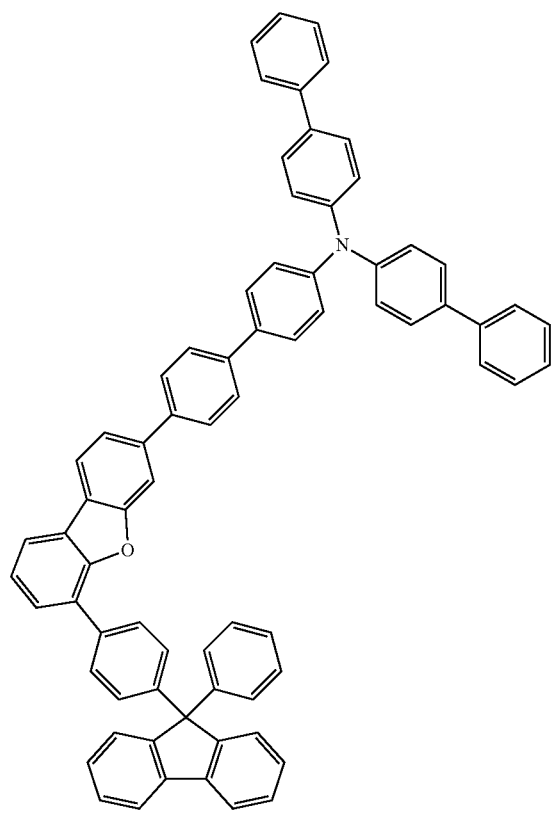
(25)
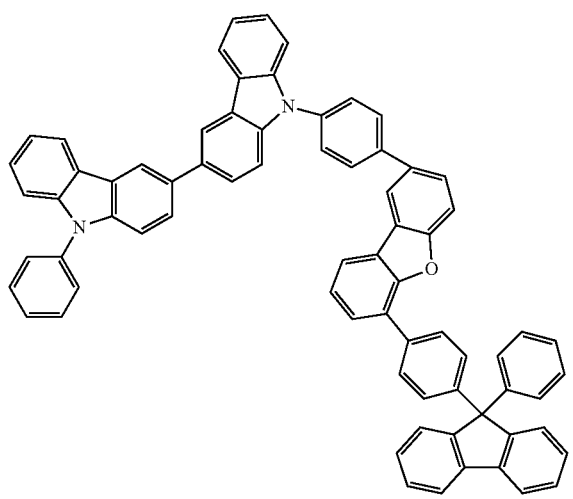
(26)
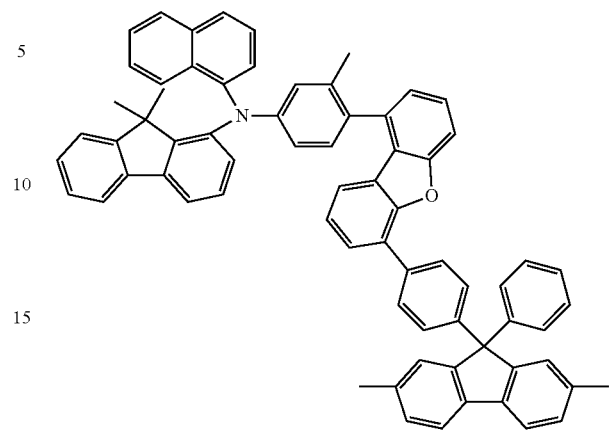
(27)
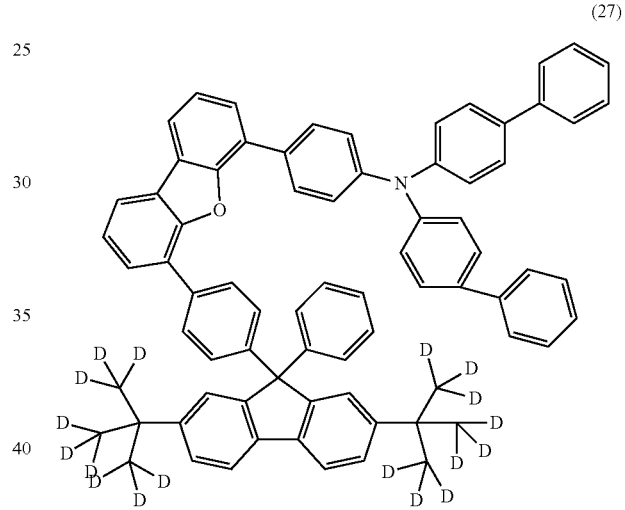
(28)
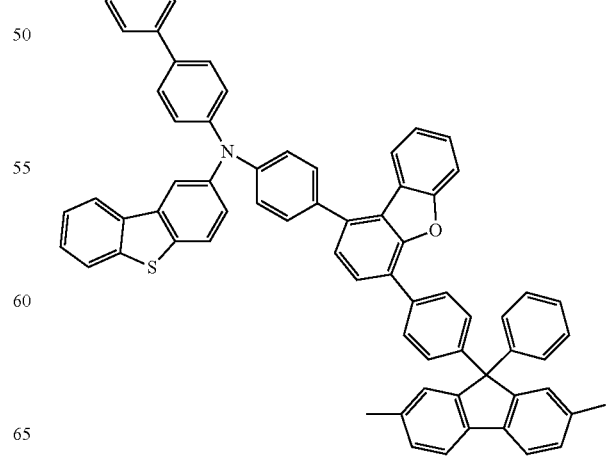

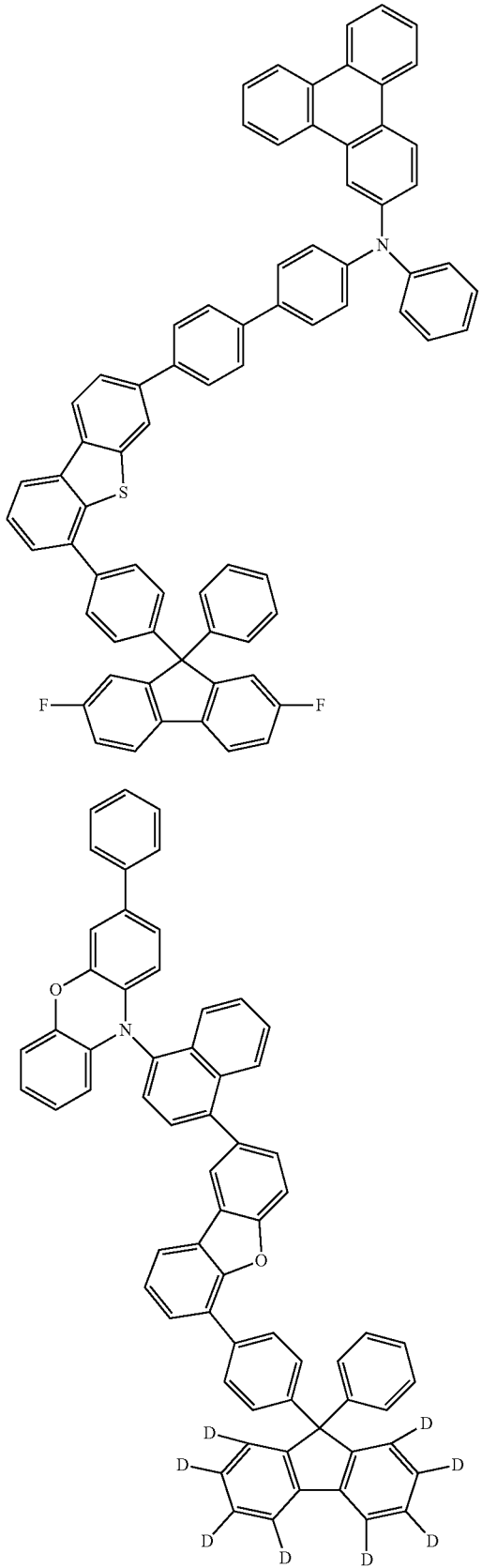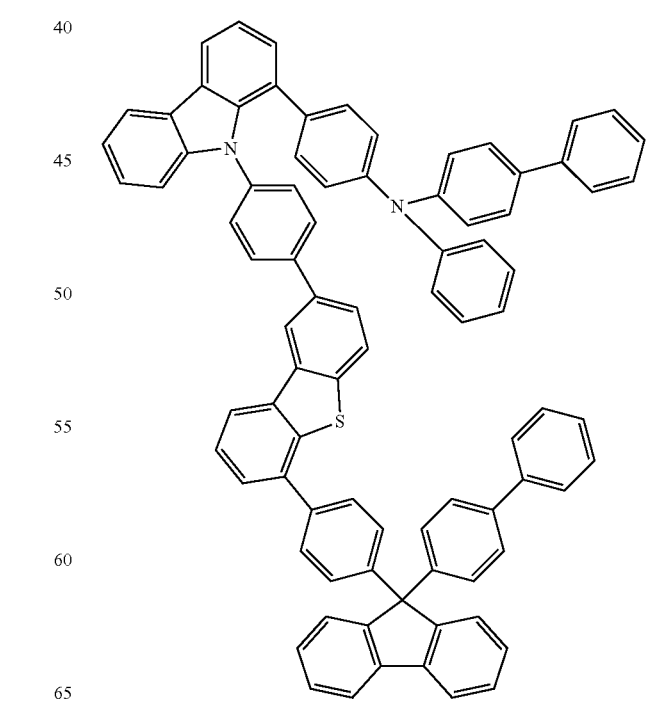

(33)
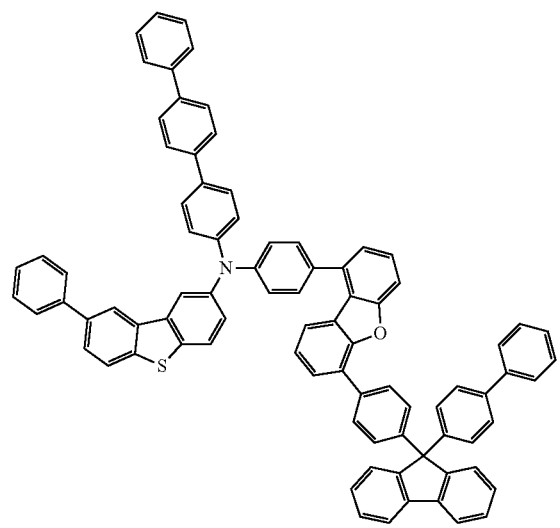
(34)
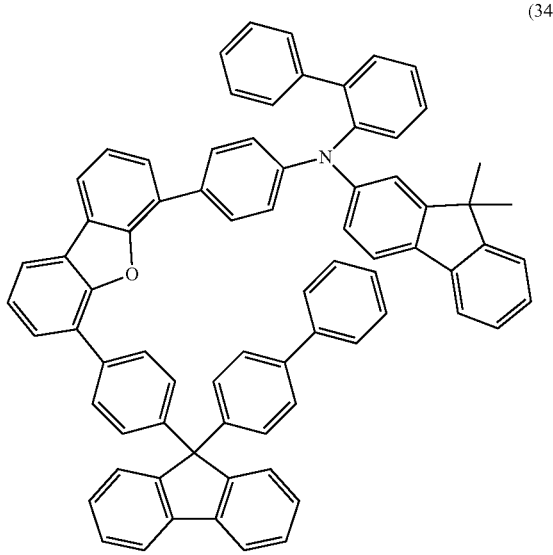
(35)
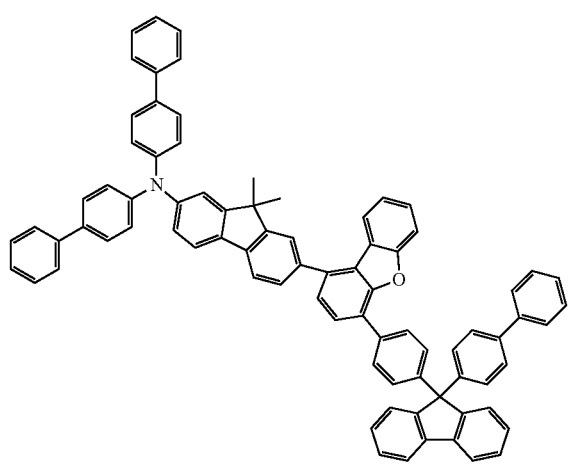
(36)
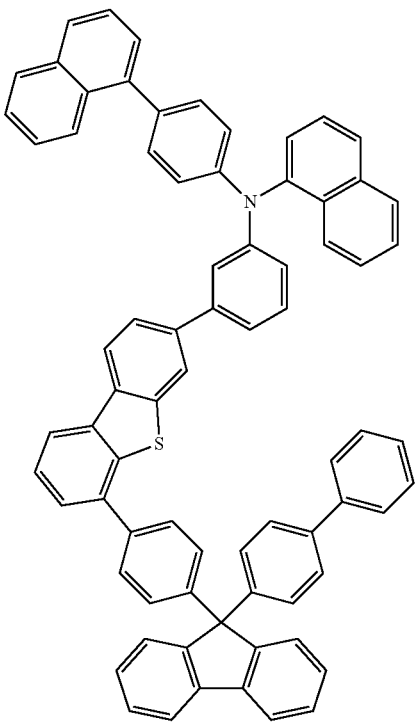
(37)
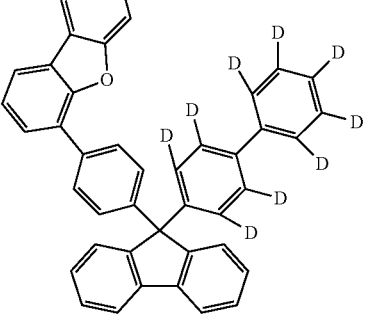

(38)
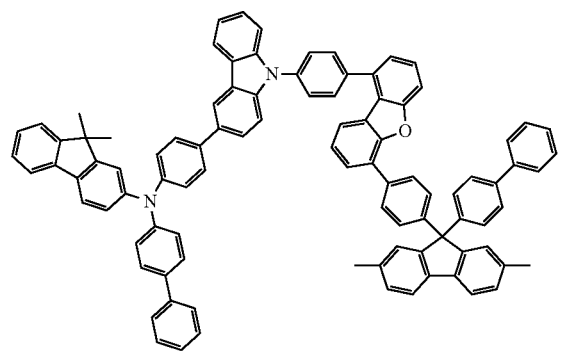
(39)
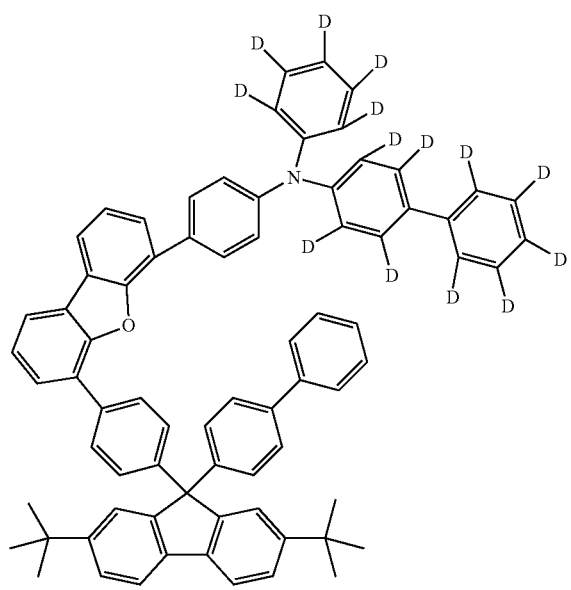
(40)
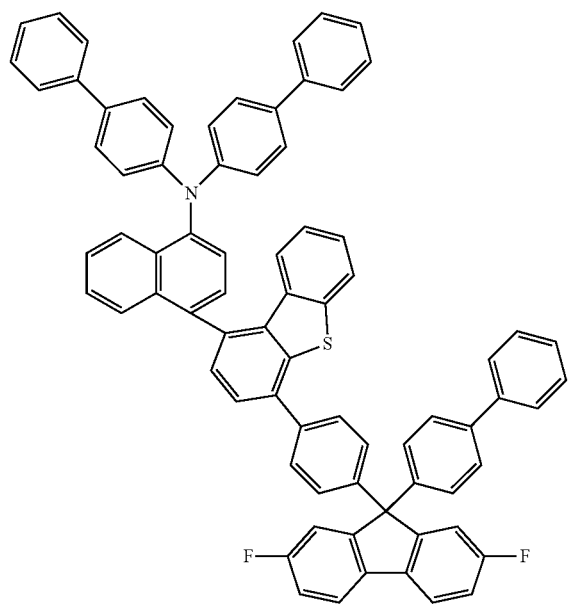
(41)
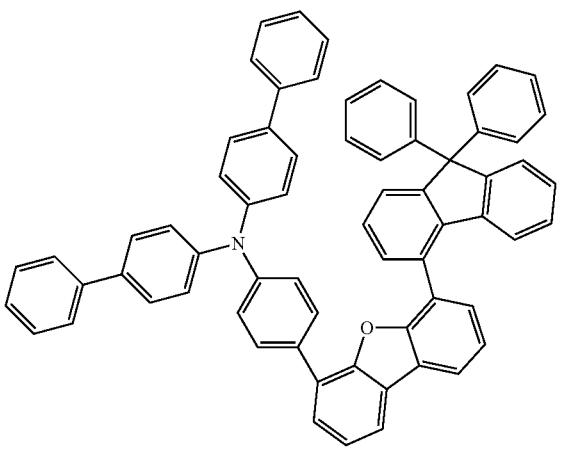
(42)
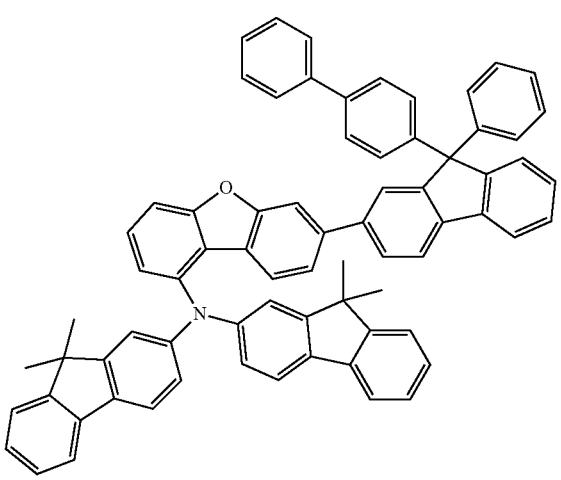
(43)
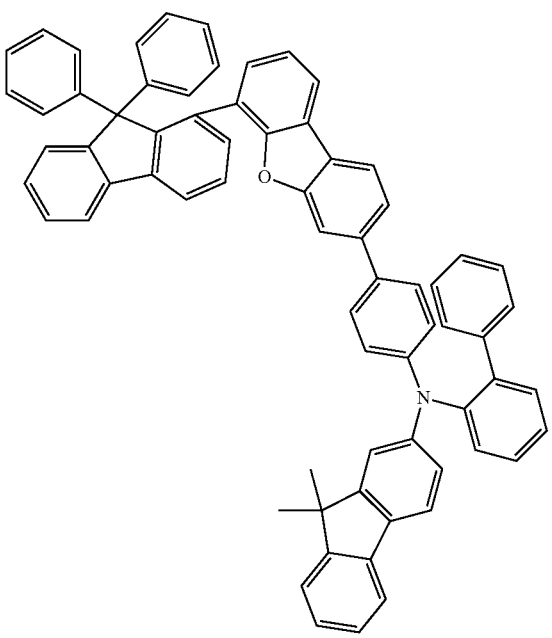

-continued
(44)
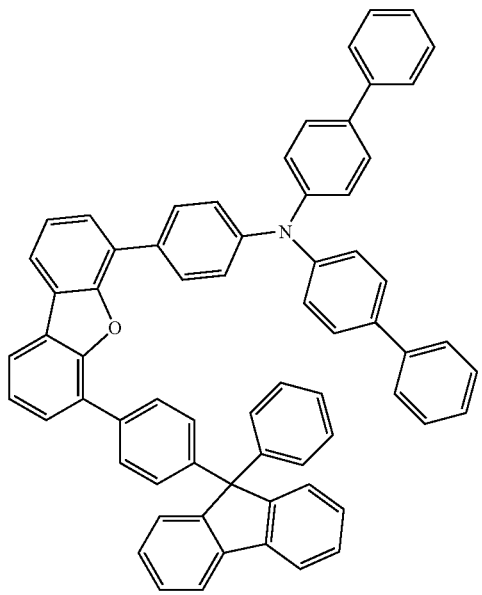
(45)
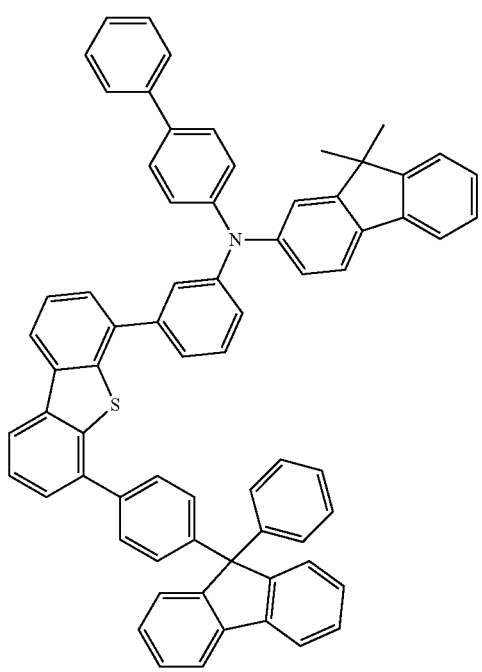
(46)
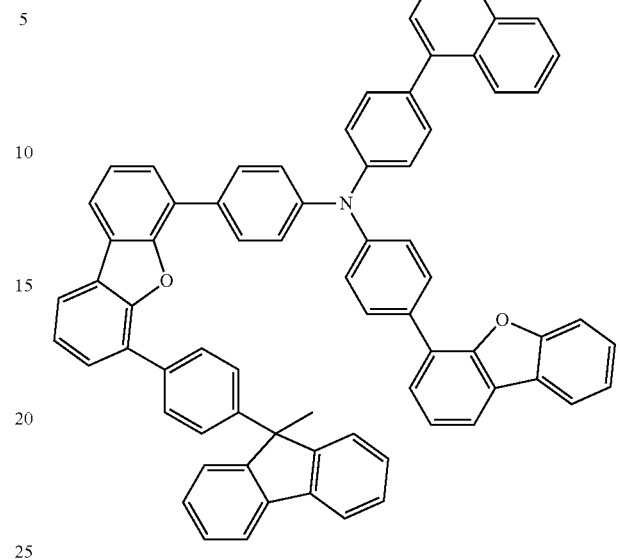
(47)
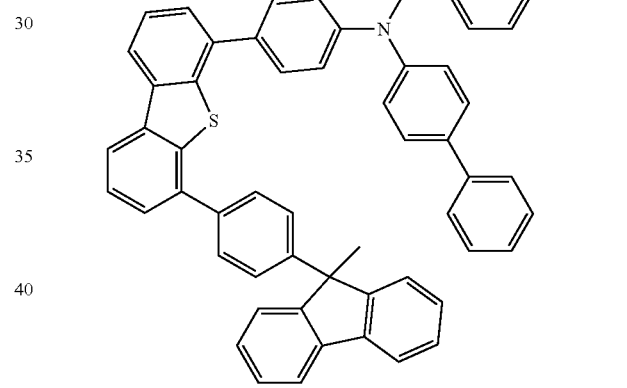
(48)
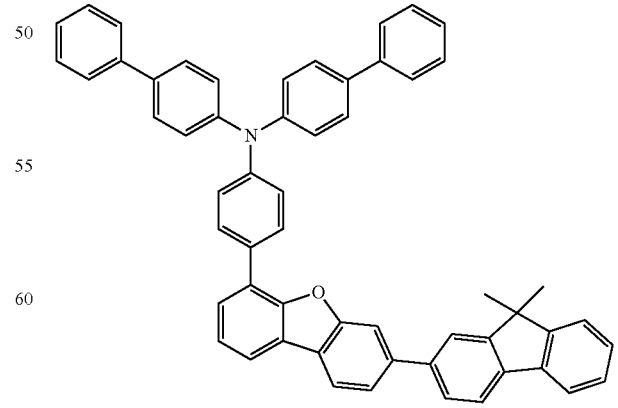

(49)
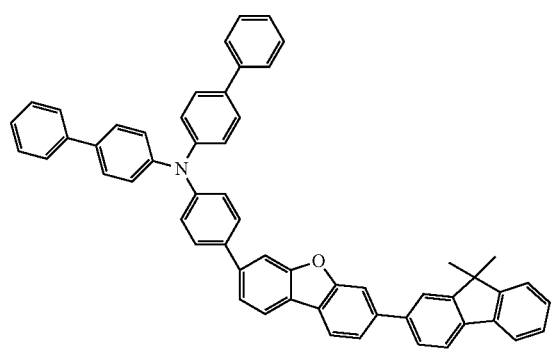
(50)
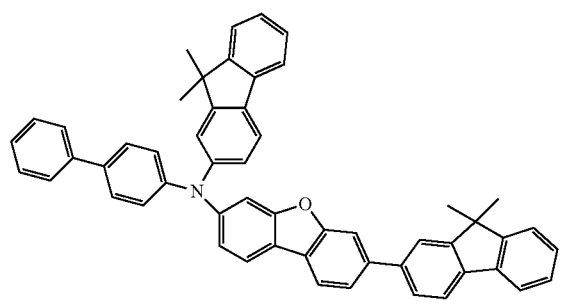
(51)
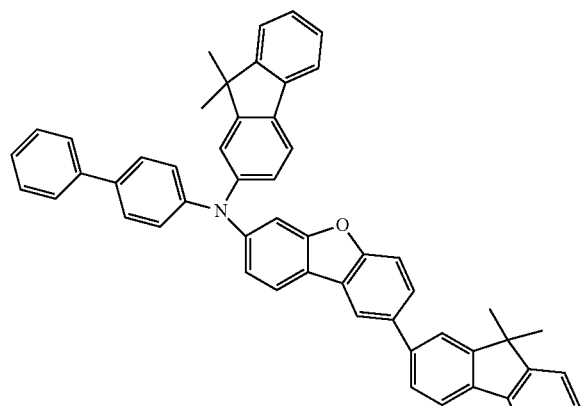
(52)
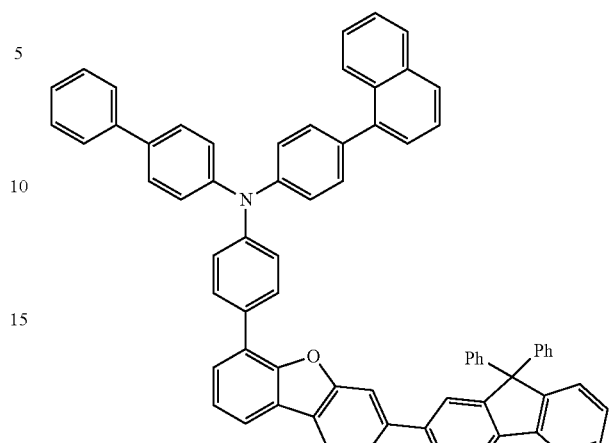
(53)
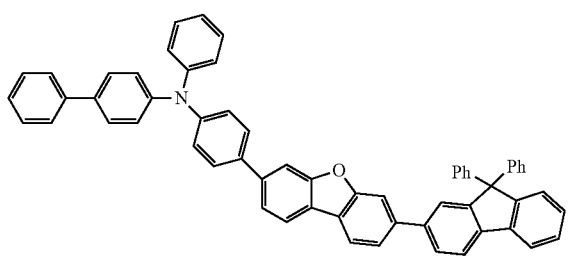
(54)
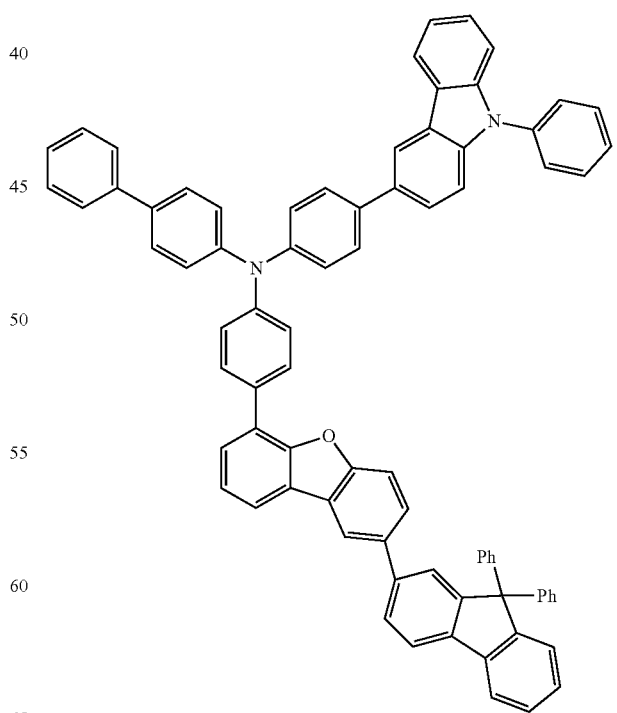

(55)
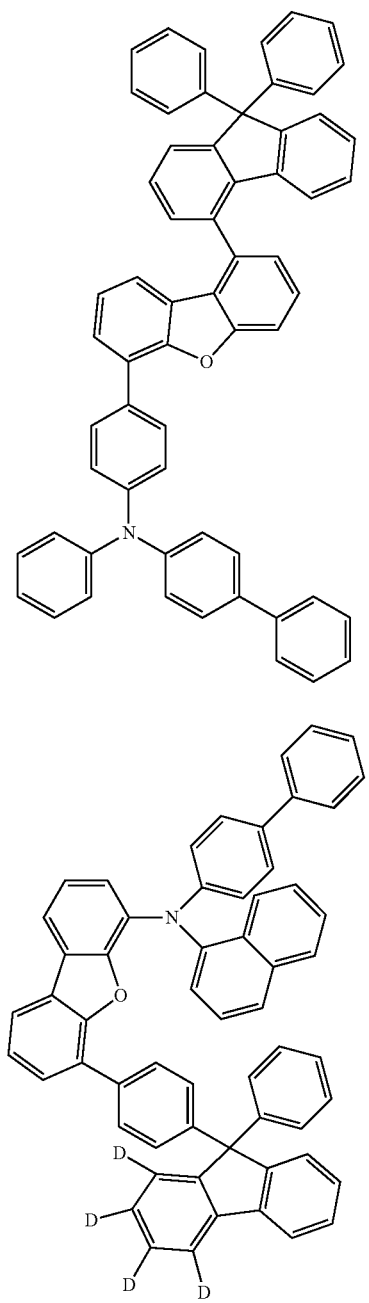
(56)
(57)
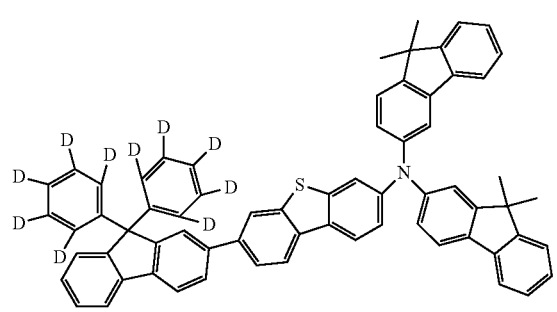
(58)
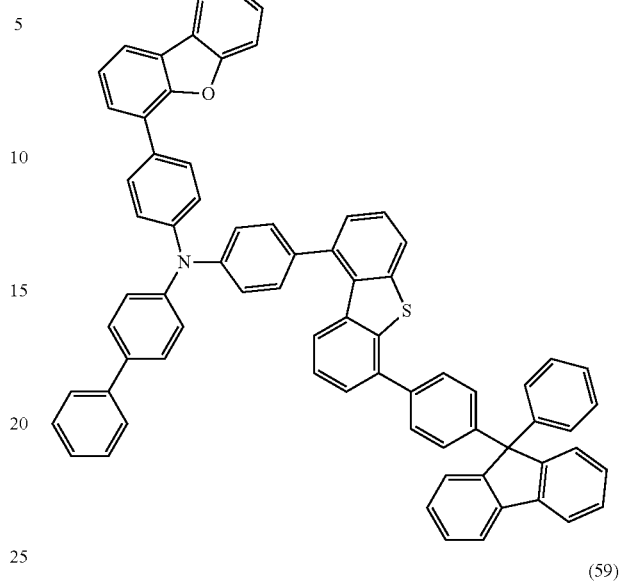
(59)
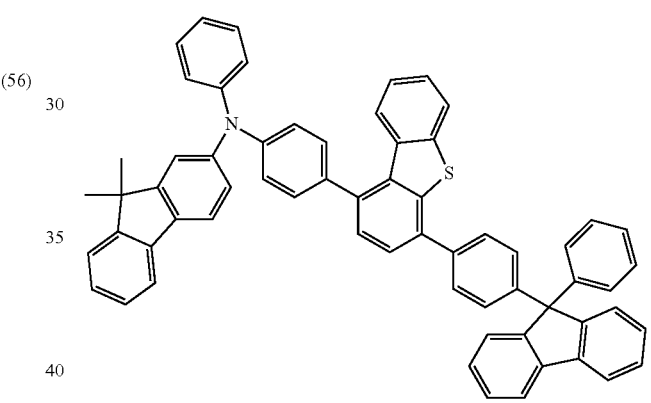
(60)
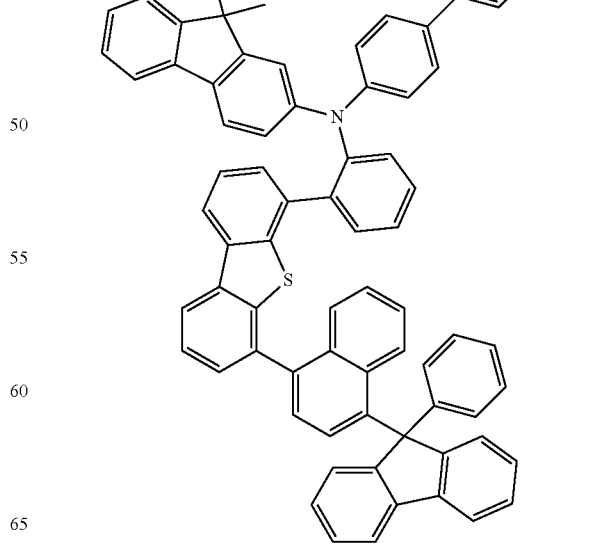

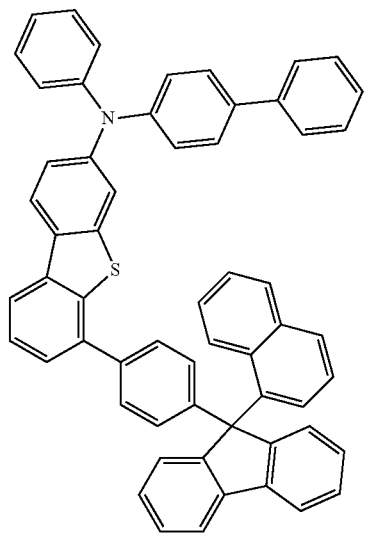
(61)
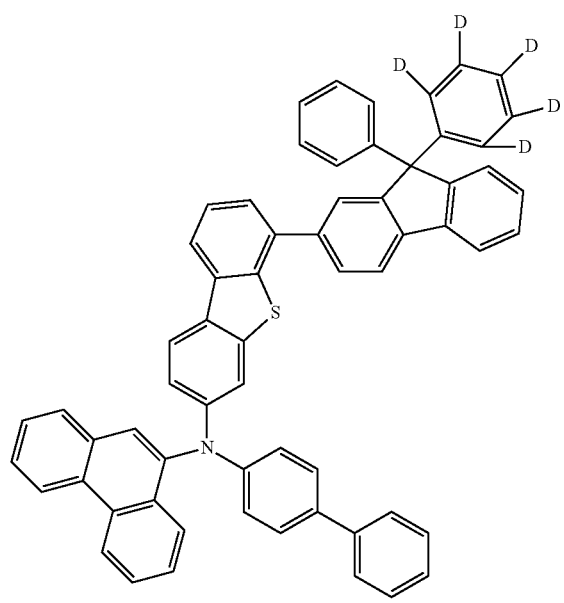
(63)
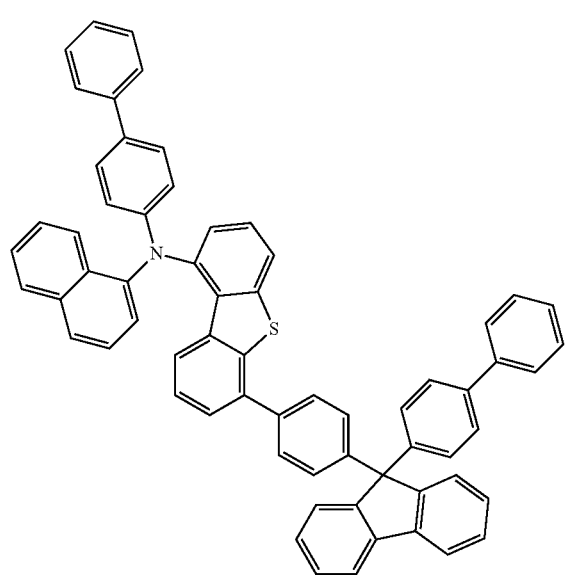
(62)
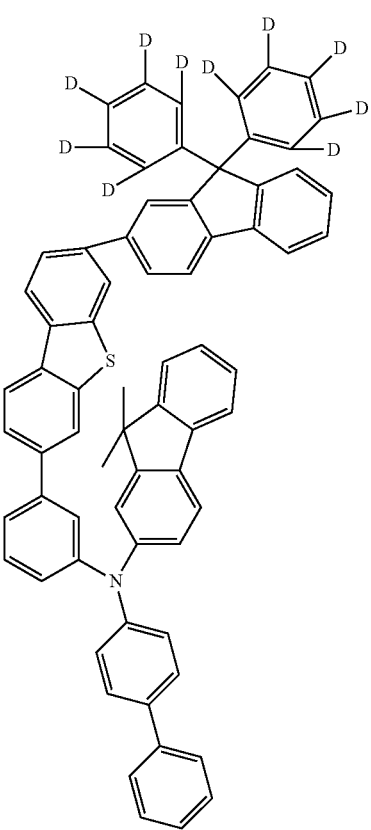
(64)

(65)
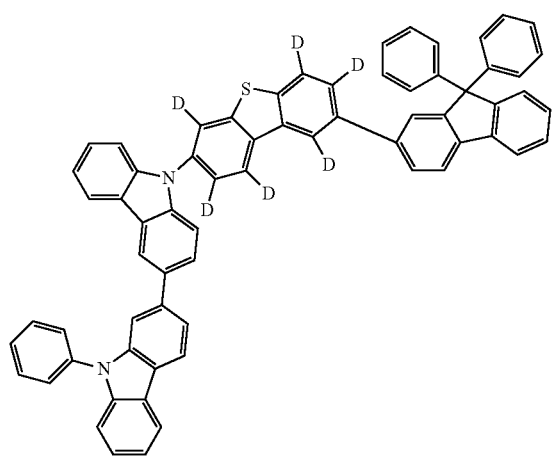
(66)
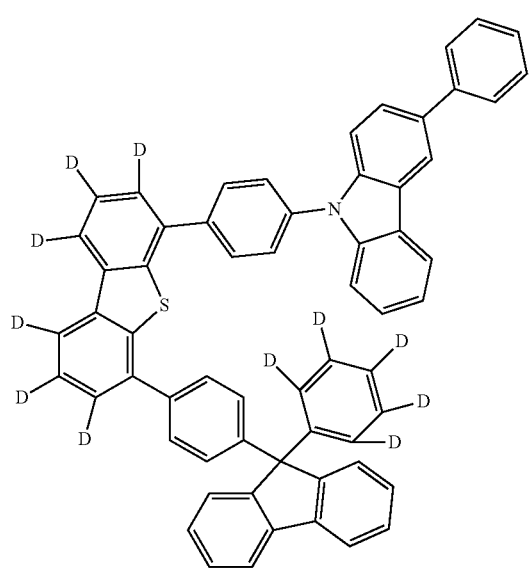
(67)
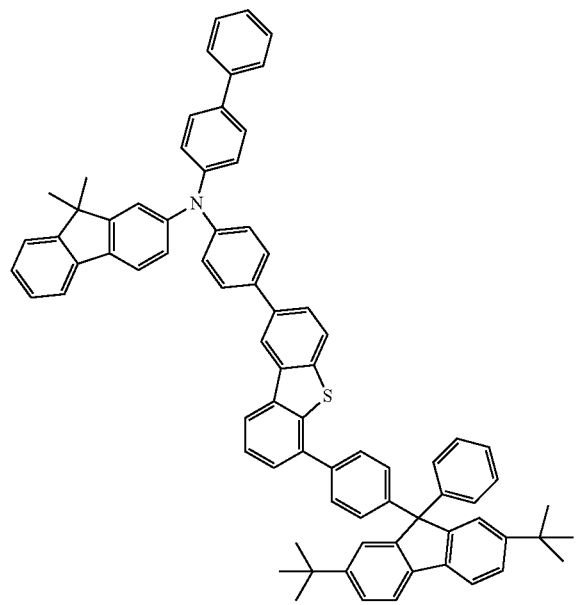
(68)
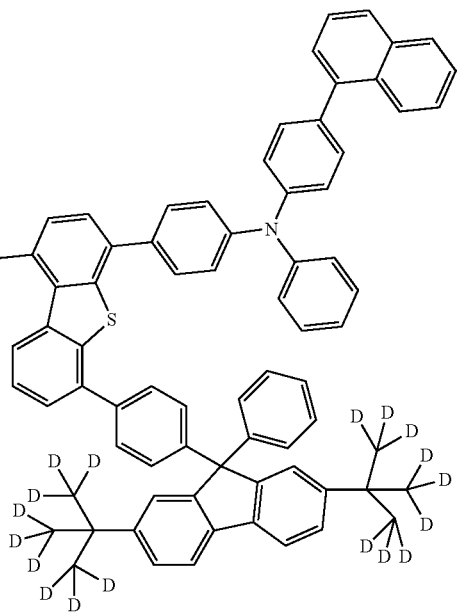
(69)
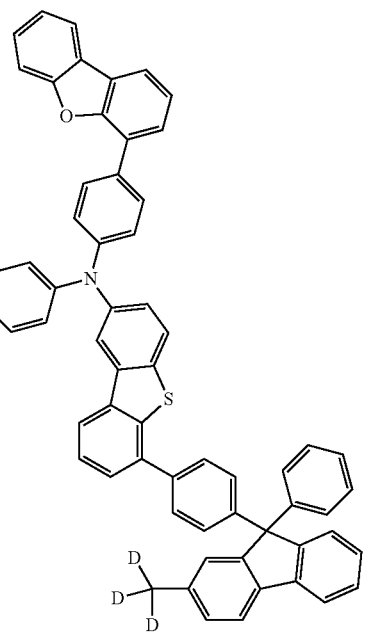

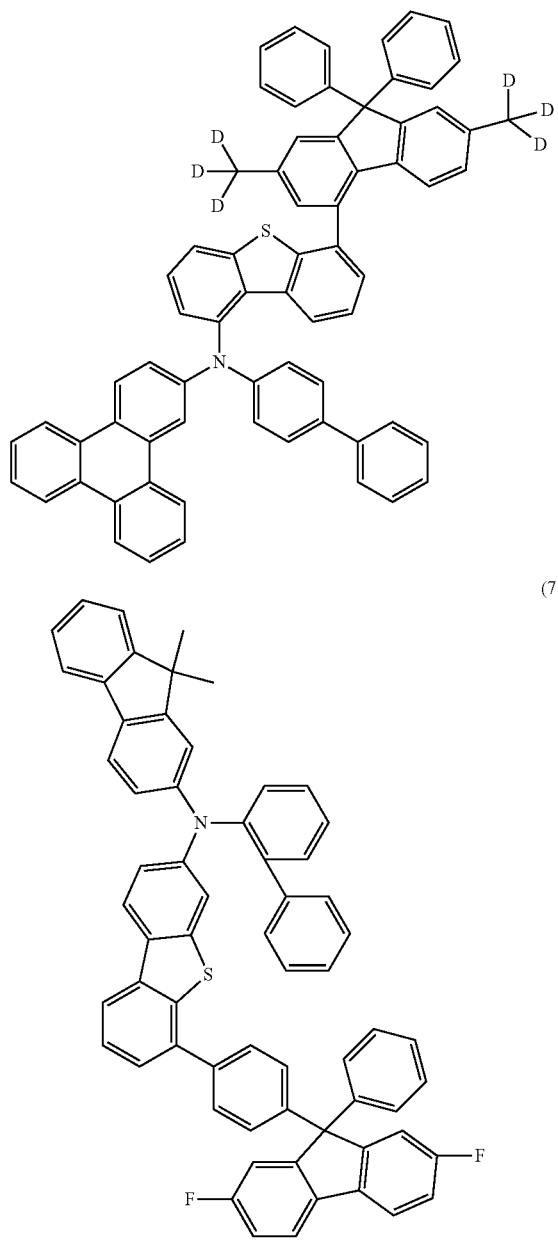
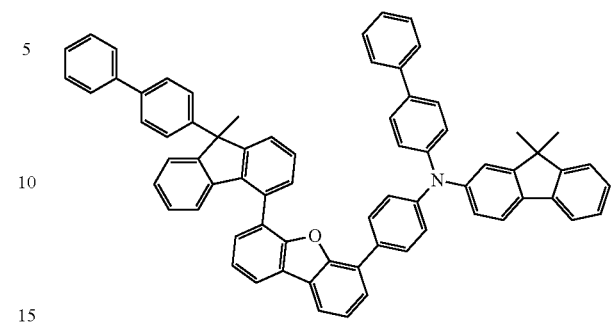
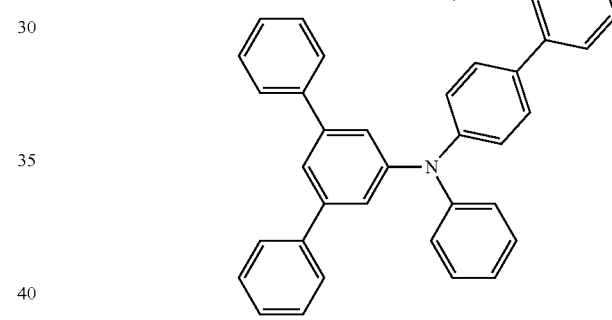
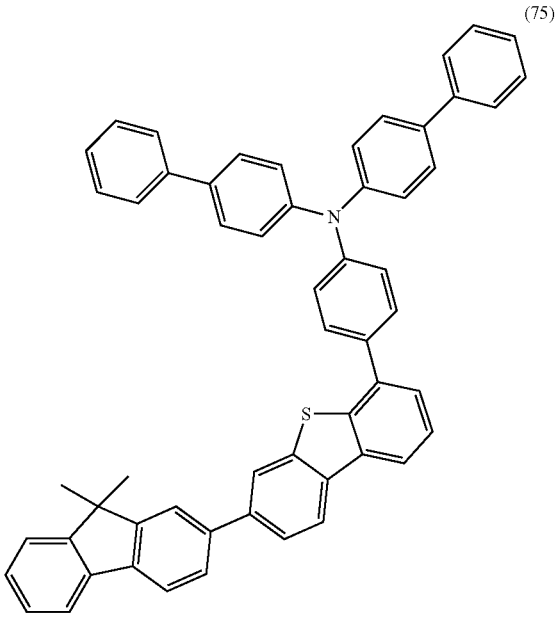

(76)
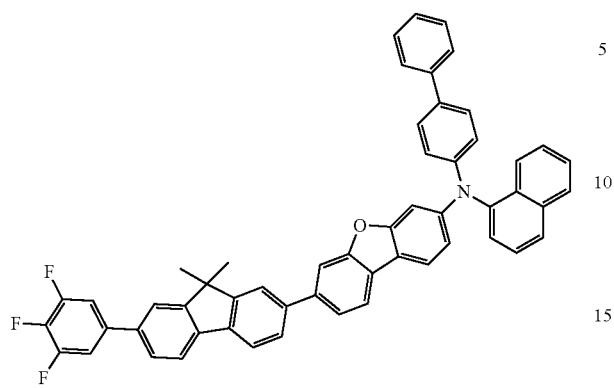
(77)
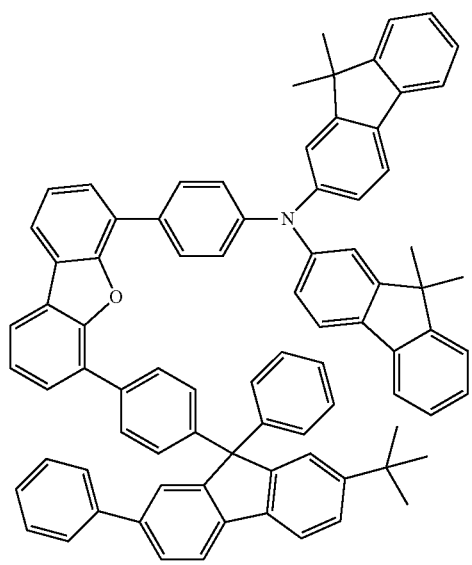
(78)
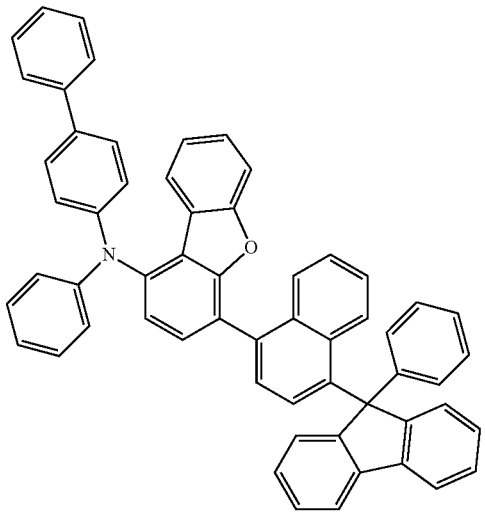
(79)
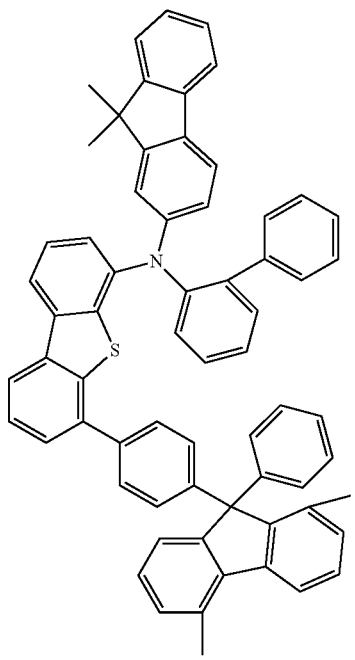
(80)

(81)
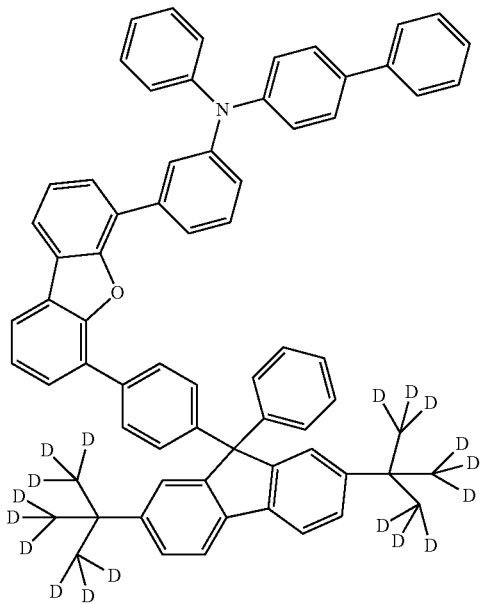
(82)
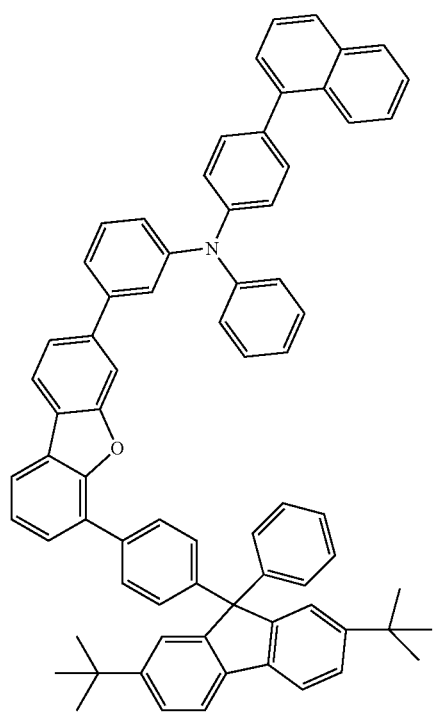
(83)
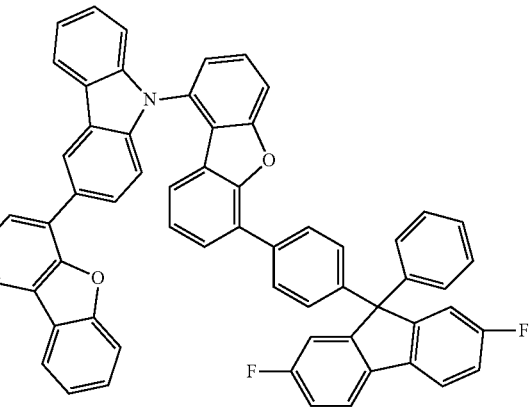
(84)
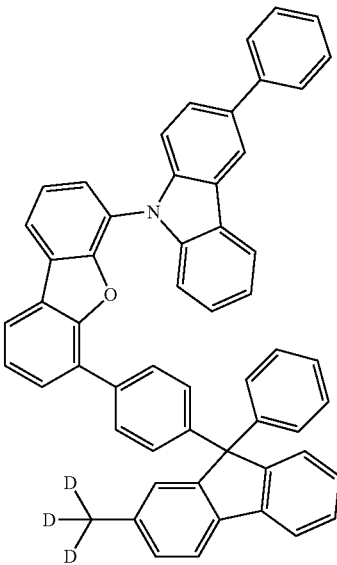

(85)
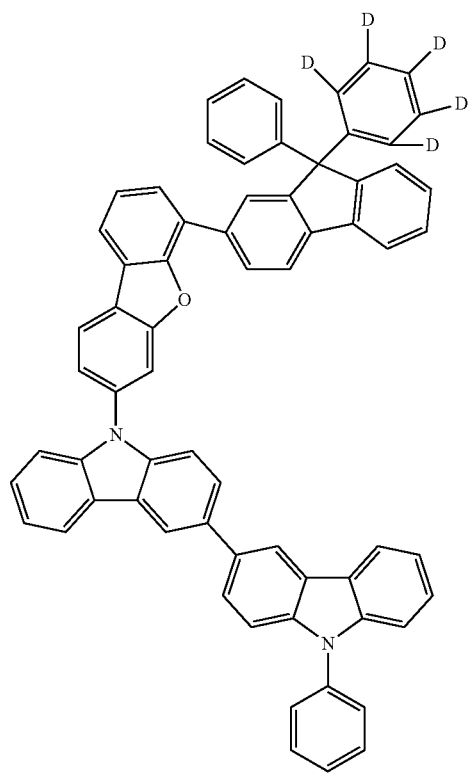
(86)
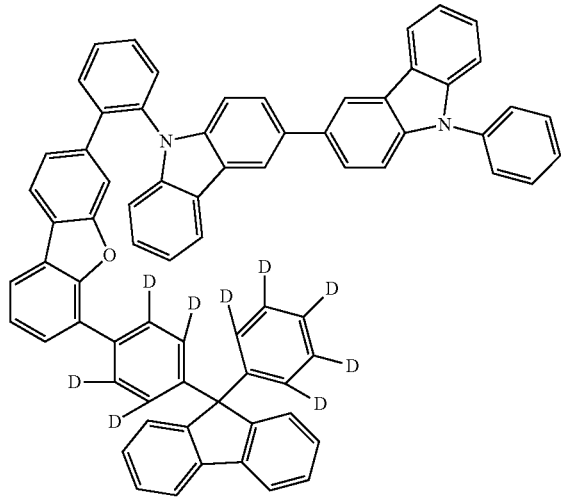
(87)
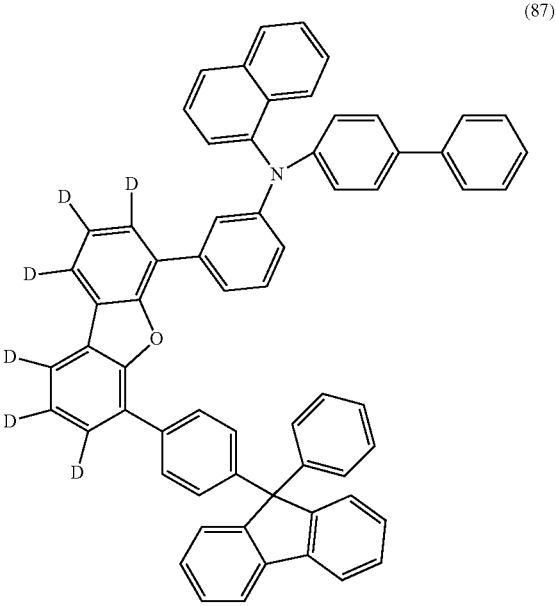
(88)
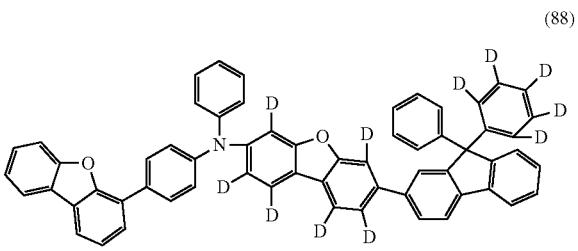
(89)
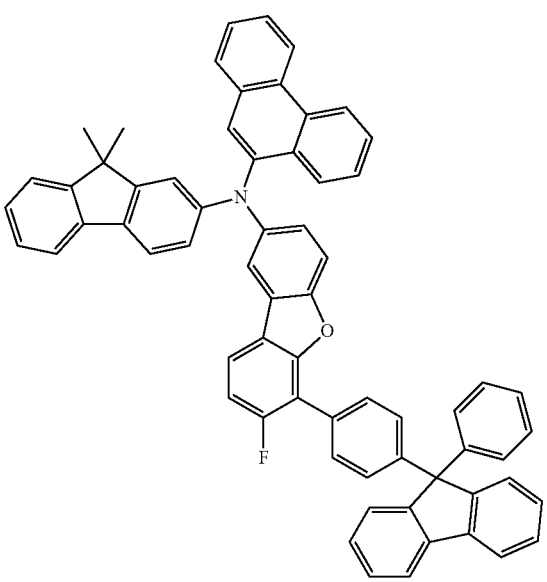

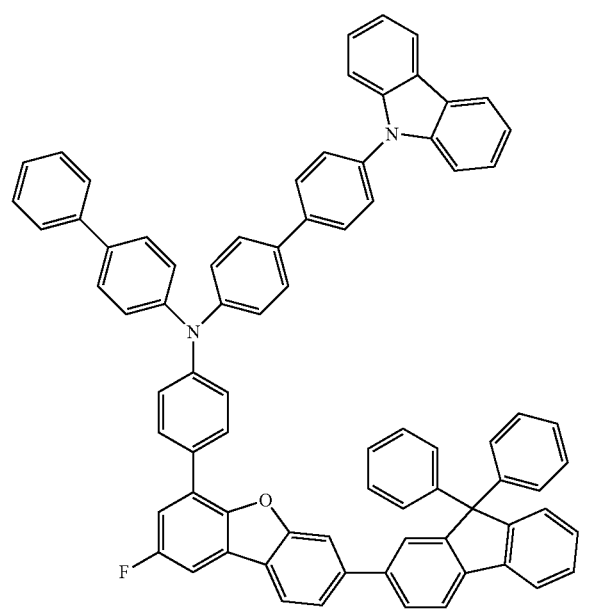
(90)
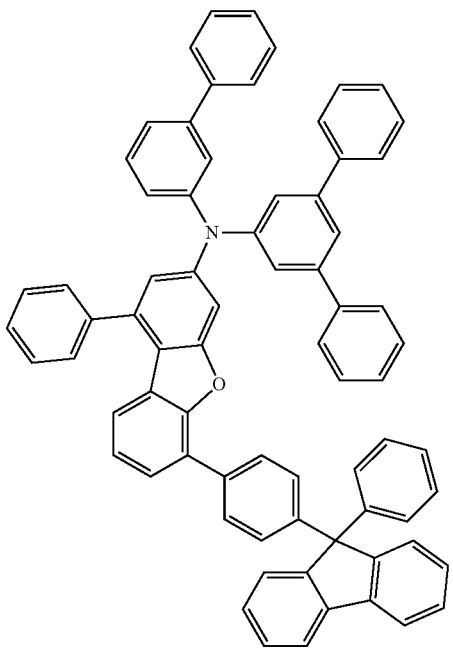
(92)
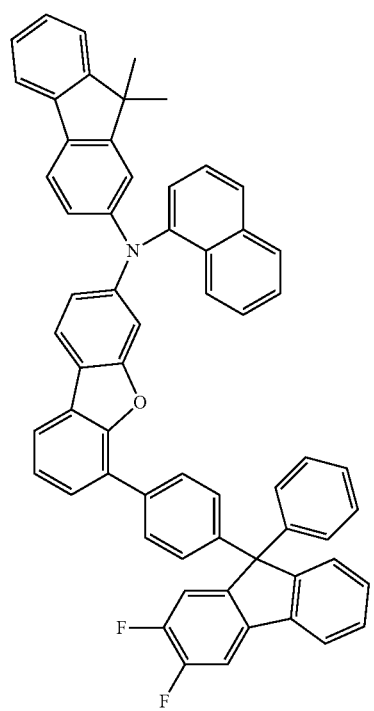
(91)
(93)

(94)
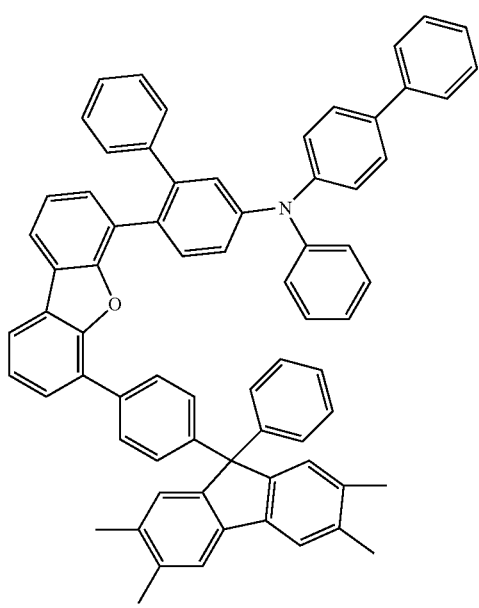

(95)
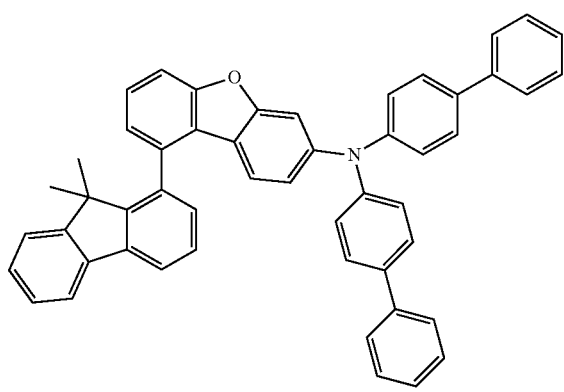

(96)
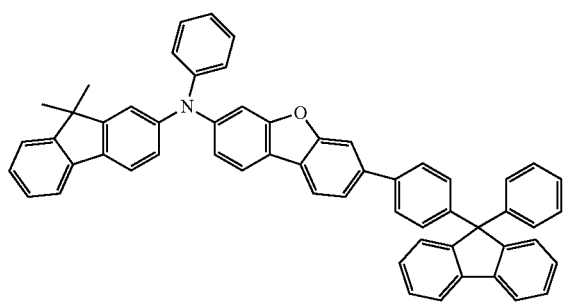

(97)
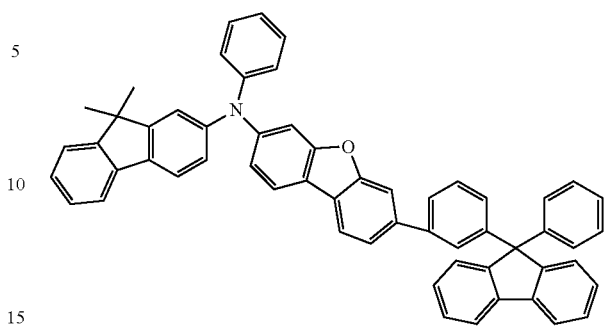

(98)
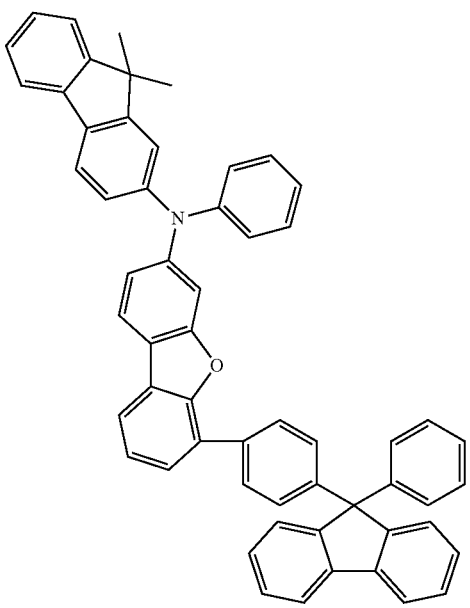

The compounds according to formula (I) are synthetically accessible for the person skilled in the art, based on the following information:

A preferred synthetic method for preparing a compound according to formula (I) is shown in Scheme 1 below. Although not shown in the scheme for reasons of simplification, the structures may be substituted with organic radicals.

Scheme 1

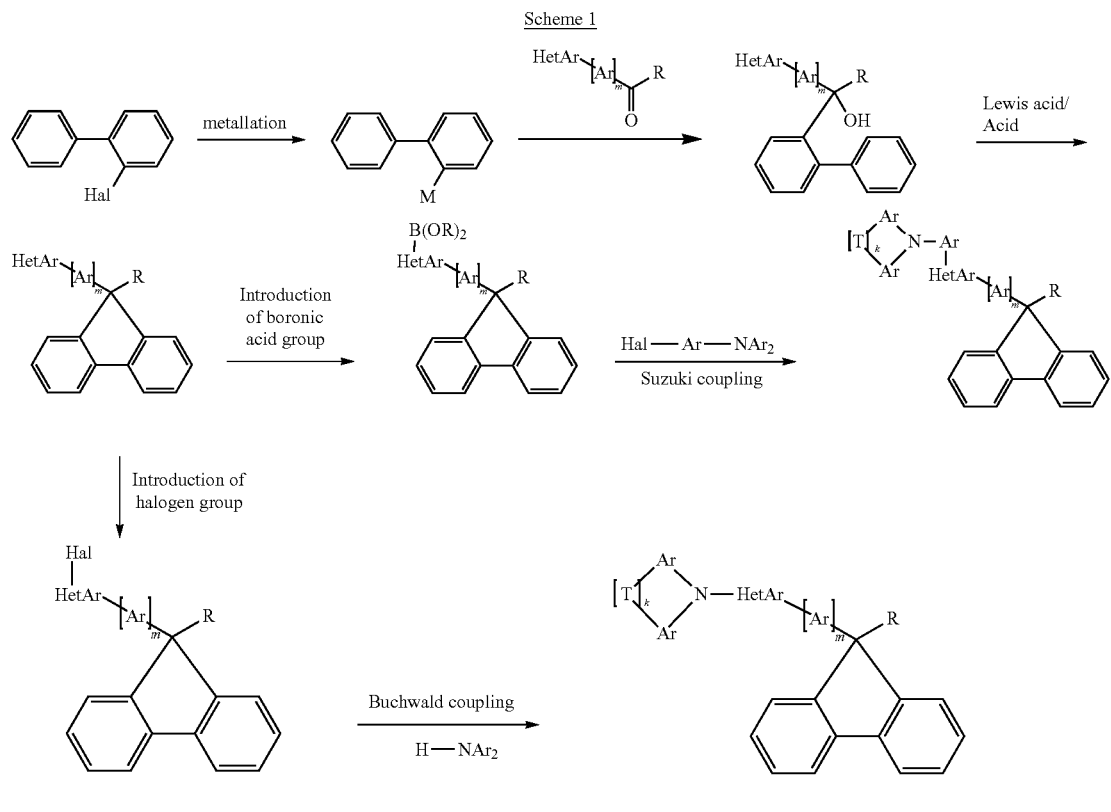

Hal=Halogen, preferably Br or I;
M=Metal, preferably Li or Mg;
Ar=aromatic group;
HetAr=optionally substituted dibenzofuran or dibenzothiophene;
R=organic radical, preferably alkyl or aromatic ring system;
T=single bond or organic linking group, preferably, O, S, $CR_2$ or $SiR_2$;
k=0 or 1, where for k=0, the groups Ar are not linked to each other;
m=0 or 1, where for m=0, the groups bonding to the group Ar are directly connected to each other.

In a first step, a biphenyl compound which is substituted with a halogen substituent, preferably Br or I, in the position ortho to the connecting bond between the two phenyl groups, is metalated in the position of the halogen substituent. The metalation reaction is preferably a lithiation reaction or a Grignard reaction. The metalated intermediate is then reacted with a carbonyl derivative, which has a dibenzofuran or dibenzothiophene group bonded to the carbonyl group, optionally via a spacer. The resulting tertiary alcohol is cyclized to a fluorene under acidic and/or lewis acidic conditions. In a following step, a boronic acid group or a halogen substituent, preferably, Br or I group, is introduced on the dibenzofuran or dibenzothiophene group. In the case of a boronic acid group on the dibenzofuran or dibenzothiophene, in a following step, a Suzuki coupling with a compound Hal-Ar—$NAr_2$, where Hal is a halogen substituent, preferably Br or I, can be performed, resulting in a product according to formula (I) in which an amine group is bonded to the dibenzofuran or dibenzothiophene group via an aryl spacer. In the case of a halogen substituent on the dibenzofuran or dibenzothiophene, in a following step, a Buchwald coupling with a compound H—$NAr_2$ can be performed, resulting in a product according to formula (I) in which an amine group is directly bonded to the dibenzofuran or dibenzothiophene group.

An alternative method for preparation of compounds according to formula (I) is shown in Scheme 2 below. Although not shown in the scheme for reasons of simplification, the structures may be substituted with organic radicals.

Scheme 2

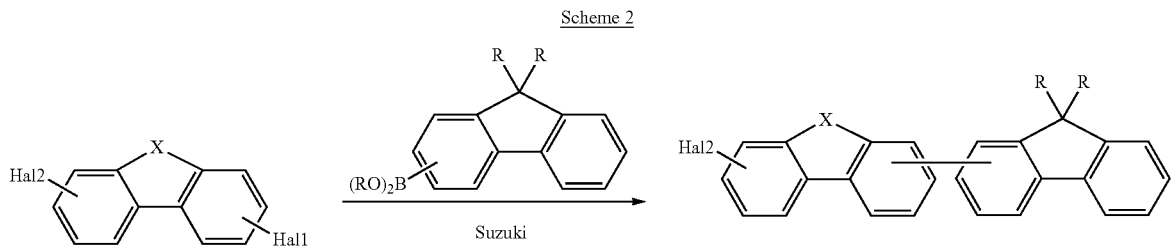

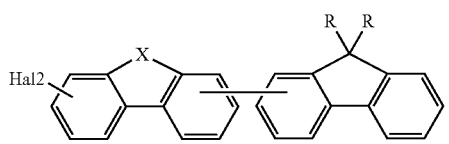 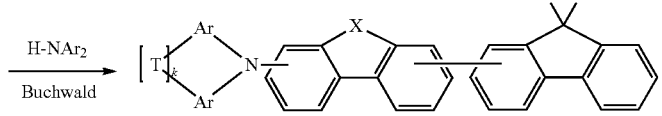

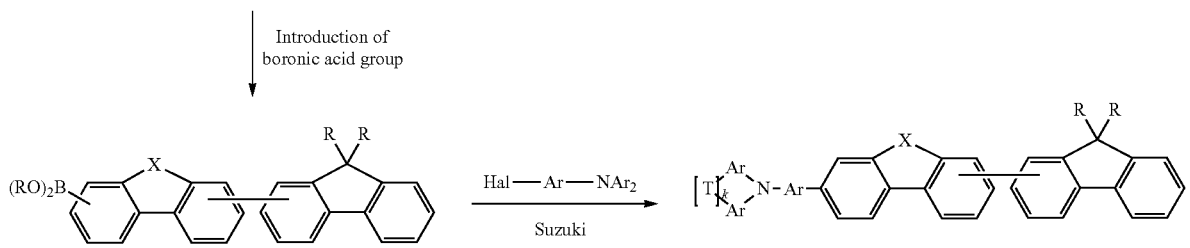

Hal1=Halogen, preferably Br or I;
Hal2=Halogen, preferably Cl or Br;
Ar=Aromatic group;
X=O or S;
R=organic radical, preferably alkyl or aromatic ring system;
T=single bond or organic linking group, preferably, O, S, $CR_2$ or $SiR_2$;
k=0 or 1, where for k=0, the groups Ar are not linked to each other.

According to this method, in a first step, a dibenzofuran or dibenzothiophene compound which has two halogen substituents, which are preferably different, and are preferably selected from Cl, Br and I, is reacted in a Suzuki coupling with a fluorenyl group which has a boronic acid group on one of its benzene rings. The resulting coupling product is according to one embodiment of the invention further reacted on the second halogen substituent in a Buchwald reaction with a diarylamine, resulting in a compound of formula (I) in which the diarylamine is directly bonded to the dibenzofuran or dibenzothiophene. According to another embodiment of the invention, the resulting coupling product is further reacted to a boronic acid intermediate compound, and this intermediate compound is reacted in a Suzuki reaction with a compound Hal-Ar—$NAr_2$, where Hal is a halogen substituent, preferably Cl, Br or I. In the Suzuki reaction, a compound of formula (I) results in which the diarylamine is bonded to the dibenzofuran or dibenzothiophene via an arylene spacer.

The present application thus relates to a method for preparation of a compound according to formula (I), characterized in that a biphenyl derivative which is substituted with a halogen substituent, preferably Br or I, which is present in the ortho-position to the phenyl-phenyl bond of the biphenyl derivative, is metalated (step 1). The metalation reaction is preferably a lithiation reaction or a Grignard reaction. Then, in step 2, the metalated biphenyl derivative is added to a carbonyl derivative, which has a dibenzofuran or dibenzothiophene group bonded to the carbonyl group, optionally via a spacer. In a step 3, the resulting intermediate is cyclized to a fluorene derivative. The cyclization reaction preferably takes place under acidic and/or Lewis-acidic conditions, most preferably by addition of a strong organic acid, such as para-toluenesulfonic acid. In a step 4, a boronic acid group (step 4a) or a halogen substituent, preferably, Br or I (step 4b), is introduced on the dibenzofuran or dibenzothiophene group. In a fifth step, in the case where the step 4a has been performed, a Suzuki coupling is performed with a compound Hal-Ar—$NAr_2$, where Hal is a halogen substituent and is preferably Cl or Br, resulting in a compound of formula (I) in which an amine group is bonded via an arylene spacer to the dibenzofuran or dibenzothiophene. In the case where the step 4b has been performed, a Buchwald coupling is performed with a compound H—$NAr_2$, resulting in a compound of formula (I), in which an amine group is directly bonded to the dibenzofuran or dibenzothiophene.

The above-described first to fifth step are preferably consecutive, meaning that there are no intermediate steps between the first and the second, the second and the third, the third and the fourth, and the fourth and the fifth step. Steps 4a and 4b are alternative steps, and steps 5a and 5b are alternative steps, where according to a first alternative, step 5a follows step 4a, and where according to a second alternative, step 5b follows step 5a.

In the alternative, the present application relates to an alternative method for preparation of a compound of formula (I), characterized in that a dibenzofuran or dibenzothiophene compound which has two halogen substituents, which are preferably different, and which are preferably selected from Cl, Br and I, where most preferably, the first halogen substituent is Br, and the other is Cl, is reacted in a Suzuki coupling with a fluorenyl group which has a boronic acid group on one of its benzene rings. According to one alternative embodiment, the second halogen substituent is then reacted in a Buchwald reaction with a diarylamine compound. According to another alternative embodiment, the second halogen substituent is transformed to a boronic acid substituent, and the boronic acid is reacted in a Suzuki reaction with a compound Hal-Ar—$NAr_2$, where Hal is preferably Cl, Br or I. The above-described steps are preferably consecutive.

The compounds according to the present application, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (I), wherein the bond(s) to the polymer, oligomer or dendrimer may be localized at any desired positions substituted by $R^1$, $R^2$, $R^3$, $R^4$, $R^5$ or $R^6$ in the formulae. According to the linkage of the compound, the compound is part of a side chain of the oligomer or polymer or part of the main chain. An oligomer in the context of this invention is understood to mean a compound formed from at least three monomer units. A polymer in the context of the invention is understood to mean a compound formed from at least ten monomer units. The polymers, oligomers or dendrimers of the invention may be conjugated, partly conjugated or nonconjugated. The oligomers or polymers of the invention may be linear, branched or dendritic. In the structures having linear linkage, the units of the above formulae may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of the above formulae to be joined via a trivalent or higher-valency group, for example via a trivalent or higher-valency aromatic or heteroaromatic group, to give a branched or dendritic oligomer or polymer.

For the repeat units of the above formulae in oligomers, dendrimers and polymers, the same preferences apply as described above for the compounds of the above formulae.

For preparation of the oligomers or polymers, the monomers of the invention are homopolymerized or copolymerized with further monomers. Suitable and preferred comonomers are chosen from fluorenes, spirobifluorenes, paraphenylenes, carbazoles, thiophenes, dihydrophenanthrenes, cis- and trans-indenofluorenes, ketones, phenanthrenes or else a plurality of these units. The polymers, oligomers and dendrimers typically contain still further units, for example emitting (fluorescent or phosphorescent) units, for example vinyltriarylamines or phosphorescent metal complexes, and/or charge transport units, especially those based on triarylamines.

The polymers and oligomers of the invention are generally prepared by polymerization of one or more monomer types, of which at least one monomer leads to repeat units of the above formulae in the polymer. Suitable polymerization reactions are known to those skilled in the art and are described in the literature. Particularly suitable and preferred polymerization reactions which lead to formation of C—C or C—N bonds are the Suzuki polymerization, the Yamamoto polymerization, the Stille polymerization and the Hartwig-Buchwald polymerization.

For the processing of the compounds according to the present application from a liquid phase, for example by spin-coating or by printing methods, formulations of the compounds according to the present application are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (-)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound according to the present application and at least one solvent, preferably an organic solvent. The way in which such solutions can be prepared is known to those skilled in the art and is described, for example, in WO 2002/072714, WO 2003/019694 and the literature cited therein.

The compounds according to the present application are suitable for use in electronic devices, especially in organic electroluminescent devices (OLEDs). Depending on the substitution, the compounds are used in different functions and layers.

The invention therefore further provides for the use of the compound in an electronic device. This electronic device is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

The invention further provides, as already set out above, an electronic device comprising at least one compound according to the present application. This electronic device is preferably selected from the abovementioned devices.

It is more preferably an organic electroluminescent device (OLED) comprising anode, cathode and at least one emitting layer, characterized in that at least one organic layer, which may be an emitting layer, a hole transport layer or another layer, preferably an emitting layer or a hole transport layer, particularly preferably a hole transport layer, comprises at least one compound according to the present application.

Apart from the cathode, anode and emitting layer, the organic electroluminescent device may also comprise further layers. These are selected, for example, from in each case one or more hole injection layers, hole transport layers, hole blocking layers, electron transport layers, electron injection layers, electron blocking layers, exciton blocking layers, interlayers, charge generation layers and/or organic or inorganic p/n junctions.

The sequence of the layers of the organic electroluminescent device comprising the compound of the above formulae is preferably as follows: anode-hole injection layer-hole transport layer-optionally further hole transport layer(s)-optionally electron blocking layer-emitting layer-optionally hole blocking layer-electron transport layer-electron injection layer-cathode. It is additionally possible for further layers to be present in the OLED.

The organic electroluminescent device of the invention may contain two or more emitting layers. More preferably, these emission layers in this case have several emission maxima between 380 nm and 750 nm overall, such that the overall result is white emission; in other words, various emitting compounds which may fluoresce or phosphoresce and which emit blue, green, yellow, orange or red light are used in the emitting layers. Especially preferred are three-layer systems, i.e. systems having three emitting layers, where the three layers show blue, green and orange or red emission. The compounds according to the present application are preferably present in the hole transport layer, hole injection layer, electron blocking layer and emitting layer. In case they are present in the emitting layer, they are preferably present as host materials.

It is preferable in accordance with the invention when the compound according to the present application is used in an electronic device comprising one or more phosphorescent emitting compounds. In this case, the compound may be present in different layers, preferably in a hole transport layer, an electron blocking layer, a hole injection layer or in an emitting layer.

The term "phosphorescent emitting compounds" typically encompasses compounds where the emission of light is effected through a spin-forbidden transition, for example a transition from an excited triplet state or a state having a higher spin quantum number, for example a quintet state.

Suitable phosphorescent emitting compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitting compounds, compounds containing copper, molybdenum, tungsten, rhenium, ruthenium, osmium, rhodium, iridium, palladium, platinum, silver, gold or europium, especially compounds containing iridium, platinum or copper. In the context of the present invention, all luminescent iridium, platinum or copper complexes are considered to be phosphorescent emitting compounds. In general, all phosphorescent complexes as used for phosphorescent OLEDs according to the prior art and as known to those skilled in the art in the field of organic electroluminescent devices are suitable. It is also possible for the person skilled in the art, without exercising inventive skill, to use further phosphorescent complexes in combination with the compounds according to the present application in organic electroluminescent devices. Further examples are listed in a table which follows.

It is also possible in accordance with the invention to use the compound according to the present application in an electronic device comprising one or more fluorescent emitting compounds.

In a preferred embodiment of the invention, the compounds according to the present application are used as hole-transporting material. In that case, the compounds are preferably present in a hole transport layer, an electron blocking layer or a hole injection layer. Particular preference is given to use in an electron blocking layer or in a hole transport layer.

A hole transport layer according to the present application is a layer having a hole-transporting function between the anode and emitting layer.

Hole injection layers and electron blocking layers are understood in the context of the present application to be specific embodiments of hole transport layers. A hole injection layer, in the case of a plurality of hole transport layers between the anode and emitting layer, is a hole transport layer which directly adjoins the anode or is separated therefrom only by a single coating of the anode. An electron blocking layer, in the case of a plurality of hole transport layers between the anode and emitting layer, is that hole transport layer which directly adjoins the emitting layer on the anode side. Preferably, the OLED of the invention comprises two, three or four hole-transporting layers between the anode and emitting layer, at least one of which preferably contains a compound according to the present application, and more preferably exactly one or two contain a such compound.

If the compound according to the present application is used as hole transport material in a hole transport layer, a hole injection layer or an electron blocking layer, the compound can be used as pure material, i.e. in a proportion of 100%, in the hole transport layer, or it can be used in combination with one or more further compounds. In a preferred embodiment, the organic layer comprising the compound of one of the above-mentioned formulae then additionally contains one or more p-dopants. p-Dopants used according to the present invention are preferably those organic electron acceptor compounds capable of oxidizing one or more of the other compounds in the mixture. Such p-dopants are preferably present in the hole-injection layer and/or hole transporting layer of the device. The electron-blocking layer preferably does not comprise any p-dopants.

Particularly preferred p-dopants are quinodimethane compounds, azaindenofluorenediones, azaphenalenes, azatriphenylenes, 12, metal halides, preferably transition metal halides, metal oxides, preferably metal oxides containing at least one transition metal or a metal of main group 3, and transition metal complexes, preferably complexes of Cu, Co, Ni, Pd and Pt with ligands containing at least one oxygen atom as bonding site. Preference is further given to transition metal oxides as dopants, preferably oxides of rhenium, molybdenum and tungsten, more preferably $Re_2O_7$, $MoO_3$, $WO_3$ and $ReO_3$. Further preferable p-dopants are selected from Bi(III)-containing metal complexes, in particular Bi(III) complexes of benzoic acid or benzoic acid derivatives.

The p-dopants are preferably in substantially homogeneous distribution in the p-doped layers. This can be achieved, for example, by coevaporation of the p-dopant and the hole transport material matrix.

Preferred p-dopants are especially the following compounds:

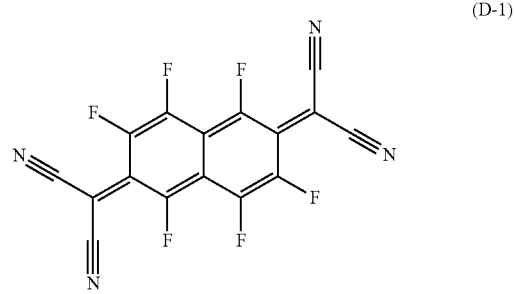

(D-1)

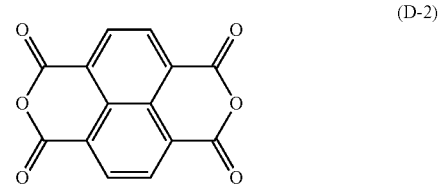

(D-2)

-continued
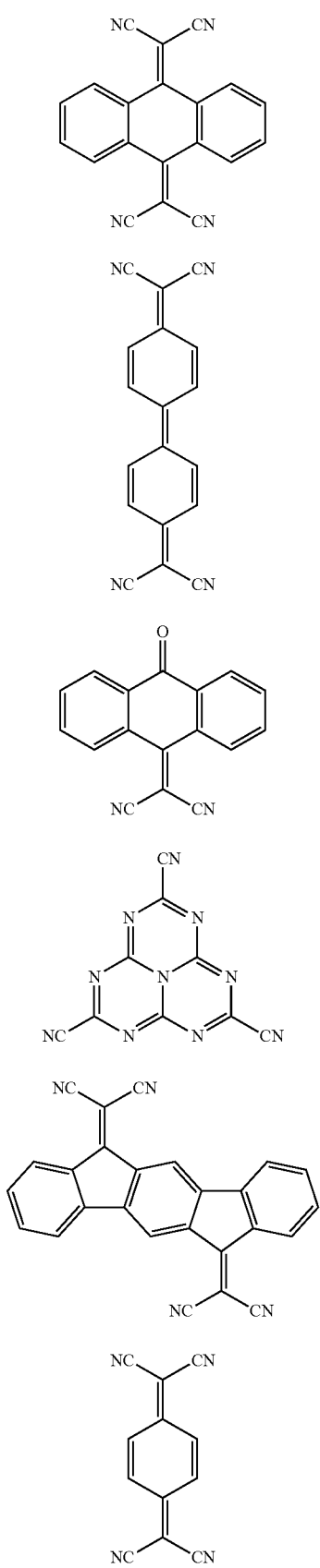
(D-3)
(D-4)
(D-5)
(D-6)
(D-7)
(D-8)
-continued
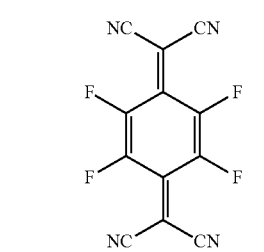
(D-9)
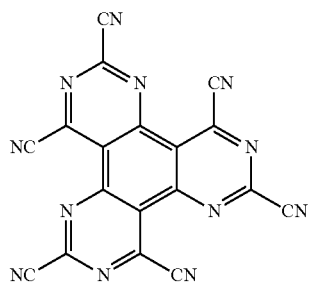
(D-10)
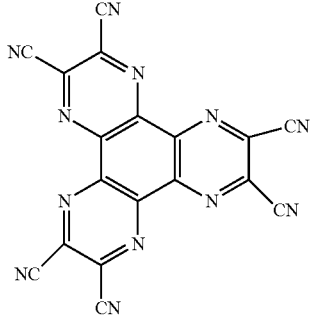
(D-11)
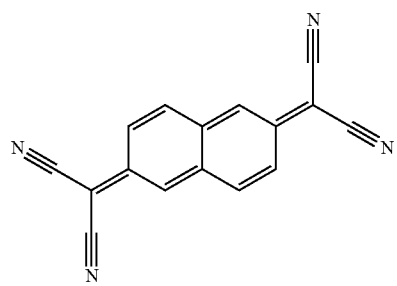
(D-12)
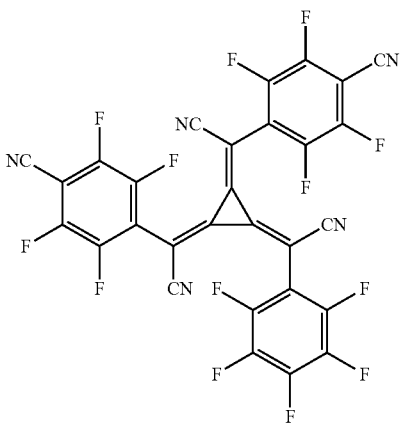
(D-13)

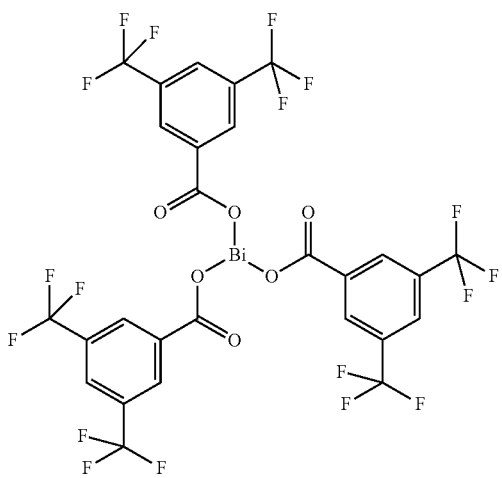

(D-14)

In a further preferred embodiment of the invention, the compound is used as hole transport material in a hole transporting layer, and there is a layer (called hole injection layer) present between anode and this hole transporting layer, which comprises an electron accepting material.

Preferably, this electron accepting material is selected from the compound classes mentioned above for use as p-dopants, particularly preferably from the compounds (D-1) to (D-14) mentioned above, most preferably from the compounds (D-6), (D-7) and (D-14). Preferably, the above-mentioned hole injection layer comprises one of the above-mentioned compounds in non-doped form, and with no other compounds admixed. Most preferably, it consists of only one of the above-mentioned compounds and comprises no other compound.

According to a preferred embodiment, a hole transporting or hole injection layer of the device comprises two or more, preferably two, different hole transporting materials (mixed layer). In such case, the two or more different hole transporting materials are preferably selected from triarylamine compounds, particularly preferred from mono-triarylamine compounds, more particularly preferably from the compounds listed below as preferred hole-transporting compounds. In case two or more different compounds are present in the layer, each of them is preferably present in a proportion of at least 10% by volume, preferably in a proportion of at least 20% by volume.

In this application, proportions are given as percent by volume. If the mixtures are applied from solution, this corresponds to percent by mass.

The above-mentioned mixed layers preferably comprise one or more compounds according to the present application.

In a further embodiment of the present invention, the compound is used in an emitting layer as matrix material in combination with one or more emitting compounds, preferably phosphorescent emitting compounds.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the emitting compound is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of emitting compounds. In this case too, the emitting compounds are generally those compounds having the smaller proportion in the system and the matrix materials are those compounds having the greater proportion in the system. In individual cases, however, the proportion of a single matrix material in the system may be less than the proportion of a single emitting compound.

It is preferable that the compound is used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The compound is preferably the matrix material having hole-transporting properties. The desired electron-transporting and hole-transporting properties of the mixed matrix components may, however, also be combined mainly or entirely in a single mixed matrix component, in which case the further mixed matrix component(s) fulfill(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices.

The mixed matrix systems may comprise one or more emitting compounds, preferably one or more phosphorescent emitting compounds. In general, mixed matrix systems are preferably used in phosphorescent organic electroluminescent devices.

Particularly suitable matrix materials which can be used in combination with the compounds according to the present application as matrix components of a mixed matrix system are selected from the preferred matrix materials specified below for phosphorescent emitting compounds or the preferred matrix materials for fluorescent emitting compounds, according to what type of emitting compound is used in the mixed matrix system.

Preferred phosphorescent emitting compounds for use in mixed matrix systems are the same as detailed further up as generally preferred phosphorescent emitter materials.

Preferred embodiments of the different functional materials in the electronic device are listed hereinafter.

Preferred phosphorescent emitting compounds are the following ones:

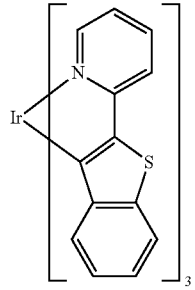

-continued
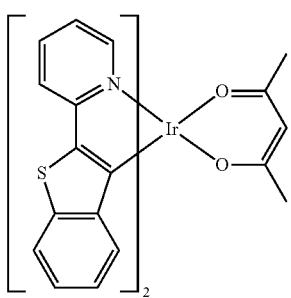
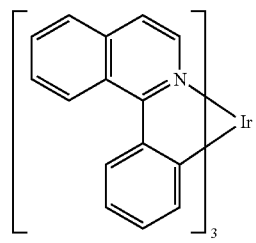
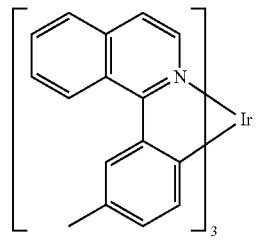
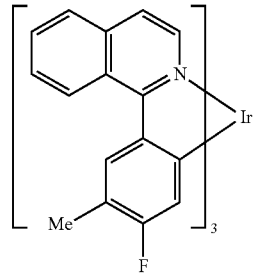
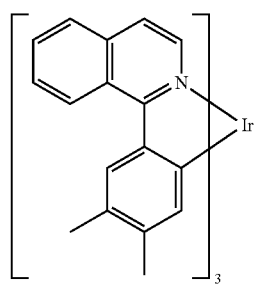
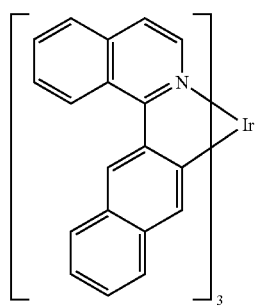
-continued
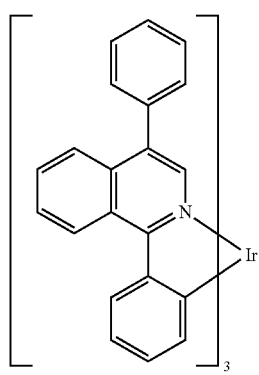
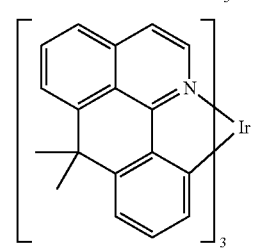
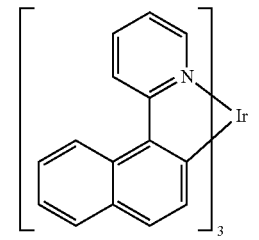
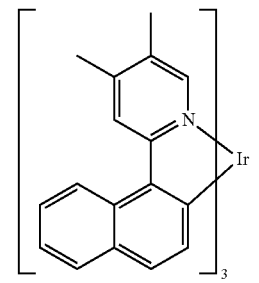
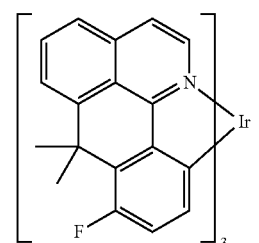
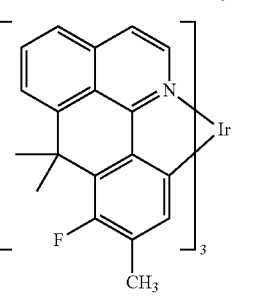

-continued
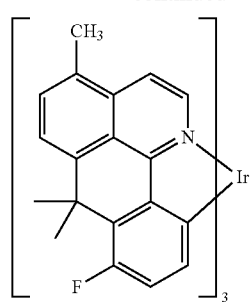
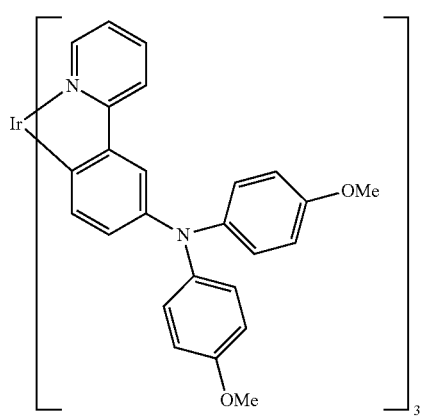
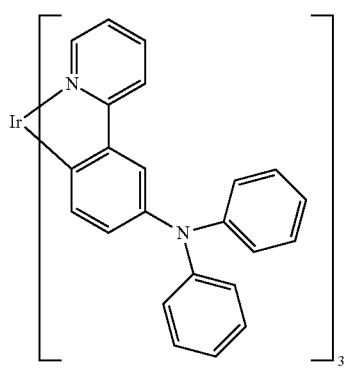
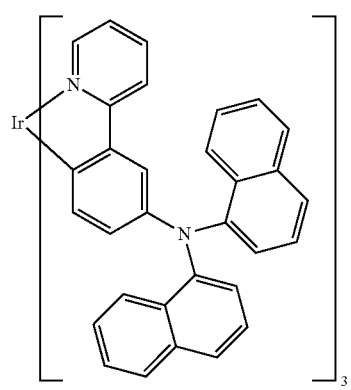
-continued
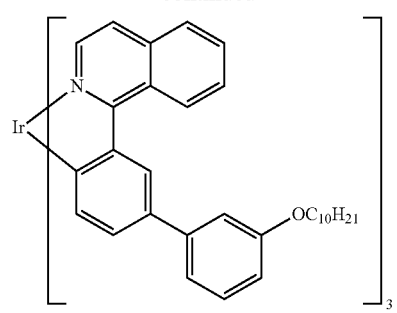
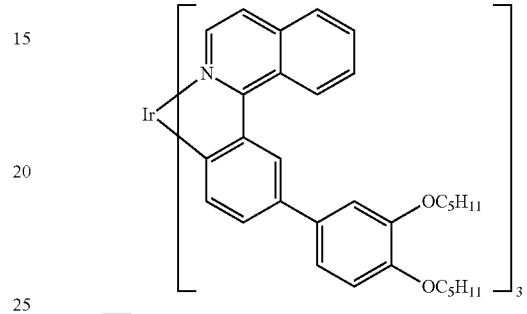
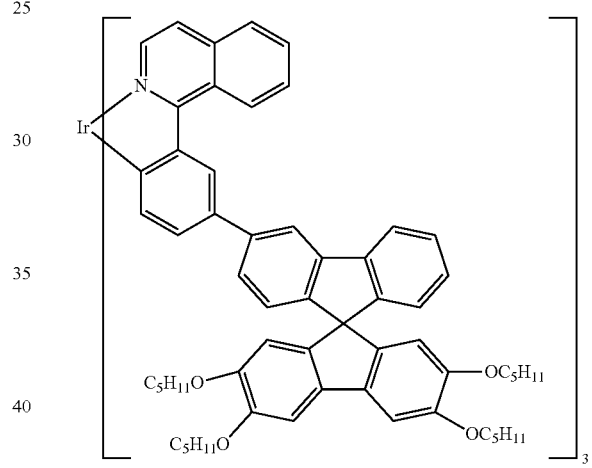
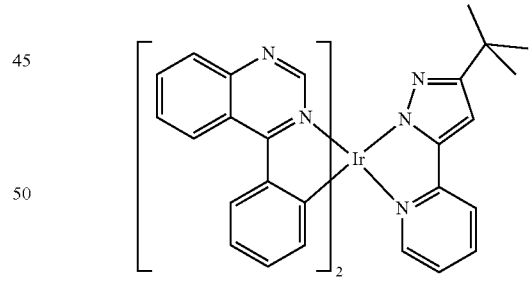
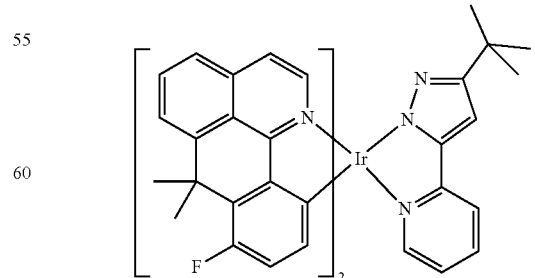

179
-continued
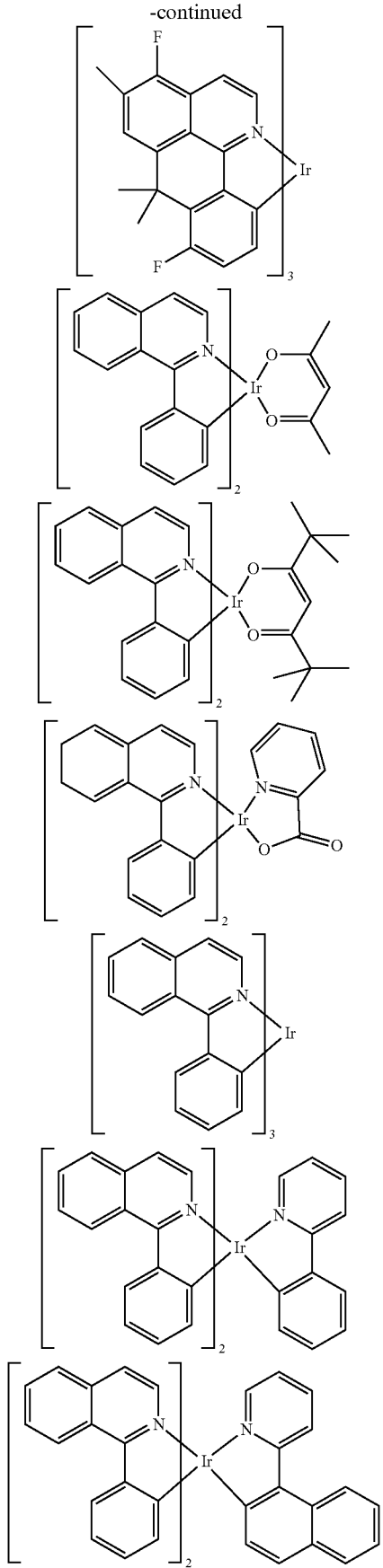
180
-continued
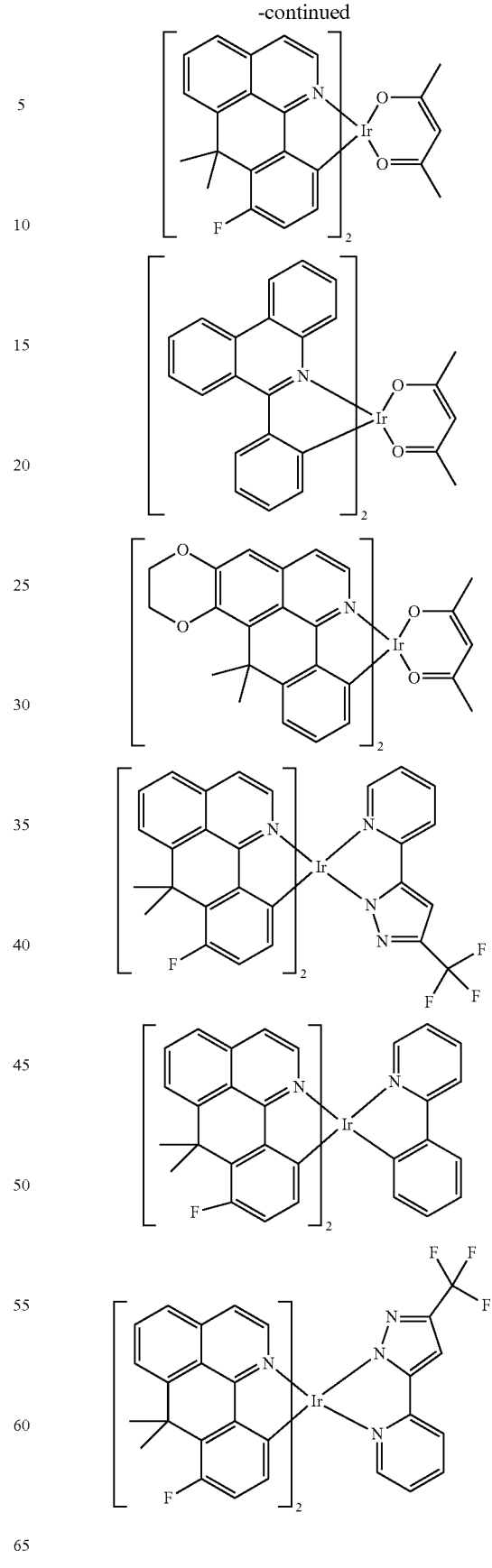

181
-continued
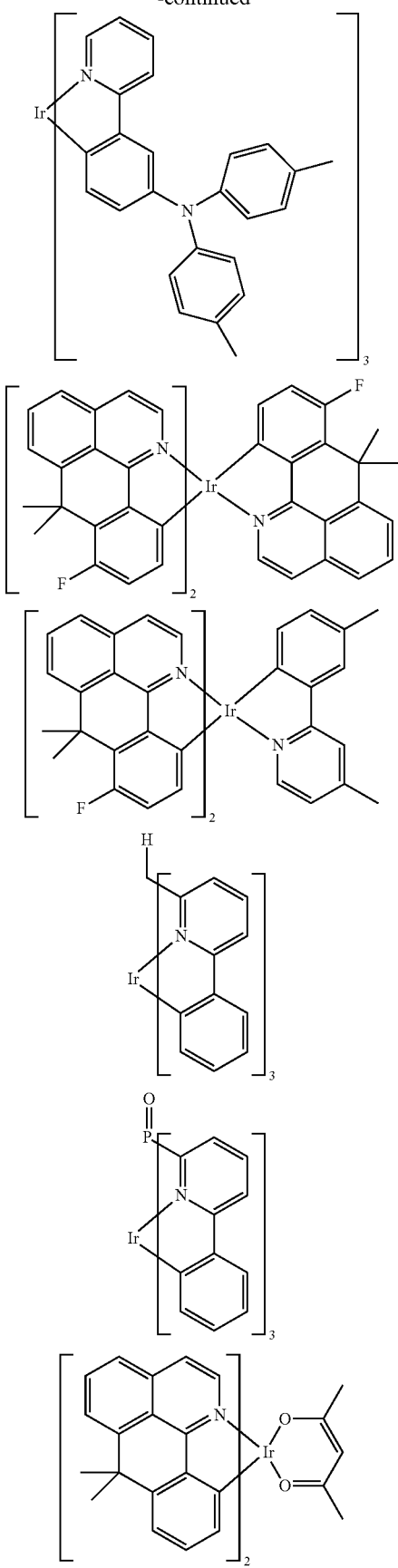
182
-continued
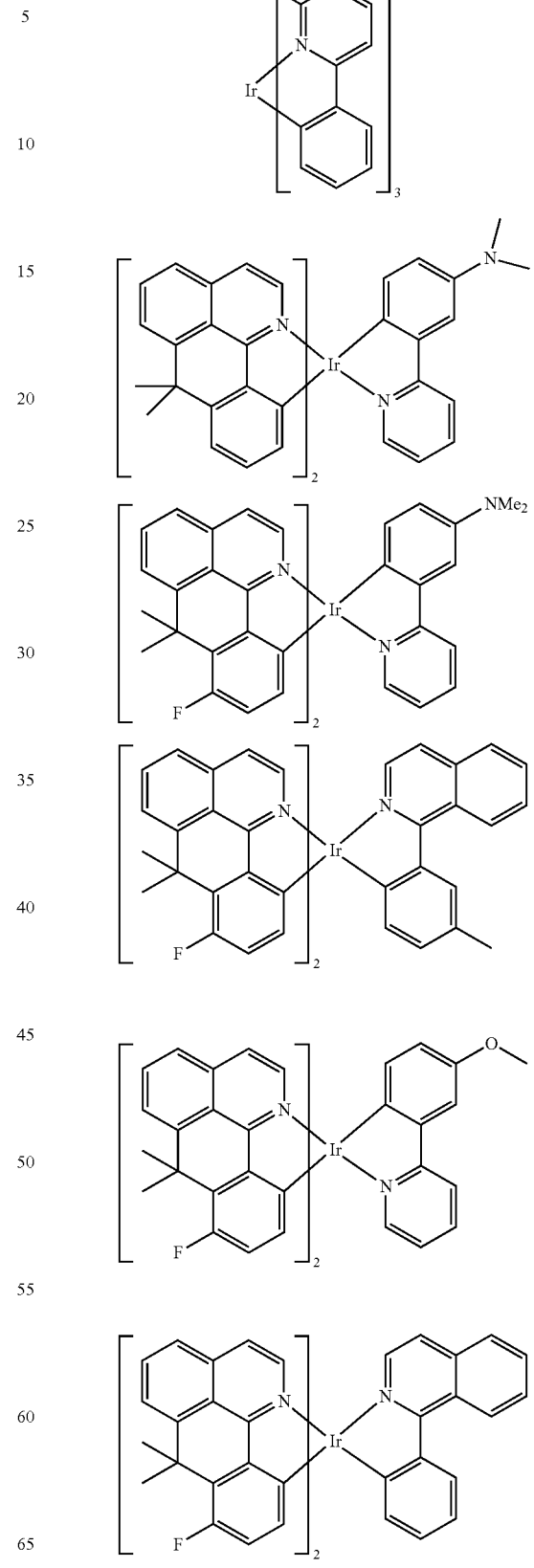

183
-continued
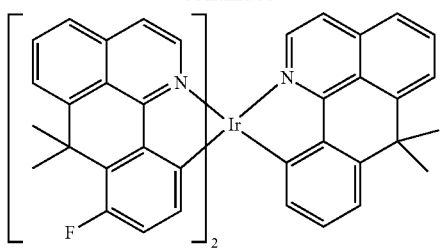
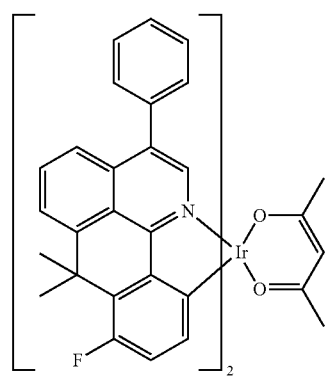
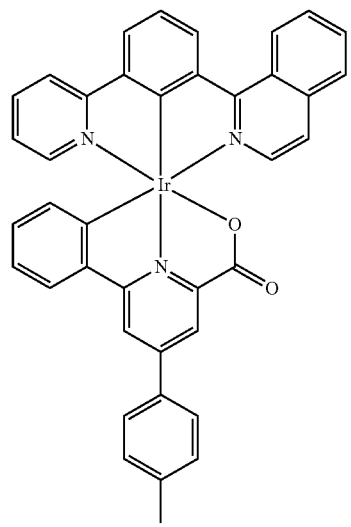
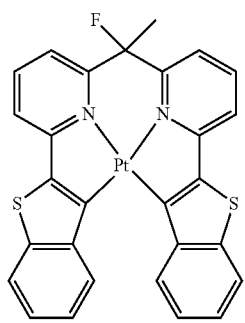
184
-continued
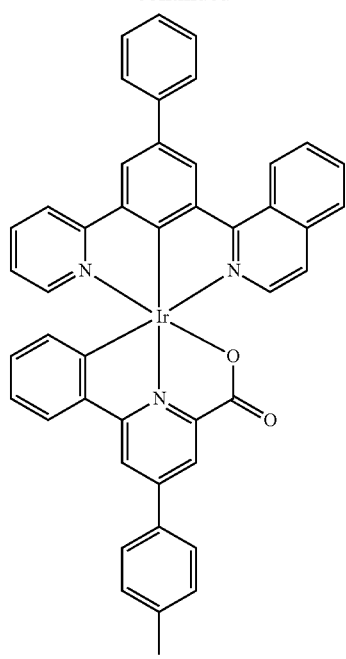
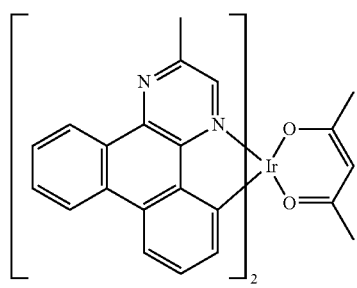
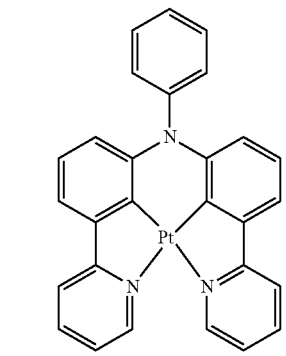
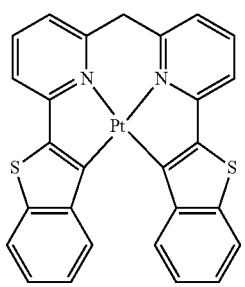

185
-continued
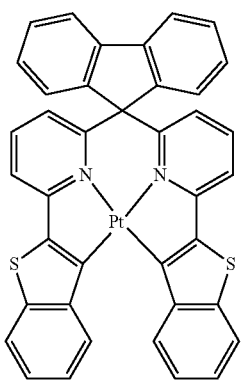
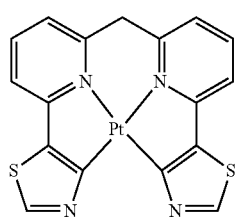
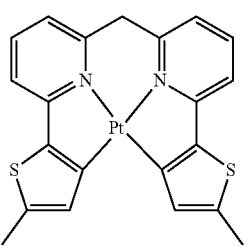
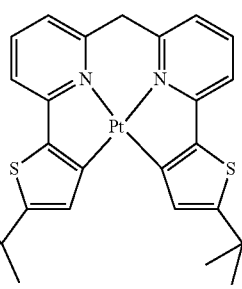
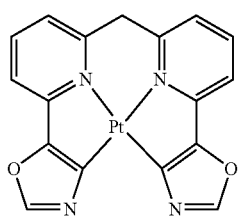
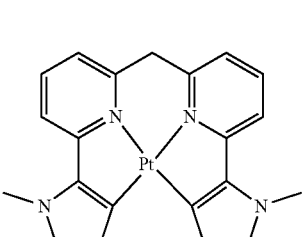
186
-continued
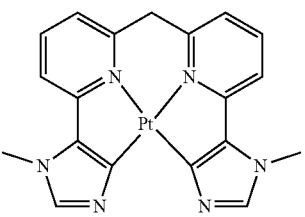
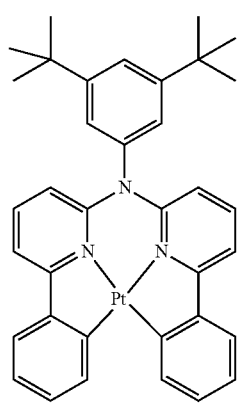
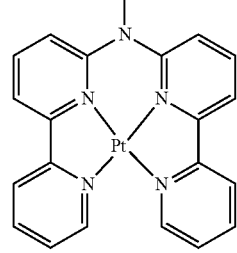
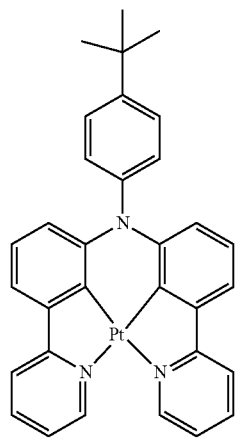

187
-continued
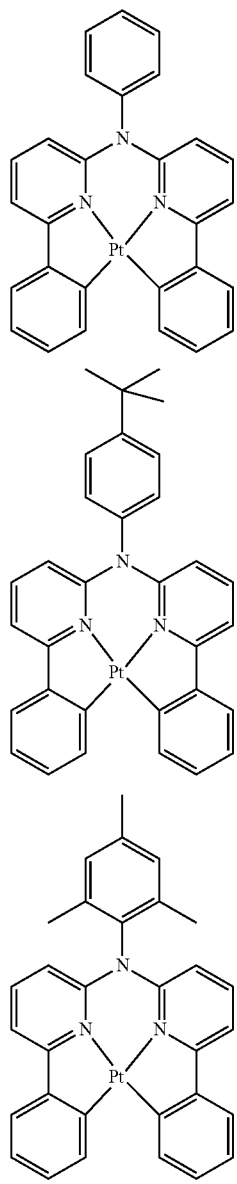
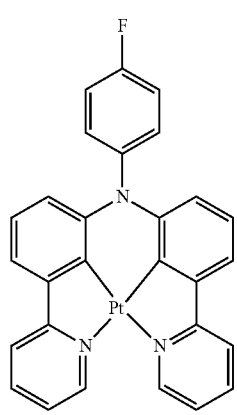
188
-continued
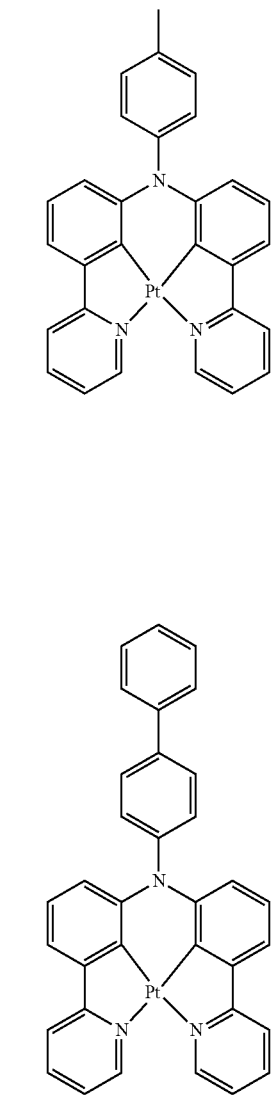
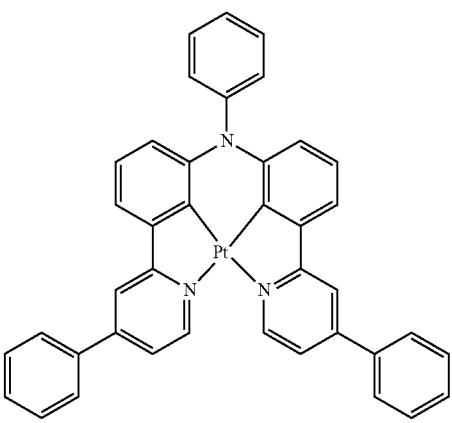

189
-continued
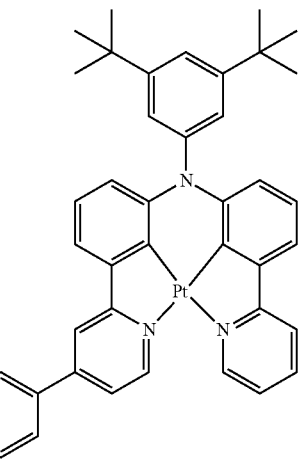
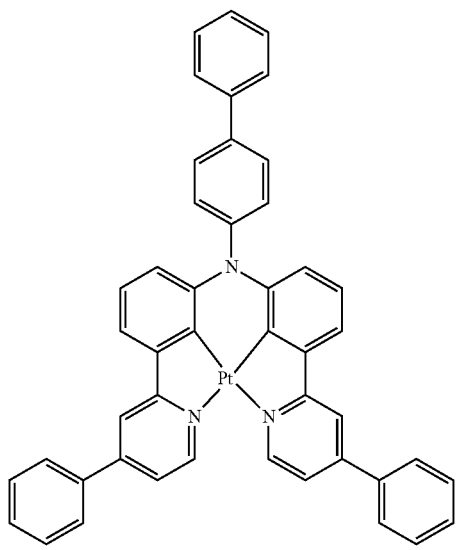
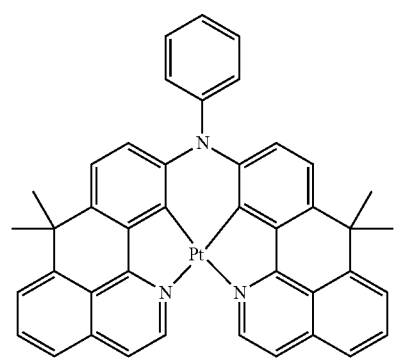
190
-continued
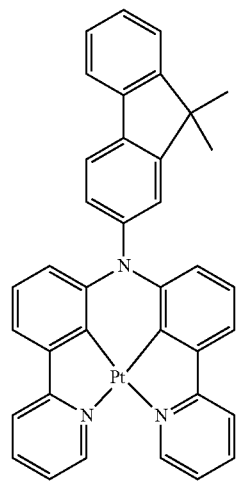
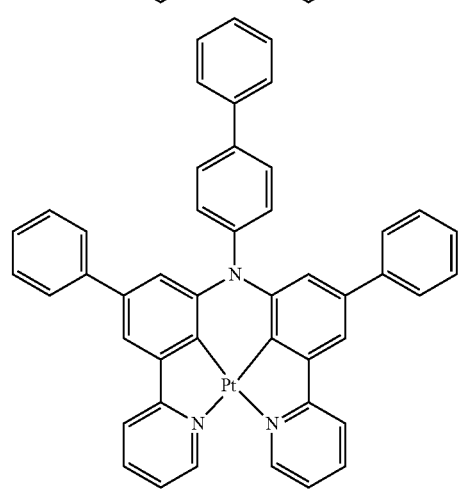
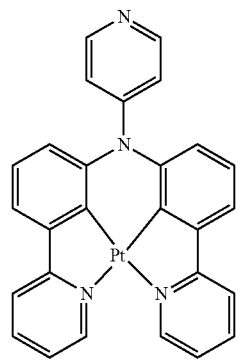
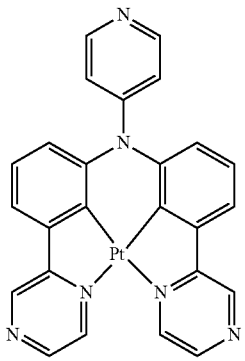

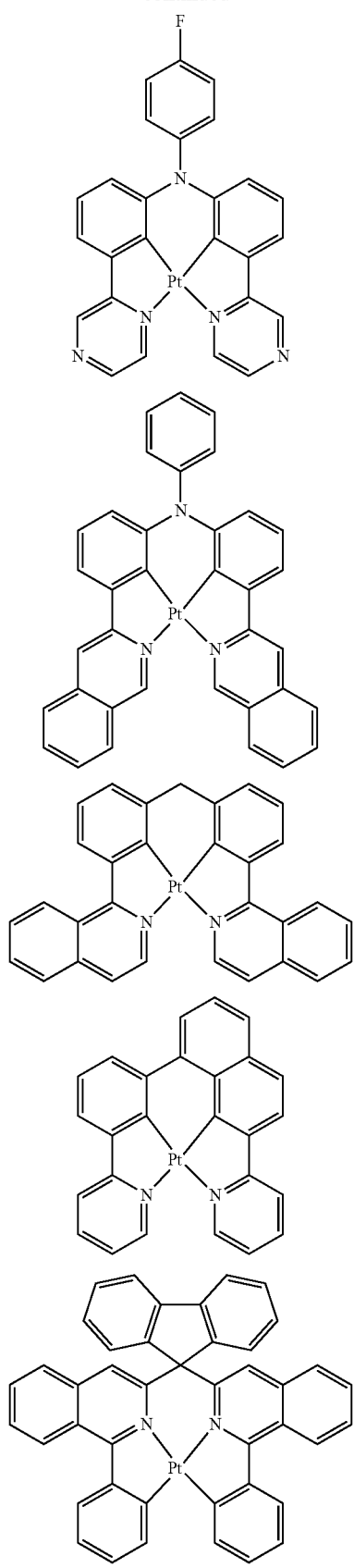
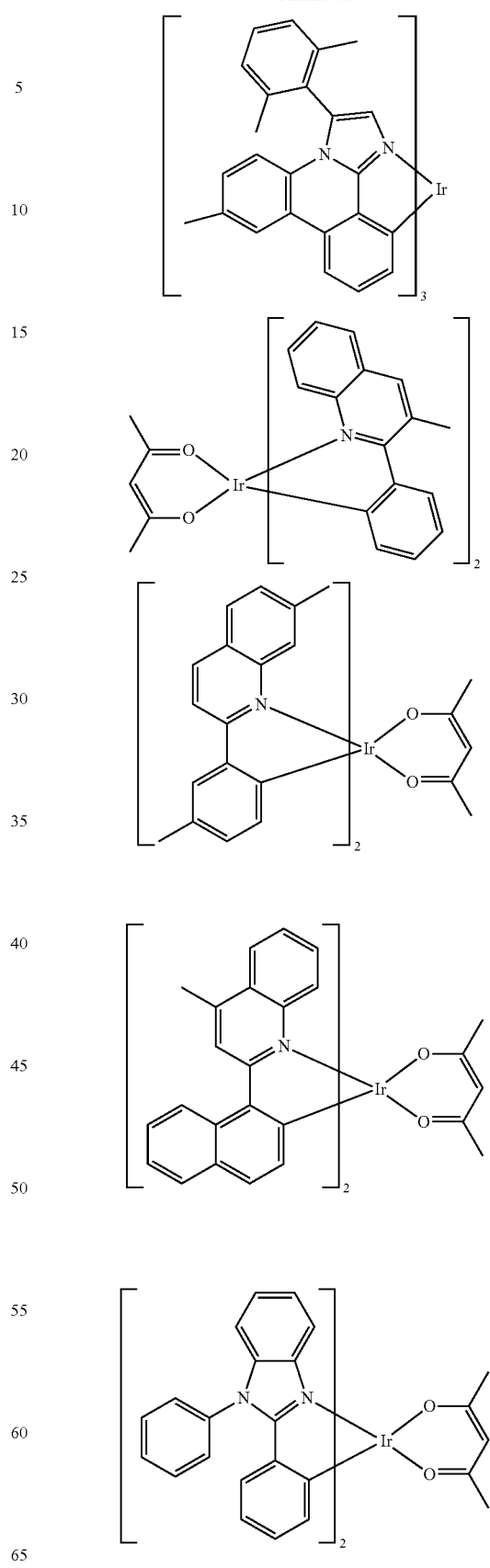

193
-continued
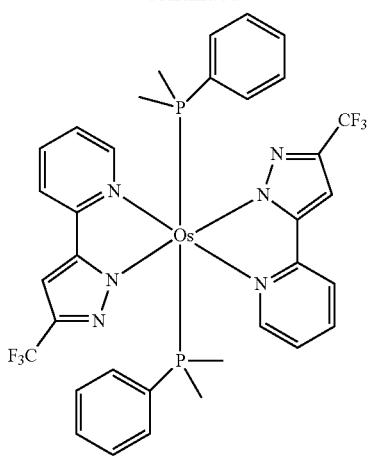
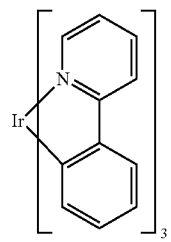
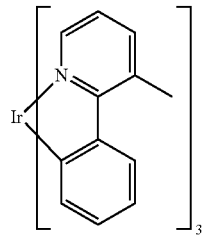
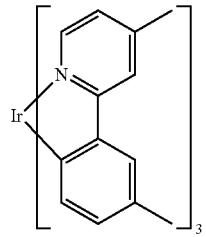
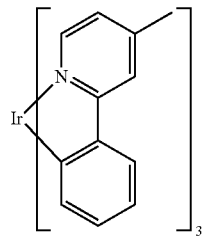
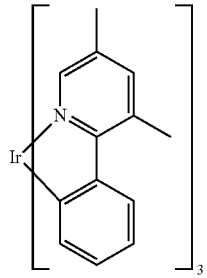
194
-continued
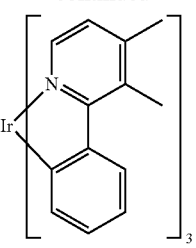
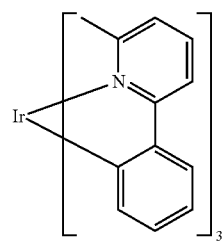
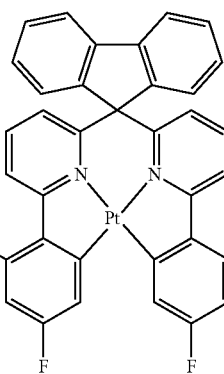
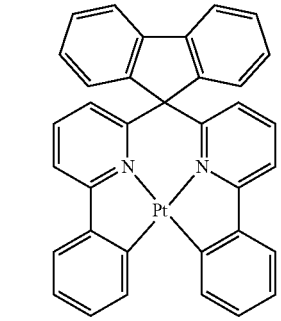
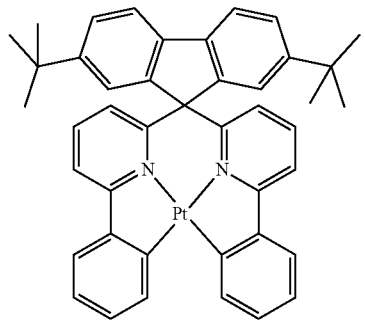

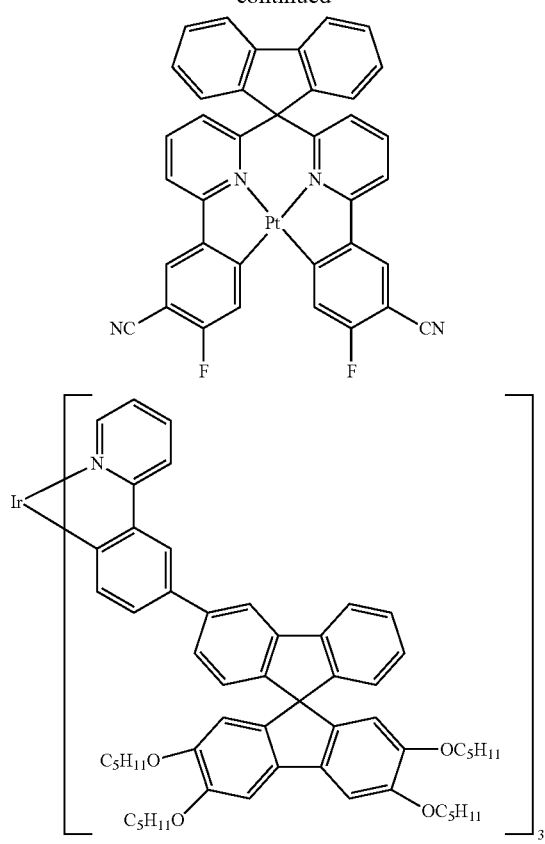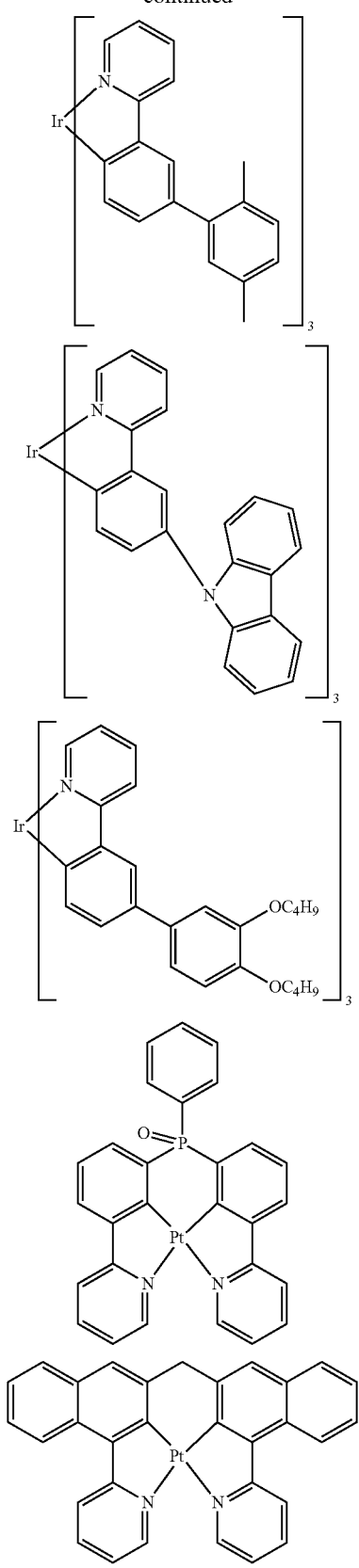

197
-continued
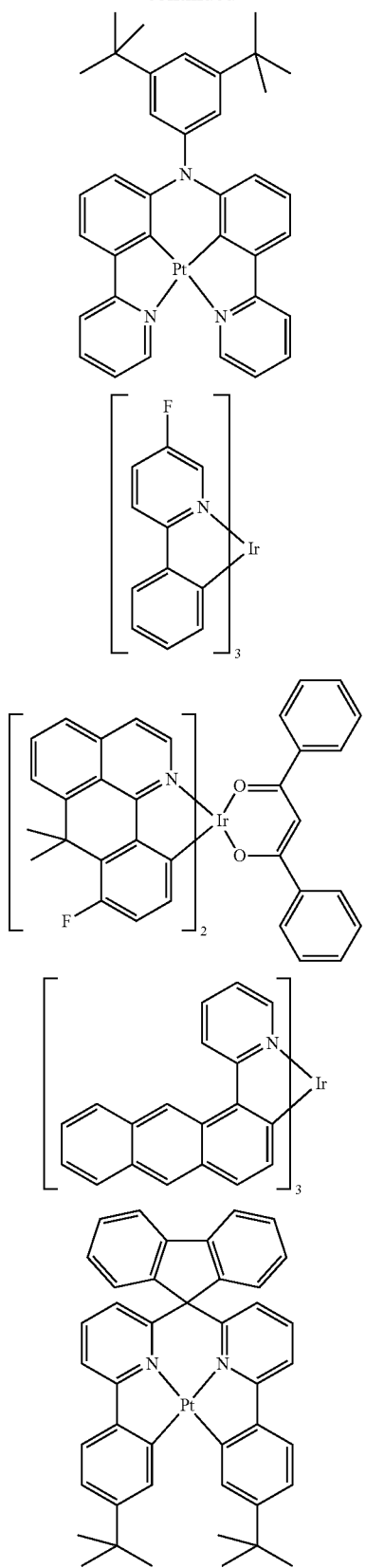
198
-continued
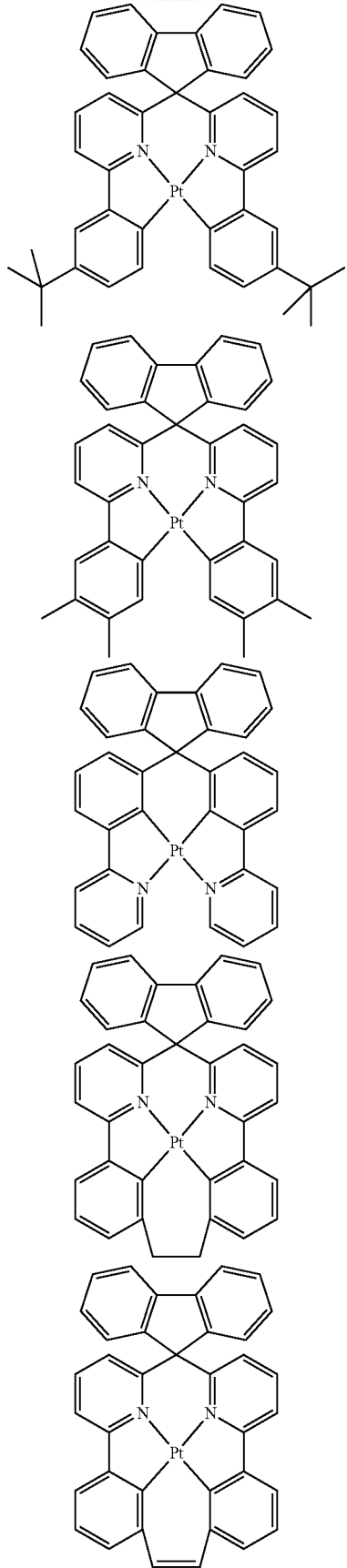

199
-continued
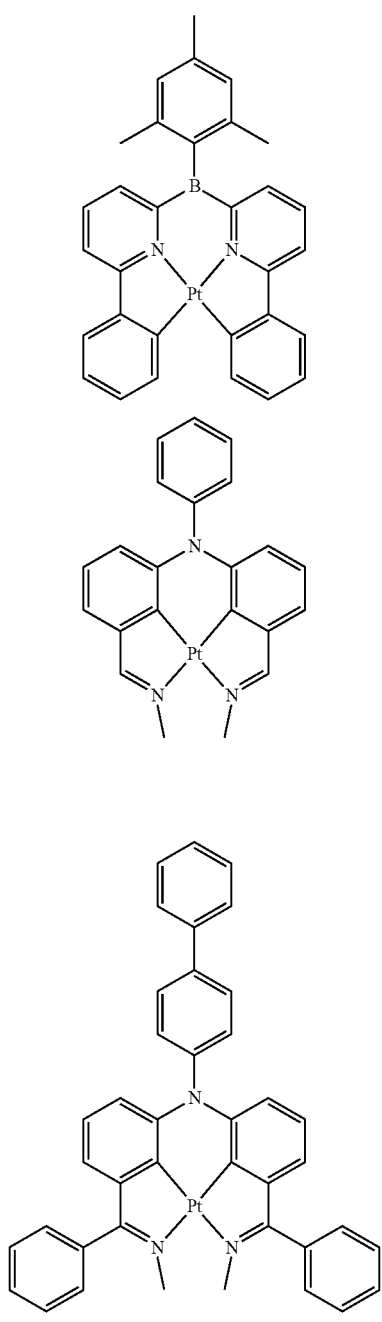
200
-continued
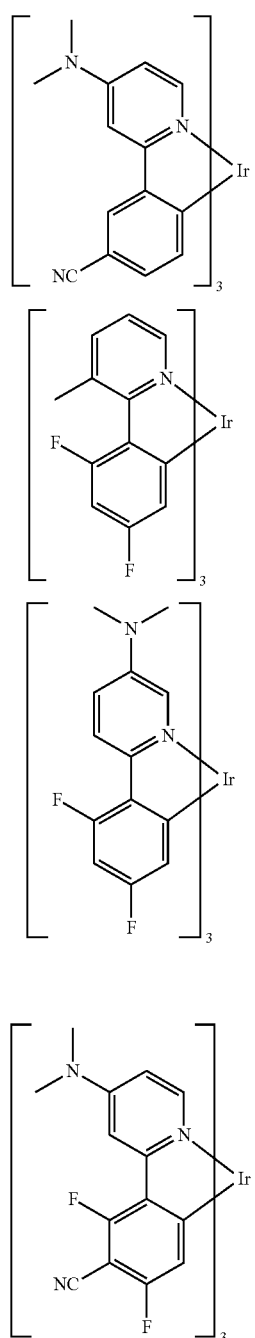
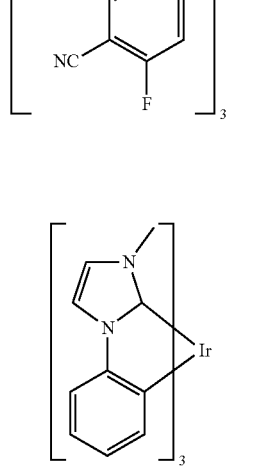

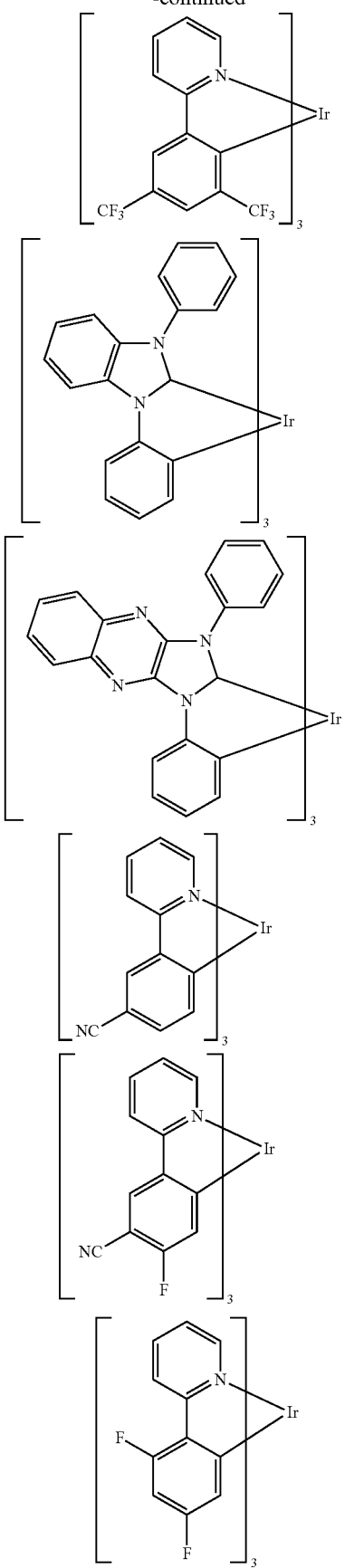
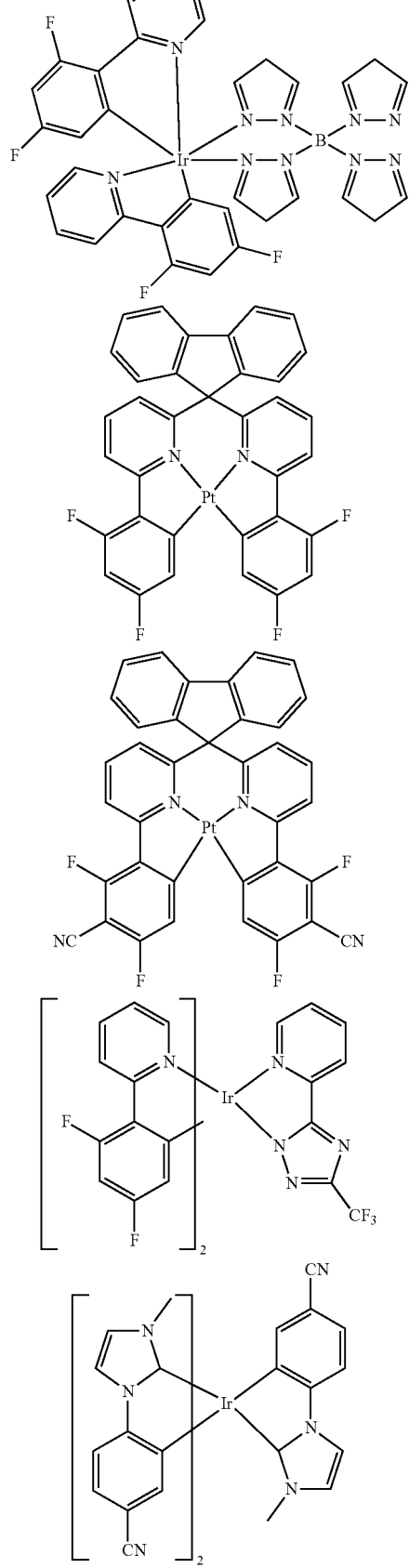

203
-continued
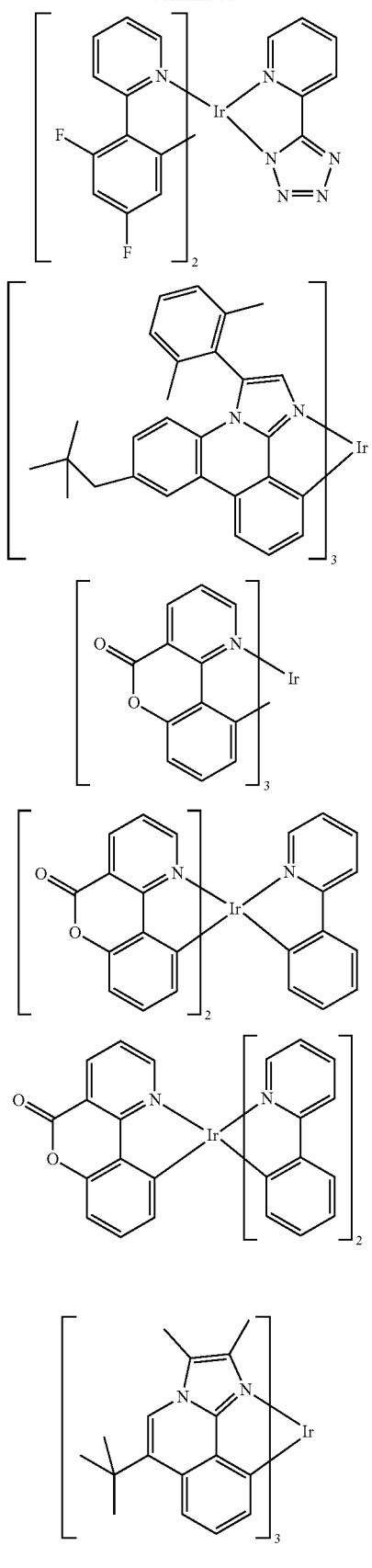
204
-continued
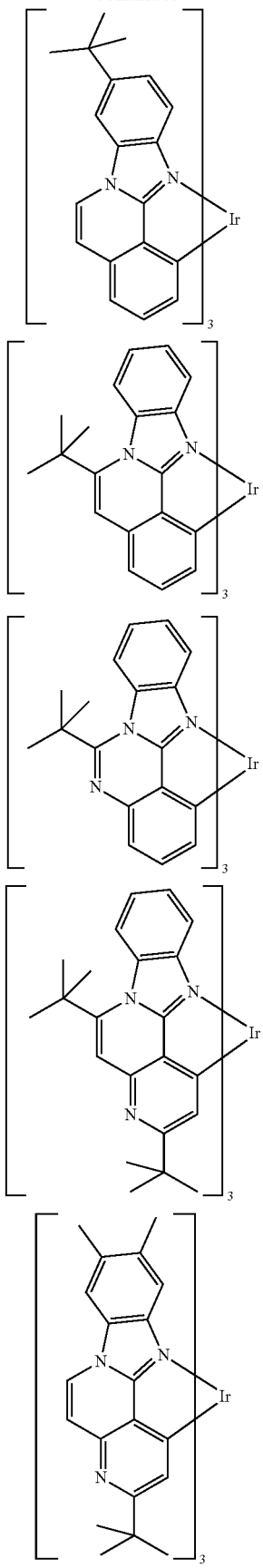

205
-continued
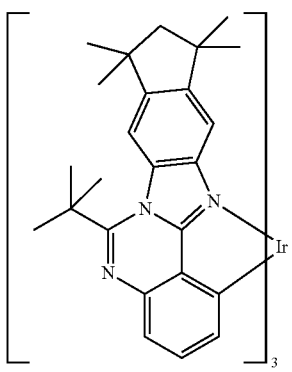
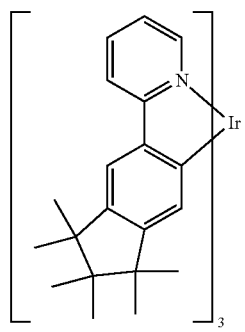
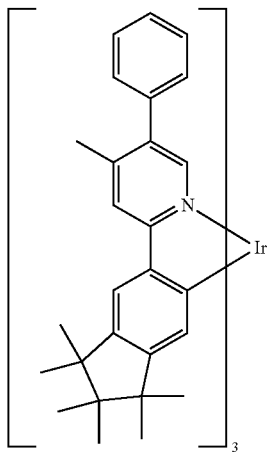
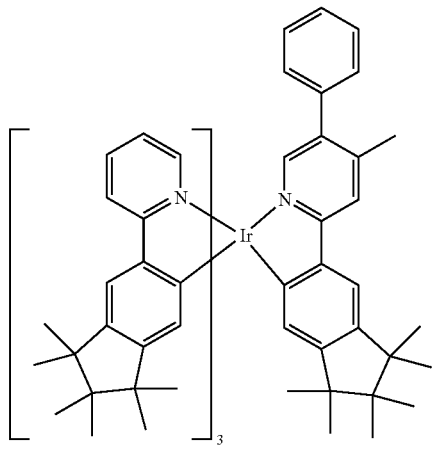
206
-continued
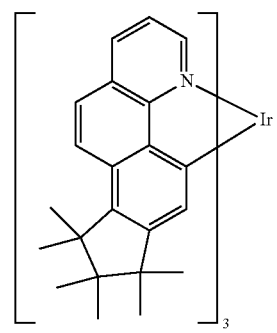
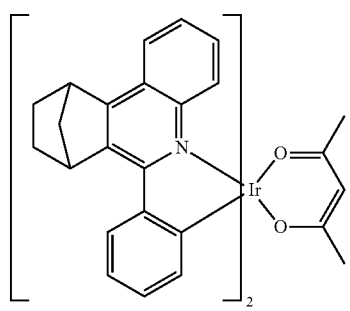
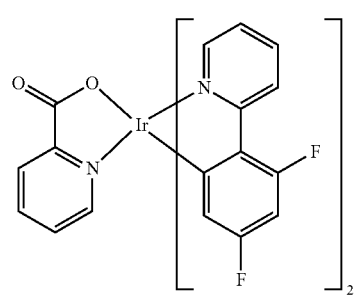
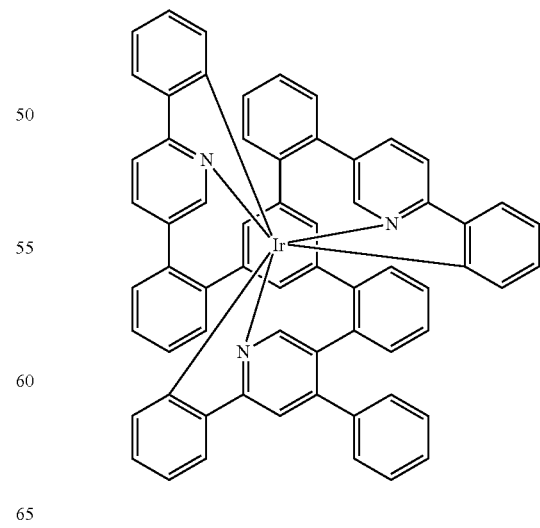

207
-continued

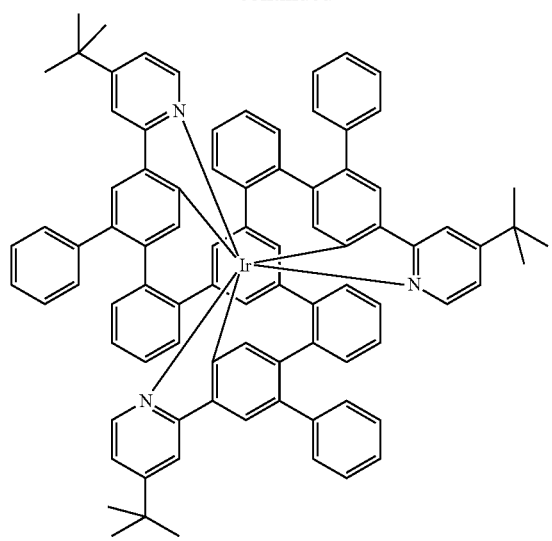

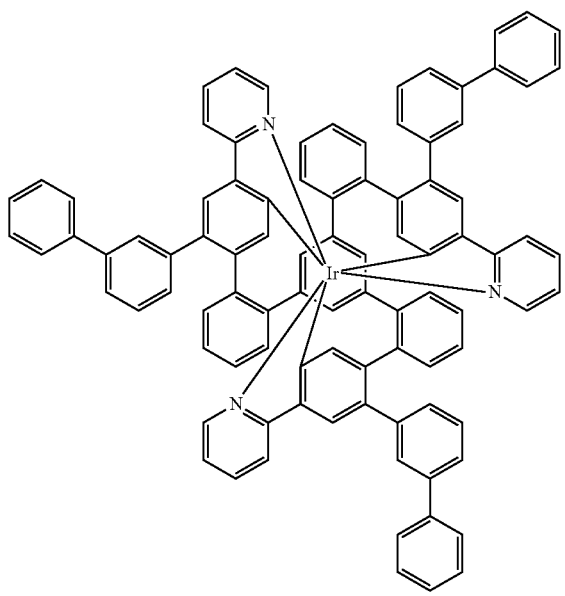

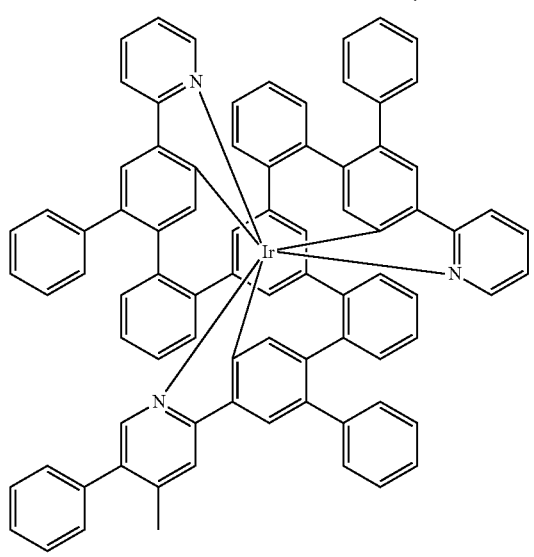

208
-continued

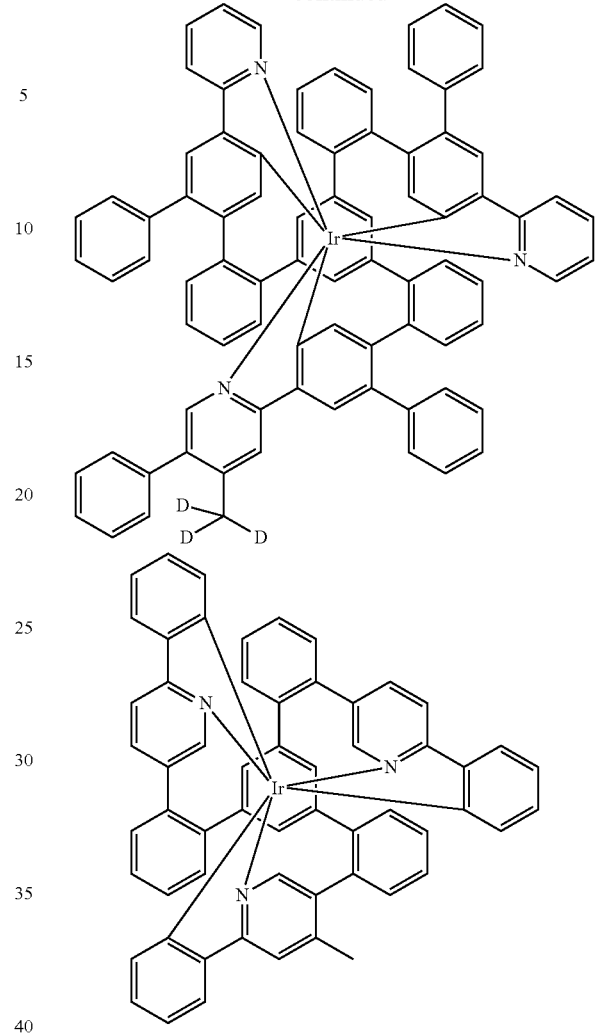

Preferred fluorescent emitting compounds are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthracenamines, aromatic anthracenediamines, aromatic pyrenamines, aromatic pyrenediamines, aromatic chrysenamines or aromatic chrysenediamines. An aromatic anthracenamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyrenamines, pyrenediamines, chrysenamines and chrysenediamines are defined analogously, where the diarylamino groups are bonded to the pyrene preferably in the 1-position or 1,6-positions. Further preferred emitting compounds are indenofluorenamines and -fluorenediamines, benzoindenofluorenamines and -fluorenediamines, dibenzoindenofluoreneamines and -diamines, and indenofluorene derivatives having fused aryl groups. Likewise preferred are pyrenearylamines. Likewise preferred are benzoindenofluorenamines, benzofluorenamines, extended benzoindenofluorenes, phenoxazines, and fluorene derivatives bonded to furan units or to thiophene units.

Useful matrix materials, preferably for fluorescent emitting compounds, include materials of various substance classes. Preferred matrix materials are selected from the classes of the oligoarylenes (e.g. 2,2',7,7'-tetraphenylspirobifluorene or dinaphthylanthracene), especially of oligoarylenes containing fused aromatic groups, oligoarylenevinylenes (e.g. DPVBi or spiro-DPVBi), polypodal metal complexes, hole-conducting compounds, electron-conducting compounds, especially ketones, phosphine oxides, and sulphoxides, and atropisomers, boronic acid derivatives or benzanthracenes. Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulphoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another.

Preferred matrix materials for phosphorescent emitting compounds are, as well as the compounds of the present application, aromatic ketones, aromatic phosphine oxides or aromatic sulphoxides or sulphones, triarylamines, carbazole derivatives, e.g. CBP (N,N-biscarbazolylbiphenyl) or carbazole derivatives, indolocarbazole derivatives, indenocarbazole derivatives, azacarbazole derivatives, bipolar matrix materials, silanes, azaboroles or boronic esters, triazine derivatives, zinc complexes, diazasilole or tetraazasilole derivatives, diazaphosphole derivatives, bridged carbazole derivatives, triphenylene derivatives, or lactams.

Suitable charge transport materials as usable in the hole injection or hole transport layer or electron blocking layer or in the electron transport layer of the electronic device of the invention are, other than the compounds of the present application, for example, the compounds disclosed in Y. Shirota et al., Chem. Rev. 2007, 107(4), 953-1010, or other materials as used in these layers according to the prior art.

Particularly preferable materials for use in a hole injection layer, a hole transport layer, an electron blocking layer or an emitting layer, of an OLED are shown below:

H-1

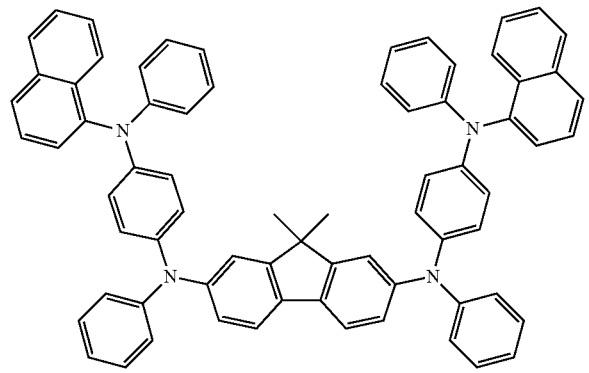

H-2

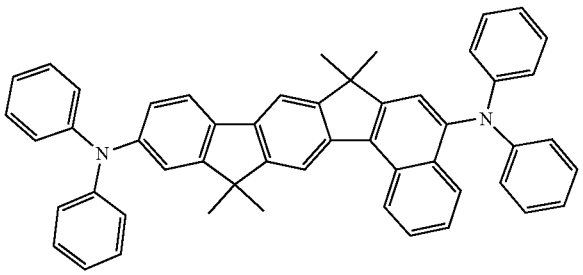

H-3

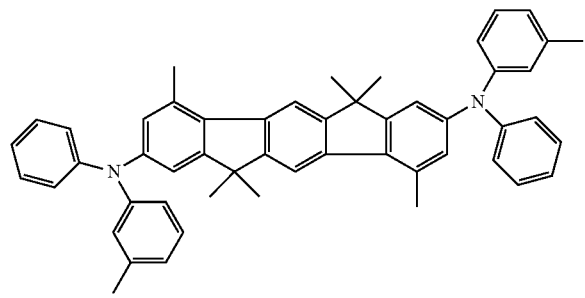

H-4

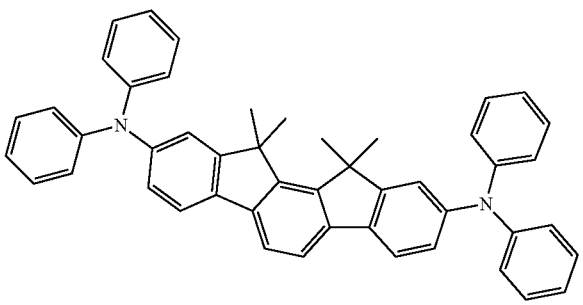

H-5

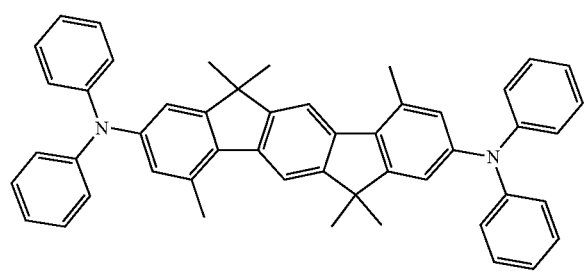

H-6

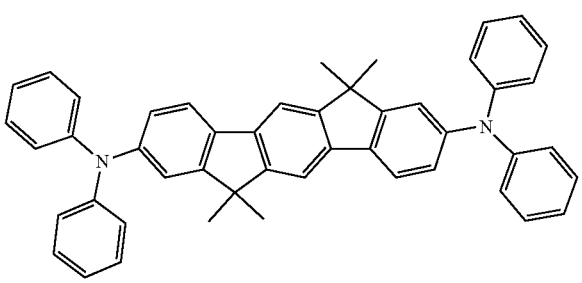

-continued
H-7
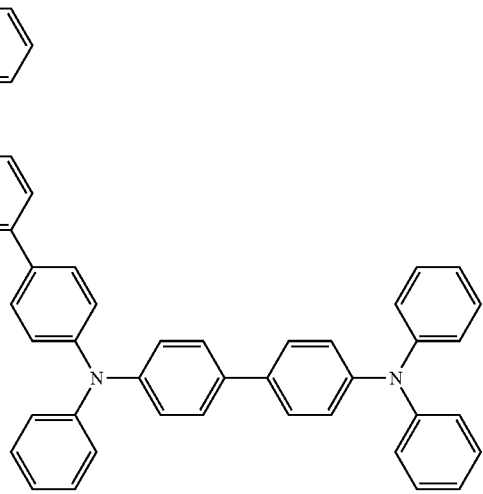
H-8
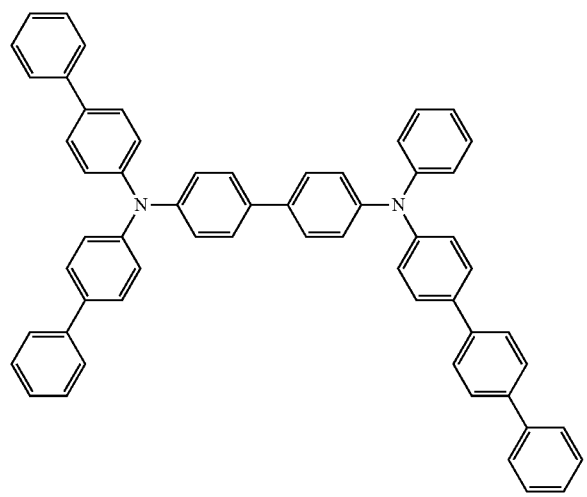
H-9
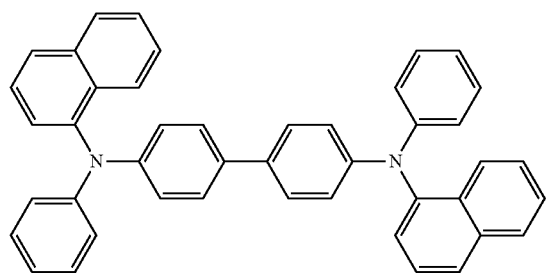
H-10
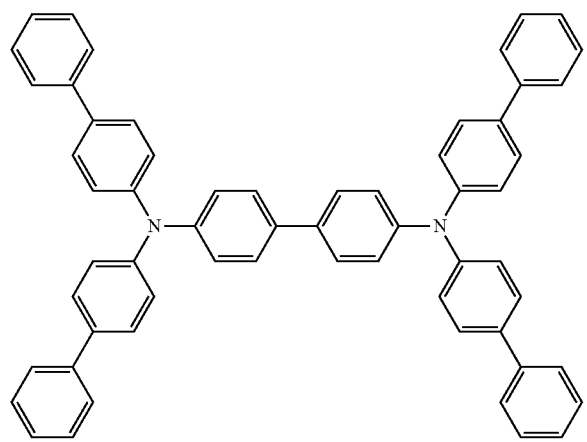
H-11
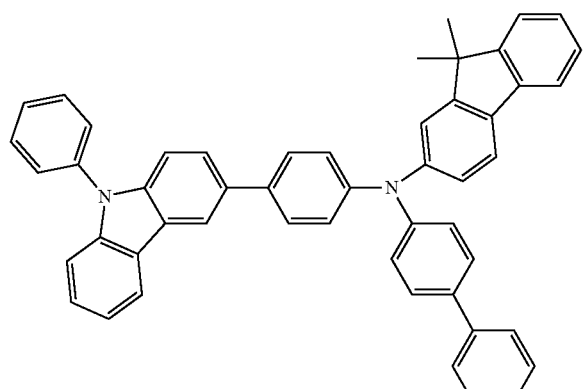

-continued
H-12
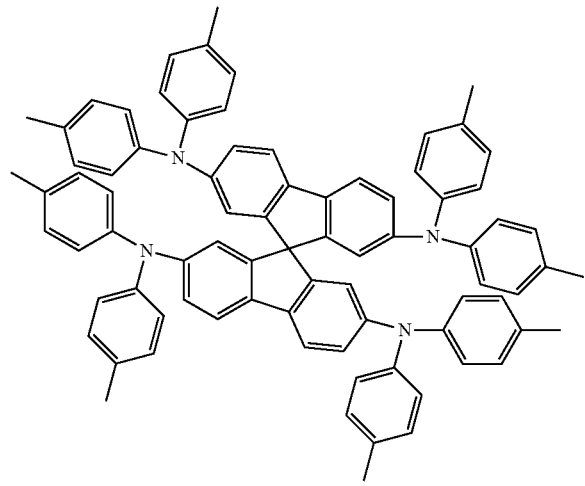
H-13
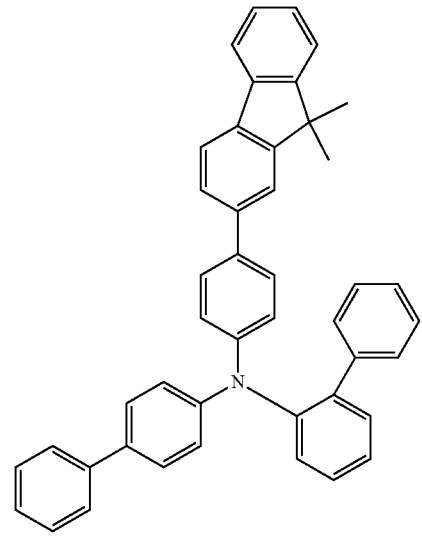
H-14
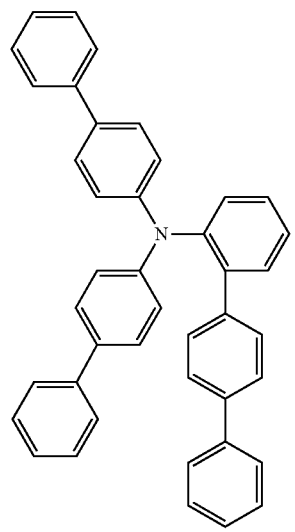
H-15
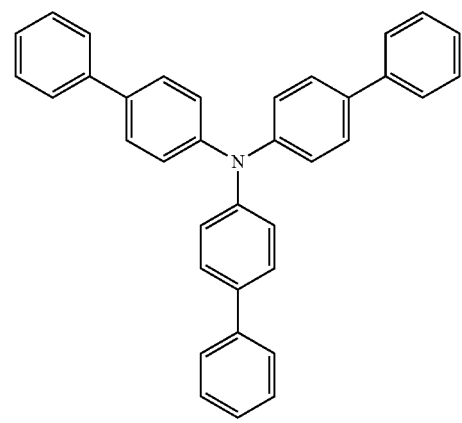
H-16
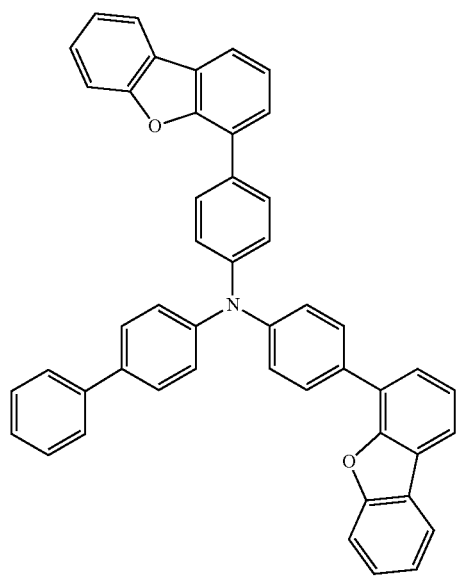
H-17
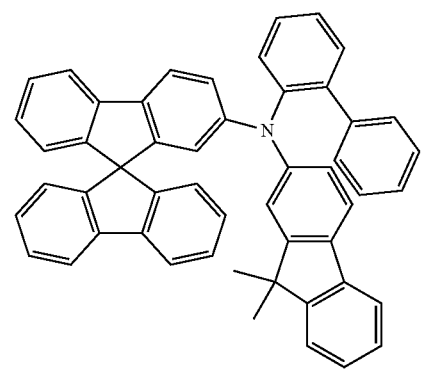

-continued
H-18
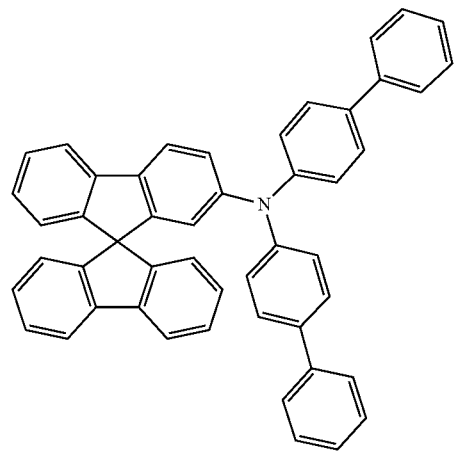
H-19
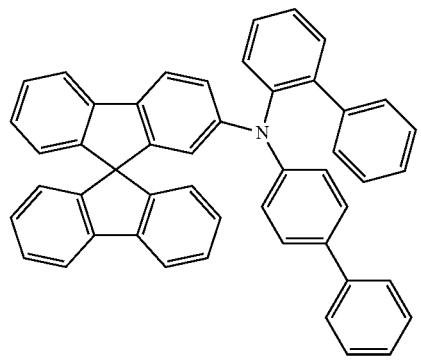
H-20
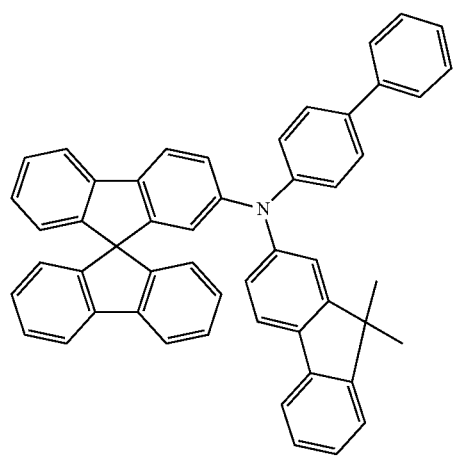
H-21
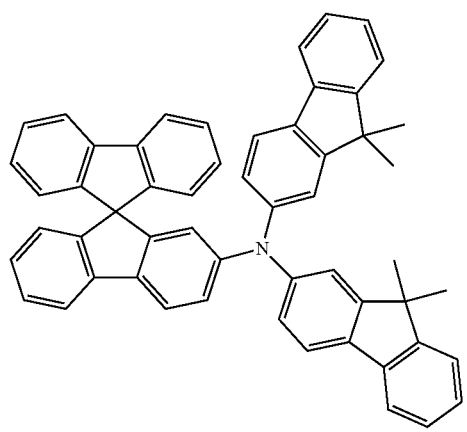
H-22
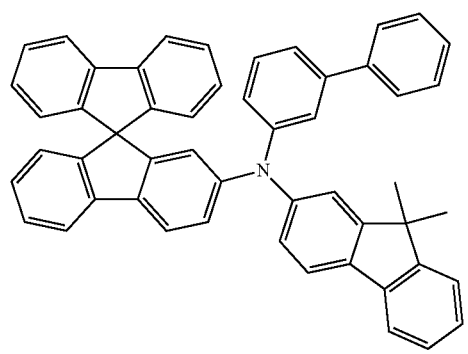
H-23
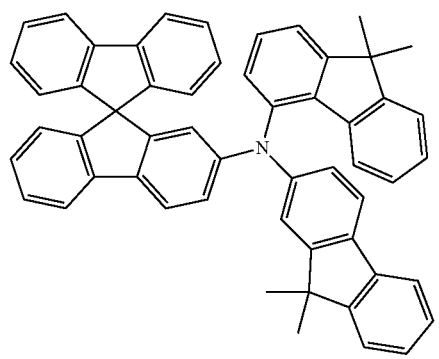

-continued
H-24
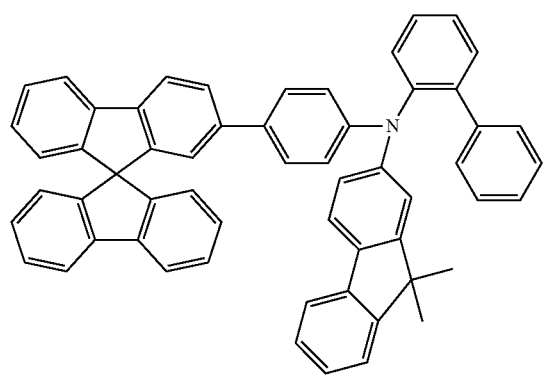
H-25
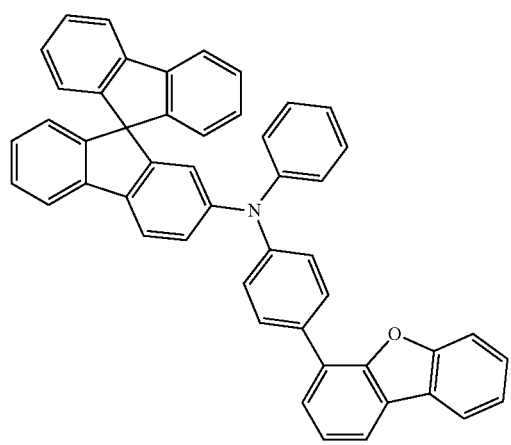
H-26
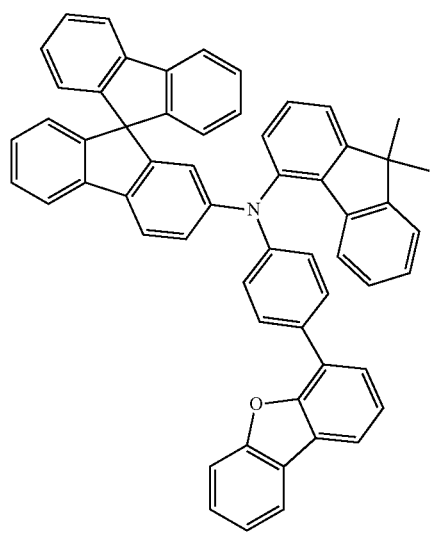
H-27
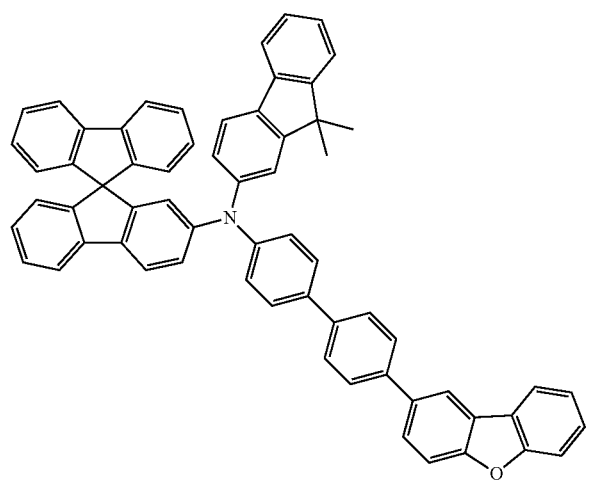
H-28
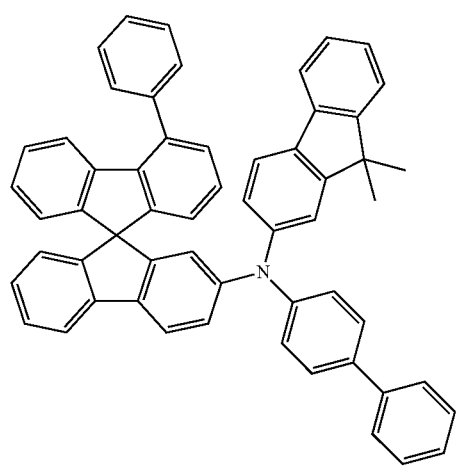
H-29
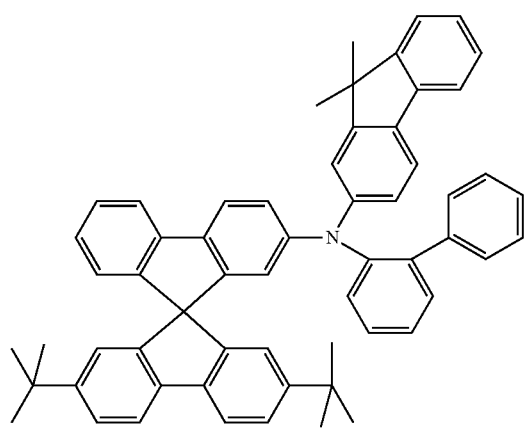

-continued
H-30
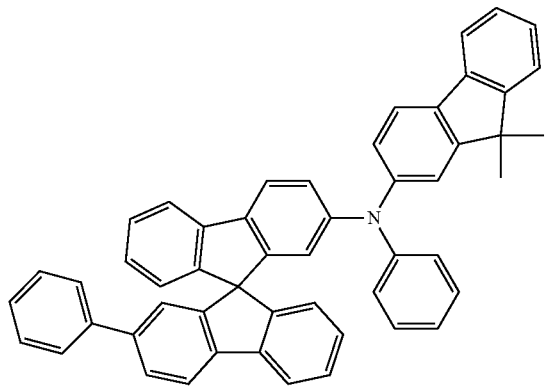
H-31
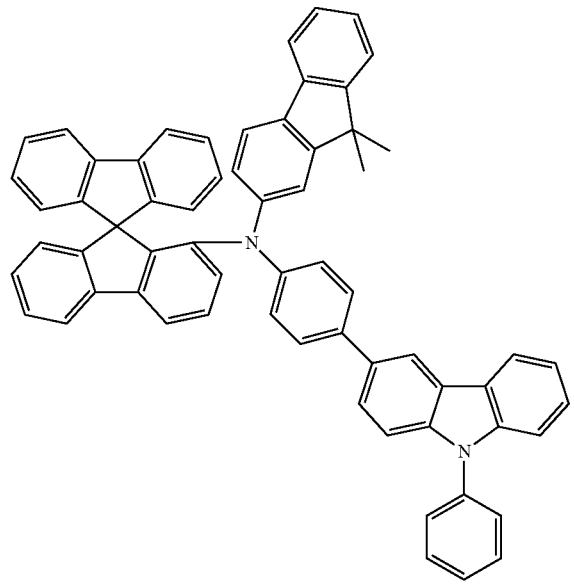
H-32
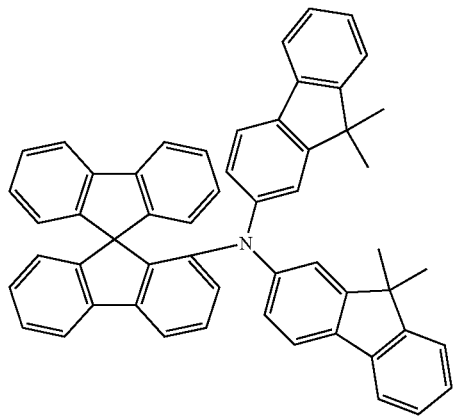
H-33
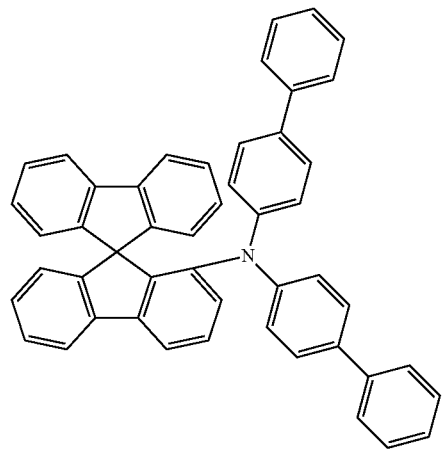
H-34
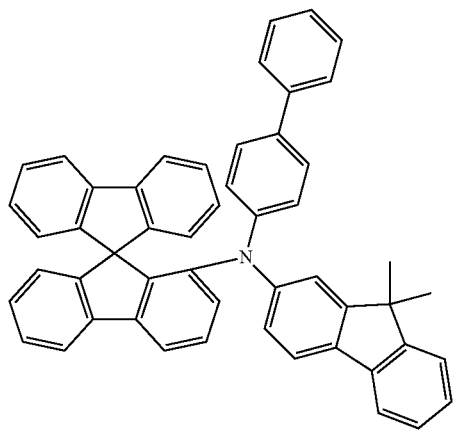
H-35
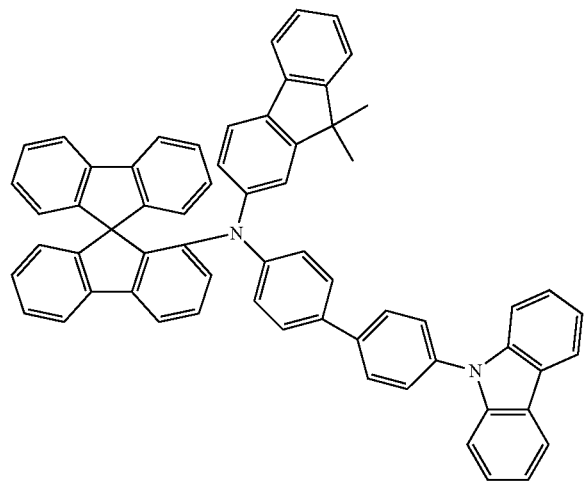

-continued
H-36
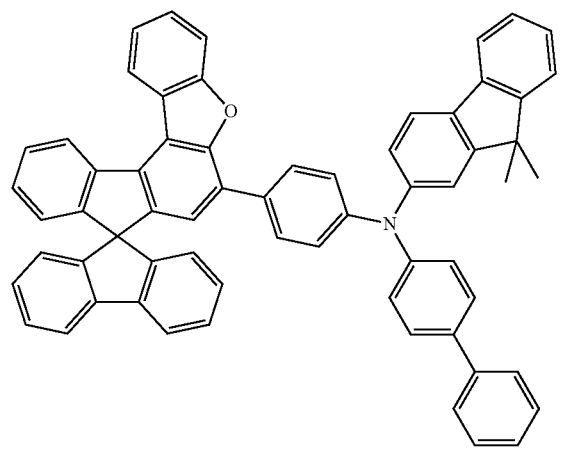
H-37
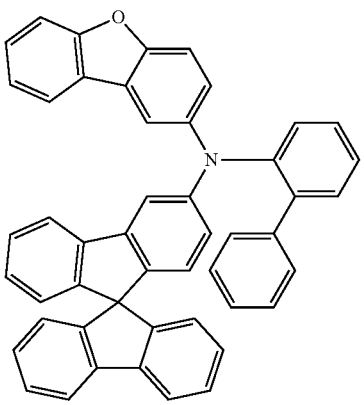
H-38
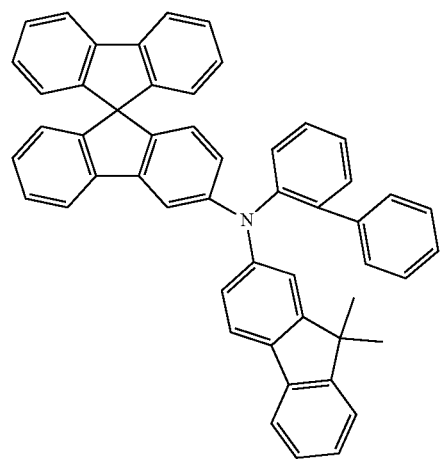
H-39
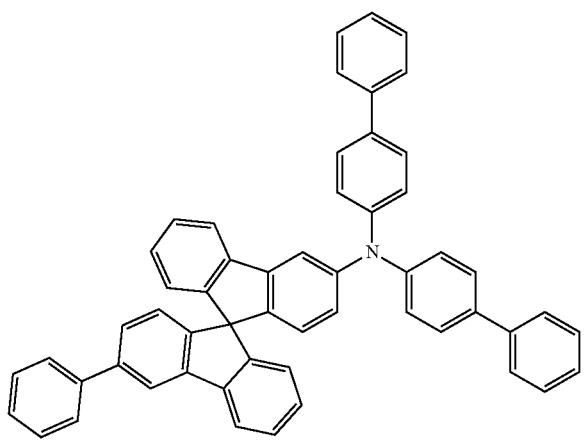
H-40
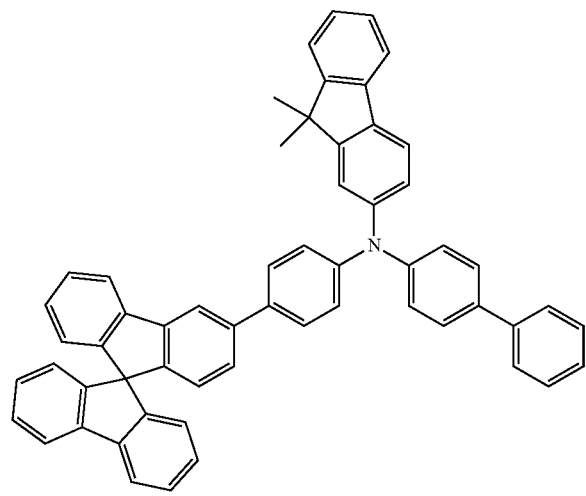
H-41
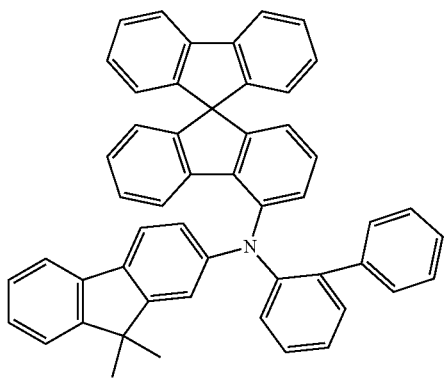

-continued
H-42
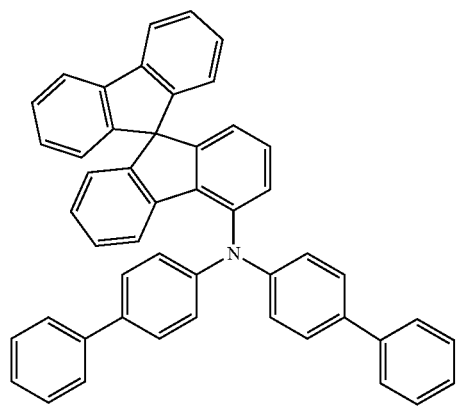
H-43
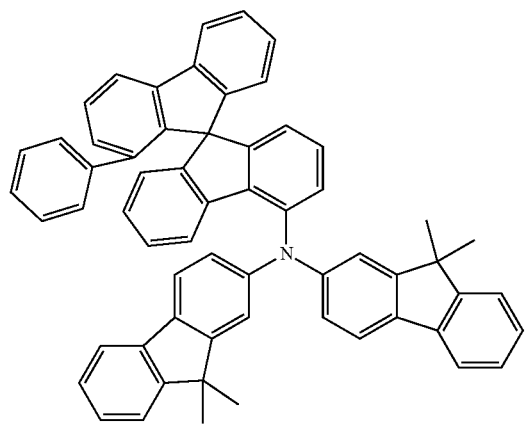
H-44
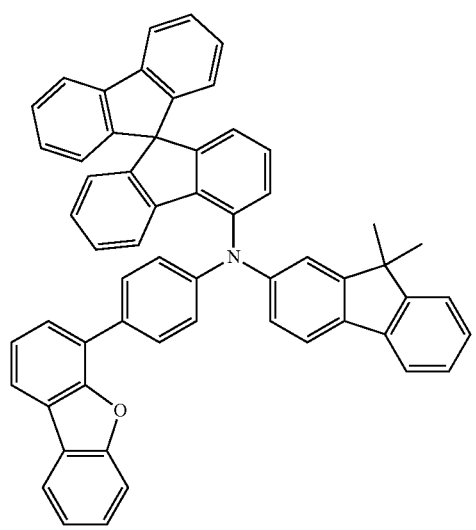
H-45
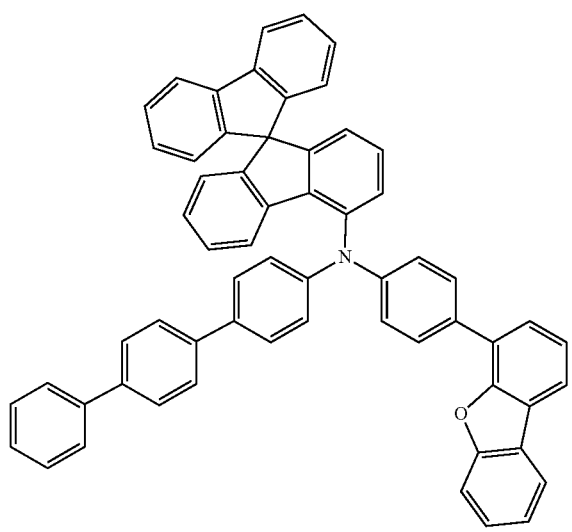
H-46
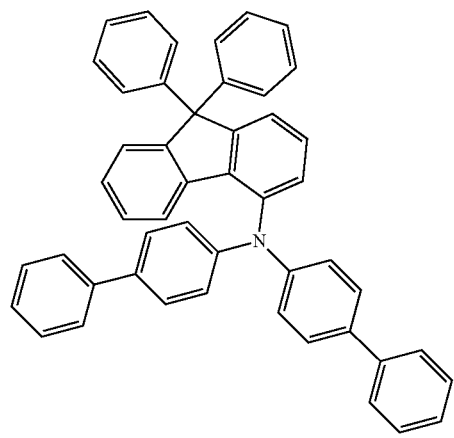
H-47
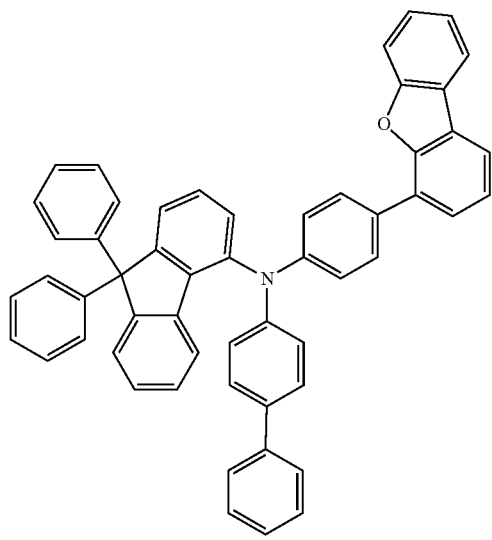

-continued
H-48
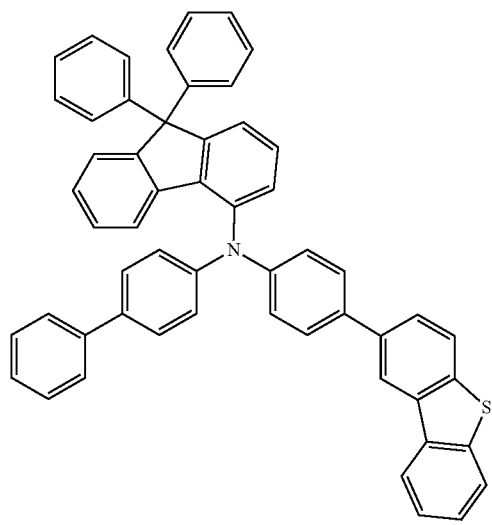
H-49
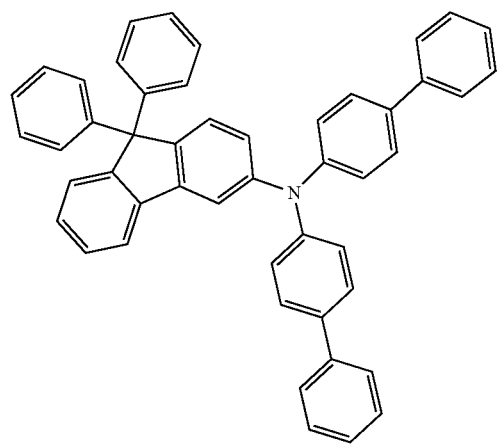
H-50
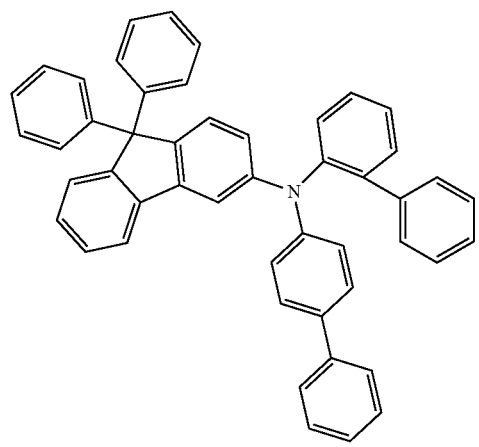
H-51
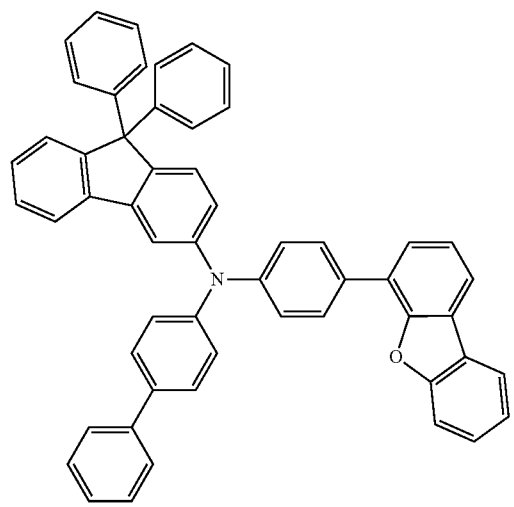
H-52
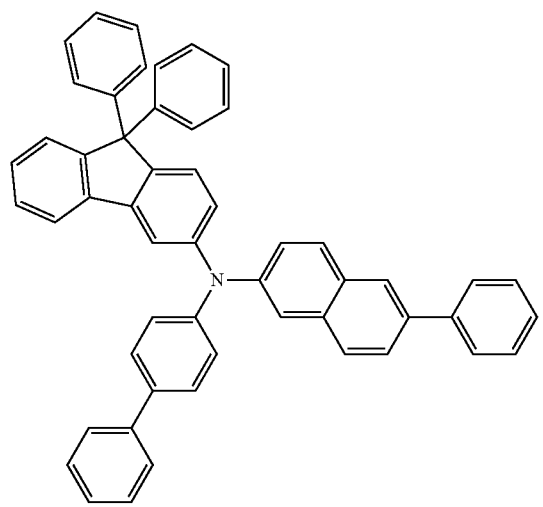
H-53
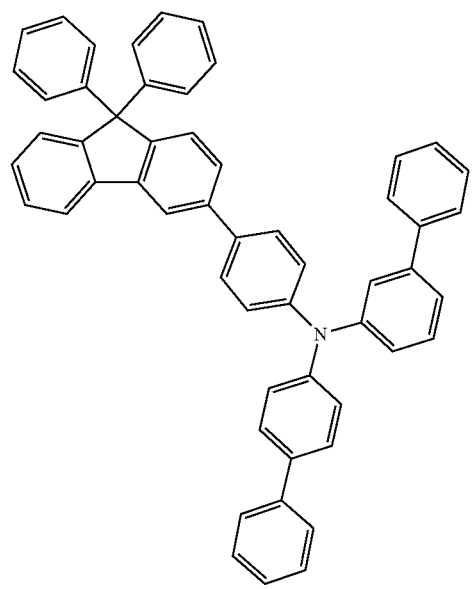

-continued
H-54
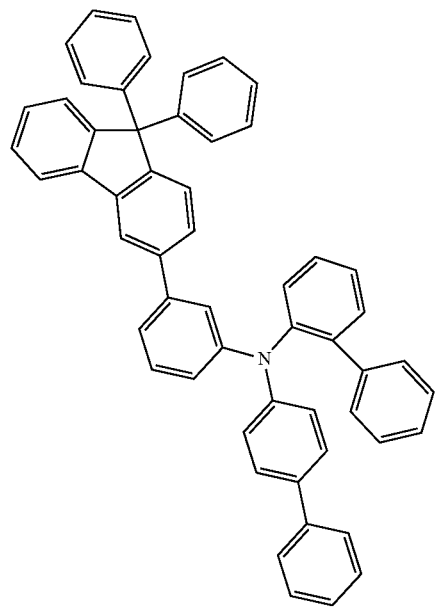
H-55
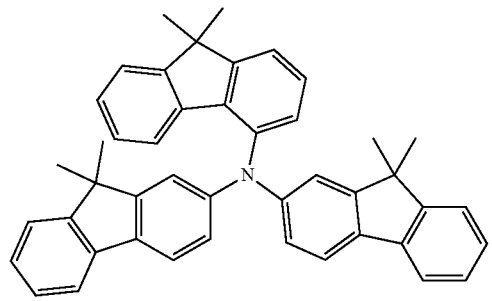
H-56
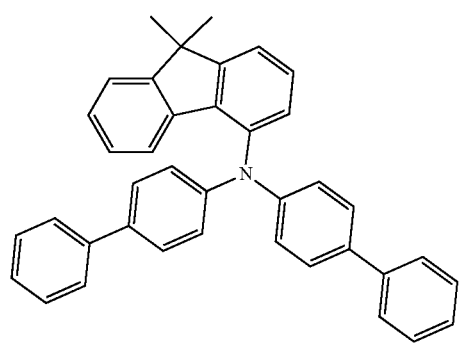
H-57
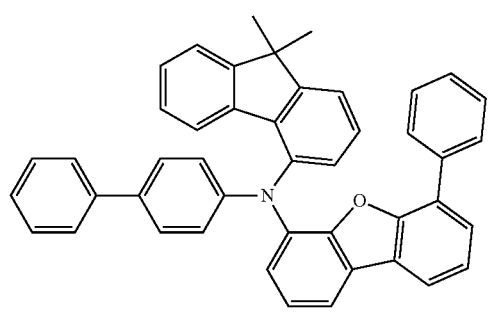
H-58
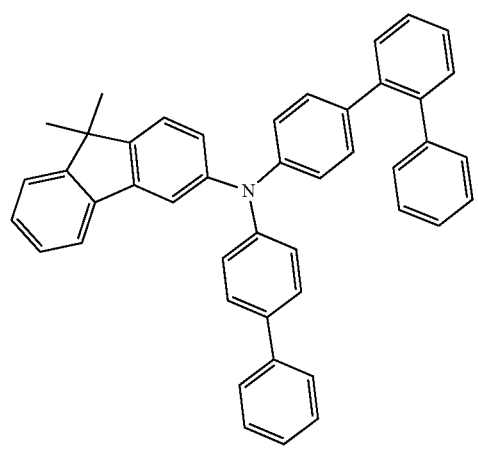
H-59
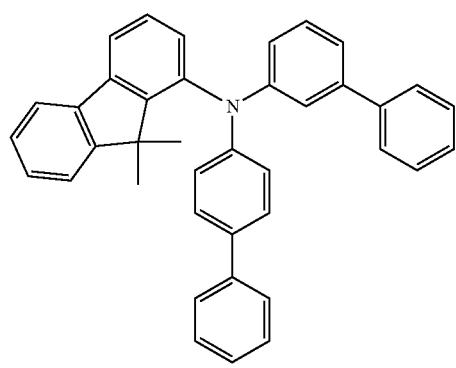

-continued
H-60
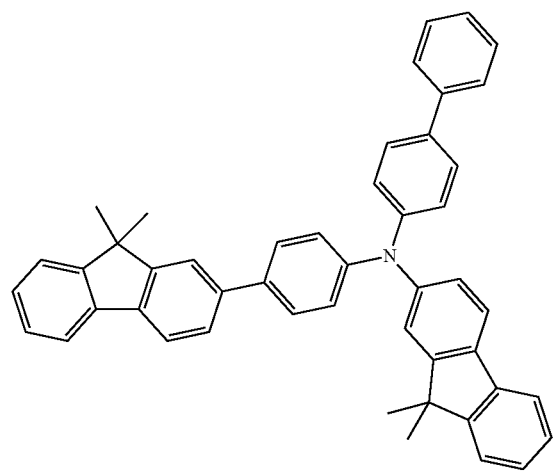
H-61
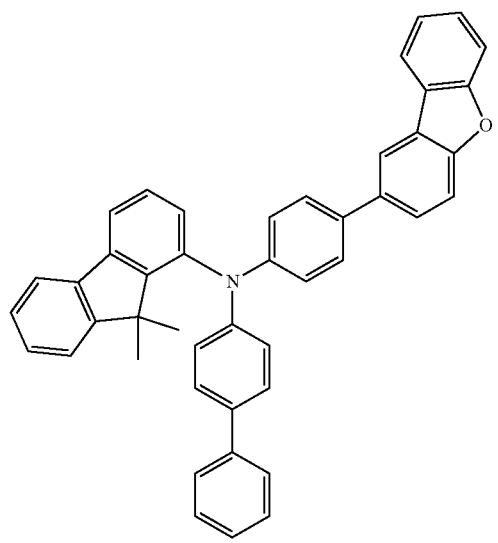
H-62
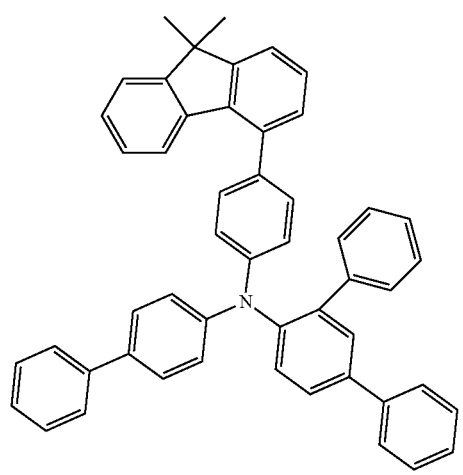
H-63
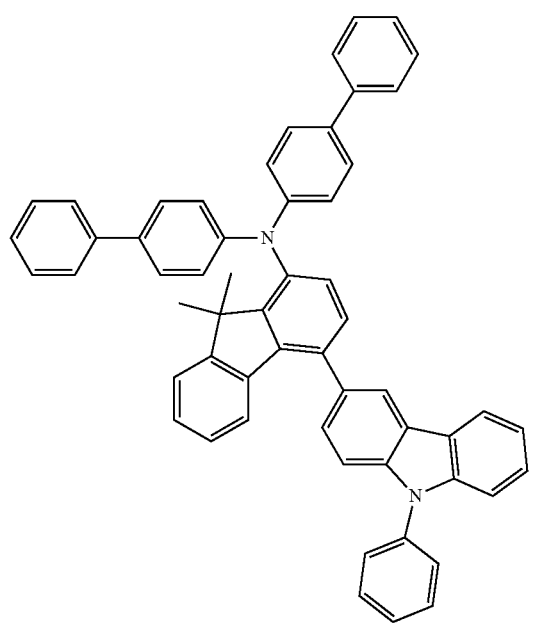

-continued
H-64
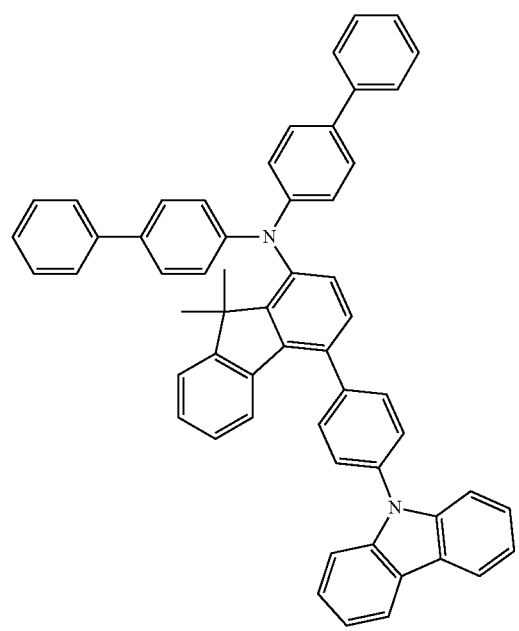
H-65
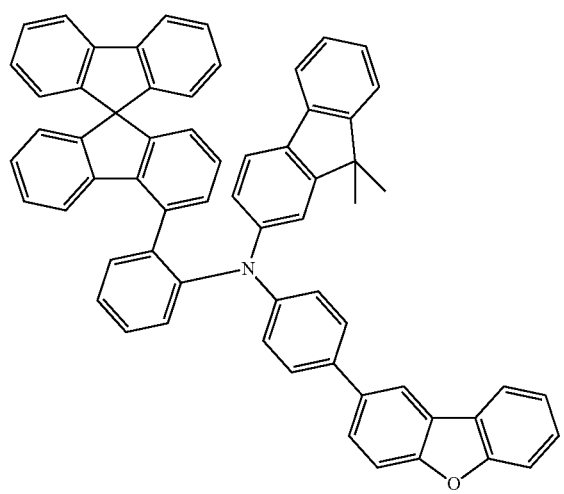
H-66
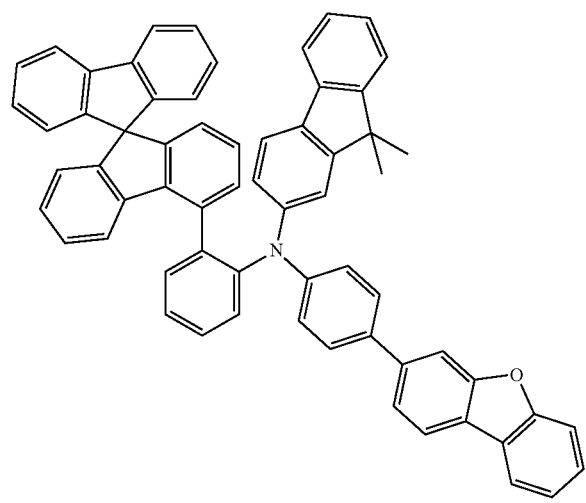
H-67
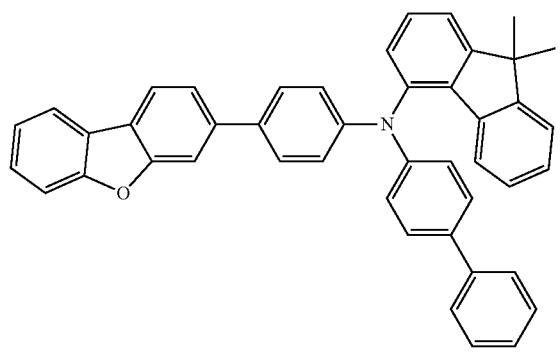

-continued

H-68

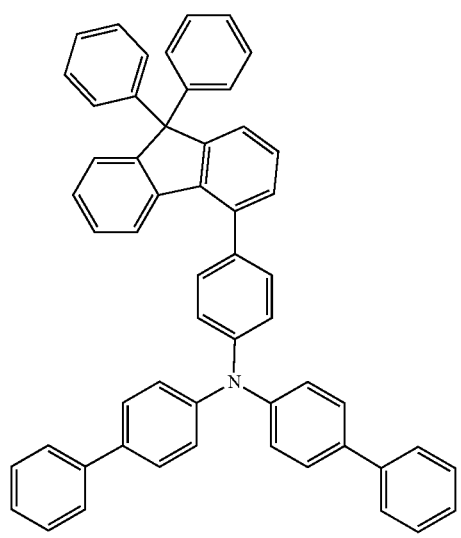

H-69

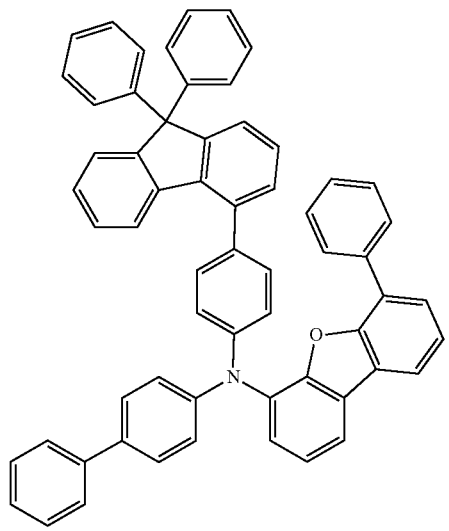

It is to be noted that the above materials can not only be used in combination with a material according to formula (I) in an OLED, but are generally highly suitable for use in OLEDs in a layer with hole transporting function, such as the layers mentioned above. The materials lead to OLEDs having good performance, in particular good lifetime and efficiency. They can be synthesized using reactions and methodology known in the art of synthesis of organic materials. For example, the fluorenyl amine compounds H-13, H-46 to H-59, H-61 to H-63 and H-67 to H-69 can be prepared using the synthesis procedures as disclosed in WO2014/015938.

Preferably, the inventive OLED comprises two or more different hole-transporting layers. The compound according to the present application may be used here in one or more of or in all the hole-transporting layers. In a preferred embodiment, the compound is used in exactly one or exactly two hole-transporting layers, and other compounds, preferably aromatic amine compounds, are used in the further hole-transporting layers present. Further compounds which are used alongside the compounds according to the present application, preferably in hole-transporting layers of the OLEDs of the invention, are especially indenofluorenamine derivatives, hexaazatriphenylene derivatives, amine derivatives with fused aromatics, monobenzoindenofluorenamines, dibenzoindenofluorenamines, spirobifluorenamines, fluorenamines, spirodibenzopyranamines, dihydroacridine derivatives, spirodibenzofurans and spirodibenzothiophenes, phenanthrenediarylamines, spirotribenzotropolones, spirobifluorenes with meta-phenyldiamine groups, spirobisacridines, xanthenediarylamines, and 9,10-dihydroanthracene spiro compounds with diarylamino groups.

Very particular preference is given to the use of spirobifluorenes substituted by diarylamino groups in the 4 position as hole-transporting compounds, and to the use of spirobifluorenes substituted by diarylamino groups in the 2 position as hole-transporting compounds.

Materials used for the electron transport layer may be any materials as used according to the prior art as electron transport materials in the electron transport layer. Especially suitable are aluminum complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives.

Particularly preferably electron transporting material for use in the OLEDs are shown below:

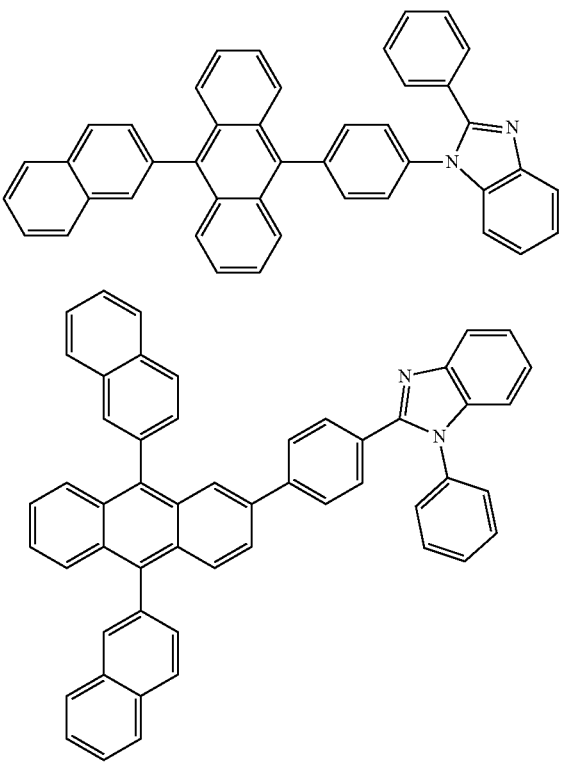

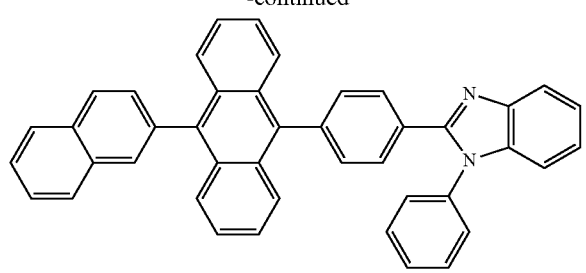
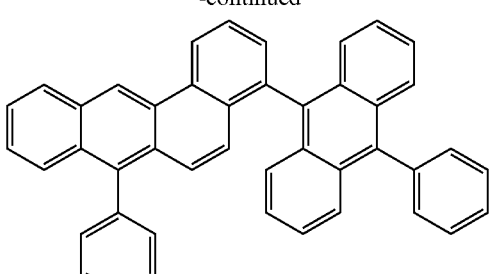
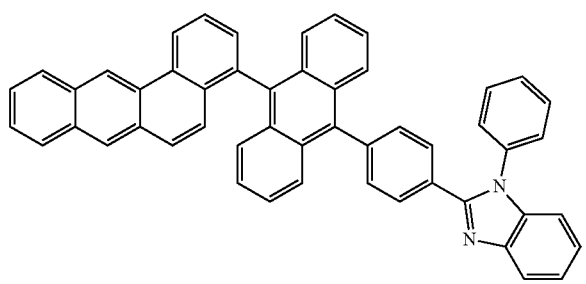
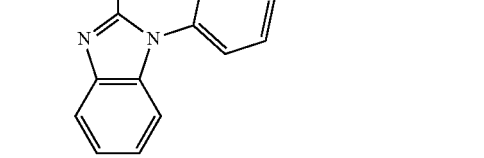
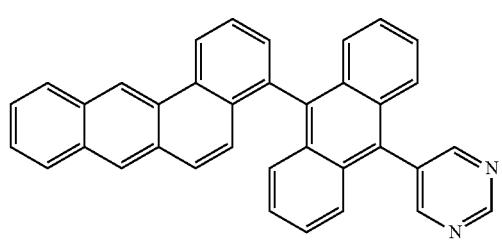
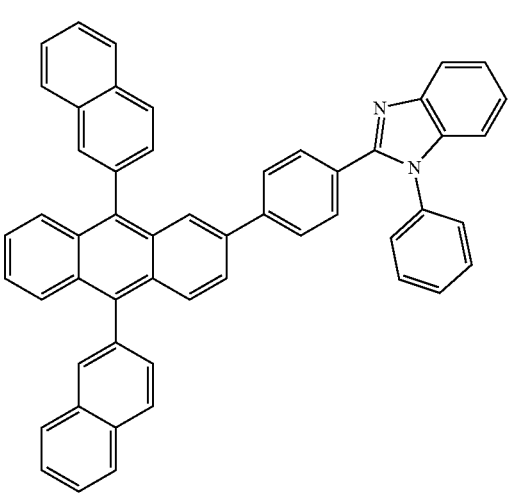
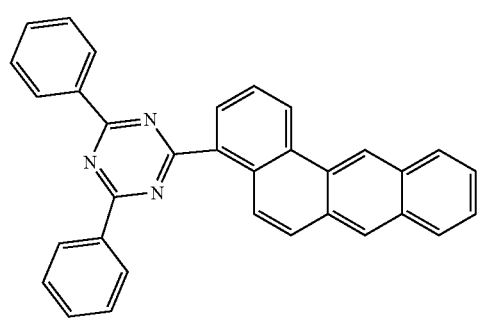
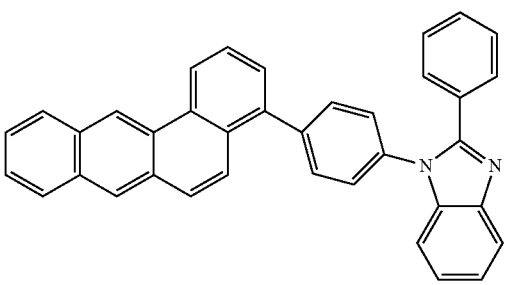
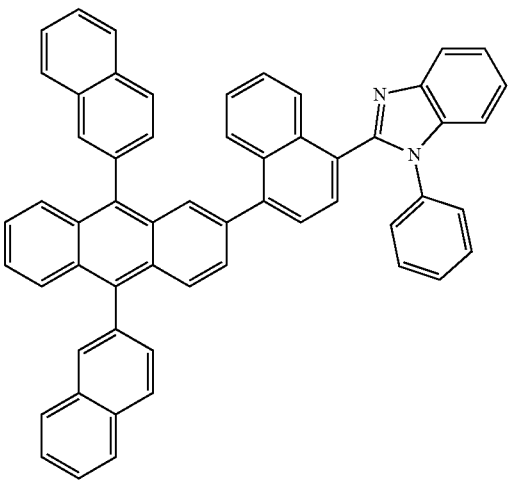

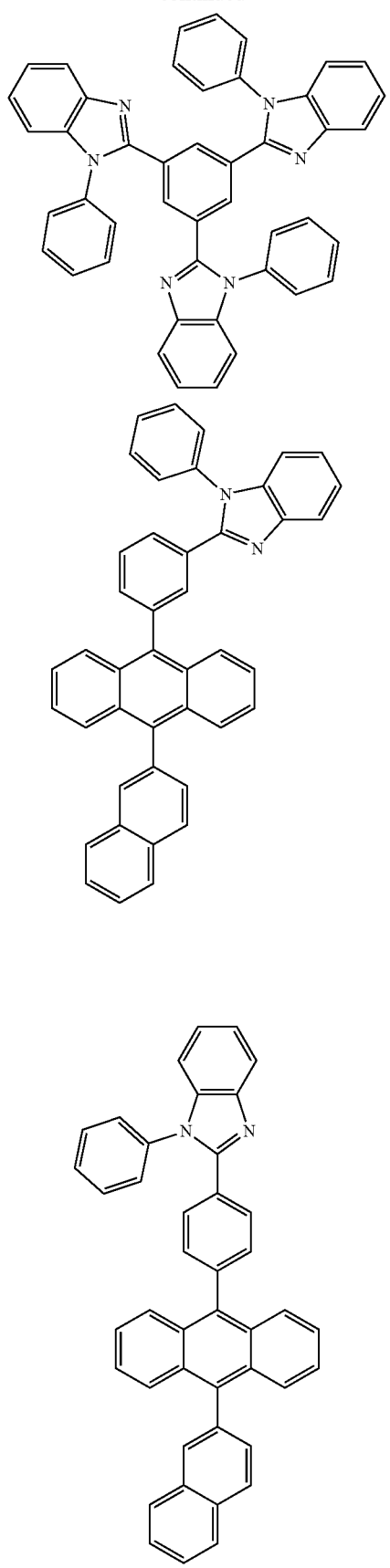
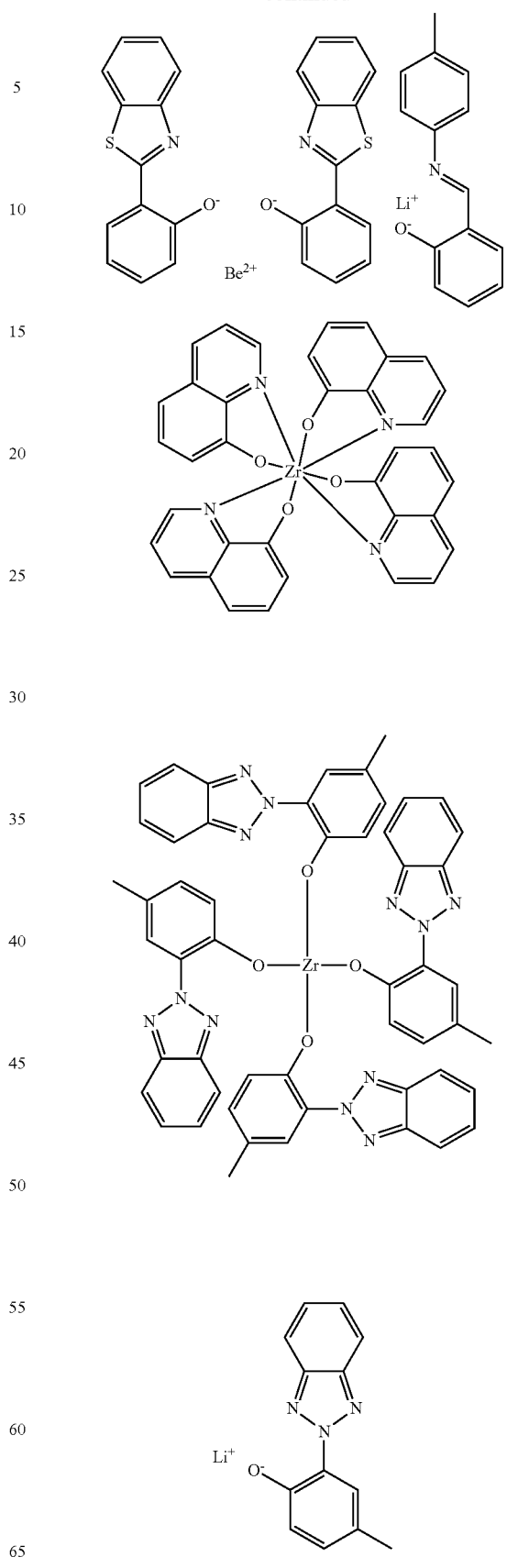

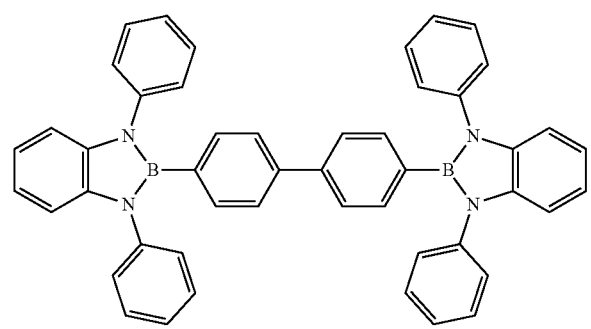
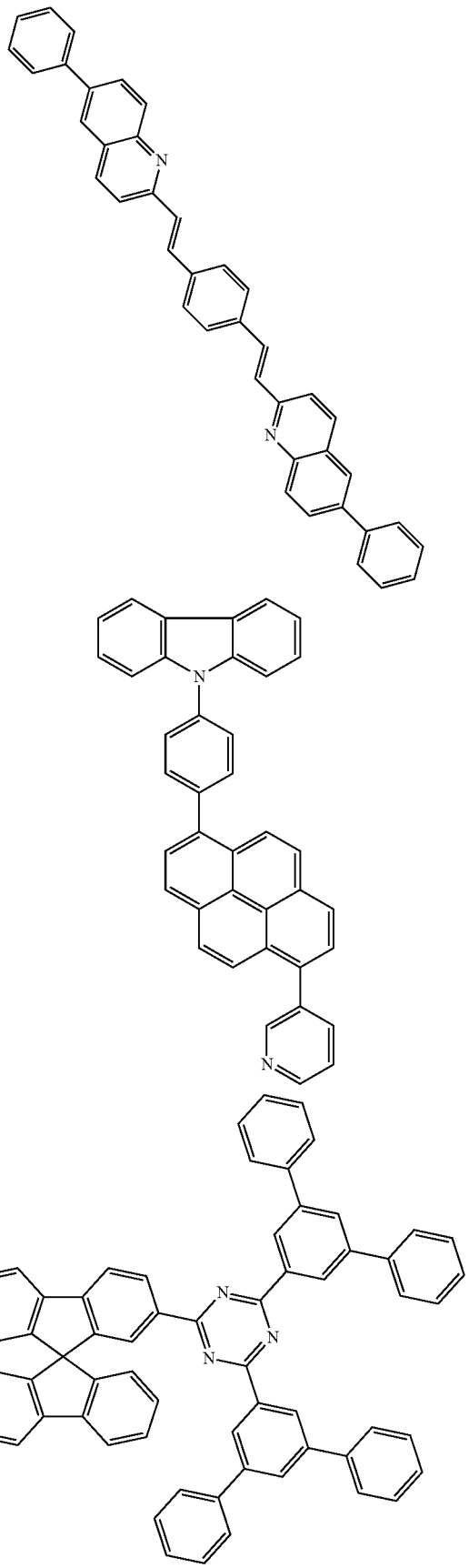

-continued

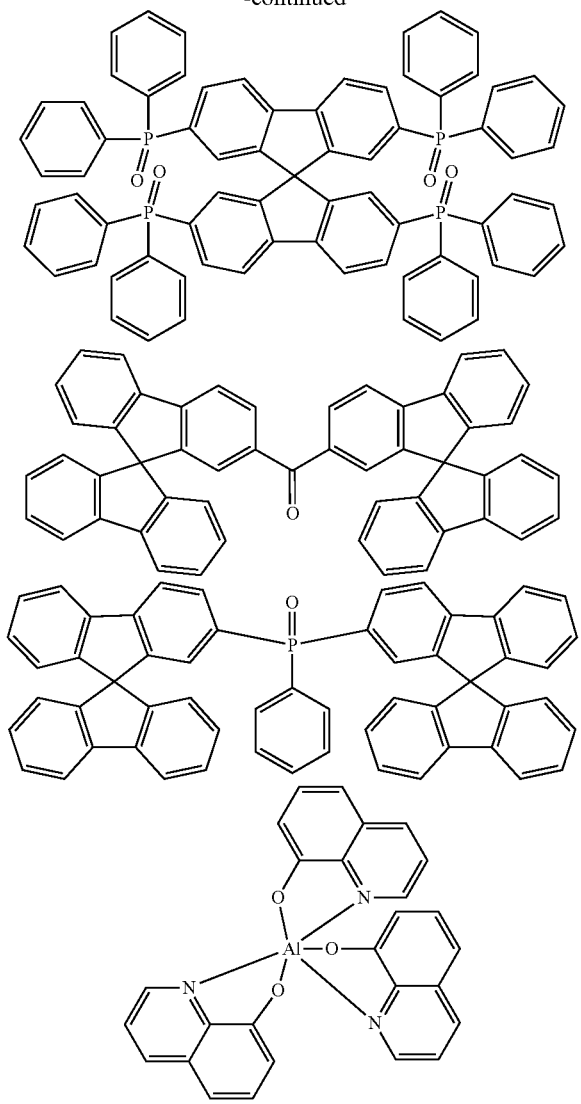

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable the irradiation of the organic material (organic solar cell) or the emission of light (OLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is structured appropriately (according to the application), contact-connected and finally sealed, in order to rule out damaging effects by water and air.

In a preferred embodiment, the electronic device is characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an electronic device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301).

Preference is additionally given to an electronic device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds are needed. High solubility can be achieved by suitable substitution of the compounds.

It is further preferable that an electronic device of the invention is produced by applying one or more layers from solution and one or more layers by a sublimation method.

According to the invention, the electronic devices comprising one or more compounds according to the present application can be used in displays, as light sources in lighting applications and as light sources in medical and/or cosmetic applications.

EXAMPLES

A) Synthesis Examples

The following syntheses are carried out under a protective-gas atmosphere, unless indicated otherwise. The starting materials can be purchased from ALDRICH or ABCR. The numbers in square brackets in the case of the starting materials known from the literature are the corresponding CAS numbers.

1) Synthesis of 6-(4-benzoylphenyl)-8-oxatricyclo[7.4.0.0²,⁷]trideca-1(13),2,4,6,9,11-hexaene 1a

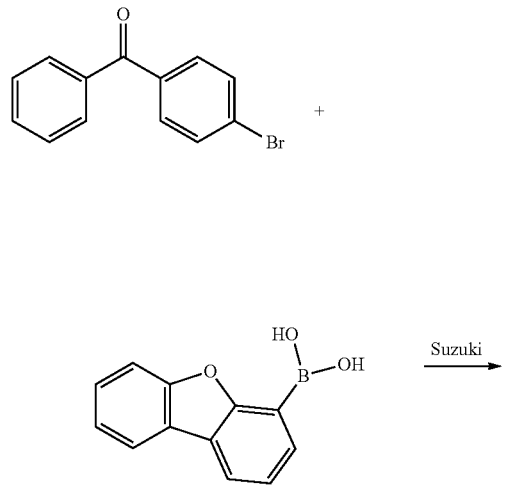

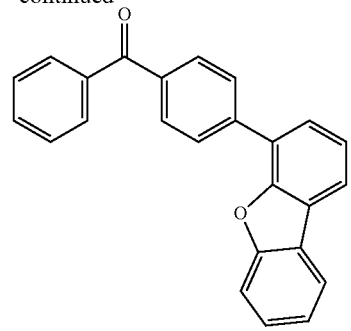

50 g (191.5 mmol) of (4-bromo-phenyl)-phenyl-methanone and 50.7 g (239.4 mmol) of dibenzofuran-4-yl-boronic acid, 26.5 g (23 mmol, 0.12 eq.) of Pd(P(Ph$_3$))$_4$, 680 mL 2M solution (1365 mmol, 7 eq.) of Na$_2$CO$_3$ are dissolved in 1300 mL of ethylenglycoldiethylether. The reaction mixture is stirred under reflux and agitated under an argon atmosphere for 12 hours. After cooling to room temperature, the mixture is extracted with ethyl acetate. The organic phase is dried with Na$_2$SO$_4$ and the filtrate is evaporated in vacuo, and the residue is purified by chromatography (mixture heptane/AcOEt). The product is isolated in the form of an off-white solid (46 g 68% of theory).

The synthesis of further derivatives is carried out analogously:

| Ex. | Boronic acid | Ketone | Product | Yield |
|---|---|---|---|---|
| 1b | | | | 76% |
| 1c | | | | 74% |

-continued

| Ex. | Boronic acid | Ketone | Product | Yield |
| --- | --- | --- | --- | --- |
| 1d | | | | 80% |
| 1f | | | | 70% |
| 1g | | | | 86% |
| 1h | | | | 71% |
| 1i | | | | 77% |

-continued
| Ex. | Boronic acid | Ketone | Product | Yield |
|---|---|---|---|---|
| 1j | 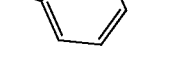 |  |  | 65% |
| 1k | 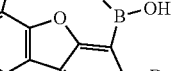 | 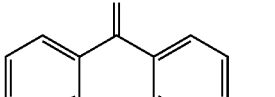 | 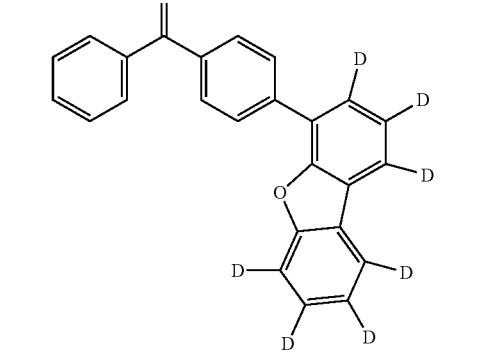 | 81% |
| 1l | 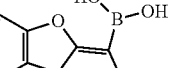 | 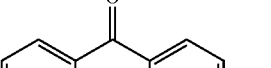 | 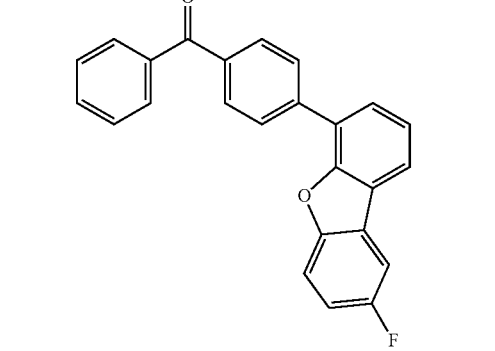 | 70% |
| 1ll | 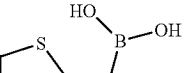 | 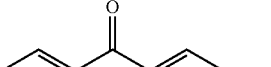 | 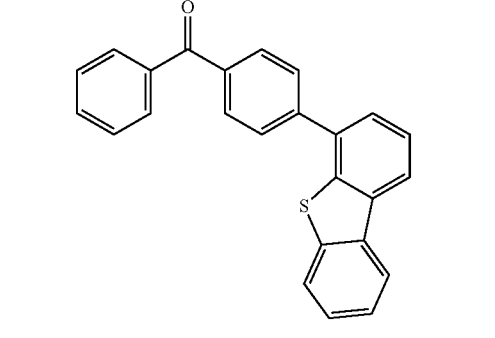 | 71% |
| 1m | 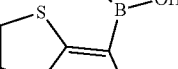 | 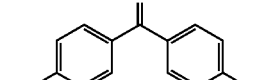 | 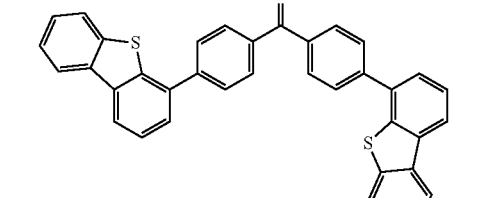 | 76% |

-continued
| Ex. | Boronic acid | Ketone | Product | Yield |
|---|---|---|---|---|
| 1n | 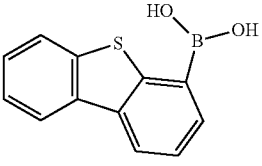 | 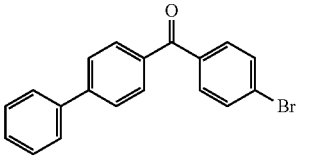 [SMILES: O=C(c1ccc(Br)cc1)c1ccc(-c2ccccc2)cc1] | 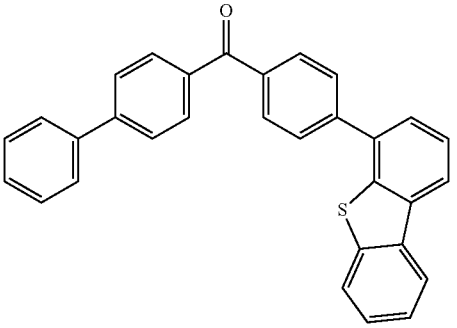 | 81% |
| 1o | 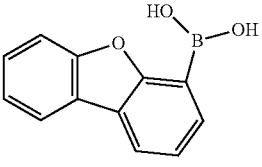 [SMILES: OB(O)c1cccc2c1oc1ccccc12] | 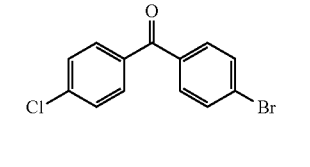 [SMILES: O=C(c1ccc(Cl)cc1)c1ccc(Br)cc1] | 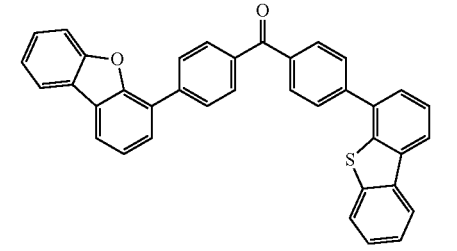 [SMILES: O=C(c1ccc(-c2cccc3c2oc2ccccc23)cc1)c1ccc(-c2cccc3c2sc2ccccc23)cc1] | 68% |
| 1p | 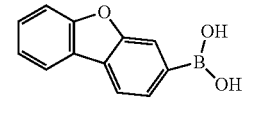 [SMILES: OB(O)c1ccc2c(c1)oc1ccccc12] | 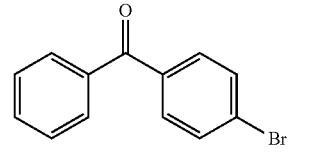 [SMILES: O=C(c1ccccc1)c1ccc(Br)cc1] | 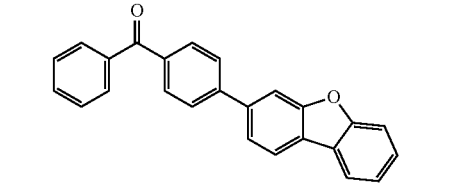 [SMILES: O=C(c1ccccc1)c1ccc(-c2ccc3c(c2)oc2ccccc23)cc1] | 80% |
| 1q | 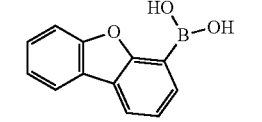 [SMILES: OB(O)c1cccc2c1oc1ccccc12] | 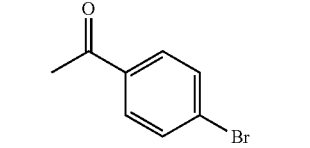 | 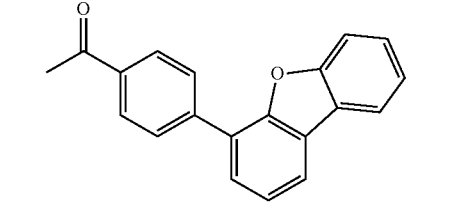 [SMILES: CC(=O)c1ccc(-c2cccc3c2oc2ccccc23)cc1] | 85% |
| 1r | 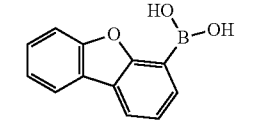 | 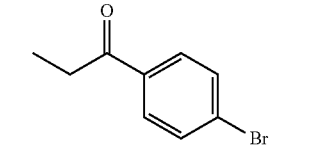 | 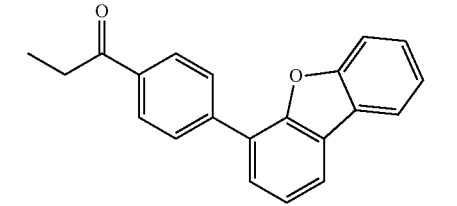 [SMILES: CCC(=O)c1ccc(-c2cccc3c2oc2ccccc23)cc1] | 78% |
| 1s | 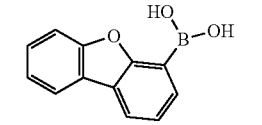 [SMILES: OB(O)c1cccc2c1oc1ccccc12] | 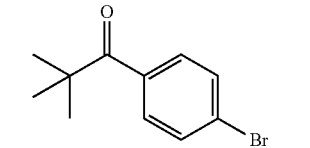 | 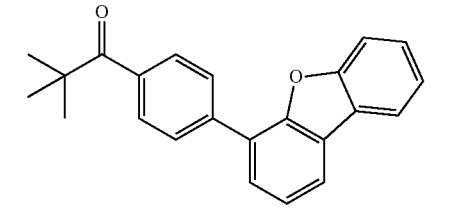 [SMILES: CC(C)(C)C(=O)c1ccc(-c2cccc3c2oc2ccccc23)cc1] | 75% |

-continued
| Ex. | Boronic acid | Ketone | Product | Yield |
|---|---|---|---|---|
| 1t | 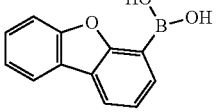 | 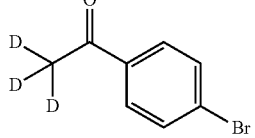 | 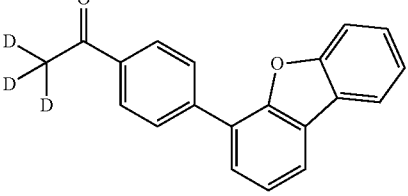 | 87% |
| 1u | 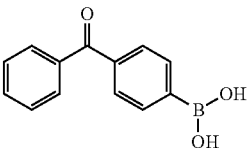 [SMILES: O=C(c1ccccc1)c1ccc(B(O)O)cc1] | 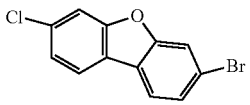 [SMILES: Clc1ccc2c(c1)oc1cc(Br)ccc12] | 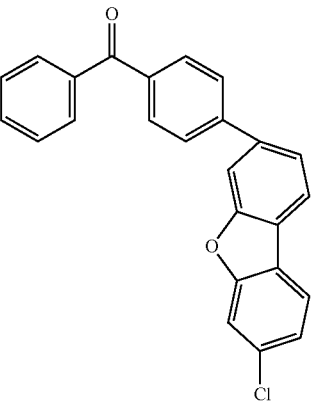 [SMILES: O=C(c1ccccc1)c1ccc(-c2ccc3c(c2)oc2cc(Cl)ccc23)cc1] | 76% |
| 1v | 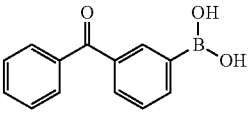 [SMILES: O=C(c1ccccc1)c1cccc(B(O)O)c1] | 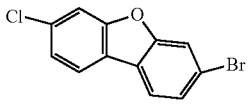 | 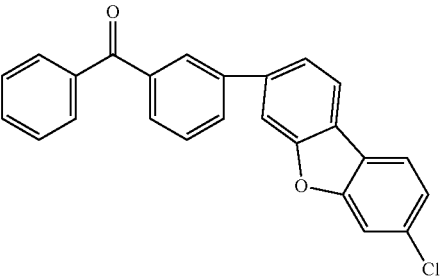 [SMILES: O=C(c1ccccc1)c1cccc(-c2ccc3c(c2)oc2cc(Cl)ccc23)c1] | 82% |
| 1w | 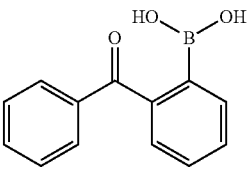 [SMILES: O=C(c1ccccc1)c1ccccc1B(O)O] | 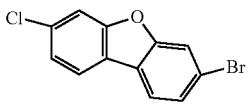 [SMILES: Clc1ccc2c(c1)oc1cc(Br)ccc12] | 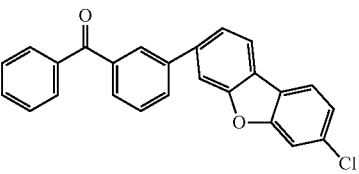 [SMILES: O=C(c1ccccc1)c1cccc(-c2ccc3c(c2)oc2cc(Cl)ccc23)c1] | 67% |
| 1x | 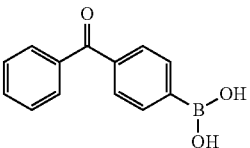 [SMILES: O=C(c1ccccc1)c1ccc(B(O)O)cc1] | 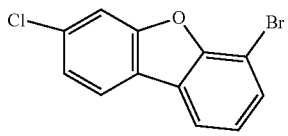 [SMILES: Clc1ccc2c(c1)oc1c(Br)cccc12] | 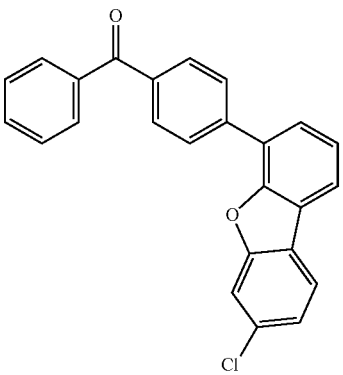 [SMILES: O=C(c1ccccc1)c1ccc(-c2cccc3c2oc2cc(Cl)ccc23)cc1] | 75% |

2) Synthesis of 6-[4-(9-phenyl-9H-fluoren-9-yl)phenyl]-8-oxatricyclo[7.4.0.0²,⁷]trideca-1(13),2,4,6,9,11-hexaene 2a

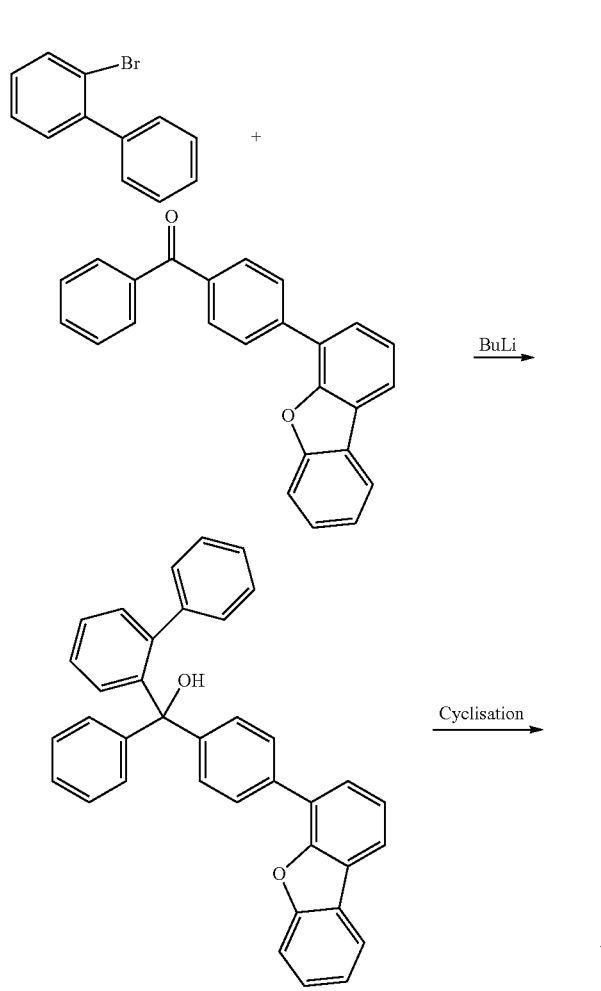

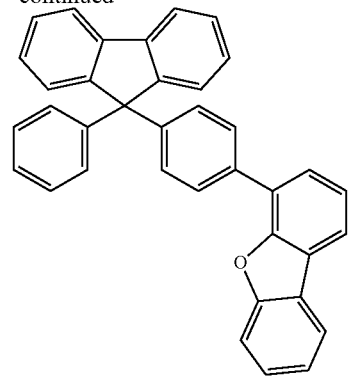

A solution of 2-bromo-biphenyl (36.8 g, 158 mmol) in THF (465 ml) is treated with 58 mL of n-BuLi (2.2 M in hexane, 144 mmol) under argon at −78° C. The mixture is stirred for 30 minutes. A solution of 1a (50 g, 144 mmol) in 230 mL THF is added dropwise. The reaction proceeds at −78° C. for 30 minutes and then is stirred at room temperature overnight. The reaction is quenched with water and the solid is filtered. Without further purification, a solution of the alcohol in 700 mL toluene and 2.9 g p-toluenesulfonic acid is refluxed overnight. After cooling, the organic phase is washed with water and the solvent is removed under vacuum. The product is isolated in the form of a white solid (55 g, 69% of theory).

The following compounds are synthesized analogously:

| Ex. | Ketone | Halogen | Product | Yield |
|---|---|---|---|---|
| 2b | (structure) | (structure) | (structure) | 81% |

-continued

| Ex. | Ketone | Halogen | Product | Yield |
|---|---|---|---|---|
| 2c | | | | 70% |
| 2d | | | | 65% |
| 2e | | | | 60% |
| 2f | | | | 80% |

-continued
| Ex. | Ketone | Halogen | Product | Yield |
|---|---|---|---|---|
| 2g | 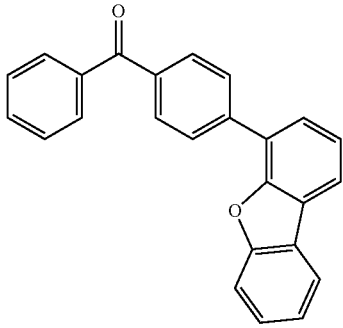 [SMILES: O=C(c1ccccc1)c1ccc(-c2cccc3c2oc2ccccc23)cc1] | 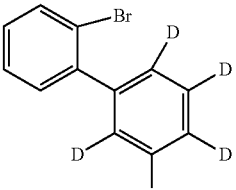 | 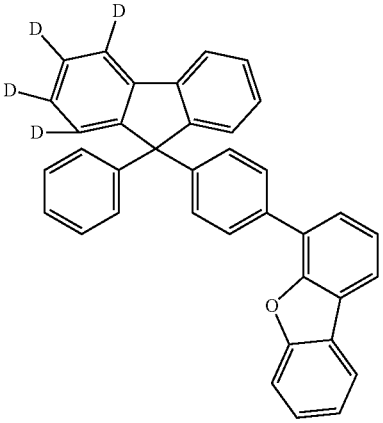 [SMILES: [2H]c1c([2H])c([2H])c2c(c1[2H])-c1ccccc1C2(c1ccccc1)c1ccc(-c2cccc3c2oc2ccccc23)cc1] | 75% |
| 2h | 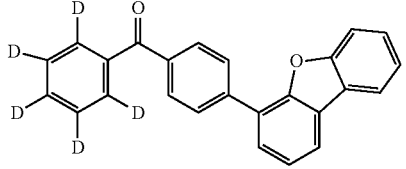 [SMILES: [2H]c1c([2H])c([2H])c(C(=O)c2ccc(-c3cccc4c3oc3ccccc34)cc2)c([2H])c1[2H]] | 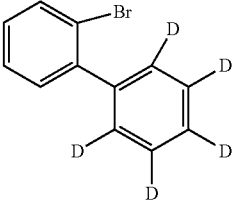 [SMILES: [2H]c1c([2H])c([2H])c(-c2ccccc2Br)c([2H])c1[2H]] | 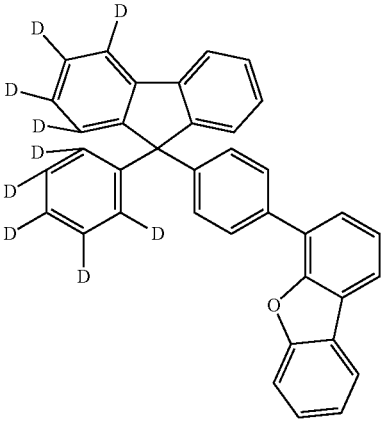 [SMILES: [2H]c1c([2H])c([2H])c(C2(c3ccc(-c4cccc5c4oc4ccccc45)cc3)c3ccccc3-c3c([2H])c([2H])c([2H])c([2H])c32)c([2H])c1[2H]] | 75% |
| 2i | 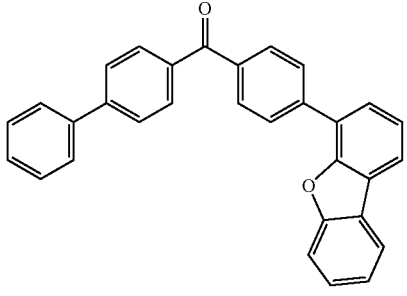 | 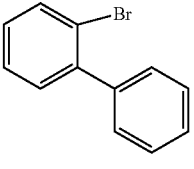 [SMILES: Brc1ccccc1-c1ccccc1] | 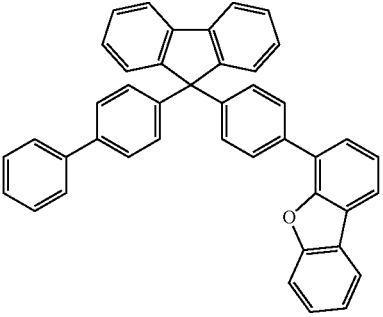 [SMILES: c1ccc(-c2ccc(C3(c4ccc(-c5cccc6c5oc5ccccc56)cc4)c4ccccc4-c4ccccc43)cc2)cc1] | 64% |
| 2j | 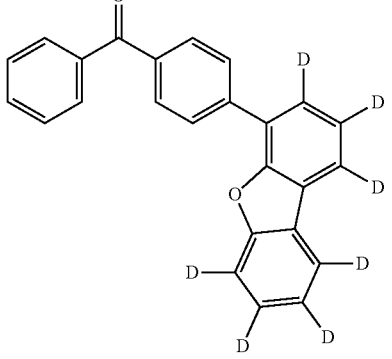 | 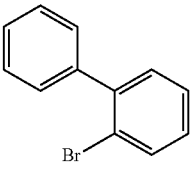 [SMILES: Brc1ccccc1-c1ccccc1] | 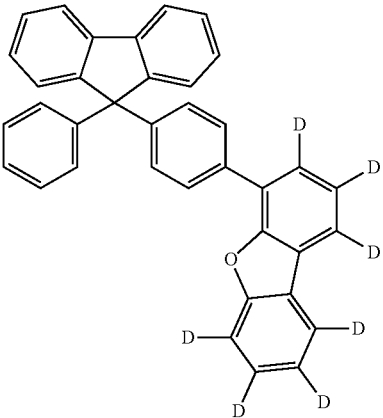 [SMILES: [2H]c1c([2H])c([2H])c2c(oc3c(-c4ccc(C5(c6ccccc6)c6ccccc6-c6ccccc65)cc4)c([2H])c([2H])c([2H])c32)c1[2H]] | 60% |

-continued
| Ex. | Ketone | Halogen | Product | Yield |
|---|---|---|---|---|
| 2k | 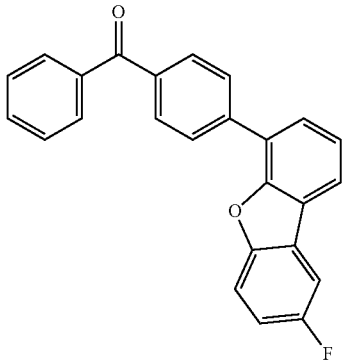 [SMILES: O=C(c1ccccc1)c1ccc(-c2cccc3c2oc2ccc(F)cc23)cc1] | 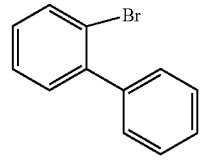 [SMILES: Brc1ccccc1-c1ccccc1] | 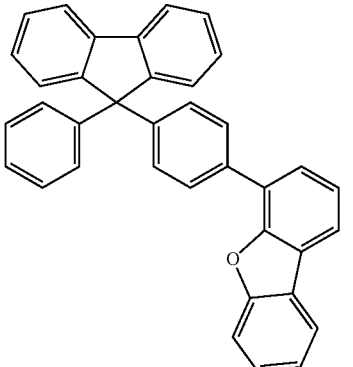 | 70% |
| 2l | 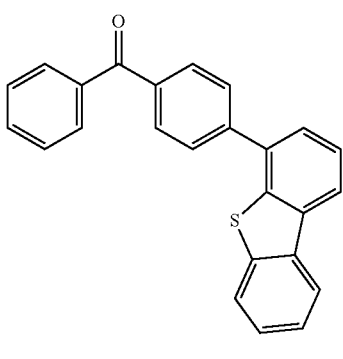 [SMILES: O=C(c1ccccc1)c1ccc(-c2cccc3c2sc2ccccc23)cc1] | 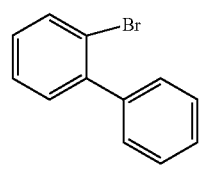 [SMILES: Brc1ccccc1-c1ccccc1] | 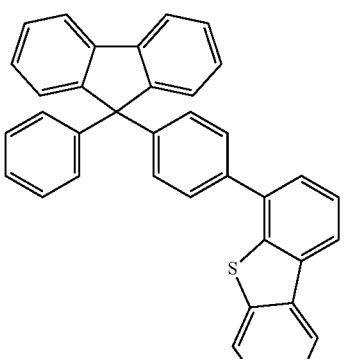 | 80% |
| 2m | 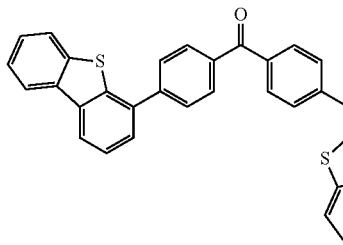 | 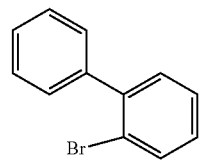 [SMILES: Brc1ccccc1-c1ccccc1] | 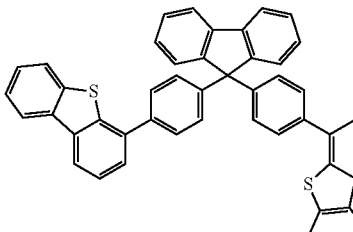 | 75% |
| 2n | 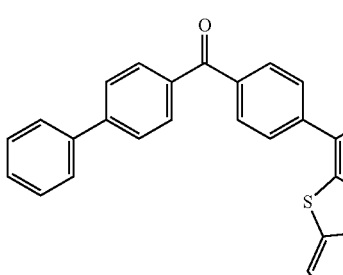 | 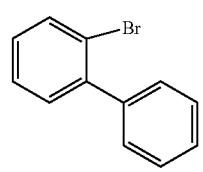 [SMILES: Brc1ccccc1-c1ccccc1] | 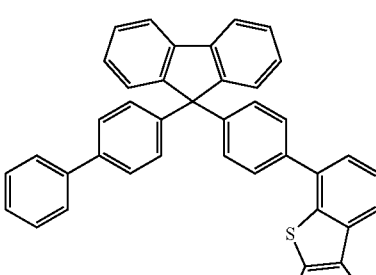 | 80% |

-continued

| Ex. | Ketone | Halogen | Product | Yield |
|---|---|---|---|---|
| 2o | | | | 77% |
| 2p | | | | 82% |
| 2q | | | | 84% |
| 2r | | | | 77% |

| Ex. | Ketone | Halogen | Product | Yield |
|---|---|---|---|---|
| 2s | 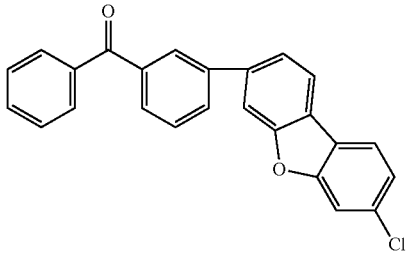 [SMILES: O=C(c1ccccc1)c1cccc(-c2ccc3c(c2)oc2cc(Cl)ccc23)c1] | 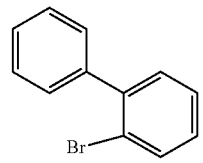 [SMILES: Brc1ccccc1-c1ccccc1] | 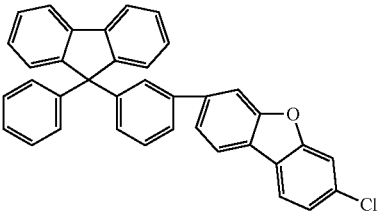 [SMILES: Clc1ccc2c(c1)oc1cc(-c3cccc(C4(c5ccccc5)c5ccccc5-c5ccccc54)c3)ccc12] | 75% |
| 2t | 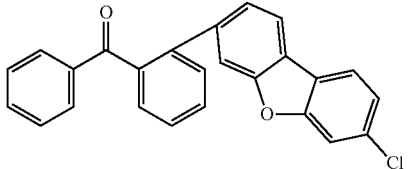 [SMILES: O=C(c1ccccc1)c1ccccc1-c1ccc2c(c1)oc1cc(Cl)ccc12] | 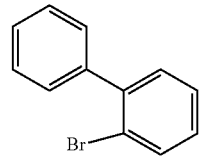 [SMILES: Brc1ccccc1-c1ccccc1] | 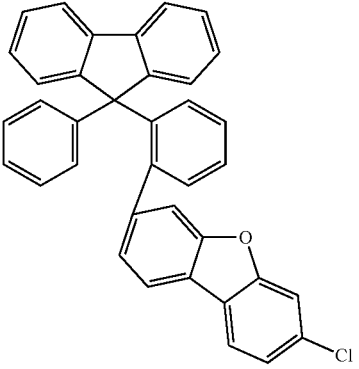 [SMILES: Clc1ccc2c(c1)oc1cc(-c3ccccc3C3(c4ccccc4)c4ccccc4-c4ccccc43)ccc12] | 68% |
| 2u | 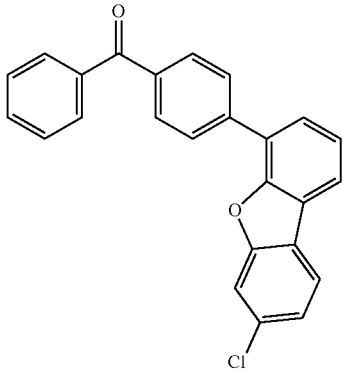 [SMILES: O=C(c1ccccc1)c1ccc(-c2cccc3c2oc2cc(Cl)ccc23)cc1] | 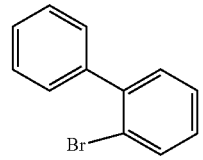 [SMILES: Brc1ccccc1-c1ccccc1] | 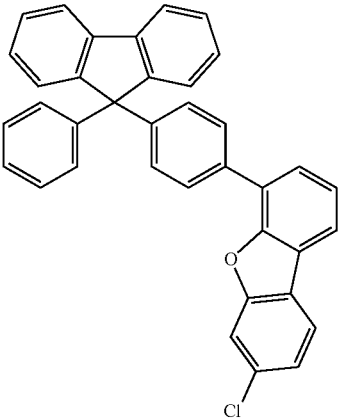 [SMILES: Clc1ccc2c(c1)oc1c(-c3ccc(C4(c5ccccc5)c5ccccc5-c5ccccc54)cc3)cccc12] | 65% |

265

3) Synthesis of 4,4,5,5-tetramethyl-2-{10-[4-(9-phenyl-9H-fluoren-9-yl)phenyl]-8-oxatricyclo[7.4.0.0²,⁷]trideca-1(9),2(7),3,5,10,12-hexaen-6-yl}-1,3,2-dioxaborolane 3a

266

-continued

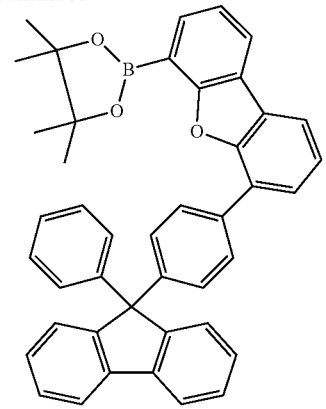

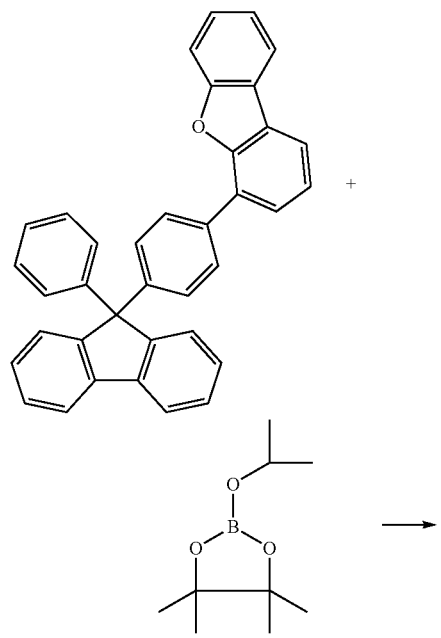

26.7 g (54.8 mmol) of fluorene 2a are dissolved in 350 ml of THF. At −10° C., 78 mL sec-BuLi (1.4 M in cyclohexane) are added dropwise. After 4 hours, 28.5 mL (137 mmol) of isopropoxy-tetramethyldioxaborolane are added dropwise. The reaction mixture is allowed to stir overnight at room temperature. After complete reaction, water and ethyl acetate are added to the crude, and the organic phase is separated, dried and concentrated. The residue is purified by chromatography on silica gel. Yield: 27.8 g (42 mmol), 77% of theory. Purity by GC>93%.

The following compounds are synthesized analogously:

| Ex. | Fluorene | Product | Yield |
|---|---|---|---|
| 3b | | | 81% |
| 3c | | | 70% |

-continued

| Ex. | Fluorene | Product | Yield |
|---|---|---|---|
| 3d | | | 65% |
| 3e | | | 60% |
| 3f | | | 80% |

-continued

| Ex. | Fluorene | Product | Yield |
|---|---|---|---|
| 3g | | | 75% |
| 3h | | | 75% |
| 3i | | | 64% |

| Ex. | Fluorene | Product | Yield |
|---|---|---|---|
| 3j | | | 60% |
| 3k | | | 70% |
| 3l | | | 80% |

-continued

| Ex. | Fluorene | Product | Yield |
|---|---|---|---|
| 3m | | | 75% |
| 3n | | | 80% |
| 3o | | | 77% |
| 3p | | | 82% |

| Ex. | Fluorene | Product | Yield |
|---|---|---|---|
| 3q | 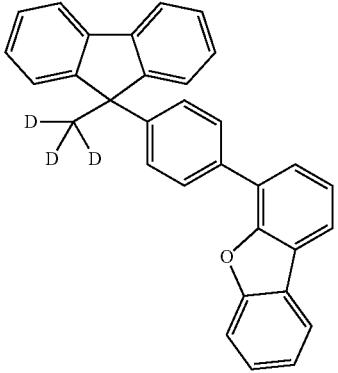 [SMILES: [2H]C([2H])([2H])C1(c2ccc(-c3cccc4c3oc3ccccc34)cc2)c2ccccc2-c2ccccc21] | 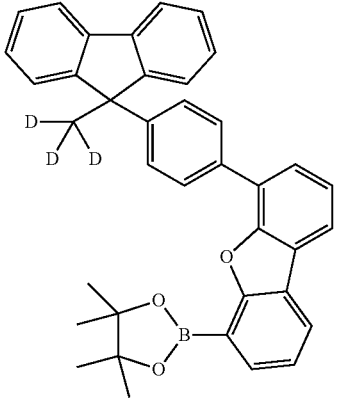 [SMILES: [2H]C([2H])([2H])C1(c2ccc(-c3cccc4c3oc3c(B5OC(C)(C)C(C)(C)O5)cccc34)cc2)c2ccccc2-c2ccccc21] | 84% |
The following compounds are synthesized analogously, with the only difference that $Br_2$ is added instead of iso-propoxy-tetramethyldioxaborolane:
| | | | |
|---|---|---|---|
| 3r | 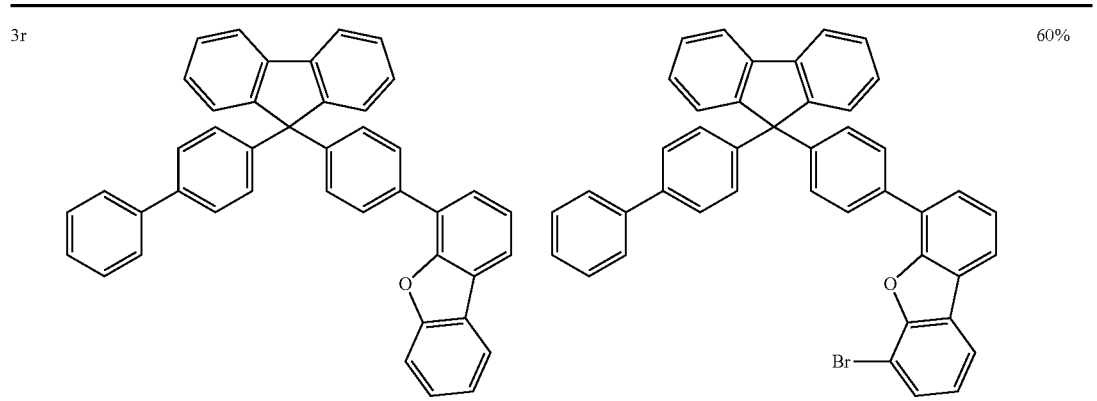 | | 60% |
| 3s | 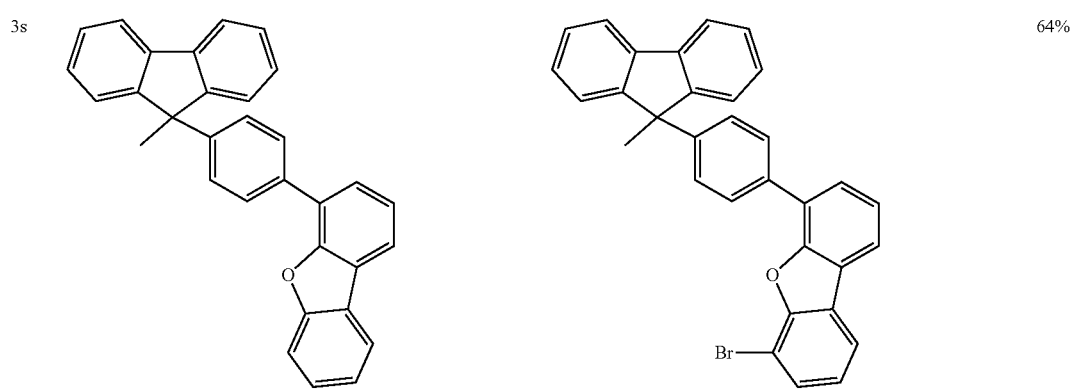 | | 64% |

| | | |
|---|---|---|
| 3t | 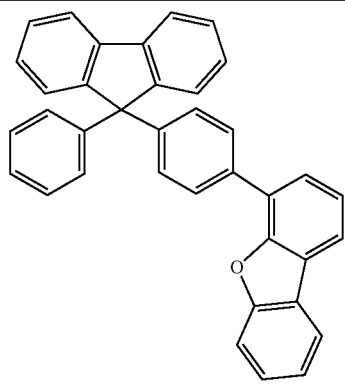 | 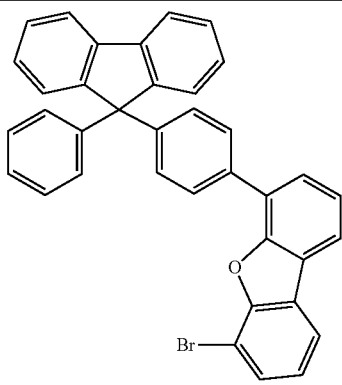 67% |
| 3u | 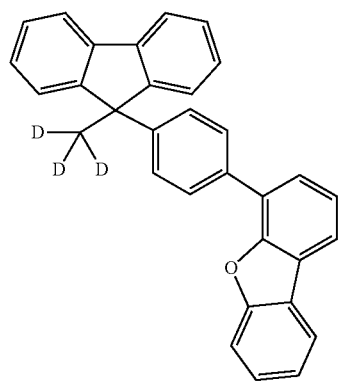 [SMILES: [2H]C([2H])([2H])C1(c2ccc(-c3cccc4c3oc3ccccc34)cc2)c2ccccc2-c2ccccc21] | 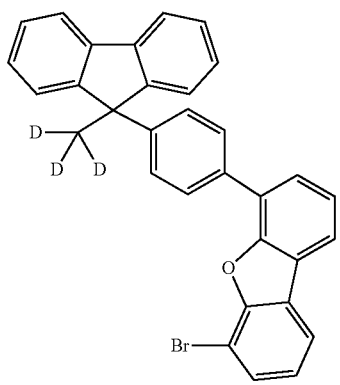 [SMILES: [2H]C([2H])([2H])C1(c2ccc(-c3cccc4c3oc3c(Br)cccc34)cc2)c2ccccc2-c2ccccc21] 62% |
4) Synthesis of N-{[1,1'-biphenyl]-4-yl}-9,9-dimethyl-N-(4-{10-[4-(9-phenyl-9H-fluoren-9-yl)phenyl]-8-oxatricyclo[7.4.0.0²,⁷]trideca-1(9),2,4,6,10,12-hexaen-6-yl}phenyl)-9H-fluoren-2-amine 4a
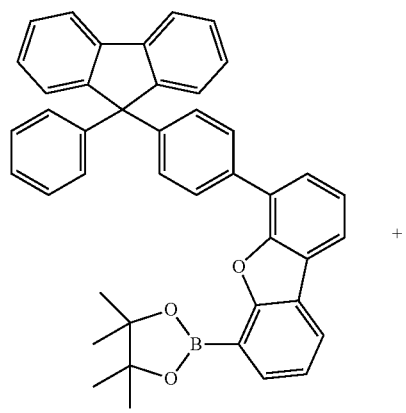
+
-continued
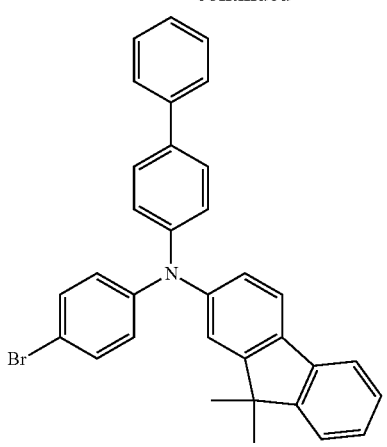
→

-continued

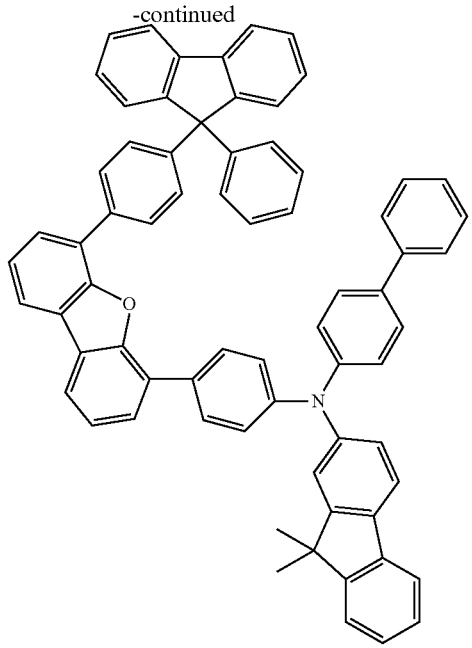

9.9 g (19.1 mmol) of N-{[1,1'-biphenyl]-4-yl}-N-(4-bromophenyl)-9,9-dimethyl-9H-fluoren-2-amine, 19.1 mmol fluorene 3a, 0.7 g (0.95 mmol) of $PdCl_2(Cy)_3$, 5.8 g (38.1 mmol) of cesium fluoride are dissolved in 115 mL of THF. The reaction mixture is refluxed and agitated under an argon atmosphere for 12 hours and after cooling to room temperature, the mixture is filtered through Celite. The filtrate is evaporated in vacuo, and the residue is crystallised from heptane. The crude product is extracted in a Soxhlet extractor (toluene) and purified by zone sublimation in vacuo twice. The product is isolated in the form of a white solid (8 g, 50% of theory).

The following compounds are synthesized analogously:

| Ex. | Boronic ester | Amine | Product | Yield |
|---|---|---|---|---|
| 4b | 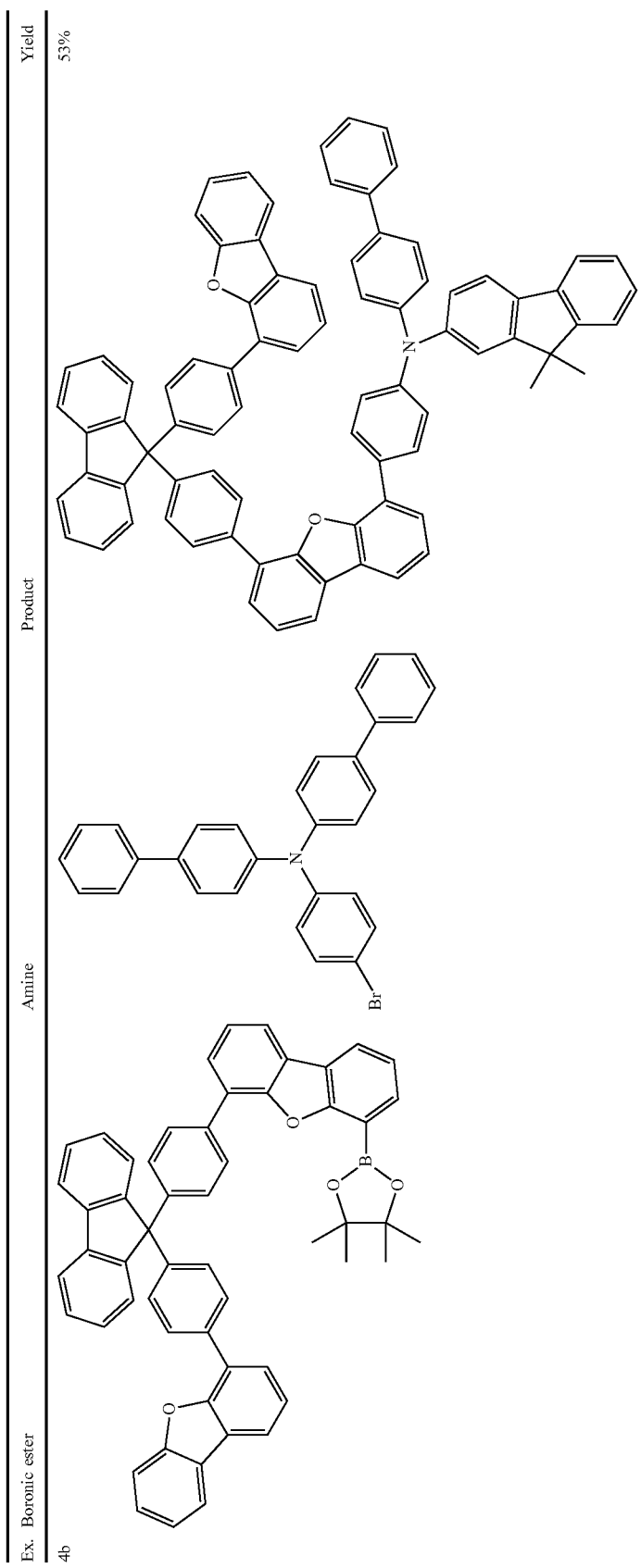 | | | 53% |

| Ex. | Boronic ester | Amine | Product | Yield |
|---|---|---|---|---|
| 4c | | | | 65% |

| Ex. | Boronic ester | Amine | Product | Yield |
|---|---|---|---|---|
| 4d | 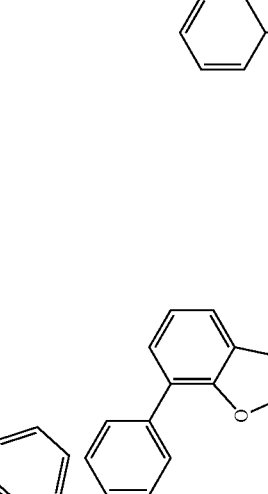 | 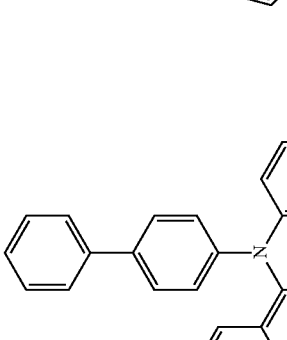 | 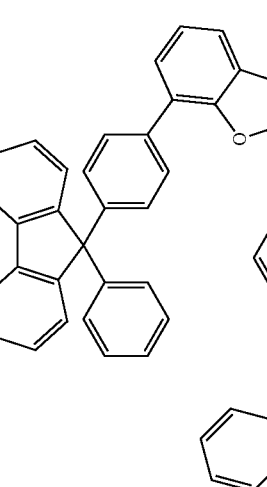 | 50% |

-continued
| Ex. | Boronic ester | Amine | Product | Yield |
|---|---|---|---|---|
| 4e | 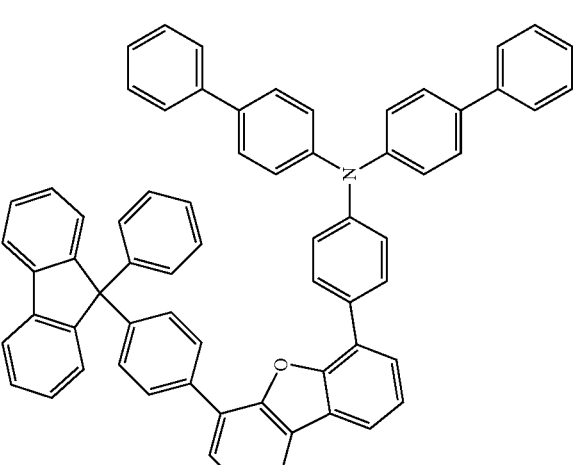 | 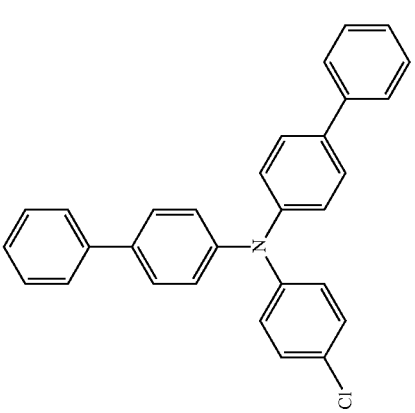 | | 53% |

| Ex. | Boronic ester | Amine | Product | Yield |
|---|---|---|---|---|
| 4f | 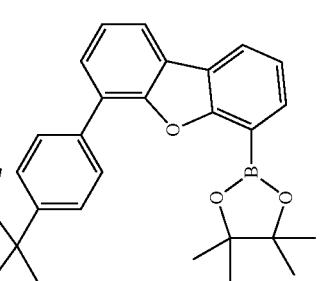 | 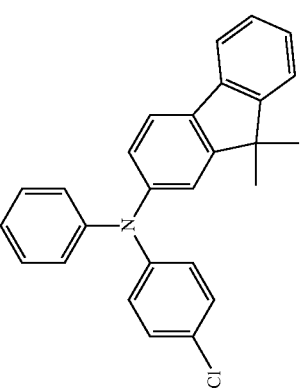 | 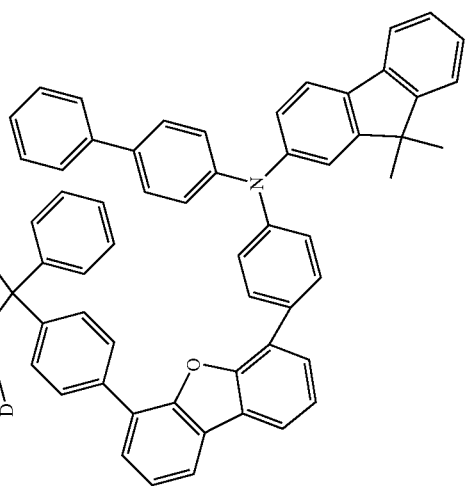 | 60% |

| Ex. | Boronic ester | Amine | Product | Yield |
|---|---|---|---|---|
| 4g | 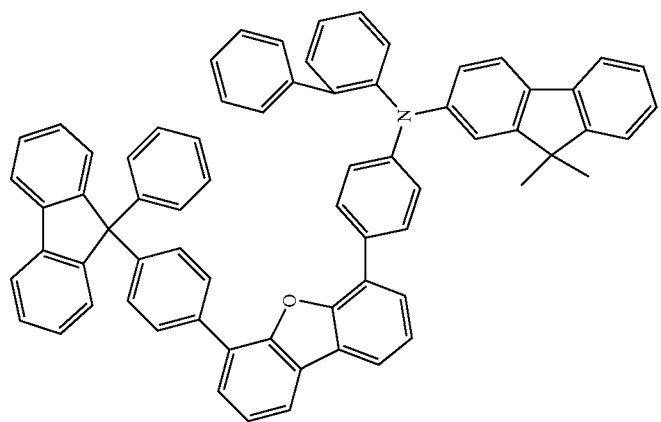 | 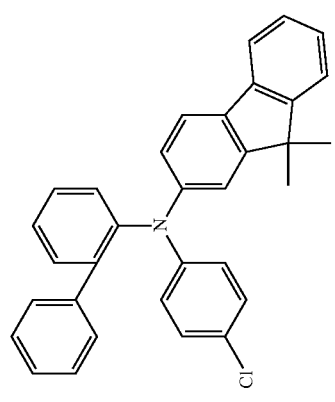 | | 55% |

| Ex. | Boronic ester | Amine | Product | Yield |
|---|---|---|---|---|
| 4h | 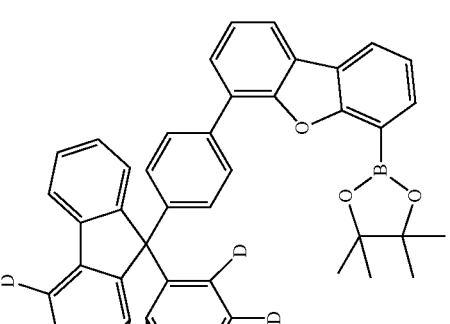 | 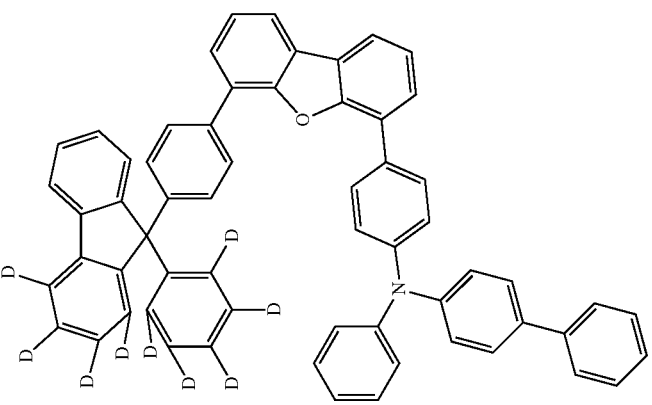 | 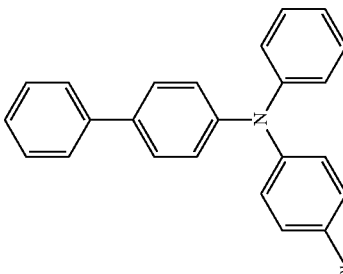 | 65% |

| Ex. | Boronic ester | Amine | Product | Yield |
|---|---|---|---|---|
| 4i | | | | 54% |

| Ex. | Boronic ester | Amine | Product | Yield |
|---|---|---|---|---|
| 4j | 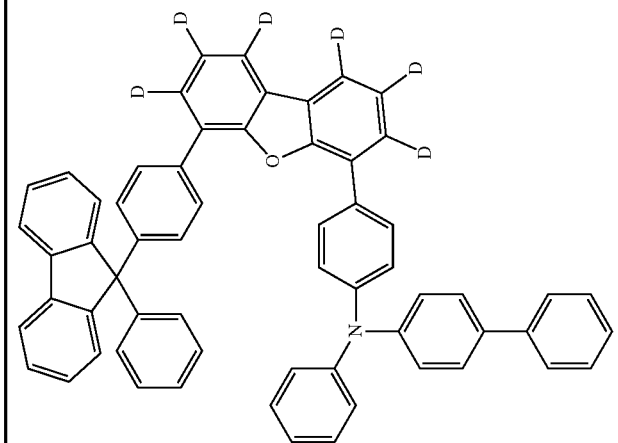 | 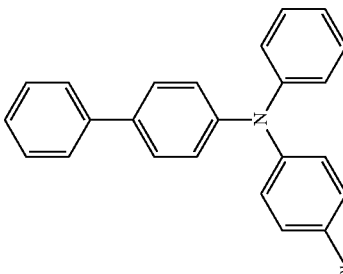 | | 65% |

| Ex. | Boronic ester | Amine | Product | Yield |
|---|---|---|---|---|
| 4k |  |  | 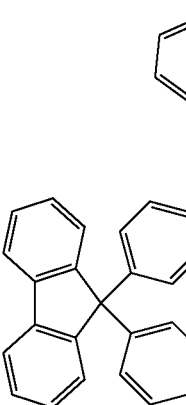 | 45% |

| Ex. | Boronic ester | Amine | Product | Yield |
|---|---|---|---|---|
| 41 | 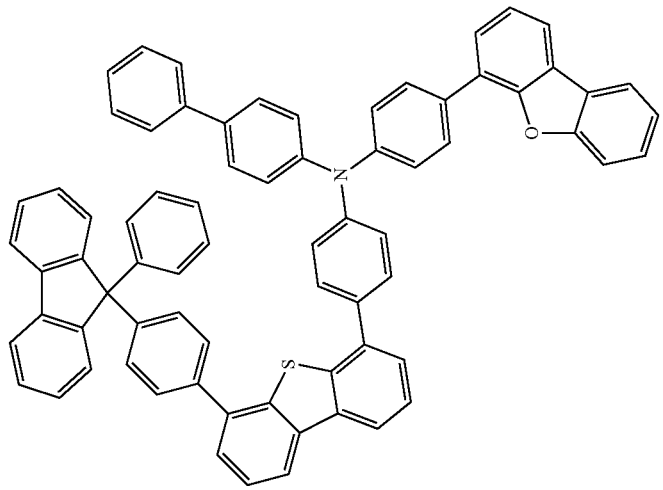 | 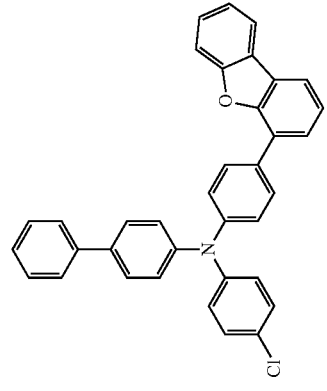 | | 80% |

| Ex. | Boronic ester | Amine | Product | Yield |
|---|---|---|---|---|
| 4m | [structure] | [structure] | [structure] | 67% |

| Ex. | Boronic ester | Amine | Product | Yield |
|---|---|---|---|---|
| 4n | 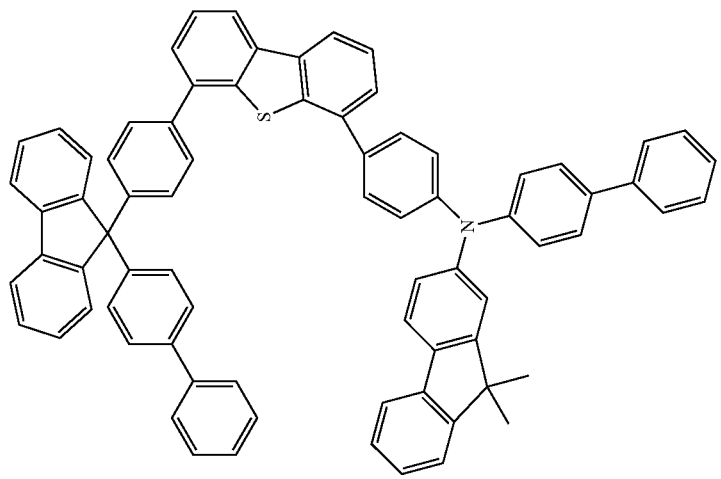 | | | 60% |

| Ex. | Boronic ester | Amine | Product | Yield |
|---|---|---|---|---|
| 4o | | | 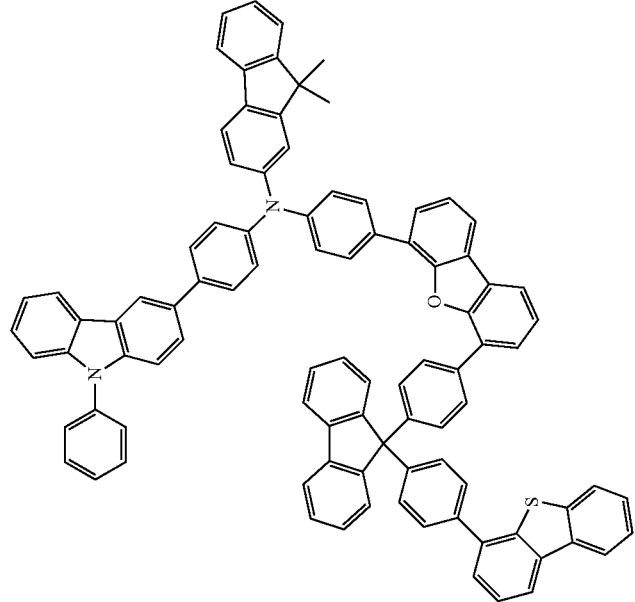 | 50% |

-continued

| Ex. | Boronic ester | Amine | Product | Yield |
|---|---|---|---|---|
| 4p | (structure) | (structure) | (structure) | 62% |

| Ex. | Boronic ester | Amine | Product | Yield |
|---|---|---|---|---|
| 4q | [structure] | [structure] | [structure] | 55% |

-continued
| Ex. | Boronic ester | Amine | Product | Yield |
|---|---|---|---|---|
| 4r | 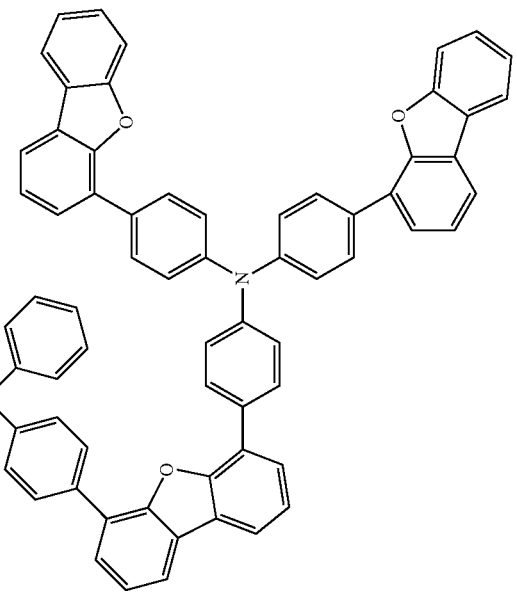 | | | 66% |

| Ex. | Boronic ester | Amine | Product | Yield |
|---|---|---|---|---|
| 4s | (structure) | (structure) | (structure) | 52% |

| Ex. | Boronic ester | Amine | Product | Yield |
|---|---|---|---|---|
| 4t | | | 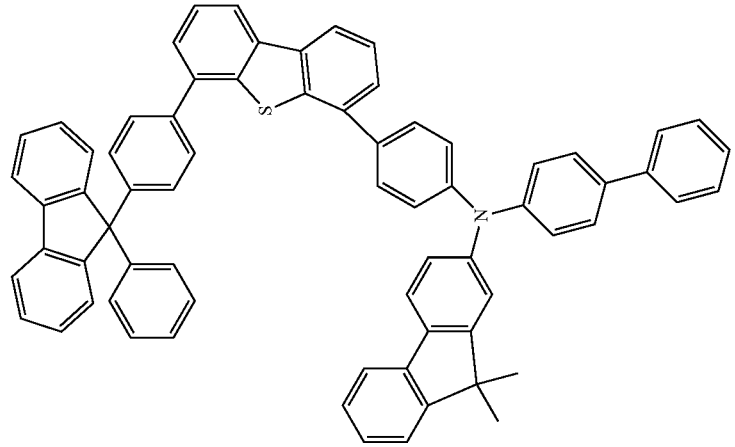 | 48% |

| Ex. | Boronic ester | Amine | Product | Yield |
|---|---|---|---|---|
| 4u | | | | 54% |

| Ex. | Boronic ester | Amine | Product | Yield |
|---|---|---|---|---|
| 4v | | | | 45% |
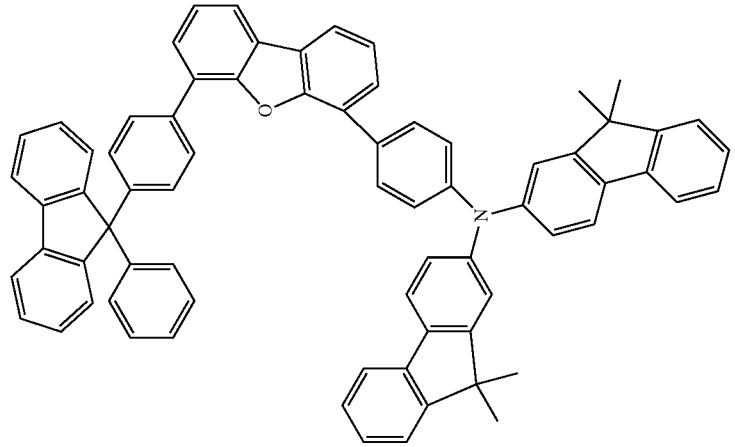

| Ex. | Boronic ester | Amine | Product | Yield |
|---|---|---|---|---|
| 4w | | | | 51% |

-continued

| Ex. | Boronic ester | Amine | Product | Yield |
|---|---|---|---|---|
| 4x | | | | 46% |
| 4y | | | | 48% |

-continued

| Ex. | Boronic ester | Amine | Product | Yield |
|---|---|---|---|---|
| 4z | | | | 51% |
| 4aa | | | | 49% |

5) Synthesis of 10-chloro-4-(9,9-dimethyl-9H-fluoren-2-yl)-8-oxatricyclo[7.4.0.0^{2,7}]trideca-1(9),2,4,6,10,12-hexaene 5a

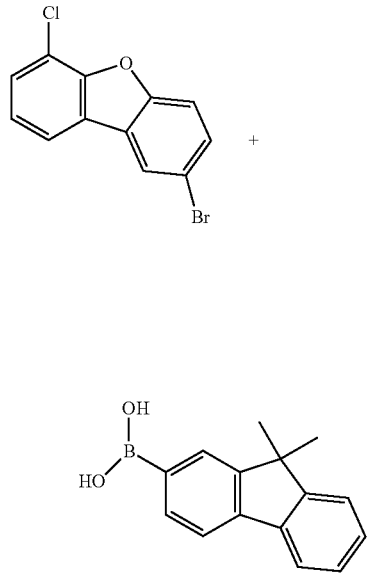

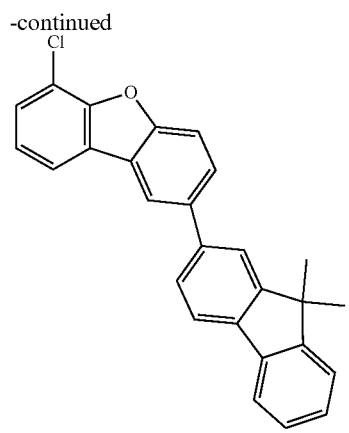

53.6 g (191.5 mmol) 4-bromo-10-chloro-8-oxatricyclo[7.4.0.0$^{2,7}$]trideca-1(9),2,4,6,10,12-hexaene, 57 g (239.4 mmol) of (9,9-dimethyl-9H-fluoren-2-yl)boronic acid, 26.5 g (23 mmol, 0.12 eq.) of Pd(P(Ph$_3$))$_4$, and 680 mL 2M solution (1365 mmol, 7 eq.) of Na$_2$CO$_3$ are dissolved in 1300 mL of ethylenglycoldiethylether. The reaction mixture is stirred under reflux and agitated under an argon atmosphere for 12 hours. After cooling to room temperature, the mixture is extracted with ethyl acetate. The organic phase is dried with Na$_2$SO$_4$ and the filtrate is evaporated in vacuo, and the residue is purified by chromatography (mixture heptane/AcOEt). The product is isolated in the form of an off-white solid (51 g, 68% of theory).

The following compounds are synthesized analogously:

| Ex. | Dibenzofurane | Boronic acid | Product | Yield |
|---|---|---|---|---|
| 5b | | | | 53% |
| 5c | | | | 65% |

-continued
| Ex. | Dibenzofurane | Boronic acid | Product | Yield |
|---|---|---|---|---|
| 5d | 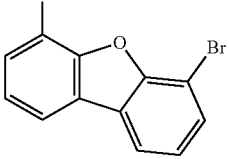 | 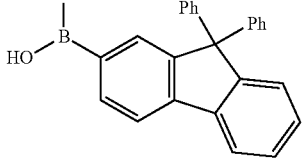 | 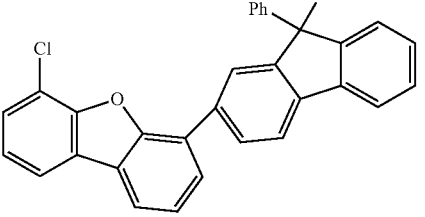 | 57% |
| 5e | 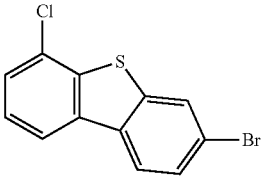 [SMILES: Clc1cccc2c1sc1cc(Br)ccc12] | 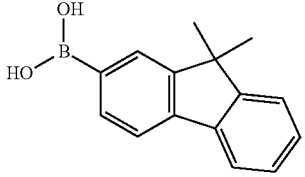 [SMILES: CC1(C)c2ccccc2-c2ccc(B(O)O)cc21] | 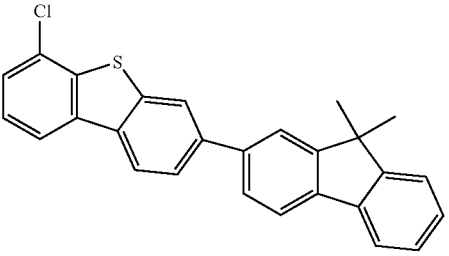 | 64% |
| 5f | 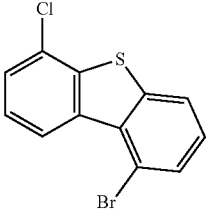 [SMILES: Clc1cccc2c1sc1cccc(Br)c12] | 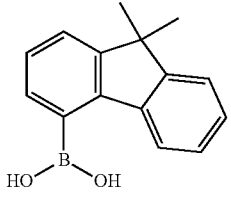 [SMILES: CC1(C)c2ccccc2-c2c(B(O)O)cccc21] | 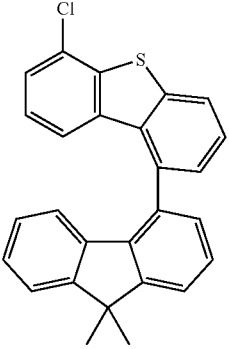 [SMILES: CC1(C)c2ccccc2-c2c(-c3cccc4sc5c(Cl)cccc5c34)cccc21] | 53% |
| 5g | 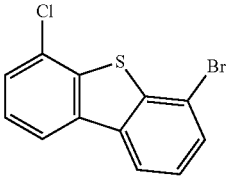 [SMILES: Clc1cccc2c1sc1c(Br)cccc12] | 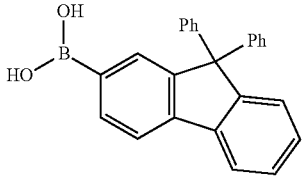 [SMILES: OB(O)c1ccc2c(c1)C(c1ccccc1)(c1ccccc1)c1ccccc1-2] | 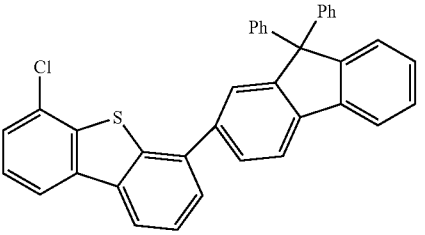 [SMILES: Clc1cccc2c1sc1c(-c3ccc4c(c3)C(c3ccccc3)(c3ccccc3)c3ccccc3-4)cccc12] | 61% |
| 5h | 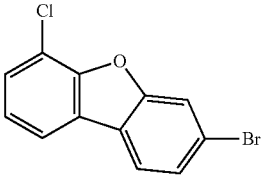 [SMILES: Clc1cccc2c1oc1cc(Br)ccc12] | 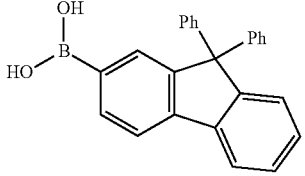 [SMILES: OB(O)c1ccc2c(c1)C(c1ccccc1)(c1ccccc1)c1ccccc1-2] | 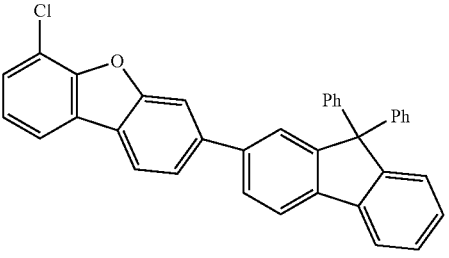 [SMILES: Clc1cccc2c1oc1cc(-c3ccc4c(c3)C(c3ccccc3)(c3ccccc3)c3ccccc3-4)ccc12] | 65% |
| 5i | 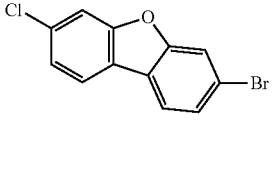 [SMILES: Clc1ccc2c(c1)oc1cc(Br)ccc12] | 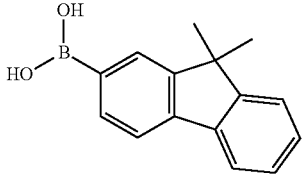 [SMILES: CC1(C)c2ccccc2-c2ccc(B(O)O)cc21] | 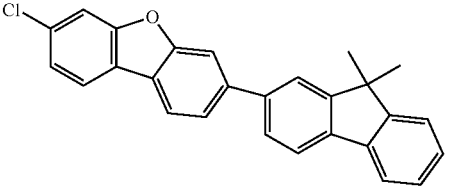 [SMILES: CC1(C)c2ccccc2-c2ccc(-c3ccc4c(c3)oc3cc(Cl)ccc34)cc21] | 57% |

-continued
| Ex. | Dibenzofurane | Boronic acid | Product | Yield |
|---|---|---|---|---|
| 5j | | | | 60% |
| 5k | | | | 65% |
| 5l | | | | 72% |
| 5m | | | | 75% |
6) Synthesis of 2-[12-(9,9-dimethyl-9H-fluoren-2-yl)-8-oxatricyclo[7.4.0.0$^{2,7}$]trideca-1(13),2(7),3,5,9,11-hexaen-6-yl]-4,4,5,5-tetramethyl-1,3,2-dioxaborolane 6a
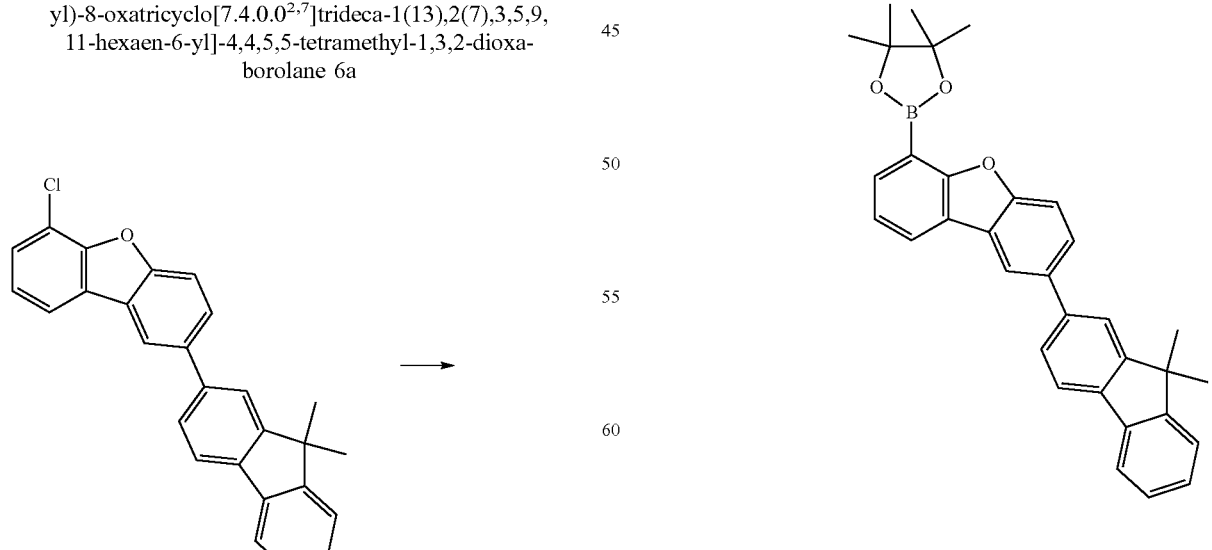
91 g (231 mmol) of 10-chloro-4-(9,9-dimethyl-9H-fluoren-2-yl)-8-oxatricyclo[7.4.0.0$^{2,7}$]trideca-1(9),2,4,6,10,12-hexaene, 4.8 g (5.9 mmol) of Pd(dppf)Cl$_2$, 61.6 g (238 mmol) of bis(pinacolato)diboron and 58.3 g (594 mmol) of potassium acetate are dissolved in 1300 mL of 1,4-dioxane. The reaction mixture is refluxed and agitated under an argon atmosphere for 12 hours and after cooling to room temperature, the mixture is filtered through Celite. The filtrate is evaporated in vacuo, and the residue is crystallised from heptane. The product is isolated in the form of a pale-yellow solid (87 g, 78% of theory).

The following compounds are synthesized analogously:

| Ex. | Halogene | Product | Yield |
|---|---|---|---|
| 6b | 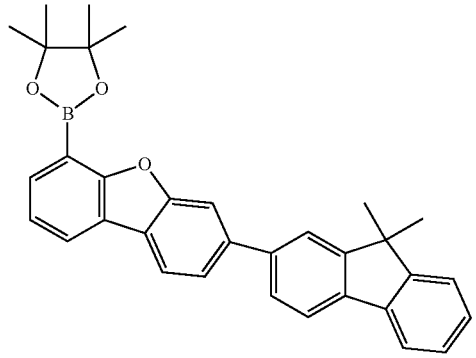 | | 81% |
| 6c | 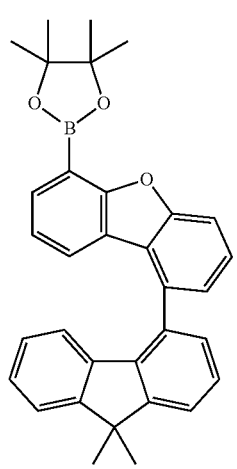 [SMILES: CC1(C)c2ccccc2-c2c(-c3cccc4oc5c(B6OC(C)(C)C(C)(C)O6)cccc5c34)cccc21] | | 76% |
| 6d | 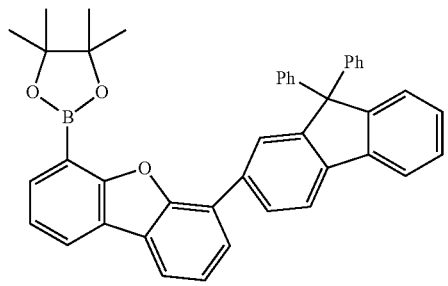 [SMILES: CC1(C)OB(c2cccc3c2oc2c(-c4ccc5c(c4)C(c4ccccc4)(c4ccccc4)c4ccccc4-5)cccc23)OC1(C)C] | | 70% |
| 6e | 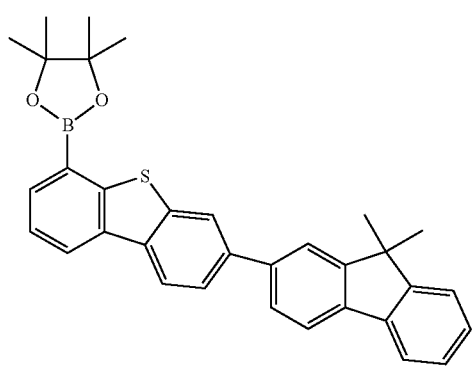 [SMILES: CC1(C)c2ccccc2-c2ccc(-c3ccc4c(c3)sc3c(B5OC(C)(C)C(C)(C)O5)cccc34)cc21] | | 68% |

| Ex. | Halogene | Product | Yield |
|---|---|---|---|
| 6f | | | 64% |
| 6g | | | 63% |
| 6h | | | 74% |
| 6i | | | 66% |

-continued

| Ex. | Halogene | Product | Yield |
|---|---|---|---|
| 6j | | | 61% |
| 6k | | | 65% |

7) Synthesis of N-{[1,1'-biphenyl]-4-yl}-N,12-bis(9,9-dimethyl-9H-fluoren-2-yl)-8-oxatricyclo[7.4.0.0$^{2,7}$]trideca-1(9),2(7),3,5,10,12-hexaen-6-amine 7a

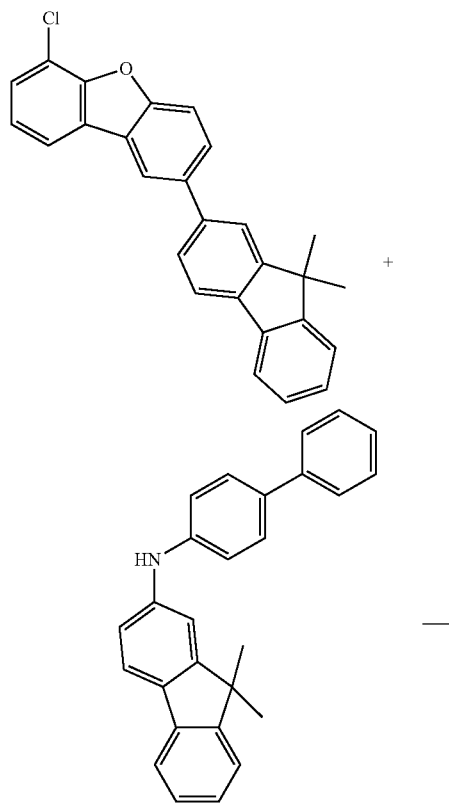

+

-continued

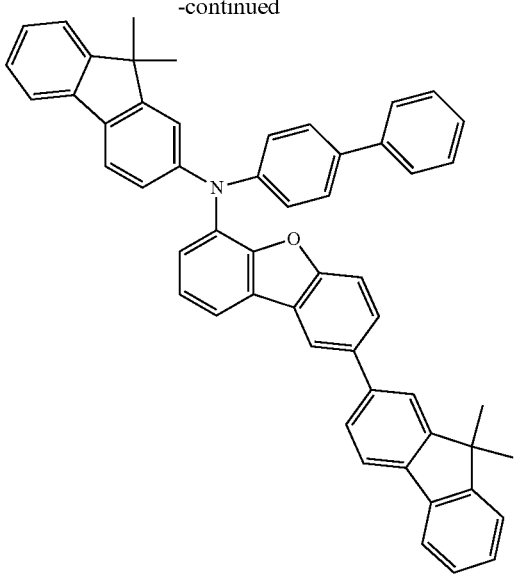

S-Phos (0.645 g, 1.6 mmol), Pd$_2$(dba)$_3$ (0.72 g, 0.8 mmol) and sodium tert-butoxide (5 g, 52.4 mmol) are added to a solution of biphenyl-4-yl-(9,9-dimethyl-9H-fluoren-2-yl)-amine (9.5 g, 26.2 mmol) and fluorene 3a (10.3 g, 6.2 mmol) in degassed toluene (140 ml), and the mixture is heated under reflux for 10 h. The reaction mixture is cooled to room temperature, extended with toluene and filtered through Celite. The filtrate is evaporated in vacuo, and the residue is crystallised from toluene/heptane. The crude product is extracted in a Soxhlet extractor (toluene) and purified by zone sublimation in vacuo twice. The product is isolated in the form of an off-white solid (7.5 g, 40% of theory).

The following compounds are obtained analogously:

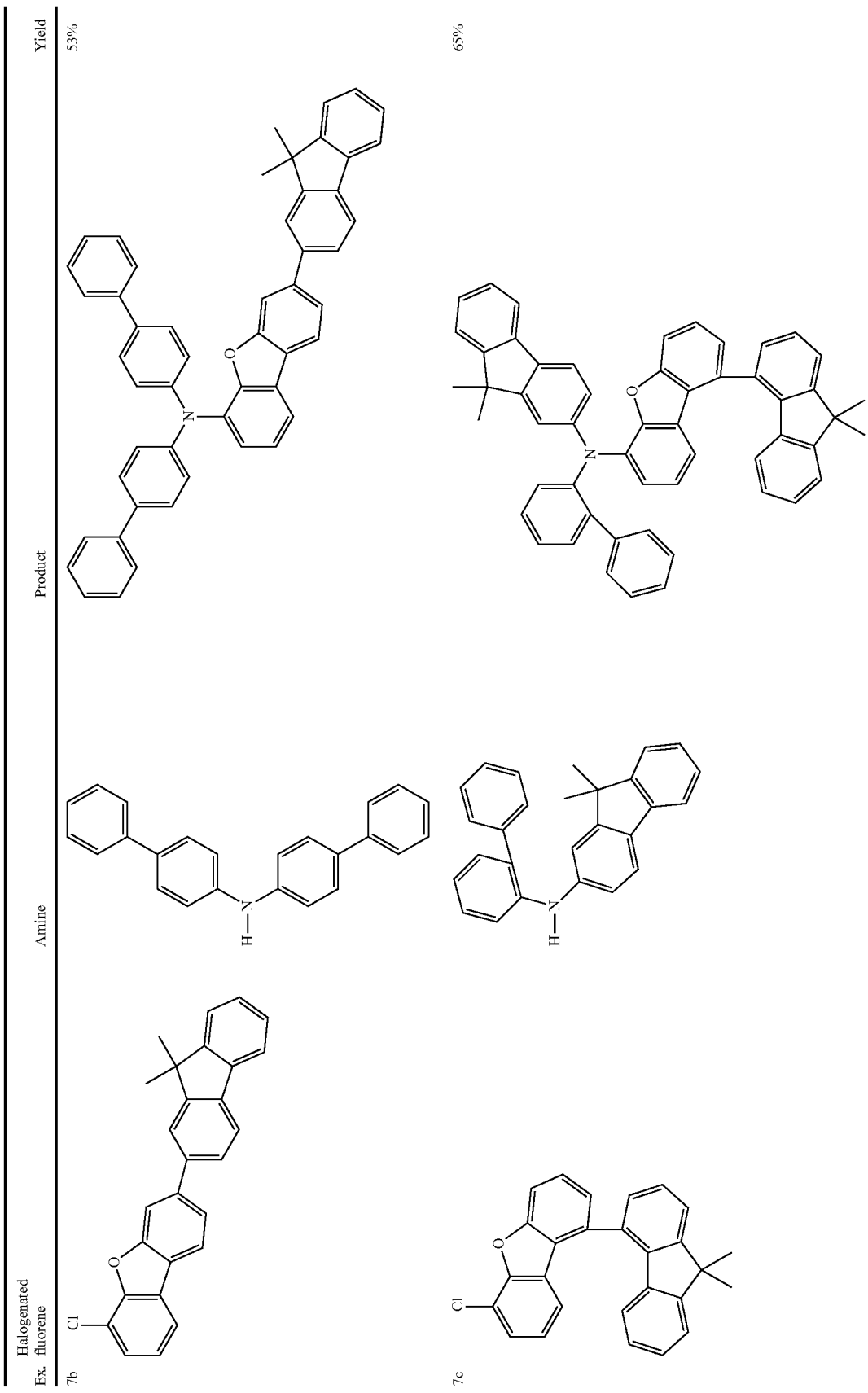

-continued
| Ex. | Halogenated fluorene | Amine | Product | Yield |
|---|---|---|---|---|
| 7d | 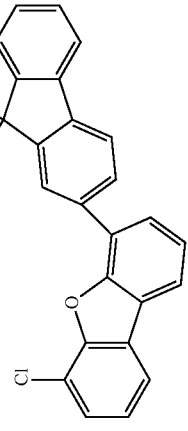 | 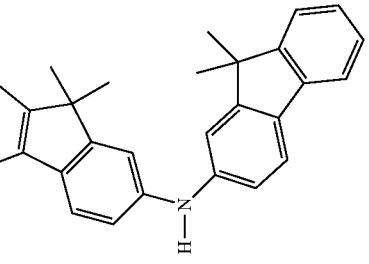 | 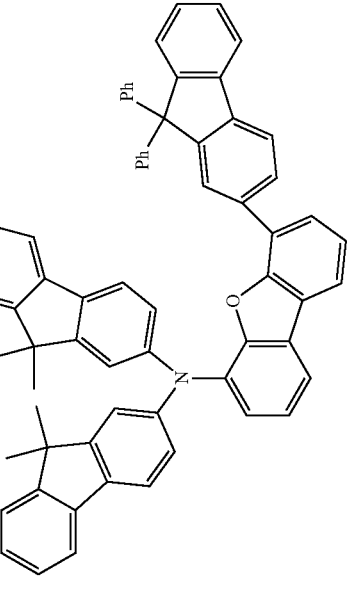 | 51% |
| 7e |  | 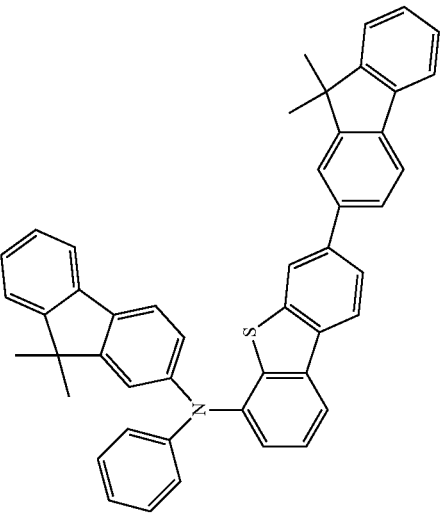 | | 62% |

-continued
| Ex. | Halogenated fluorene | Amine | Product | Yield |
|---|---|---|---|---|
| 7f | 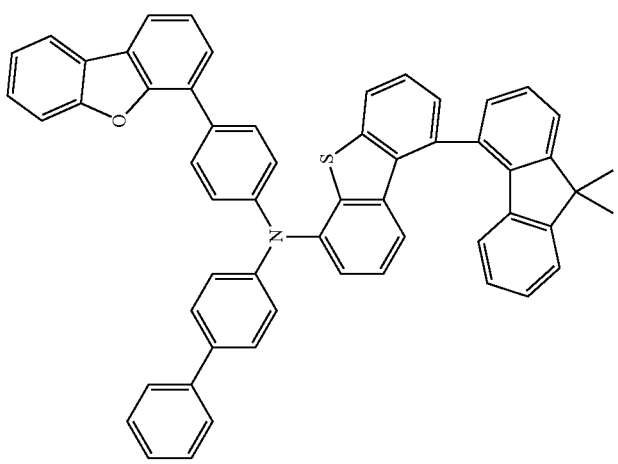 | 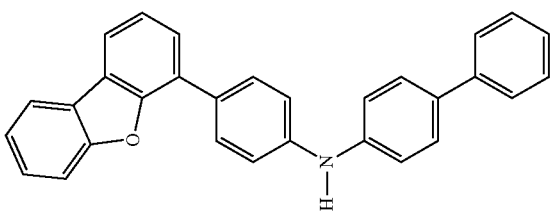 | 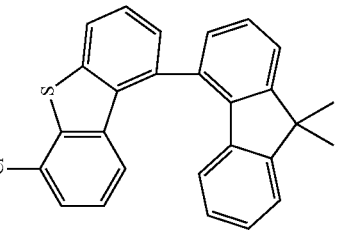 | 58% |

-continued

| Ex. | Halogenated fluorene | Amine | Product | Yield |
|---|---|---|---|---|
| 7g | *(4-chlorodibenzothiophene with 9,9-diphenylfluorene substituent)* | *(dibenzofuran-phenyl-N(H)-9,9-dimethylfluorene amine)* | *(triarylamine product)* | 63% |
| 7h | *(4-chlorodibenzofuran with 9,9-diphenylfluorene substituent)* | *(N-(1-naphthyl)-N-(4-biphenyl)amine)* | *(triarylamine product)* | 55% |

-continued

| Ex. | Halogenated fluorene | Amine | Product | Yield |
|---|---|---|---|---|
| 7i | | | | 77% |
| 7j | | | | 76% |

-continued
| Ex. | Halogenated fluorene | Amine | Product | Yield |
|---|---|---|---|---|
| 7k | 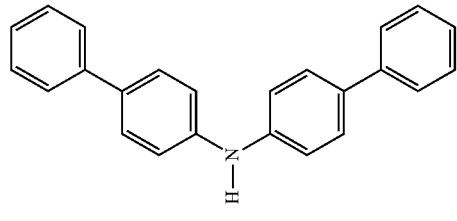 | 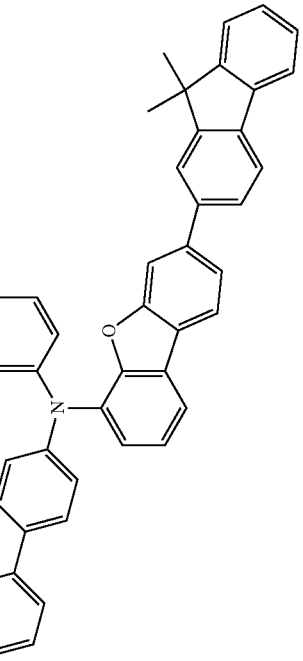 | 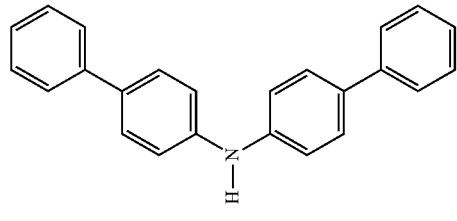 | 65% |
| 7l | 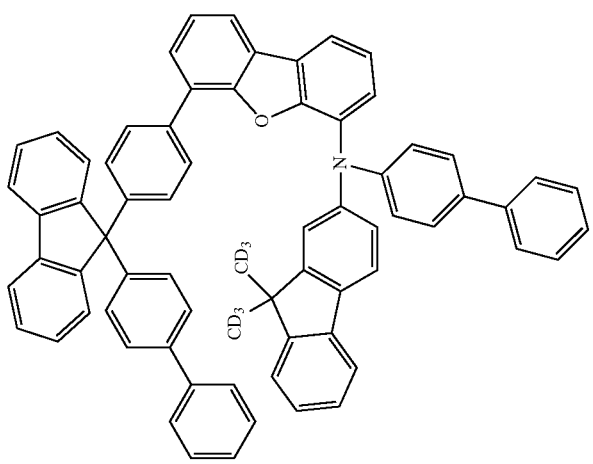 | | | 52% |

-continued
| Ex. | Halogenated fluorene | Amine | Product | Yield |
|---|---|---|---|---|
| 7m | 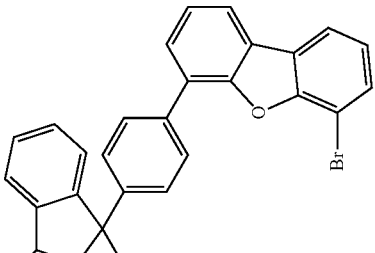 | 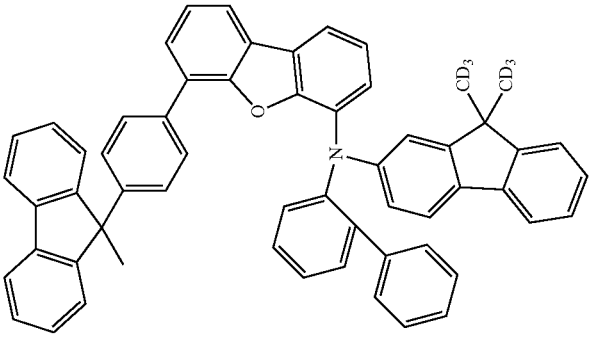 | 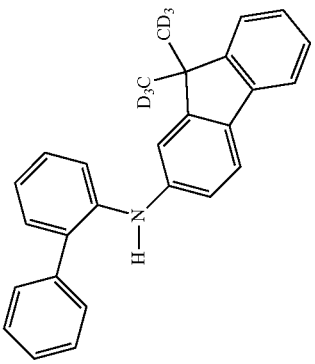 | 73% |

-continued
| Ex. | Halogenated fluorene | Amine | Product | Yield |
|---|---|---|---|---|
| 7n | 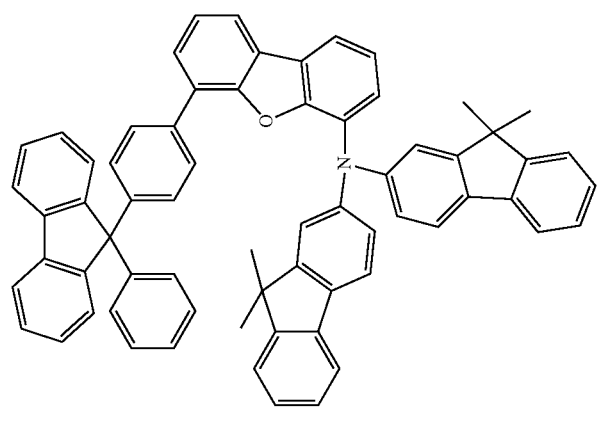 | 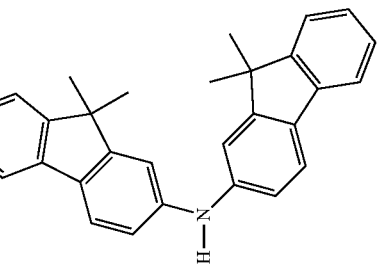 | 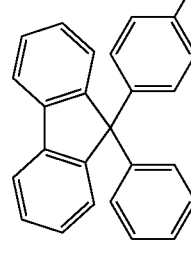 | 59% |

-continued
| Ex. | Halogenated fluorene | Amine | Product | Yield |
|---|---|---|---|---|
| 7o | 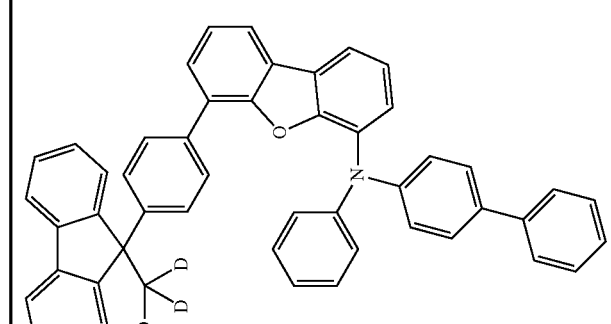 | 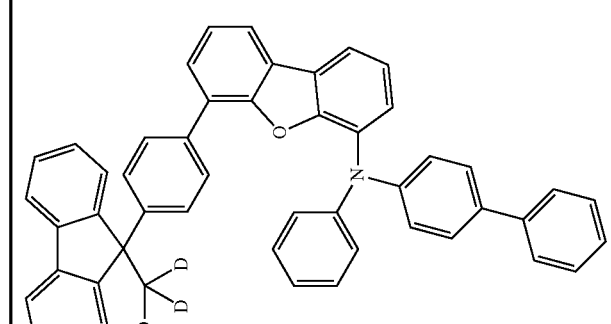 | 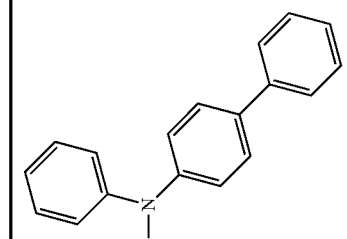 | 55% |

| Ex. | Halogenated fluorene | Amine | Product | Yield |
|---|---|---|---|---|
| 7p | 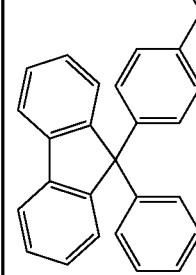 | 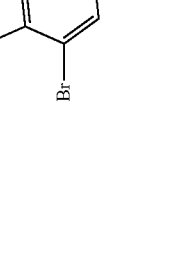 | 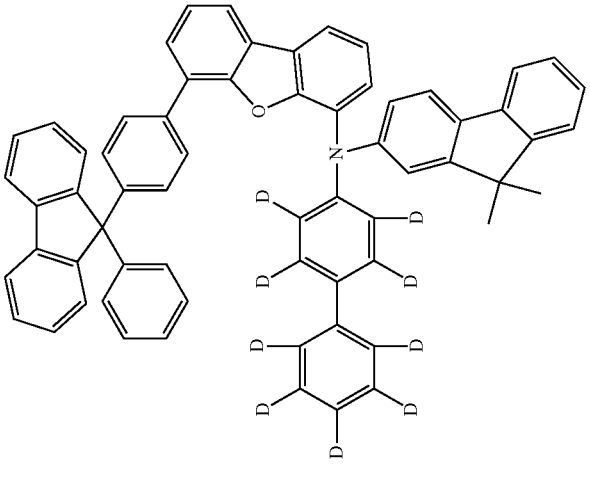 | 55% |

-continued

| Ex. | Halogenated fluorene | Amine | Product | Yield |
|---|---|---|---|---|
| 7q | (structure) | (structure) | (structure) | 75% |

-continued

| Ex. | Halogenated fluorene | Amine | Product | Yield |
|---|---|---|---|---|
| 7r | (structure) | (structure) | (structure) | 70% |

-continued

| Ex. | Halogenated fluorene | Amine | Product | Yield |
|---|---|---|---|---|
| 7s | (9,9-dimethylfluorene-dibenzofuran-Cl) | (N-phenylcarbazole-carbazole-NH) | (product structure) | 72% |

-continued
| Ex. | Halogenated fluorene | Amine | Product | Yield |
|---|---|---|---|---|
| 7t | 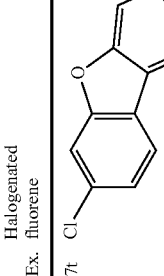 | 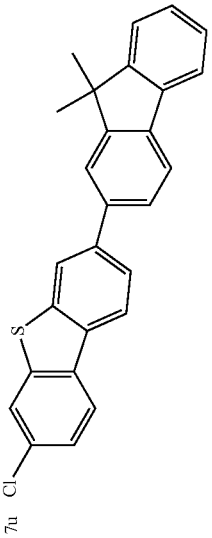 | 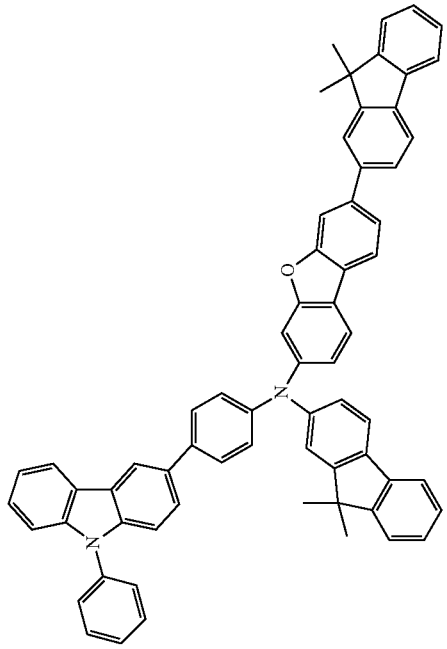 | 62% |
| 7u | 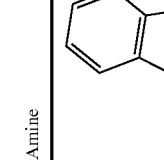 | 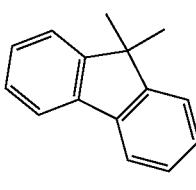 | 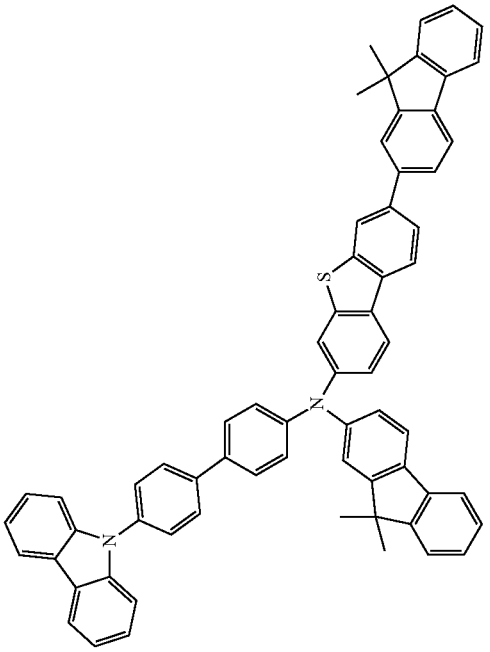 | 45% |

-continued

| Ex. | Halogenated fluorene | Amine | Product | Yield |
|---|---|---|---|---|
| 7v | (structure with Cl-dibenzothiophene-fluorene) | (structure with carbazole-biphenyl-amine) | (product structure) | 66% |
| 7w | (structure with Cl-dibenzofuran-fluorene) | (phenyl-carbazole amine) | (product structure) | 66% |

-continued
| Ex. | Halogenated fluorene | Amine | Product | Yield |
|---|---|---|---|---|
| 7x | 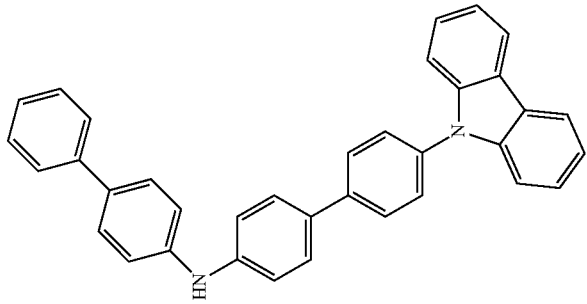 | 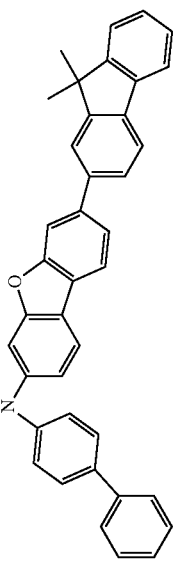 | 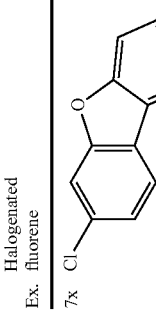 | 71% |
| 7y | 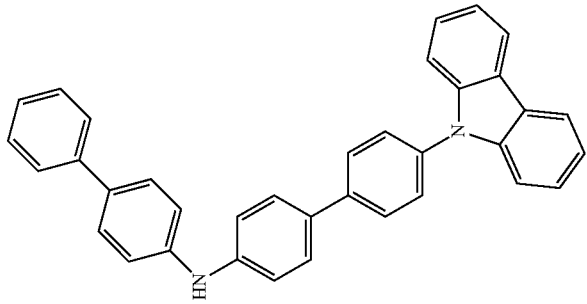 | 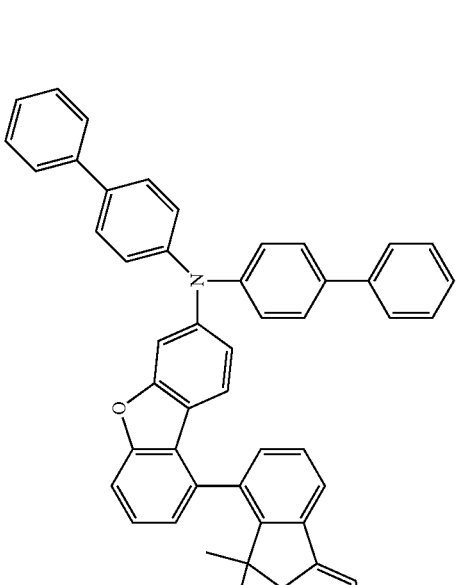 | | 70% |

| Ex. | Halogenated fluorene | Amine | Product | Yield |
|---|---|---|---|---|
| 7z | 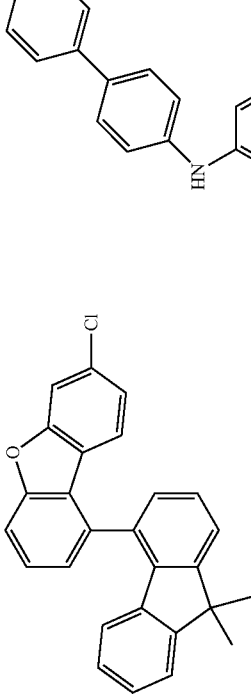 | 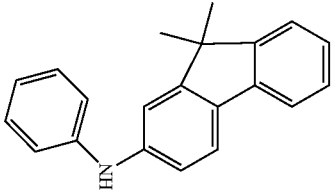 | 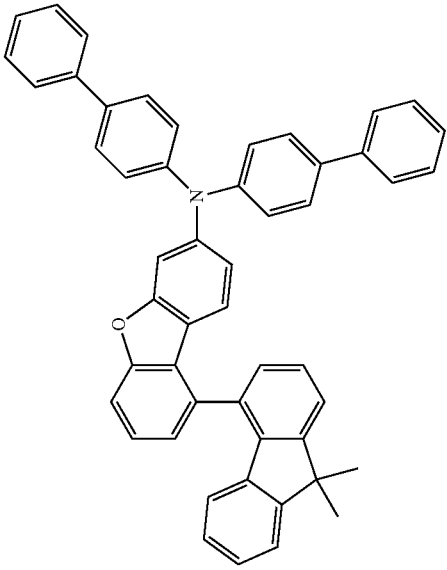 | 65% |
| 7aa | 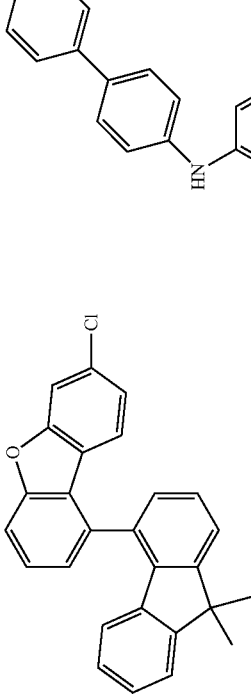 | 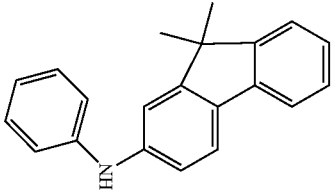 | 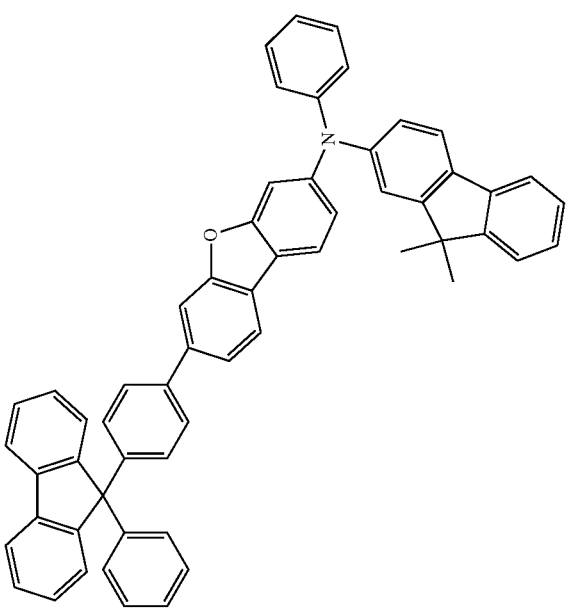 | 57% |

| Ex. | Halogenated fluorene | Amine | Product | Yield |
|---|---|---|---|---|
| 7ab | 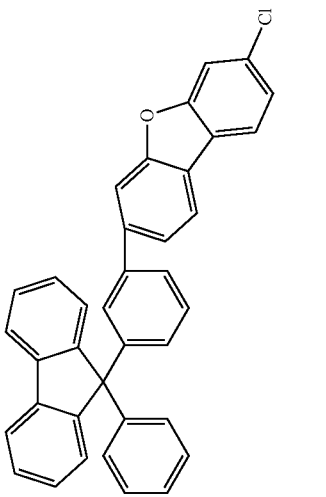 | 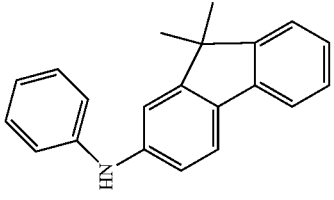 | 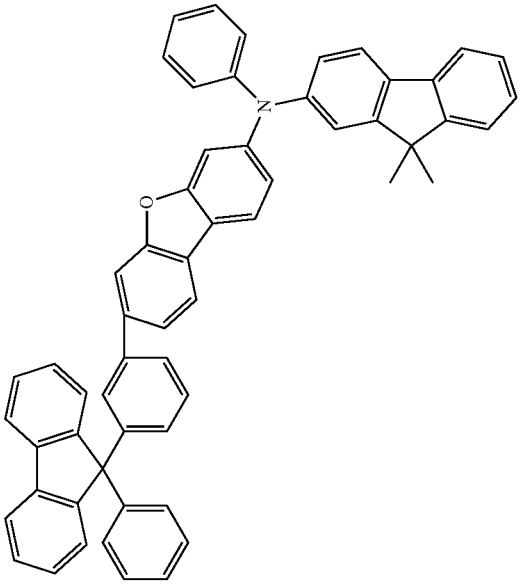 | 60% |

| Ex. | Halogenated fluorene | Amine | Product | Yield |
|---|---|---|---|---|
| 7ac | 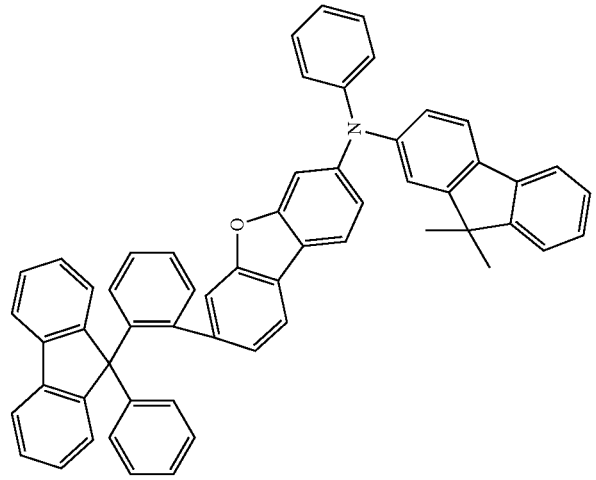 | 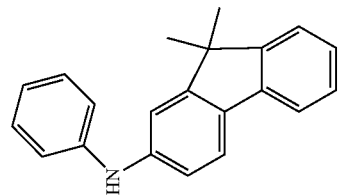 | 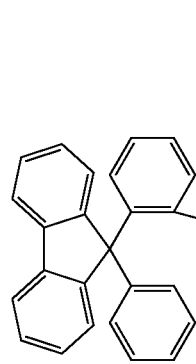 | 48% |

-continued
| Ex. | Halogenated fluorene | Amine | Product | Yield |
|---|---|---|---|---|
| 7ad | 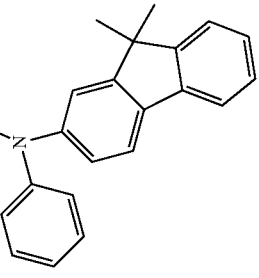 | 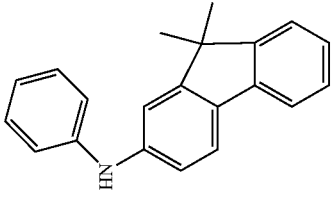 | 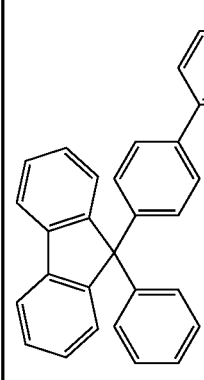 | 55% |

B) Device Examples

B-1) General Preparation and Characterization Methods

OLEDs comprising compounds according to the present application are prepared by the following general process: The substrates used are glass plates coated with structured ITO (indium tin oxide) in a thickness of 50 nm. The OLEDs have the following layer structure: substrate/hole-injection layer (HIL)/hole-transport layer (HTL)/electron-blocking layer (EBL)/emission layer (EML)/electron-transport layer (ETL)/electron-injection layer (EIL) and finally a cathode. The cathode is formed by an aluminium layer with a thickness of 100 nm. The specific device setup of the OLEDs is shown in Tables 1a to 1c, and the materials for the various layers of the OLEDs are shown in Table 3.

All materials are applied by thermal vapour deposition in a vacuum chamber. The emission layer always consists of at least one matrix material (host material) and an emitting dopant (emitter), which is admixed with the matrix material or matrix materials in a certain proportion by volume by coevaporation. An expression such as H:SEB (5%) here means that material H is present in the layer in a proportion by volume of 95% and SEB is present in the layer in a proportion by volume of 5%. Analogously, other layers may also consist of a mixture of two or more materials.

The OLEDs are characterised by standard methods. For this purpose, the electroluminescence spectra and the external quantum efficiency (EQE, measured in percent) as a function of the luminous density, calculated from current/voltage/luminous density characteristic lines (IUL characteristic lines) assuming Lambert emission characteristics, and the lifetime are determined. The expression EQE @ 10 mA/cm$^2$ denotes the external quantum efficiency at an operating current density of 10 mA/cm$^2$. LT80 @ 60 mA/cm$^2$ is the lifetime until at a current density of 60 mA/cm$^2$, the OLED has dropped from its initial luminance of e.g. 5000 cd/m$^2$ to 80% of the initial intensity, i.e. to 4000 cd/m$^2$, without using any acceleration factor.

B-2) Use of the Compounds in the EBL of Green Phosphorescent OLEDs

The compounds HTM-1 to HTM-4 according to the present application are used in the EBL of a green phosphorescent OLED stack, as shown below in Table 1a.

In such device setup, very good results for EQE, lifetime and voltage are obtained with the compounds, as shown in the table below.

TABLE 2a

Data of the OLEDs

|    | U @ 10 mA/cm$^2$ (V) | EQE @ 10 mA/cm$^2$ (%) | LT80 @ 40 mA/cm$^2$ (h) |
|----|---|---|---|
| E1 | 3.7 | 16.4 | 270 |
| E2 | 3.9 | 17.6 | 280 |
| E3 | 3.8 | 15.9 | 350 |
| E4 | 4.0 | 17.7 | 320 |

B-3) Use of the Compounds in the EBL of Blue Fluorescent OLEDs

The compounds HTM-1 and HTM-2 according to the present application are used in the EBL of a blue fluorescent OLED stack, as shown below in Table 1b.

TABLE 1a

Device Setup

| Ex. | HIL Thickness/nm | HTL Thickness/nm | EBL Thickness/nm | EML Thickness/nm | ETL Thickness/nm | EIL Thickness/nm |
|---|---|---|---|---|---|---|
| E1 | HTM: p-dopant (5%) 20 nm | HTM 220 nm | HTM-1 10 nm | TMM-1:TMM-2(28%):TEG(12%) 30 nm | ETM:LiQ(50%) 30 nm | LiQ 1 nm |
| E2 | HTM: p-dopant (5%) 20 nm | HTM 220 nm | HTM-2 10 nm | TMM-1:TMM-2(28%):TEG(12%) 30 nm | ETM:LiQ(50%) 30 nm | LiQ 1 nm |
| E3 | HTM: p-dopant (5%) 20 nm | HTM 220 nm | HTM-3 10 nm | TMM-1:TMM-2(28%):TEG(12%) 30 nm | ETM:LiQ(50%) 30 nm | LiQ 1 nm |
| E4 | HTM: p-dopant (5%) 20 nm | HTM 220 nm | HTM-4 10 nm | TMM-1:TMM-2(28%):TEG(12%) 30 nm | ETM:LiQ(50%) 30 nm | LiQ 1 nm |

TABLE 1b

| | | | Device Setup | | | |
|---|---|---|---|---|---|---|
| Ex. | HIL Thickness/nm | HTL Thickness/nm | EBL Thickness/nm | EML Thickness/nm | ETL Thickness/nm | EIL Thickness/nm |
| E5 | HTM: p-dopant (5%) 20 nm | HTM 180 nm | HTM-1 10 nm | H:SEB(5%) 20 nm | ETM:LiQ(50%) 30 nm | LiQ 1 nm |
| E6 | HTM: p-dopant (5%) 20 nm | HTM 180 nm | HTM-2 10 nm | H:SEB(5%) 20 nm | ETM:LiQ(50%) 30 nm | LiQ 1 nm |

In such device setup, very good results for EQE, lifetime and voltage are obtained with the compounds, as shown in the table below.

TABLE 2b

| | Data of the OLEDs | | |
|---|---|---|---|
| | U @ 10 mA/cm$^2$ (V) | EQE @ 10 mA/cm$^2$ (%) | LT80 @ 60 mA/cm$^2$ (h) |
| E5 | 3.8 | 8.3 | 250 |
| E6 | 3.9 | 9.1 | 280 |

B-4) Use of the Compounds in the HTL of Blue Fluorescent OLEDs

The compounds HTM-1 and HTM-3 according to the present application are used in the HTL of a blue fluorescent OLED stack, as shown below in Table 1c.

TABLE 1c

| | | | Device Setup | | | |
|---|---|---|---|---|---|---|
| Ex. | HIL Thickness/nm | HTL Thickness/nm | EBL Thickness/nm | EML Thickness/nm | ETL Thickness/nm | EIL Thickness/nm |
| E7 | HTM-1: p-dopant (5%) 20 nm | HTM-1 180 nm | EBM 10 nm | H:SEB(5%) 20 nm | ETM:LiQ(50%) 30 nm | LiQ 1 nm |
| E8 | HTM-3: p-dopant (5%) 20 nm | HTM-3 180 nm | EBM 10 nm | H:SEB(5%) 20 nm | ETM:LiQ(50%) 30 nm | LiQ 1 nm |

In such device setup, very good results for EQE, lifetime and voltage are obtained with the compounds, as shown in the table below.

TABLE 2c

| | Data of the OLEDs | | |
|---|---|---|---|
| | U @ 10 mA/cm$^2$ (V) | EQE @ 10 mA/cm$^2$ (%) | LT80 @ 60 mA/cm$^2$ (h) |
| E7 | 4.5 | 8.8 | 190 |
| E8 | 4.5 | 8.7 | 120 |

TABLE 3

Materials used

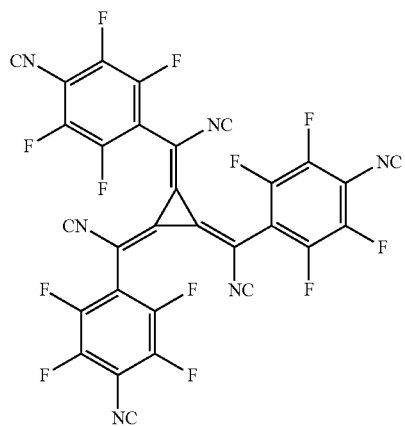

p-dopant

TABLE 3-continued
Materials used
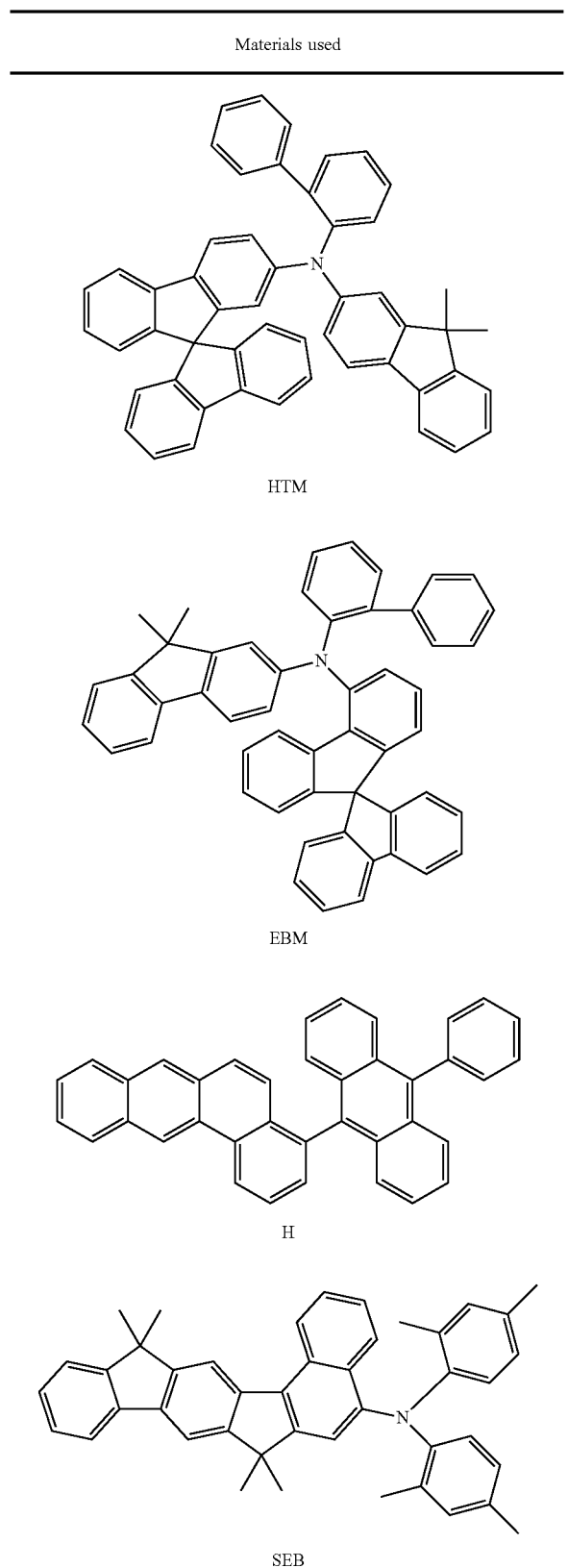
HTM
EBM
H
SEB
TABLE 3-continued
Materials used
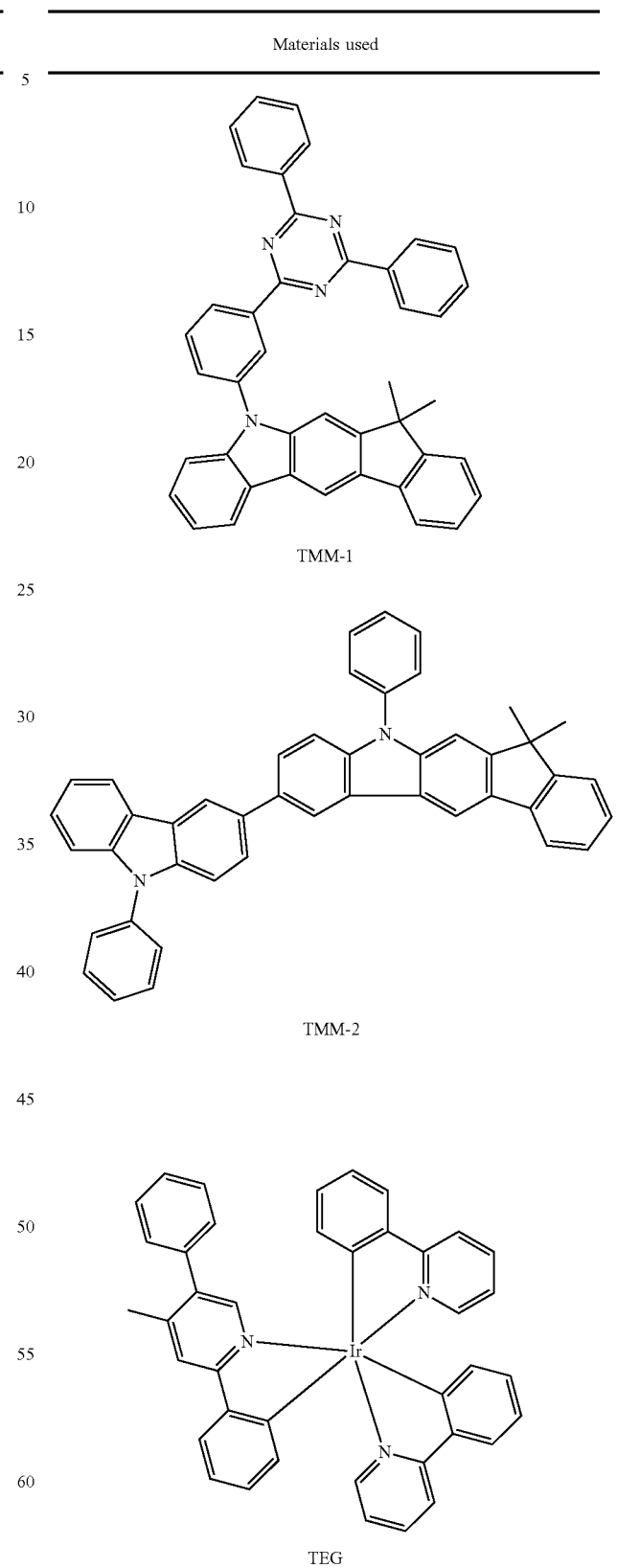
TMM-1
TMM-2
TEG TABLE 3-continued
Materials used
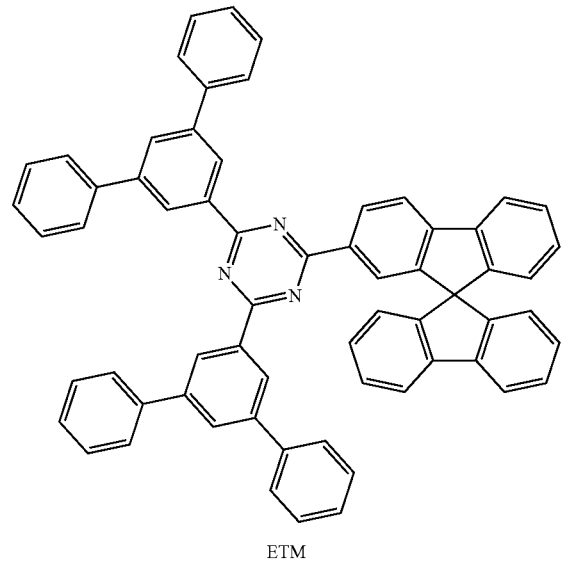 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ETM
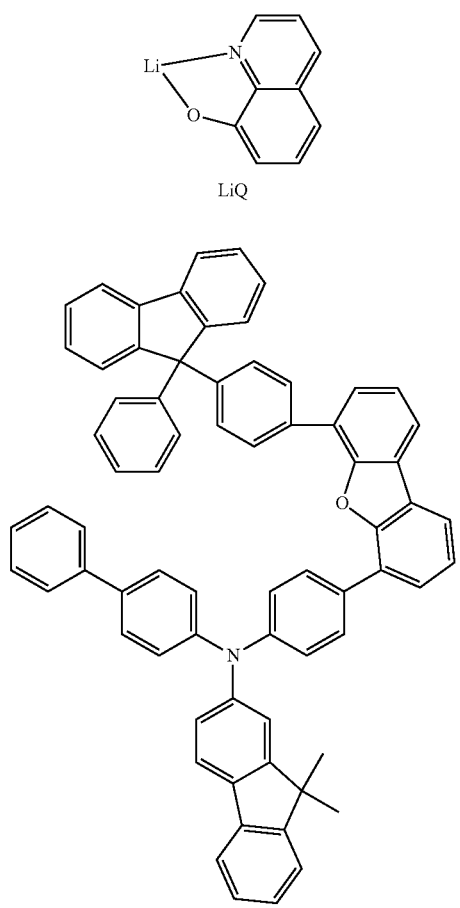
LiQ
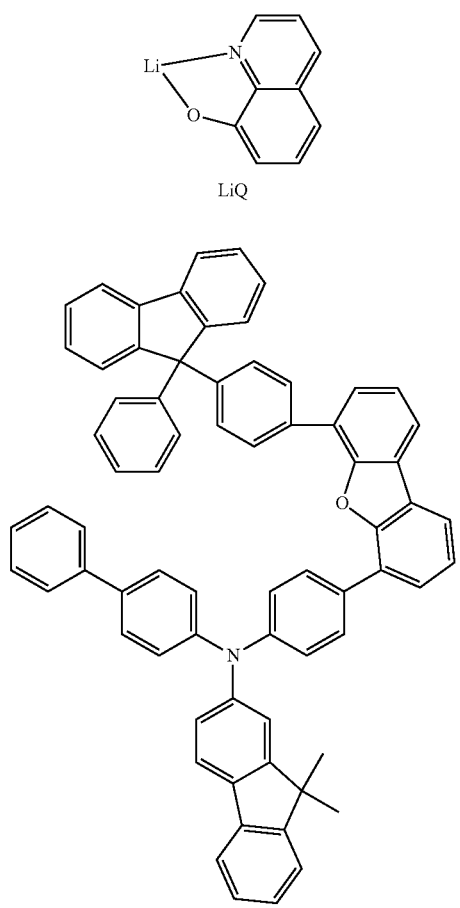
HTM-1
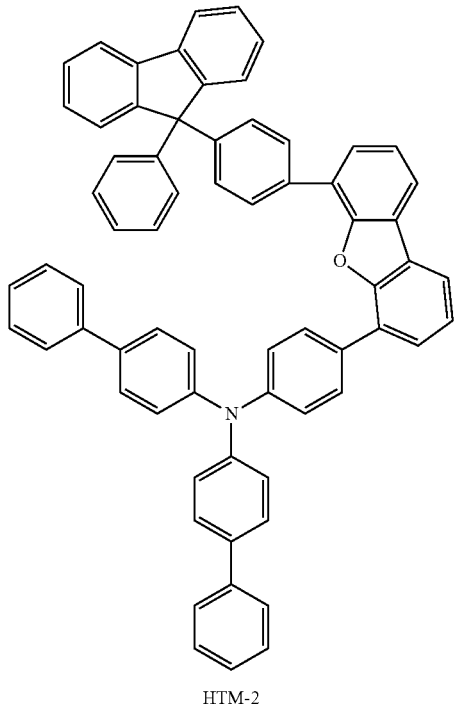
HTM-2
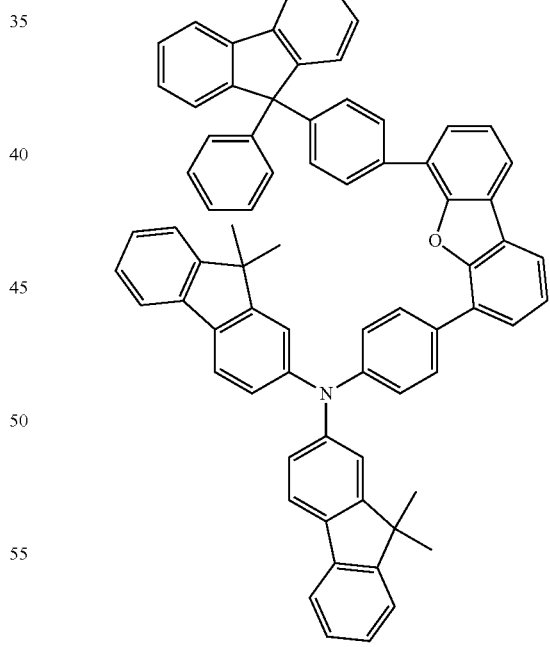
HTM-3

TABLE 3-continued

Materials used

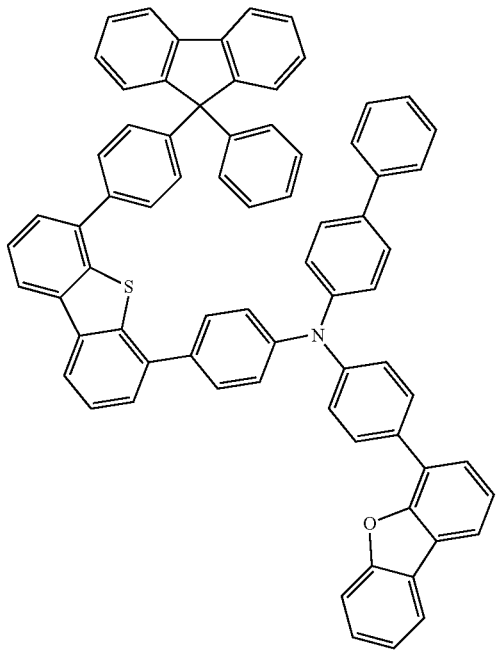

HTM-4

The invention claimed is:

1. A compound of formula (I)

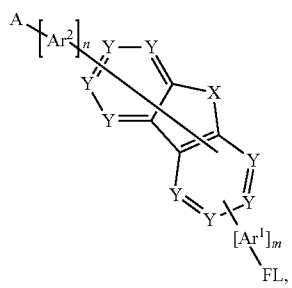

formula (I)

where:

FL is a group of formulae (FL-1)

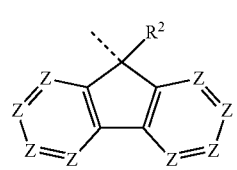

formula (FL-1)

where the dotted bond is the bond to the rest of formula (I);

Z is identically or differently at each occurrence, selected from CR¹ and N;

Y is C if a group —[Ar²]ₙ—N(Ar³)(Ar⁴) or —[Ar¹]ₘ-FL is bonded in this position; and Y is in all other cases selected, identically or differently at each occurrence, from CR³ and N;

X is O or S;

Ar¹ is, identically or differently at each occurrence, selected from aromatic ring systems having 6 to 40 aromatic ring atoms, which are substituted by radicals R⁴, and heteroaromatic ring systems having 5 to 40 aromatic ring atoms, which are substituted by radicals R⁴;

Ar² is, identically or differently at each occurrence, selected from aromatic ring systems having 6 to 40 aromatic ring atoms, which are substituted by radicals R⁵, and heteroaromatic ring systems having 5 to 40 aromatic ring atoms, which are substituted by radicals R⁵;

A corresponds to the following formula

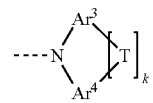

which is bonded via the dotted line;

Ar³ and Ar⁴ are, identically or differently at each occurrence, selected from aromatic ring systems having 6 to 40 aromatic ring atoms, which are substituted by radicals R⁶, and heteroaromatic ring systems having 5 to 40 aromatic ring atoms, which are substituted by radicals R⁶;

k is 0 which means that T does not occur and the groups Ar³ and Ar⁴ are not connected;

R¹ is selected, identically or differently at each occurrence, from H, D, F, Cl, Br, I, C(=O)R⁷, CN, Si(R⁷)₃, N(R⁷)₂, P(=O)(R⁷)₂, OR⁷, S(=O) R⁷, S(=O)₂R⁷, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals R¹ may be connected to each other to form a ring; where the said alkyl, alkoxy, alkenyl and alkynyl groups and the said aromatic and heteroaromatic ring systems are in each case substituted by radicals R⁷, and where one or more CH₂ groups in the said alkyl, alkoxy, alkenyl and alkynyl groups may in each case be replaced by —R⁷C=CR⁷—, —C≡C—, Si(R⁷)₂, C=O, C=NR⁷, —C(=O)O—, —C(=O)NR⁷—, NR⁷, P(=O)(R⁷), —O—, —S—, SO or SO₂;

R² is selected, identically or differently at each occurrence, from straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl, groups and the said aromatic and heteroaromatic ring systems are in each case substituted by radicals R⁷;

R³ is selected, identically or differently at each occurrence, from H, D, F, Cl, Br, I, C(=O)R⁷, CN, Si(R⁷)₃, N(R⁷)₂, P(=O)(R⁷)₂, OR⁷, S(=O)R⁷, S(=O)₂R⁷, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals R³ may be connected to each other to form a ring; where the said alkyl, alkoxy, alkenyl and alkynyl groups and the said aromatic and heteroaromatic ring systems are in each case substituted by radicals $R^7$, and where one or more $CH_2$ groups in the said alkyl, alkoxy, alkenyl and alkynyl groups may in each case be replaced by —$R^7C$═$CR^7$—, —C≡C—, $Si(R^7)_2$, C═O, C═$NR^7$, —C(═O)O—, —C(═O)$NR^7$—, $NR^7$, P(═O)($R^7$), —O—, —S—, SO or $SO_2$;

$R^4$ is selected, identically or differently at each occurrence, from H, D, F, Cl, Br, I, C(═O)$R^7$, CN, $Si(R^7)_3$, $N(R^7)_2$, P(═O)($R^7$)$_2$, $OR^7$, S(═O)$R^7$, S(═O)$_2R^7$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^4$ may be connected to each other to form a ring; where the said alkyl, alkoxy, alkenyl and alkynyl groups and the said aromatic and heteroaromatic ring systems are in each case substituted by radicals $R^7$, and where one or more $CH_2$ groups in the said alkyl, alkoxy, alkenyl and alkynyl groups may in each case be replaced by —$R^7C$═$CR^7$—, —C≡C—, $Si(R^7)_2$, C═O, C═$NR^7$, —C(═O)O—, —C(═O)$NR^7$—, $NR^7$, P(═O)($R^7$), —O—, —S—, SO or $SO_2$;

$R^5$ is selected, identically or differently at each occurrence, from H, D, F, Cl, Br, I, C(═O)$R^7$, CN, $Si(R^7)_3$, $N(R^7)_2$, P(═O)($R^7$)$_2$, $OR^7$, S(═O)$R^7$, S(═O)$_2R^7$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where the said alkyl, alkoxy, alkenyl and alkynyl groups and the said aromatic and heteroaromatic ring systems are in each case substituted by radicals $R^7$, and where one or more $CH_2$ groups in the said alkyl, alkoxy, alkenyl and alkynyl groups may in each case be replaced by —$R^7C$═$CR^7$—, —C≡C—, $Si(R^7)_2$, C═O, C═$NR^7$, —C(═O)O—, —C(═O)$NR^7$—, $NR^7$, P(═O)($R^7$), —O—, —S—, SO or $SO_2$;

$R^6$ is selected, identically or differently at each occurrence, from H, D, F, Cl, Br, I, C(═O)$R^7$, CN, $Si(R^7)_3$, $N(R^7)_2$, P(═O)($R^7$)$_2$, $OR^7$, S(═O)$R^7$, S(═O)$_2R^7$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^6$ may be connected to each other to form a ring; where the said alkyl, alkoxy, alkenyl and alkynyl groups and the said aromatic and heteroaromatic ring systems are in each case be substituted by radicals $R^7$, and where one or more $CH_2$ groups in the said alkyl, alkoxy, alkenyl and alkynyl groups may in each case be replaced by —$R^7C$═$CR^7$—, —C≡C—, $Si(R^7)_2$, C═O, C═$NR^7$, —C(═O)O—, —C(═O)$NR^7$—, $NR^7$, P(═O)($R^7$), —O—, —S—, SO or $SO_2$;

$R^7$ is selected, identically or differently at each occurrence, from H, D, F, Cl, Br, I, C(═O)$R^8$, CN, $Si(R^8)_3$, $N(R^8)_2$, P(═O)($R^8$)$_2$, $OR^8$, S(═O)$R^8$, S(═O)$_2R^8$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where the said alkyl, alkoxy, alkenyl and alkynyl groups and the said aromatic and heteroaromatic ring systems are in each case be substituted by radicals $R^8$, and where one or more $CH_2$ groups in the said alkyl, alkoxy, alkenyl and alkynyl groups may in each case be replaced by —$R^8C$═$CR^8$—, —C≡C—, $Si(R^8)_2$, C═O, C═$NR^8$, —C(═O)O—, —C(═O)$NR^8$—, $NR^8$, P(═O)($R^8$), —O—, —S—, SO or $SO_2$;

$R^8$ is selected, identically or differently at each occurrence, from H, D, F, Cl, Br, I, CN, alkyl groups having 1 to 20 C atoms, aromatic ring systems having 6 to 40 C atoms, or heteroaromatic ring systems having 5 to 40 aromatic ring atoms; and where the said alkyl groups, aromatic ring systems and heteroaromatic ring systems may be substituted by one or more radicals selected from F and CN;

m is 1, 2, 3, or 4;

n is 0, 1, 2, 3, or 4.

2. The compound according to claim 1, wherein it is a monoamine.

3. The compound according to claim 1, wherein X is O.

4. The compound according to claim 1, wherein m is 1.

5. The compound according to claim 1, wherein —[$Ar^1$]$_m$— for the case of m=1 is 1,4-phenylene, which is substituted with radicals $R^4$.

6. The compound according to claim 1, wherein groups —[$Ar^2$]$_n$— for the case of n=1 are selected from divalent groups derived from phenyl, biphenyl, terphenyl, naphthalene, fluorene, indenofluorene, indenocarbazole, spirobifluorene, dibenzofuran, dibenzothiophene, and carbazole, which are substituted with radicals $R^5$.

7. The compound according to claim 1, wherein $Ar^3$ and $Ar^4$ are selected, identically or differently, from phenyl, biphenyl, terphenyl, quaterphenyl, naphthyl, fluorenyl, particularly 9,9'-dimethylfluorenyl and 9,9'-diphenylfluorenyl, benzofluorenyl, spirobifluorenyl, indenofluorenyl, indenocarbazolyl, dibenzofuranyl, dibenzothiophenyl, carbazolyl, benzofuranyl, benzothiophenyl, benzo-condensed dibenzofuranyl, benzo-condensed dibenzothiophenyl, phenyl substituted with naphthyl, phenyl substituted with fluorenyl, phenyl substituted with spirobifluorenyl, phenyl substituted with dibenzofuranyl, phenyl substituted with dibenzothiophene, phenyl substituted with carbazolyl, phenyl substituted with pyridyl, phenyl substituted with pyrimidyl, and phenyl substituted with triazinyl, where the groups are each substituted with radicals $R^6$.

8. The compound according to claim 1, wherein
$R^1$ is selected, identically or differently, from H, D, F, CN, $Si(R^7)_3$, $N(R^7)_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$; and $R^2$ is selected, identically or differently, from a straight-chain alkyl group having 1 to 20 C atoms, a branched or cyclic alkyl group having 3 to 20 C atoms, and an aromatic ring system having 6 to 40 aromatic ring atoms; where the said alkyl group and the said aromatic ring system are substituted by radicals $R^7$; and $R^3$ is selected, identically or differently, from H, D, F, CN, $Si(R^7)_3$, $N(R^7)_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$; and $R^4$ is selected, identically or differently, from H, D, F, CN, $Si(R^7)_3$, $N(R^7)_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$; and $R^5$ is selected, identically or differently, from H, D, F, CN, $Si(R^7)_3$, $N(R^7)_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$; and $R^6$ is selected, identically or differently, from H, D, F, CN, $Si(R^7)_3$, $N(R^7)_2$, straight-chain alkyl groups having 1 to 20 C atoms, branched or cyclic alkyl alkoxy groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$; and $R^7$ is selected, identically or differently, from H, D, F, CN, $Si(R^8)_3$, $N(R^8)_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^8$;

n=1;

—$Ar^2$— is selected from divalent groups derived from phenyl, biphenyl, naphthyl and fluorene, which are substituted with radicals $R^5$;

$Ar^3$ and $Ar^4$ are selected, identically or differently, from phenyl, biphenyl, terphenyl quaterphenyl, naphthyl, fluorenyl, particularly 9,9'-dimethylfluorenyl and 9,9'-diphenylfluorenyl, benzofluorenyl, spirobifluorenyl, indenofluorenyl, indenocarbazolyl, dibenzofuranyl dibenzothiophenyl, carbazolyl, benzofuranyl, benzothiophenyl, benzo-condensed dibenzofuranyl, benzo-condensed dibenzothiophenyl, phenyl substituted with naphthyl, phenyl substituted with fluorenyl, phenyl substituted with spirobifluorenyl, phenyl substituted with dibenzofuranyl, phenyl substituted with dibenzothiophene, phenyl substituted with carbazolyl, phenyl substituted with pyridyl, phenyl substituted with pyrimidyl, and phenyl substituted with triazinyl, where the groups are each substituted with radicals $R^6$.

9. The compound according to claim 1, wherein $R^2$ is selected, identically or differently on each occurrence, from the following groups

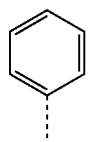
R²-1

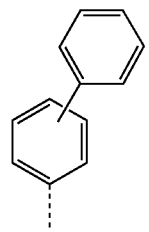
R²-2

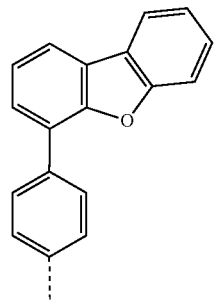
R²-3

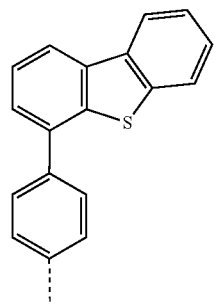
R²-4

—CH₃ R²-5 where the dotted bond represents the bond to the rest of the formula.

10. The compound according to claim 1, wherein it conforms to the following formulae

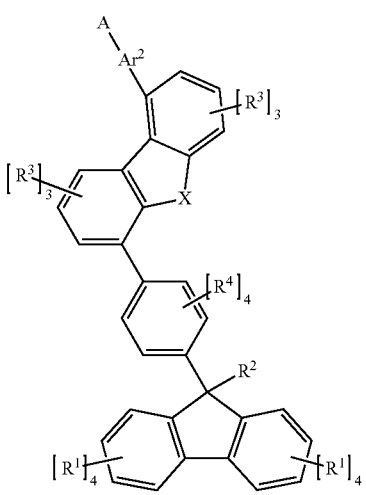
Formula (I-A-1-1)

Formula (I-A-1-2)
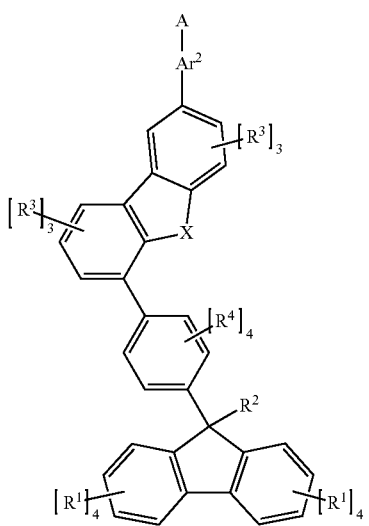
Formula (I-A-1-3)
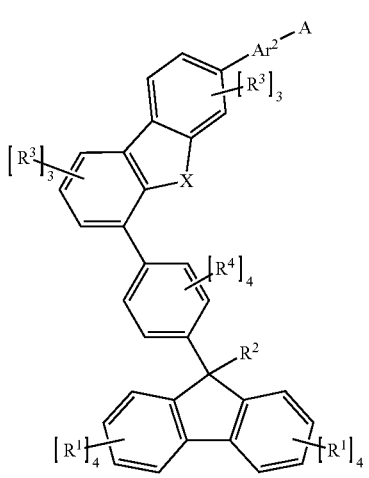
Formula (I-A-1-4)
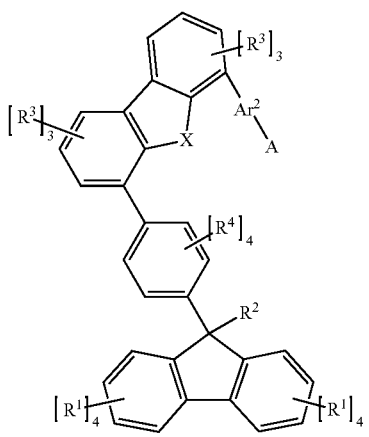
Formula (I-A-1-5)
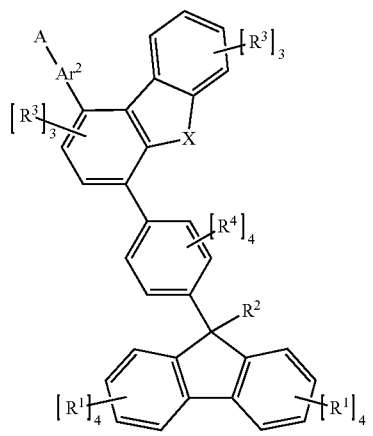
Formula (I-A-1-6)
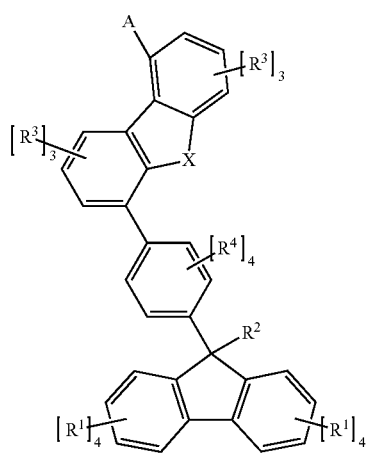
Formula (I-A-1-7)
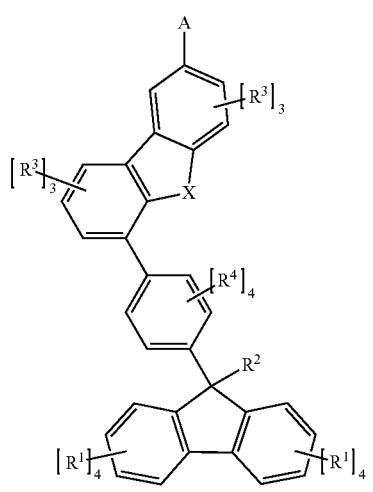

-continued

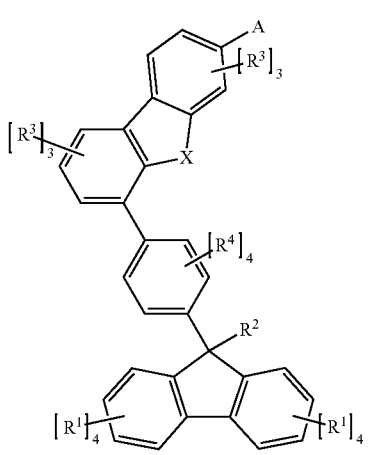
Formula (I-A-1-8)

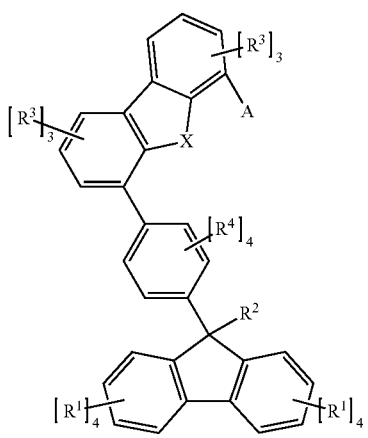
Formula (I-A-1-9)

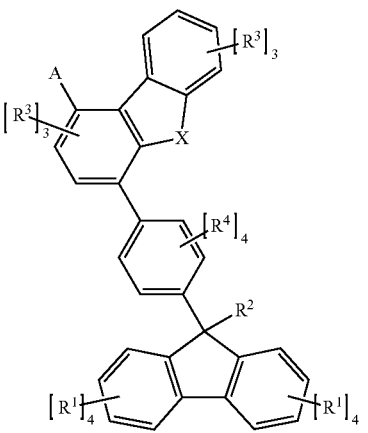
Formula (I-A-1-10)

where the variables occurring are defined as in claim 1.

11. The compound according to claim 10, wherein the compound conforms to formula (I-A-1-4) or (I-A-1-9).

12. An oligomer, polymer or dendrimer, comprising one or more compounds of formula (I) according to claim 1, where the bond(s) to the polymer, oligomer or dendrimer may be localised at any desired positions in formula (I) substituted by $R^1$, $R^2$, $R^3$, $R^4$, $R^5$ or $R^6$.

13. A formulation, comprising at least one compound of formula (I) according to claim 1, and at least one solvent.

14. An electronic device, comprising at least one compound according to claim 1.

15. The electronic device according to claim 14, wherein the device is an organic electroluminescent device, comprising anode, cathode and at least one emitting layer, where at least one organic layer of the device, which is a hole transport layer, an electron blocking layer or a hole injection layer, comprises the at least one compound.

16. A method comprising incorporating the compound according to claim 1 in an electronic device.

17. The compound according to claim 10, wherein $R^1$ is selected, identically or differently, from H, D, F, CN, $Si(R^7)_3$, $N(R^7)_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$; and $R^2$ is selected, identically or differently, from a straight-chain alkyl group having 1 to 20 C atoms, a branched or cyclic alkyl group having 3 to 20 C atoms, and an aromatic ring system having 6 to 40 aromatic ring atoms; where the said alkyl group and the said aromatic ring system are substituted by radicals $R^7$; and $R^3$ is selected, identically or differently, from H, D, F, CN, $Si(R^7)_3$, $N(R^7)_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$; and $R^4$ is selected, identically or differently, from H, D, F, CN, $Si(R^7)_3$, $N(R^7)_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$; and $R^5$ is selected, identically or differently, from H, D, F, CN, $Si(R^7)_3$, $N(R^7)_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$; and $R^6$ is selected, identically or differently, from H, D, F, CN, $Si(R^7)_3$, $N(R^7)_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$;

$R^7$ is selected, identically or differently, from H, D, F, CN, $Si(R^8)_3$, $N(R^8)_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^8$;

n=1;

—Ar$^2$— is selected from divalent groups derived from phenyl, biphenyl, naphthyl and fluorene, which are substituted with radicals $R^5$; and Ar$^3$ and Ar$^4$ are selected, identically or differently, from phenyl, biphenyl, terphenyl, quaterphenyl, naphthyl, fluorenyl, particularly 9,9'-dimethylfluorenyl and 9,9'-diphenylfluorenyl, benzofluorenyl, spirobifluorenyl, indenofluorenyl, indenocarbazolyl, dibenzofuranyl dibenzothiophenyl, carbazolyl, benzofuranyl, benzothiophenyl, benzo-condensed dibenzofuranyl, benzo-condensed dibenzothiophenyl, phenyl substituted with naphthyl, phenyl substituted with fluorenyl, phenyl substituted with spirobifluorenyl, phenyl substituted with dibenzofuranyl, phenyl substituted with dibenzothiophene, phenyl substituted with carbazolyl, phenyl substituted with pyridyl, phenyl substituted with pyrimidyl, and phenyl substituted with triazinyl, where the groups are each substituted with radicals $R^6$.

18. The compound according to claim 11, wherein $R^1$ is selected, identically or differently, from H, D, F, CN, Si($R^7$)$_3$, N($R^7$)$_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$; and $R^2$ is selected, identically or differently, from a straight-chain alkyl group having 1 to 20 C atoms, a branched or cyclic alkyl group having 3 to 20 C atoms, and an aromatic ring system having 6 to 40 aromatic ring atoms; where the said alkyl group and the said aromatic ring system are substituted by radicals $R^7$; and $R^3$ is selected, identically or differently, from H, D, F, CN, Si($R^7$)$_3$, N($R^7$)$_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$; and $R^4$ is selected, identically or differently, from H, D, F, CN, Si($R^7$)$_3$, N($R^7$)$_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$; and $R^5$ is selected, identically or differently, from H, D, F, CN, Si($R^7$)$_3$, N($R^7$)$_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$; and $R^6$ is selected, identically or differently, from H, D, F, CN, Si($R^7$)$_3$, N($R^7$)$_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^7$; and $R^7$ is selected, identically or differently, from H, D, F, CN, Si($R^8$)$_3$, N($R^8$)$_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems are substituted by radicals $R^8$ n=1;

—Ar$^2$— is selected from divalent groups derived from phenyl, biphenyl, naphthyl and fluorene, which are substituted with radicals $R^5$;

Ar$^3$ and Ar$^4$ are selected, identically or differently, from phenyl, biphenyl, terphenyl, quaterphenyl, naphthyl, fluorenyl, particularly 9,9'-dimethylfluorenyl and 9,9'-diphenylfluorenyl, benzofluorenyl, spirobifluorenyl, indenofluorenyl, indenocarbazolyl, dibenzofuranyl dibenzothiophenyl, carbazolyl, benzofuranyl, benzothiophenyl, benzo-condensed dibenzofuranyl, benzo-condensed dibenzothiophenyl, phenyl substituted with naphthyl, phenyl substituted with fluorenyl, phenyl substituted with spirobifluorenyl, phenyl substituted with dibenzofuranyl, phenyl substituted with dibenzothiophene, phenyl substituted with carbazolyl, phenyl substituted with pyridyl, phenyl substituted with pyrimidyl, and phenyl substituted with triazinyl, where the groups are each substituted with radicals $R^6$.

\* \* \* \* \*